United States Patent
Wohlgemuth et al.

(10) Patent No.: US 8,110,364 B2
(45) Date of Patent: Feb. 7, 2012

(54) METHODS AND COMPOSITIONS FOR DIAGNOSING OR MONITORING AUTOIMMUNE AND CHRONIC INFLAMMATORY DISEASES

(75) Inventors: Jay Wohlgemuth, Menlo Park, CA (US); Kirk Fry, Palo Alto, CA (US); Robert Woodward, Pleasanton, CA (US); Ngoc Ly, Albany, CA (US)

(73) Assignee: XDx, Inc., Brisbane, CA (US)

( * ) Notice: Subject to any disclaimer, the term of this patent is extended or adjusted under 35 U.S.C. 154(b) by 0 days.

(21) Appl. No.: 12/958,344

(22) Filed: Dec. 1, 2010

(65) Prior Publication Data

US 2011/0262914 A1 Oct. 27, 2011

Related U.S. Application Data

(60) Continuation of application No. 12/235,969, filed on Sep. 23, 2008, now abandoned, which is a division of application No. 10/990,298, filed on Nov. 15, 2004, now Pat. No. 7,579,148, which is a division of application No. 10/131,827, filed on Apr. 24, 2002, now Pat. No. 6,905,827, which is a continuation-in-part of application No. 10/006,290, filed on Oct. 22, 2001, now abandoned.

(60) Provisional application No. 60/296,764, filed on Jun. 8, 2001.

(51) Int. Cl.
C12Q 1/68 (2006.01)
(52) U.S. Cl. ............. 435/6.17; 435/6.11; 435/6.12
(58) Field of Classification Search .................. None
See application file for complete search history.

(56) References Cited

U.S. PATENT DOCUMENTS

| | | |
|---|---|---|
| 4,190,535 A | 2/1980 | Luderer et al. |
| 4,215,051 A | 7/1980 | Schroeder et al. |
| 4,350,593 A | 9/1982 | Kessler |
| 4,358,535 A | 11/1982 | Falkow et al. |
| 4,376,110 A | 3/1983 | David et al. |
| 4,582,789 A | 4/1986 | Sheldon, III et al. |
| 4,683,195 A | 7/1987 | Mullis et al. |
| 4,683,202 A | 7/1987 | Mullis |
| 4,751,001 A | 6/1988 | Saunders |
| 4,762,780 A | 8/1988 | Spector et al. |
| 4,789,630 A | 12/1988 | Bloch et al. |
| 4,800,159 A | 1/1989 | Mullis et al. |
| 4,818,418 A | 4/1989 | Saunders |
| 4,843,155 A | 6/1989 | Chomczynski |
| 4,889,818 A | 12/1989 | Gelfand et al. |
| 4,908,318 A | 3/1990 | Lerner |
| 4,946,778 A | 8/1990 | Ladner et al. |
| 4,946,952 A | 8/1990 | Kiefer |
| 4,965,188 A | 10/1990 | Mullis et al. |
| 5,053,134 A | 10/1991 | Luderer et al. |
| 5,063,162 A | 11/1991 | Kiefer |
| 5,066,584 A | 11/1991 | Gyllensten et al. |
| 5,075,216 A | 12/1991 | Innis et al. |
| 5,079,352 A | 1/1992 | Gelfand et al. |
| 5,091,310 A | 2/1992 | Innis |
| 5,120,525 A | 6/1992 | Goldenberg |
| 5,142,033 A | 8/1992 | Innis |
| 5,143,854 A | 9/1992 | Pirrung et al. |
| 5,210,015 A | 5/1993 | Gelfand et al. |
| 5,212,071 A | 5/1993 | Fearon et al. |
| 5,215,882 A | 6/1993 | Bahl et al. |
| 5,219,727 A | 6/1993 | Wang et al. |
| 5,264,351 A | 11/1993 | Harley |
| 5,278,043 A | 1/1994 | Bannwarth et al. |
| 5,310,652 A | 5/1994 | Gelfand et al. |
| 5,314,809 A | 5/1994 | Erlich et al. |
| 5,322,770 A | 6/1994 | Gelfand |
| 5,340,720 A | 8/1994 | Stetler |
| 5,346,994 A | 9/1994 | Chomczynski |
| 5,352,600 A | 10/1994 | Gelfand et al. |
| 5,374,553 A | 12/1994 | Gelfand et al. |
| 5,385,824 A | 1/1995 | Hoet et al. |
| 5,389,512 A | 2/1995 | Kwok et al. |
| 5,393,672 A | 2/1995 | Ness et al. |
| 5,405,774 A | 4/1995 | Abramson et al. |
| 5,407,800 A | 4/1995 | Gelfand et al. |
| 5,411,876 A | 5/1995 | Bloch et al. |
| 5,418,149 A | 5/1995 | Gelfand et al. |
| 5,420,029 A | 5/1995 | Gelfand et al. |
| 5,426,039 A | 6/1995 | Wallace et al. |
| 5,445,940 A | 8/1995 | Brenner et al. |
| 5,455,170 A | 10/1995 | Abramson et al. |
| 5,459,037 A | 10/1995 | Sutcliffe et al. |
| 5,464,937 A | 11/1995 | Sims et al. |
| 5,466,591 A | 11/1995 | Abramson et al. |
| 5,468,613 A | 11/1995 | Erlich et al. |

(Continued)

FOREIGN PATENT DOCUMENTS

EP 0217102 A1 4/1987

(Continued)

OTHER PUBLICATIONS

Shulzhenko, "Monitoring of Intragraft and Peripheral Blood TIRC7 Expression as a Diagnostic Tool for Acute Cardiac Rejection in Humans", Human Immunology, vol. 62, 2001, pp. 342-347.

Dudek, et al., "Platelet Factor 4 Promotes Adhesion of Hematopoietic Progenitor Cells and Binds IL-8: Novel Mechanisms for Modulation of Hematopoiesis", Blood, vol. 101, No. 12, Jun. 2003, pp. 4687-4694.

Dugre, F. J., "Cytokine and Cytotoxic Molecule Gene Expression Determined in Peripheral Blood Mononuclear Cells in the Diagnosis of Acute Renal Rejection", Transplantation, vol. 70, No. 7, Oct. 2000, pp. 1074-1080.

Smith-Norowitz, et al., "Lymphocyte Activation in Angina Pectoris", Clinical Immunology, vol. 93, No. 2, 1999, pp. 168-175.

Staudt, et al., "Genomic Views of the Immune System", Annual Review of Immunology, vol. 18, 2000, pp. 829-859.

(Continued)

Primary Examiner — James Martinell
(74) Attorney, Agent, or Firm — Morrison & Foerster LLP

(57) ABSTRACT

Methods of diagnosing or monitoring an autoimmune or chronic inflammatory disease, particularly SLE in a patient by detecting the expression level of one or more genes or surrogates derived therefrom in the patient are described. Diagnostic oligonucleotides for diagnosing or monitoring chronic inflammatory disease, particularly SLE infection and kits or systems containing the same are also described.

8 Claims, 12 Drawing Sheets

U.S. PATENT DOCUMENTS

| | | | |
|---|---|---|---|
| 5,476,774 A | 12/1995 | Wang et al. |
| 5,487,970 A | 1/1996 | Rowley et al. |
| 5,487,972 A | 1/1996 | Gelfand et al. |
| 5,491,063 A | 2/1996 | Fisher et al. |
| 5,491,086 A | 2/1996 | Gelfand et al. |
| 5,501,963 A | 3/1996 | Burckhardt |
| 5,506,145 A | 4/1996 | Bull et al. |
| 5,512,462 A | 4/1996 | Cheng |
| 5,514,556 A | 5/1996 | Shearer et al. |
| 5,538,848 A | 7/1996 | Livak et al. |
| 5,561,058 A | 10/1996 | Gelfand et al. |
| 5,565,339 A | 10/1996 | Bloch et al. |
| 5,569,583 A | 10/1996 | Greenberg et al. |
| 5,571,673 A | 11/1996 | Picone |
| 5,573,906 A | 11/1996 | Bannwarth et al. |
| 5,604,099 A | 2/1997 | Erlich et al. |
| 5,618,703 A | 4/1997 | Gelfand et al. |
| 5,618,711 A | 4/1997 | Gelfand et al. |
| 5,624,833 A | 4/1997 | Gelfand et al. |
| 5,635,365 A | 6/1997 | Ansari et al. |
| 5,641,864 A | 6/1997 | Gelfand |
| 5,658,744 A | 8/1997 | Ochoa et al. |
| 5,665,551 A | 9/1997 | Gelfand et al. |
| 5,674,738 A | 10/1997 | Abramson et al. |
| 5,677,152 A | 10/1997 | Birch et al. |
| 5,693,517 A | 12/1997 | Gelfand et al. |
| 5,707,807 A | 1/1998 | Kato |
| 5,716,787 A | 2/1998 | Dunn et al. |
| 5,721,351 A | 2/1998 | Levinson |
| 5,728,822 A | 3/1998 | Macfarlane |
| 5,766,585 A | 6/1998 | Evans et al. |
| 5,773,258 A | 6/1998 | Birch et al. |
| 5,789,224 A | 8/1998 | Gelfand et al. |
| 5,795,762 A | 8/1998 | Abramson et al. |
| 5,804,375 A | 9/1998 | Gelfand et al. |
| 5,807,522 A | 9/1998 | Brown et al. |
| 5,811,284 A | 9/1998 | Chang et al. |
| 5,837,832 A | 11/1998 | Chee et al. |
| 5,939,270 A | 8/1999 | Haunso et al. |
| 5,939,292 A | 8/1999 | Gelfand et al. |
| 5,958,342 A | 9/1999 | Gamble et al. |
| 5,958,688 A | 9/1999 | Eberwine et al. |
| 5,965,366 A | 10/1999 | Ochoa et al. |
| 5,968,799 A | 10/1999 | Gelfand et al. |
| 5,973,137 A | 10/1999 | Heath |
| 5,981,481 A | 11/1999 | Fearon et al. |
| 5,994,056 A | 11/1999 | Higuchi |
| 5,994,076 A | 11/1999 | Chenchik et al. |
| 6,001,611 A | 12/1999 | Will |
| 6,004,755 A | 12/1999 | Wang |
| 6,010,853 A | 1/2000 | Kanteti et al. |
| 6,020,186 A | 2/2000 | Henco et al. |
| 6,033,860 A | 3/2000 | Lockhart et al. |
| 6,040,138 A | 3/2000 | Lockhart et al. |
| 6,040,166 A | 3/2000 | Erlich et al. |
| 6,045,996 A | 4/2000 | Cronin et al. |
| 6,048,695 A | 4/2000 | Bradley et al. |
| 6,048,709 A | 4/2000 | Falb |
| 6,060,240 A | 5/2000 | Kamb et al. |
| 6,066,322 A | 5/2000 | Levinson |
| 6,066,498 A | 5/2000 | Levinson |
| 6,084,083 A | 7/2000 | Levinson |
| 6,087,112 A | 7/2000 | Dale |
| 6,087,477 A | 7/2000 | Falb et al. |
| 6,090,556 A | 7/2000 | Kato |
| 6,099,823 A | 8/2000 | Falb |
| 6,124,433 A | 9/2000 | Falb et al. |
| 6,127,155 A | 10/2000 | Gelfand et al. |
| 6,132,997 A | 10/2000 | Shannon |
| 6,146,828 A | 11/2000 | Lapidus et al. |
| 6,150,121 A | 11/2000 | Hamawy et al. |
| 6,156,887 A | 12/2000 | Levinson |
| 6,162,604 A | 12/2000 | Jacob |
| 6,168,933 B1 | 1/2001 | Kaser et al. |
| 6,171,785 B1 | 1/2001 | Higuchi |
| 6,177,254 B1 | 1/2001 | Rattner et al. |
| 6,187,534 B1 | 2/2001 | Strom et al. |
| 6,190,857 B1 | 2/2001 | Ralph et al. |
| 6,190,872 B1 | 2/2001 | Slotman |
| 6,194,158 B1 | 2/2001 | Kroes et al. |
| 6,197,563 B1 | 3/2001 | Erlich et al. |
| 6,203,987 B1 | 3/2001 | Friend et al. |
| 6,204,371 B1 | 3/2001 | Levinson |
| 6,214,979 B1 | 4/2001 | Gelfand et al. |
| 6,218,122 B1 | 4/2001 | Friend et al. |
| 6,222,093 B1 | 4/2001 | Marton et al. |
| 6,225,084 B1 | 5/2001 | Falb et al. |
| 6,225,093 B1 | 5/2001 | Grant et al. |
| 6,228,628 B1 | 5/2001 | Gelfand et al. |
| 6,242,185 B1 | 6/2001 | Kaser et al. |
| 6,245,334 B1 | 6/2001 | Seilhammer et al. |
| 6,245,526 B1 | 6/2001 | Yue et al. |
| 6,245,527 B1 | 6/2001 | Busfield et al. |
| 6,248,527 B1 | 6/2001 | Chen et al. |
| 6,248,528 B1 | 6/2001 | Chen et al. |
| 6,251,597 B1 | 6/2001 | Shyjan |
| 6,262,244 B1 | 7/2001 | Houchins et al. |
| 6,274,312 B1 | 8/2001 | Gish et al. |
| 6,280,941 B1 | 8/2001 | Tsao et al. |
| 6,303,321 B1 | 10/2001 | Tracey et al. |
| 6,306,602 B1 | 10/2001 | Sillekens et al. |
| 6,365,352 B1 | 4/2002 | Yerramilli et al. |
| 6,403,304 B1 | 6/2002 | Stashenko et al. |
| 6,410,319 B1 | 6/2002 | Raubitschek et al. |
| 6,811,973 B1 | 11/2004 | Reich |
| 6,905,827 B2 | 6/2005 | Wohlgemuth et al. |
| 6,964,850 B2 | 11/2005 | Bevilacqua et al. |
| 7,026,121 B1 | 4/2006 | Wohlgemuth et al. |
| 7,118,865 B2 | 10/2006 | Behrens et al. |
| 7,235,358 B2 | 6/2007 | Wohlgemuth et al. |
| 7,514,209 B2 | 4/2009 | Dai et al. |
| 7,879,556 B2 | 2/2011 | Wohlgemuth et al. |
| 7,960,121 B2 | 6/2011 | Wohlgemuth et al. |
| 2001/0021700 A1 | 9/2001 | Moore et al. |
| 2002/0042386 A1 | 4/2002 | Rosen et al. |
| 2002/0128436 A1 | 9/2002 | Strom et al. |
| 2002/0132235 A1 | 9/2002 | Avihingsanon et al. |
| 2003/0139466 A1 | 7/2003 | Peritt et al. |
| 2003/0224426 A1 | 12/2003 | Li |
| 2003/0225526 A1 | 12/2003 | Golub et al. |
| 2004/0023246 A1 | 2/2004 | Meuer et al. |
| 2004/0033498 A1 | 2/2004 | Behrens et al. |
| 2004/0072181 A1 | 4/2004 | Whitehead et al. |
| 2004/0197786 A1 | 10/2004 | Sugita et al. |
| 2005/0186637 A1 | 8/2005 | Yu et al. |
| 2005/0281815 A1 | 12/2005 | Eshel et al. |
| 2006/0051803 A1 | 3/2006 | Wohlgemuth et al. |
| 2006/0088836 A1 | 4/2006 | Wohlgemuth et al. |
| 2006/0216707 A1 | 9/2006 | Stuhlmuller et al. |
| 2006/0263813 A1 | 11/2006 | Rosenberg et al. |
| 2007/0037144 A1 | 2/2007 | Wohlgemuth |
| 2007/0037166 A1 | 2/2007 | Wohlgemuth |
| 2007/0037167 A1 | 2/2007 | Wohlgemuth et al. |
| 2007/0248978 A1 | 10/2007 | Lal et al. |
| 2008/0038746 A1 | 2/2008 | Rosenberg et al. |
| 2009/0263796 A1 | 10/2009 | Wohlgemuth et al. |
| 2009/0263800 A1 | 10/2009 | Wohlgemuth et al. |
| 2010/0009377 A1 | 1/2010 | Wohlgemuth et al. |
| 2010/0092989 A1 | 4/2010 | Wohlgemuth et al. |
| 2010/0099098 A1 | 4/2010 | Wohlgemuth et al. |
| 2010/0136564 A1 | 6/2010 | Lal et al. |
| 2010/0151467 A1 | 6/2010 | Wohlgemuth et al. |
| 2011/0070584 A1 | 3/2011 | Wohlgemuth et al. |

FOREIGN PATENT DOCUMENTS

| | | |
|---|---|---|
| EP | 0217992 A2 | 4/1987 |
| EP | 1077254 A2 | 2/2001 |
| EP | 1162276 A2 | 12/2001 |
| SG | 200302150-8 | 7/2002 |
| WO | 91/18626 A1 | 12/1991 |
| WO | 93/06864 A1 | 4/1993 |
| WO | 94/23023 A1 | 10/1994 |
| WO | 95/17506 A1 | 6/1995 |
| WO | 96/39536 A1 | 12/1996 |
| WO | 97/16568 A1 | 5/1997 |
| WO | 97/30065 A1 | 8/1997 |
| WO | 98/24935 A1 | 6/1998 |

| | | |
|---|---|---|
| WO | 99/04251 A1 | 1/1999 |
| WO | 99/10536 A1 | 3/1999 |
| WO | 99/11782 A1 | 3/1999 |
| WO | 99/11822 A1 | 3/1999 |
| WO | 99/15700 A1 | 4/1999 |
| WO | 99/52541 A2 | 10/1999 |
| WO | 99/57130 A1 | 11/1999 |
| WO | 00/04191 A1 | 1/2000 |
| WO | 00/12753 A1 | 3/2000 |
| WO | 00/29574 A2 | 5/2000 |
| WO | 00/46372 A2 | 8/2000 |
| WO | 00/23573 A3 | 9/2000 |
| WO | 00/52209 A1 | 9/2000 |
| WO | 00/55375 A1 | 9/2000 |
| WO | 00/58473 A2 | 10/2000 |
| WO | 00/63372 A1 | 10/2000 |
| WO | 00/73498 A1 | 12/2000 |
| WO | 00/78808 A1 | 12/2000 |
| WO | 01/14557 A1 | 3/2001 |
| WO | 01/20004 A2 | 3/2001 |
| WO | 01/23426 A2 | 4/2001 |
| WO | 01/23564 A1 | 4/2001 |
| WO | 01/25473 A1 | 4/2001 |
| WO | 01/29269 A2 | 4/2001 |
| WO | 01/32927 A2 | 5/2001 |
| WO | 01/40302 A2 | 6/2001 |
| WO | 01/47944 A2 | 7/2001 |
| WO | 01/54733 A1 | 8/2001 |
| WO | 01/55164 A1 | 8/2001 |
| WO | 01/55201 A1 | 8/2001 |
| WO | 01/55203 A1 | 8/2001 |
| WO | 01/55205 A1 | 8/2001 |
| WO | 01/55328 A2 | 8/2001 |
| WO | 01/55368 A1 | 8/2001 |
| WO | 01/57182 A2 | 8/2001 |
| WO | 01/60860 A3 | 8/2001 |
| WO | 01/71005 A2 | 9/2001 |
| WO | 01/81916 A2 | 11/2001 |
| WO | 01/86003 A2 | 11/2001 |
| WO | 02/00677 A1 | 1/2002 |
| WO | 02/00928 A1 | 1/2002 |
| WO | 02/28999 A2 | 4/2002 |
| WO | 02/057414 A2 | 7/2002 |
| WO | 03/004612 A2 | 1/2003 |
| WO | 03/072035 A2 | 9/2003 |
| WO | 03/090694 A2 | 11/2003 |
| WO | 2004/042346 A2 | 5/2004 |
| WO | 2004/074815 A2 | 9/2004 |
| WO | 2004/108899 A2 | 12/2004 |
| WO | 2006/122295 A2 | 11/2006 |

OTHER PUBLICATIONS

Morita, et al., "Early Chemokine Cascades in Murine Cardiac Grafts Regulate T Cell Recruitment and Progression of Acute Allograft Rejection", The Journal of Immunology, vol. 167, 2001, pp. 2979-2984.

Stellrecht, et al., "Expression Pattern of a Hematopoietic Proteoglycan Core Protein Gene During Human Hematopoiesis", Differentiation, vol. 48, 1991, pp. 127-135.

Abdallah, et al., "Evaluation of Plasma Levels of Tumor Necrosis Factor Alpha and Interleukin-6 as Rejection Markers in a Cohort of 142 Heart-Grafted Patients Followed by Endomyocardial Biopsy", European Heart Journal, vol. 18, 1997, pp. 1024-1029.

Doi, et al., "Polymerase Chain Reaction Quantification of Cytokine Messenger RNA Expression in Peripheral Blood Monoculear Cells of Patients with Acute Exacerbations of Asthma: Effect of Glucocorticoid Therapy", Clinical and Experimental Allergy, vol. 24, 1994, pp. 854-867.

Ahern, H., "Biochemical, Reagent Kits Offer Scientists Good Return on Investment", The Scientist, vol. 9, No. 15, Jul. 24, 1995, pp. 20-22.

Ajjan, et al., "Intrathyroidal Cytokine Gene Expression in Hashimoto's Thyroiditis", Clinical and Experimental Immunology, vol. 105 1996, pp. 523-528.

Akalin, et al., "Gene Expression Analysis in Human Renal Allograft Biopsy Samples Using High-Density Oligoarray Technology", Transplantation, vol. 72, No. 5, Sep. 2001, pp. 948-953.

Alizadeh, et al., "Genomic-Scale Gene Expression Profiling of Normal and Malignant Immune Cells", Current Opinion in Immunology, vol. 12, 2000, pp. 219-225.

Alizadeh, et al., "Distinct types of diffuse large B-cell lymphoma identified by gene expression profiling", Nature vol. 403, No. 6769, 2000, pp. 503-511.

Alizadeh, et al., "Probing Lymphocyte Biology by Genomic-Scale Gene Expression Analysis", Journal of Clinical Immunology, vol. 18, No. 6, 1998, pp. 373-379.

Alizadeh, et al., "The Lymphochip: A Specialized cDNA Microarray for the Genomic-scale Analysis of Gene Expression in Normal and Malignant Lymphocytes", Cold Spring Harbor Symposia on Quantitative Biology, vol. 54, 1999, pp. 71-78.

Alpert, et al., "The Relationship of Granzyme A and Perforin Expression to Cardiac Allograft Rejection and Dysfunction", Transplantation, vol. 60, No. 12, Dec. 1995, pp. 1478-1485.

Amaro, et al., "Plasma Leukocyte Elastase Concentration in Angiographically Diagnosed Coronary Artery Disease", European Heart Journal, vol. 16, 1995, pp. 615-622.

Arnett, et al., "The American Rheumatism Association 1987 Revised Criteria for the Classification of Rheumatoid Arthritis", Arthritis and Rheumatism, vol. 31, No. 3, Mar. 1988, pp. 315-324.

Aukrust, et al., "Enhanced Levels of Soluble and Membrane-Bound CD40 Ligand in Patients with Unstable Angina. Possible Reflection of T Lymphocyte and Platelet Involvement in the Pathogenesis of Acute Coronary Syndromes", Circulation, vol. 100, 1999, pp. 614-620.

Autieri, et al., "Allograft Inflammatory Factor-1 Expression Correlates with Cardiac Rejection and Development of Cardiac Allograft Vasculopathy", Circulation, vol. 106 2002, pp. 2218-2223.

Baechler, et al., "Interferon-Inducible Gene Expression Signature in Peripheral Blood Cells of Patients with Severe Lupus", Proceedings of the National Academy of Sciences, vol. 100, No. 5 Mar. 2003, pp. 2610-2615.

Bakke, et al., "Neutrophil CD64 Expression Distinguishing Acute Inflammatory Autoimmune Disease from Systemic Infections", Clinical and Applied Immunology Reviews, vol. 1, 2001, pp. 267-275.

Bass, C. A., "Clinical Evaluation of a New Polymerase Chain Reaction Assay for Detection of Chlamydia trachomatis in Endocervical Specimens", Journal of Clinical Microbiology, vol. 31, No. 10, Oct. 1993, pp. 2648-2653.

Bave, U., "Activation of Natural Interferon-Alpha Producing Cells by Apoptotic U937 Cells Combined with Lupus IgG and its Regulation by Cytokines", Journal of Autoimmunity, vol. 17, 2001, pp. 71-80.

Bave, U., "The Combination of Apoptotic U937 Cells and Lupus IgG is a Potent IFN-Alpha Inducer", The Journal of Immunology, vol. 165, 2000, pp. 3519-3526.

Belch, et al., "The White Blood Cell Adhesion Molecule E-Selectin Predicts Restenosis in Patients With Intermittent Claudication Undergoing Percutaneous Transluminal Angioplasty", Circulation, vol. 95, No. 8, Apr. 1997, pp. 2027-2031.

Morris, et al., "Thymic Lymphocytes in Male and Female Rats", Immunophenotyping Analysis of Peripheral Blood, Splenic, and Journal of Pharmacological and Toxicological Methods, vol. 37, No. 1, 1997, pp. 37-46.

Neto, et al., "Shotgun Sequencing of the Human Transcriptome with ORF Expressed Sequences Tags", Proceedings of the National Academy of Sciences, vol. 97, No. 7, 2000, pp. 3491-3496.

Newton, et al., "On Differential Variability of Expression Ratios: Improving Statistical Inference about Gene Expression Changes from Microarray Data", Journal of Computational Biology, vol. 8, No. 1, 2001, pp. 37-52.

Bertone, et al., "Global Identification of Human Transcribed Sequences with Genome Tiling Arrays", Science, vol. 306, Dec. 24, 2004, pp. 2242-2246.

Bittner, et al., "Molecular Classification of Cutaneous Malignant Melanoma by Gene Expression Profiling", Nature, vol. 406, Aug. 2000, pp. 536-540.

Boelaert, et al., "Latent Class Analysis Permits Unbiased Estimates of the Validity of DAT for the Diagnosis of Visceral Leishmaniasis", Tropical Medicine & International Health, vol. 4, No. 5, May 1999, pp. 395-401.

Bombardier, et al., "Derivation of the SLEDAI—A Disease Activity Index for Lupus Patients", Arthritis and Rheumatism, vol. 35, No. 6, Jun. 1992, pp. 630-640.

Bustin, S. A. , "Absolute Quantification of mRNA Using Real-Time Reverse Transcription Polymerase Chain Reaction Assays", Journal of Molecular Endocrinology, vol. 25, 2000, pp. 169-193.

Loftus, et al., "Genome Duplications and Other Features in 12 Mb of DNA sequence from Human Chromosome 16p and 16q", Genomics, vol. 60, 1999, pp. 295-308.

Nickel, et al., "Cytotoxic Effector Molecule Gene Expression in Acute Renal Allograft Rejection", Transplantation, vol. 72, No. 6, 2001, pp. 1158-116.

Chang, et al., "Cytokines and Cell Surface Markers in Prediction of Cardiac Allograft Rejection", Immunological Investigations, vol. 25, No. 1&2, 1996 , pp. 13-21.

Chebath, et al., "Four Different Forms of Interferon-Induced 2', 5'-Oligo(A) Synthetase Identified by Immunoblotting in Human Cells", The Journal of Biological Chemistry, vol. 262, No. 8, Mar. 1987 , pp. 3852-2857.

Chen, et al., "Identification of Differentially Expressed Genes in Rat Aortic Allograft Vasculopathy", American Journal of Pathology, vol. 149, No. 2, Aug. 1996, pp. 597-611.

Cheung, et al., "Natural Variation in Human Gene Expression Assessed in Lymphoblastoid Cells", Nature Genetics, vol. 33, Mar. 2003, pp. 422-425.

Creemers, et al., "Evaluation of Peripheral Blood CD4 and CD8 Lymphocyte Subsets, CD69 Expression and Histologic Rejection Grade as Diagnostic Markers for the Presence of Cardiac Allograft Rejection", Transplant Immunology, vol. 10, 2002, pp. 285-292.

Oh, et al., "Correlation of Fas and Fas Ligand Expression with Rejection Status of Transplanted Heart in Human", Transplantation, vol. 71, No. 7, 2001, pp. 906-909.

Damas, et al., "Enhanced Gene Expression of Chemokines and their Corresponding Receptors in Mononuclear Blood Cells in Chronic Heart Failure—Modulatory Effect of Intravenous Immunoglobin", Journal of the American College of Cardiology, vol. 38, No. 1 2001, pp. 187-193.

Davas, et al., "Serum IL-6, TNF-alpha, p55 srTNF-alpha, p75srTNF-alpha, srIL-2-alpha Levels and Disease Activity in Systemic Lupus Erythematosus", Clinical Rheumatology, vol. 18, 1999 , pp. 17-22.

International Search Report received for PCT Application No. PCT/US00/17846, mailed on Mar. 1, 2001, 2 pages.

Stites, et al., Basic and Clinical Immunology. 7th Edition, Appleton & Lange: East Norwalk, CT., 1991, 6 pages (Table of Contents).

Deuel, et al., "Amino Acid Sequence of Human Platelet Factor 4", Proceedings of the National Academy of Sciences, vol. 74, No. 6, Jun. 1977 , pp. 2256-2258.

Deuel, et al., "Platelet Factor 4 is Chemotactic for Neutrophils and Monocytes", Proceedings of the National Academy of Sciences, vol. 78, No. 7, Jul. 1981 , pp. 4584-4587.

Dietz, et al., "Maturation of Human Monocyte-Derived Dendritic Cells Studied by Microarray Hybridization", Biochemical and Biophysical Research Communications, vol. 275, 2000, pp. 731-738.

"EMBL-EBI Accession No. AA053887", Available at: <http://www.ebi.ac.uk/cgi-bin/dbfetch?db=embl&id=AA053887&style=raw> last updated Aug. 31, 2006, visited on Oct. 31, 2007, 3 pages.

"EMBL-EBI Accession No. AAC77576", Available at: <http://www.ebi.ac.uk/cgi-bin/dbfetch?db=emblcds&id=AAC77576&style=raw> visited on Oct. 31, 2007, 1 page.

"EMBL-EBI Accession No. AAK80490", Available at: <http://www.ebi.ac.uk/cgi-bin/dbfetch?db=emblcds&id=AAK80490&style=raw> visited on Oct. 31, 2007, 1 page.

"EMBL-EBI Accession No. AI775145", Available at: <http://www.ebi.ac.uk/cgi-bin/dbfetch?db=embl&id=AI755145&style=raw> visited on Oct. 31, 2007, last updated Jun. 21, 2002, 2 pages.

"EMBL-EBI Accession No. AK000354", Available at : <http://www.ebi.ac.uk/cgi-bin/dbfetch?db=embl&id=AK000354&style=raw> last updated Sep. 12, 2006, visited on Oct. 31, 2007, 3 pages.

"EMBL-EBI Accession No. AV742425", Available at : <http://www.ebi.ac.uk/cgi-bin/dbfetch?db=embl&id=AV742425&style=raw> last updated Oct. 10, 2000, visited on Oct. 31, 2007, 2 pages.

"EMBL-EBI Accession No. AW969353", Available at : <http://www.ebi.ac.uk/cgi-bin/dbfetch?db=embl&id=AW969353&style=raw> last updated Jun. 8, 2000, visited on Oct. 31, 2007, 1 page.

"EMBL-EBI Accession No. G06338", Available at : <http://www.ebi.ac.uk/cgi-bin/dbfetch?db=embl&id=G06338&style=raw> last updated Mar. 4, 2000, visited on Oct. 31, 2007, 2 pages.

"EMBL-EBI Accession No. L26474", Available at : <http://www.ebi.ac.uk/cgi-bin/dbfetch?db=embl&id=L26474&style=raw> last updated Jan. 9, 2007, visited on Oct. 31, 2007, 6 pages.

"EMBL-EBI Accession No. M23068", Available at : <http://www.ebi.ac.uk/cgi-bin/dbfetch?db=embl&id=M23068&style=raw> last updated Nov. 14, 2006, visited on Oct. 31, 2007, 2 pages.

"EMBL-EBI Accession No. V00497", Available at : <http://www.ebi.ac.uk/cgi-bin/dbfetch?db=embl&id=V00497&style=raw> last updated Nov. 20, 2004, visited on Oct. 31, 2007, 5 pages.

International Search Report received for PCT Application No. PCT/US01/47856, mailed on Jul. 18, 2002, 3 pages.

"GenBank Accssion No. AL591031", Available at : <http://www.ncbi.nlm.nih.gov/entrez/viewer.fcgi?db=nuccore&id=16073692> visited on Jun. 27, 2007, 41 pages.

"GenBank Accession No. Y10376", Available at : <http://www.ncbi.nlm.nih.gov/entrez/viewer.fcgi?db=nuccore&id=2052057> last updated May 14, 1997, visited on Apr. 8, 2008, 3 pages.

Edman, et al., "Electric Field Directed Nucleic Acid Hybridization on Microchips", Nucleic Acids Research, vol. 25, No. 24, 1997, pp. 4907-4914.

Metler, "Expression of the Chemokine Receptor CXCR3 and Its Ligand IP-10 During Human Cardiac Allograft Rejection" , Circulation, vol. 104, 2001, pp. 2558-2564.

Galon, et al., "Gene-Profiling Reveals Unknown Enhancing and Suppressive Actions of Glucocorticoids on Immune Cells", The FASEB Journal, vol. 16, Jan. 2002, pp. 61-71.

Gabay, et al., "Circulating Levels of Tumor Necrosis Factor Soluble Receptors in Systemic Lupus Erythematosus are Significantly Higher than in Other Rheumatic Diseases and Correlate with Disease Activity", The Journal of Rheumatology, vol. 24, No. 2, 1997, pp. 303-308.

Fullerton, et al., "Molecular and Population Genetic Analysis of Allelic Sequence Diversity at the Human Beta-Globin Locus", Proceedings of the National Academy of Sciences, vol. 91, Mar. 1994, pp. 1805-1809.

Supplemental Partial European Search Report received for European Patent Application No. 01997055.7, mailed on Jul. 9, 2007, 6 pages.

Supplementary European Search Report received for European Patent Application No. 03799755.8, mailed on Oct. 18, 2007, 17 pages.

Ghosh, et al., "A Specific Isozyme of 2'-5' Oligoadenylate Synthetase is a Dual Function Proapoptotic Protein of the Bcl-2 Family", The Journal of Biological Chemistry, vol. 276, No. 27, Jul. 2001, pp. 25477-25455.

International Search Report received for PCT Application No. PCT/US03/12946, mailed on Sep. 23, 2005, 4 pages.

Strehlau, et al., "Quantitative Detection of Immune Activation Transcripts as a Diagnostic Tool in Kidney Transplantation", Proceedings of the National Academy of Sciences 94, 1997 , pp. 695-700.

Mohler III, et al., "Role of Cytokines in the Mechanism of Action of Amlodipine: The PRAISE Heart Failure Trial", Journal of the American College of Cardiology, vol. 30, No. 1, 1997, pp. 35-41.

International Search Report received for PCT Application No. PCT/US03/13015, mailed on Sep. 30, 2004, 5 pages.

International Search Report and Written Opinion received for PCT Application No. PCT/US05/31806, mailed on Mar. 27, 2008, 14 pages.

U.S. Appl. No. 10/512,028, filed Apr. 24, 2003.

International Search Report and Written Opinion received for PCT Application No. PCT/US06/18381, mailed on Jun. 25, 2008, 8 pages.

Office Action received for U.S. Appl. No. 10/990,275, mailed on Oct. 3, 2007, 6 pages.

International Search Report and Written Opinion received for PCT Application No. PCT/US07/08909, mailed on Aug. 25, 2008, 10 pages.

Perou, et al., "Molecular Portraits of Human Breast Tumours", Nature, vol. 406, 2000, pp. 747-752.

Pickles, et al., "Latent-Class Analysis of Recurrence Risks for Complex Phenotypes with Selection and Measurement Error: A Twin and Family History Study of Autism", American Journal of Human Genetics, vol. 57, 1995, pp. 717-726.
Office Action received for U.S. Appl. No. 11/223,492, mailed on Jun. 15, 2007, 20 pages.
Office Action received for U.S. Appl. No. 11/223,492, mailed on Mar. 5, 2008, 13 pages.
Preble, et al., "Systemic Lupus Erythematosus: Presence in Human Serum of an Unusual Acid-Labile Leukocyte Interferon", Science, vol. 216, 1982, pp. 429-431.
Pruitt, et al., "Introducing RefSeq and LocusLink: Curated Human Genome Resources at the NCBI", Trends in Genetics, vol. 16, No. 1, 2000, pp. 44-47.
Quattrone, et al., "Quantitation of bcl-2 Oncogene in Cultured Lymphoma/Leukemia Cell Lines and in Primary Leukemia B-Cells by a Highly Sensitive RT-PCR Method", Haematologica, vol. 80, 1995, pp. 495-504.
Marcelin, et al., "Effects of Cyclosporine and Hydrocortisone on Kaposi's Sarcoma-Associated Herpesvirus Genome Replication and Cell Apoptosis Induction," Transplantation, vol. 72, No. 10 2001, pp. 1700-1703.
U.S. Appl. No. 11/938,227, filed Nov. 9, 2007.
Raychaudhuri, et al., "Basic Microarray Analysis: Grouping and Feature Reduction", Trends in Biotechnology, vol. 19, No. 5, 2001, pp. 189-193.
Fu, et al., "Representational Difference Analysis in a Lupus-Prone Mouse Strain Results in the Identification of an Unstable Region of the Genome on Chromosome 11", Nucleic Acids Research, vol. 30, No. 6, 2002, pp. 1394-1400.
Flechner, et al., "Kidney Transplant Rejection and Tissue Injury by Gene Profiling of Biopsies and Peripherals Blood Lymphocytes", American Journal of Transplantation, vol. 4, 2004, pp. 1475-1489.
Finger, et al., "The Human PD-1 Gene: Complete cDNA, Genomic Organization, and Developmentally Regulated Expression in B Cell Progenitors", Gene.vol. 197, 1997, pp. 177-18.
Rebouillat, et al., "The 100-kDa 2',5'-Oligoadenylate Synthase Catalyzing Preferentially the Synthesis of Dimeric pppA2'p5'A Molecules Is Composed of Three Homologous Domains", The Journal of Biological Chemistry, vol. 274, No. 3, 1999, pp. 1557-1565.
Felson, et al., "American College of Rheumatology. Preliminary Definition of Improvement in Rheumatoid Arthritis", Arthritis and Rheumatism, vol. 38, No. 6, Jun. 1995, pp. 727-735.
Eisen, et al., "Cluster Analysis and Display of Genome-Wide Expression Patterns", Proceedings of the National Academy of Sciences of the United States of America, vol. 95, Dec. 1998, pp. 14863-14868.
Ross, et al., "Reduced Neutrophil Infiltration Protects Against Lung Reperfusion Injury After Transplantation", The Annals of Thoracic Surgery, vol. 67, 1999, pp. 1428-1434.
Rus, et al., "Expression of Cytokine- and Chemokine-Related Genes in Peripheral Blood Mononuclear Cells from Lupus Patients by cDNA Array", Clinical Immunology, vol. 102, No. 3, 2002, pp. 283-290.
Saiura, "A Comparison of Gene Expression in Murine Cardiac Allografts and Isografts by Means DNA Microarray Analysis", Transplantation, vol. 72, No. 2, 2001, pp. 320-329.
Liossis, "B-cell Kinase Lyn Deficiency in Patients with Systemic Lupus Erythematosus", Journal of Investigative Medicine, vol. 49, No. 2, 2001, pp. 157-165.
Li, et al., "Noninvasive Diagnosis of Renal-Allograft Rejection by Measurement of Messenger RNA for Perforin and Granzyme B in Urine", The New England Journal of Medicine, vol. 344, No. 13, 2001, pp. 947-954.
Legros-Maida, et al., "Granzyme B and Perforin Can Be Used as Predictive Markers of Acute Rejection in Heart Transplantation", European Journal of Immunology, vol. 24, 1994, pp. 229-233.
Lee, et al., "Importance of Replication in Microarray Gene Expression Studies: Statistical Methods and Evidence from Repetitive cDNA Hybridizations", Proceedings of the National Academy of Sciences, vol. 9, No. 18, 2000, pp. 9834-9839.
Le, et al., "Profiling Changes in Gene Expression During Differentiation and Maturation of Monocyte-Derived Dendritic Cells Using Both Oligonucleotide Microarrays and Proteomics", The Journal of Biological Chemistry, vol. 276, No. 21, 2001, pp. 17920-17931.

Kumar, et al., "Expansion and Molecular Evolution of the Interferon-Induced 2'-5' Oligoadenylate Synthetase Gene Family", Molecular Biology and Evolution, vol. 17, No. 5, 2000, pp. 738-750.
Kumar, et al., "Cell Cycle-Dependent Modulation of Alpha-Interferon-Inducible Gene Expression and Activation of Signaling Components in Daudi Cells", The Journal of Biological Chemistry, vol. 269, No. 41 1994, pp. 25437-25441.
Mansfield, et al., "Arraying the Orchestration of Allograft Pathology", American Journal of Transplantation, vol. 4, 2004, pp. 853-862.
Salmon, "Fc-gamma-RIIa Alleles are Heritable Risk Factors for Lupus Nephritis in African Americans", The Journal of Clinical Investigation, vol. 97, No. 5, 1996, pp. 1348-1354.
Krause, "Carboxypeptidase M as a Marker of Macrophage Maturation", Immunological Reviews, vol. 161 1998, pp. 119-127.
Kobashigawa, et al., "A Randomized Active-Controlled Trial of Mycophenolate Mofetil in Heart Transplant Recipients", Transplantation, vol. 66, No. 4, 1998, pp. 507-515.
Schena, et al., "Parallel Human Genome Analysis: Microarray-based Expression Monitoring of 1000 Genes", Proceedings of the National Academy of Sciences, vol. 93, Oct. 1996, pp. 10614-10619.
Kimball, et al., "Cytokine Panel Predicts Early Rejection of Therapeutic Response After Cardiac Transplantation", Transplantation Proceedings, vol. 27, No. 1, 1995, pp. 1286-1287.
Khan, et al., "Classification and Diagnostic Prediction of Cancers Using Gene Expression Profiling and Artificial Neural Networks", Nature Medicine, vol. 7, No. 6, 2001, pp. 673-679.
Kendler, et al., "The Structure of Psychosis Latent Class Analysis of Probands from the Roscommon Family Study", Archives of General Psychiatry, vol. 55. 1998, pp. 492-499.
Schena, et al., "Quantitative Monitoring of Gene Expression Patterns with a Complementary DNA Microarray", Science 270, Oct. 20, 1995, pp. 467-470.
Marrack, et al., "Genomic-Scale Analysis of Gene Expression in Resting and Activated T Cells", Current Opinion in Immunology, vol. 12, 2000, pp. 208-209.
Schowengerdt, et al., "Increased Expression of the Lymphocyte Early Activation Marker CD69 in Peripheral Blood Correlates with Histologic Evidence of Cardiac Allograft Rejection", Transplantation, vol. 69, No. 10, 2000, pp. 2102-2107.
Katz, "Assumptions of Multiple Linear Regression, Multiple Logistic Regression, and Proportional Hazards Analysis", In Multivariable Analysis: A Practical Guide for Clinicians. Cambridge University Press: Cambridge, United Kingdom. 1999, pp. 36-42.
Kassirer, et al., "Increased Expression of the CD11b/CD18 Antigen on the Surface of Peripheral White Blood Cells in Patients with Ischemic Heart Disease: Further Evidence for Smoldering Inflammation in Patients with Atherosclerosis", American Heart Journal, vol. 138, No. 3, Sep. 1999, pp. 555-559.
Kasprzycka, et al., "Expression of FasL Gene in T cells of Renal Allograft Recipients", Immunology Letters, vol. 80, 2002, pp. 9-13.
Kang, et al., "Transcript Quantitation in Total Yeast Cellular RNA Using Kinetic PCR", Nucleic Acids Research, vol. 28, No. 2, e2, 2000, 8 pages.
Jude, et al., "Evidence for Time-Dependent Activation of Monocytes in the Systemic Circulation in Unstable Angina but Not in Acute Myocardial Infarction or in Stable Angina", Circulation, vol. 90, No. 4, Oct. 1994, pp. 1662-1668.
Joulin, et al., "Isolation and Characterization of the Human 2, 3-Bisphosphoglycerate Mutase Gene", The Journal of Biological Chemistry, vol. 263, No. 30, Oct. 25, 1988, pp. 15785-15790.
Jardi, et al., "Urokinase Receptor (UPAR) Expression During Hematopoietic Maturation", Journal of Drug Targeting, vol. 8 (Suppl. 1), 1994, p. 51.
Jagota, et al., "Nearest Neighbor Classifiers", Chapter 11 In Data Analysis and Classification for Bioinformatics. Department of Computer Science, University of California, Santa Cruz, 2000, pp. 92-93.
Australian Written Opinion and Search Report received for Singapore Application No. SG 200406287-3, mailed on Oct. 7, 2005, 2 pages.
Iida, et al., "Complement Receptor (CR1) Deficiency in Erythrocytes from Patients with Systemic Lupus Erythematosus", The Journal of Experimental Medicine, vol. 155, May 1982, pp. 1427-1438.

Hsieh, et al., "IL-17 Expression as a Possible Predictive Parameter for Subclinical Renal Allograft Rejection", Transplant International, vol. 14, 2001, pp. 287-298.

Sharma, et al., "Molecular Executors of Cell Death—Differential Intrarenal Expression of Fas Ligand, Fas, Granzyme B, and Perforin During Acute and/or Chronic Rejection of Human Renal Allografts", Transplantation, vol. 62, No. 12, 1996, pp. 1860-1866.

Hooks, et al., "Multiple Interferons in the Circulation of Patients with Systemic Lupus Erythematosus and Vasculitis", Arthritis and Rheumatism, vol. 25, No. 4, Apr. 1982, pp. 396-400.

Hooks, et al., "Immune Interferon in the Circulation of Patients with Autoimmune Disease", The New England Journal of Medicine, vol. 301, No. 1, 1979, pp. 5-8.

Higuchi, et al., "Serum 2'-5' Oligoadenylate Synthetase Activity in Children. 2. Serum 2'-5' Oligoadenylate Synthetase in Childhood Collagen Disease", 342625a, Chemical Abstracts, vol. 129, No. 26, 1998, p. 40.

Hendricks, et al., "Quantitation of HBV DNA in Human Serum Using a Branched DNA (bDNA) Signal Amplification Assay", American Journal of Clinical Pathology, vol. 104, No. 5, Nov. 1995, pp. 537-546.

Heller, et al., "Discovery and Analysis of Inflammatory Disease-Related Genes Using cDNA Microarrays", Proceedings of the National Academy of Sciences, vol. 94, Mar. 1997, pp. 2150-2155.

Hayward-Lester, et al., "Accurate and Absolute Quantitative Measurement of Gene Expression by Single Tube RT-PCR and HPLC", Genome Research, vol. 5 1995, pp. 494-499.

Hayward, et al., "Modeling and Analysis of Competitive RT-PCR", Nucleic Acids Research, vol. 26, No. 11, 1998, pp. 2511-2518.

Magnusson, et al., "Importance of CpG Dinucleotides in Activation of Natural IFN-Alpha-Producing Cells by a Lupus-Related Oligodeoxynucleotide", Scandinavian Journal of Immunology, vol. 54, 2001, pp. 543-550.

Hastie, et al., "Supervised Harvesting of Expression Trees", Genome Biology, vol. 2, No. 1, Jan. 2001.

Hastie, et al., "Gene Shaving as a Method for Identifying Distinct Sets of Genes with Similar Expression Patterns", Genome Biology, vol. 1, No. 2, Aug. 2000.

Harlow, et al., "Antibodies: A Laboratory Manual", Cold Spring Harbor Laboratory: New York, NY, 1988, 9 pages, (Table of Contents).

Gullestad, et al., "Effect of High- Versus Low-Dose Angiotensin Converting Enzyme Inhibition on Cytokine Levels in Chronic Heart Failure", Journal of the American College of Cardiology, vol. 34, No. 7 1999, pp. 2061-2067.

Griffiths, et al., "Granzyme A and Perforin as Markers for Rejection in Cardiac Transplantation", European Journal of Immunology, vol. 21, 1991, pp. 687-692.

Grant, et al., "Serum Cytokines in Human Heart Transplant Recipients", Transplantation, vol. 62, No. 4, Aug. 1996, pp. 480-491.

Gorczynski, R. M., "Correlation of Peripheral Blood Lymphocyte and Intragraft Cytokine mRNA Expression with Rejection in Orthotopic Liver Transplantation", Surgery, vol. 120, No. 3, 1996, pp. 496-502.

Golub, et al., "Molecular Classification of Cancer: Class Discovery and Class Prediction by Gene Expression Monitoring", Science, vol. 286, Oct. 1999, pp. 531-537.

Golden-Mason, et al., "Differential Expression of Lymphoid and Myeloid Markers on Differentiating Hematopoietic Stem Cells in Normal and Tumor-Bearing Adult Human Liver", Hepatology, vol. 31, No. 6, 2000, pp. 1251-1256.

Glynne, et al., "Genomic-Scale Gene Expression Analysis of Lymphocyte Growth, Tolerance and Malignancy", Current Opinion in Immunology, vol. 12, 2000, pp. 210-214.

Glynne, et al., "B-Lymphocyte Quiescence, Tolerance and Activation as Viewed by Global Gene Expression Profiling on Microarrays", Immunological Reviews, vol. 176, 2000, pp. 216-246.

Shin, et al., "Expression of Leukemia-Associated Antigen, JL1, in Bone Marrow and Thymus", American Journal of Pathology, vol. 158, No. 4, 2001, pp. 1473-1480.

Morgun et al., "Cytokine and TLRC7 MRNA expression during acute rejection in cardiac allograft recipients", Transplantation Proceedings, Orlando, Florida, USA, vol. 33. Feb. 1, 2001, pp. 1610-1611.

Nishimura et al., "Development of Lupus-like autoimmune diseases by distruption of the PD-1 gene encoding an ITIM motif-carrying immunoreceptor", Immunity, vol. 11, No. 2. Aug. 1999, pp. 141-151.

International Search Report and Written Opinion received for PCT Application No. PCT/US07/18135, mailed on Sep. 10, 2008, 12 pages.

Invitation to Pay Additional Fees for PCT Application No. PCT/US2007/023675, mailed on Apr. 27, 2009, 6 pages.

Schoels et al., "Detection of cardia allograft rejection by real time PCR analysis of circulating mononuclear cells", Clinical Transplantation, vol. 18, 2004, pp. 513-517.

Seiter et al., "CD44 Variant Isoform Expression in a Variety of Skin-Associated Autoimmune Diseases", Clinical Immunology and Immunopathology, vol. 89, No. 1, 1998, pp. 79-93.

Smith, A. D. et al., "Oxford Dictionary of Biochemistry and Molecular Biology", Oxford Dictionary of Biochemistry and Molecular Biology, 1997, Oxford University Press, Oxford, New York, p. 618. 1997, 618.

Su et al., "A gene atlas of the mouse and human protein-encoding transcriptomes", Proceedings National Academy of Sciences, vol. 101, No. 16, 2004, pp. 6062-6067.

Tanaka et al., "Cytokine Receptor Gene Expression in Peripheral Blood Mononuclear Cells During Graft-Versus-Host Disease After Allogeneic Bone Marrow Transplantation", Leukemia and Lymphoma, vol. 19. 1995, pp. 281-287.

Vamvakopoulos et al., "Genetic Control of IL-1β Bioactivity Through Differential Regulation of the IL-1 Receptor Antagonist", European Journal of Immunology, vol. 32, 2002, pp. 2988-2996.

Vermeer et al., "An in vitro bioassay to determine individual sensitivity to glucocorticoids : induction of FKBP51 mRNA in peripheral blood mononuclear cells", Molecular and Cellular Endocrinology, Elsevier Ireland Ltd, IE, vol. 218, Jan. 2004, pp. 49-55.

Wang et al., "Heart, but Not Skin, Allografts from Donors Lackin Flt3 Ligand Exhibit Markedly Prolonged Survival Time", J. Immunol., vol. 172, 2004, p. 5924.

Yeung et al., "From co-expression to co-regulation: how many microarray experiments do we need?", Genome Biology, vol. 5, No. 7, 2004.

Zanders et al., "Analysis of Immune System Gene Expression in Small", Journal of Immunological Methods, vol. 233(1-2), 2000, pp. 131-140.

Zeigler et al., "Cellular and Molecular Characterization of the Role of the Flk-2/Flt-3 Receptor Tyrosine Kinase in Hematopoietic Stem Cells", Blood, American Society of Hematology, vol. 84, No. 8, 1994, pp. 2422-2430.

Zhu et al., "The Role of Hyaluronan Receptor CD44 in MSC Migration in the Extracellular Matrix", Stem Cells Express, 2005, pp. 1-32.

Extended European Search Report received for European Patent Application No. 10183179.0, mailed on Mar. 15, 2011, 10 pages.

Kimball et al., "The paradox of cytokine monitoring-predictor of immunologic activity as well as immunologic silence following cardiac transplantation", Transplantation, vol. 61, No. 6, 1996, pp. 909-915.

Lagoo et al., "Semiquantitative measurement of cytokine messenger RNA in endomyocardium and peripheral blood mononuclear cells from human heart transplant recipients", Journal of Heart and Lung Transplantation, vol. 15, No. 2, 1996, pp. 206-217.

Zhang et al., "Quantitative assessment of cell adhesion molecule gene expression in endomyocardial biopsy specimens from cardiac transplant recipients using competitive polymerase chain reaction", Transplantation, vol. 70, No. 3, 2000, pp. 505-513.

Subar et al., "Acute Leukaemia Following Renal Transplantation", Medical Oncology, vol. 13, No. 1, 1996, pp. 9-13.

Office Action received for European Patent Application No. 03799755.8, mailed on Feb. 24, 2011, 7 pages.

Office Action received for European Patent Application No. 08016970.9, mailed on Feb. 24, 2011, 7 pages.

Non-Final Office Action received for U.S. Appl. No. 11/433,191, mailed on Mar. 31, 2011, 13 pages.

Notice of Allowance received for U.S. Appl. No. 11/893,236, mailed on Mar. 28, 2011, 11 pages.

Non Final Office Action received for U.S. Appl. No. 12/635,438, mailed on May 19, 2011, 18 pages.

Whitehead et al., "Variation in Tissue-Specific Gene Expression Among Natural Populations", Genome Biology, vol. 6, No. 2, Article R13, 2005, pp. R13.1-R13.14.

Zucker, et al., "Increased Serum Stromelysin-1 Levels in Systemic Lupus Erythematosus: Lack of Correlation with Disease Activity", Journal of Rheumatology, vol. 26, No. 1, 1999, pp. 78-80.

Shirali, et al., "Association of Viral Genome with Graft Loss in Children after Cardiac Transplantation", The New England Journal of Medicine vol. 344, No. 20, May 2001, pp. 1498-1503.

Zhang, "IRC-7, a New Interferon Regulatory Factor Associated with Epstein-Barr Virus Latency", Molecular and Cellular Biology, vol. 17, No. 10, 1997, pp. 5748-5757.

Zeigler, et al., "Cellular and Molecular Characterization of the Role of the Flk-2/Flt-3 Receptor Tyrosine Kinase in Hematopoietic Stem Cells", Blood, American Society of Hematology, vol. 84, No. 8, 1994, pp. 2422-2430.

Xia, et al., "Real-Time Polymerase Chain Reaction Analysis Reveals an Evolution of Cytokine mRNA Production in Allograft Acceptor Mice", Transplantation, vol. 72, No. 5, Sep. 2001, pp. 907-914.

Yu, et al., "Protein Synthesis-Dependent and Independent Induction of p69 2'-5'-Oligoadenylate Synthetase by Interferon-Alpha", Cytokine, vol. 11, No. 10, 1999, pp. 744-750.

Office Action received for U.S. Appl. No. 10/511,937, mailed on Apr. 1, 2008, 6 pages.

Wu, et al., "Fas Ligand Mutation in a Patient with Systemic Lupus Erythematosus and Lymphoproliferative Disease", The Journal of Clinical Investigation, vol. 98, No. 5, Sep. 1996, pp. 1107-1113.

Wu, "Analysing Gene Expression Data from DNA Microarrays to Identify Candidate Genes", Journal of Pathology, vol. 195, 2001, pp. 53-65.

Fandrey, et al., "In Vivo and In Vitro Regulation of Erythropoietin mRNA: Measurement by Competitive Polymerase Chain Reaction", Blood, vol. 81, No. 3, Feb. 1, 1993, pp. 617-623.

Willems, et al., "Decrease in Nucleoside Diphosphate Kinase (NDPK/nm23) Expression During Hematopoietic Maturation", The Journal of Biological Chemistry, vol. 273, No. 22, 1998, pp. 13663-13668.

Whitehead, et al., "An Introduction to Logistic Regression", Department of Economics, East Carolina University, Available at <http://arts.uwaterloo.ca/~wnrr/Soc710_421/Whiteheadc/020Logistic%20Regression.ppt> 2002, 48 pages.

Westin, et al., "Anchored Multiplex Amplification on a Microelectronic Chip Array", Nature Biotechnology, vol. 18, Feb. 2000, pp. 199-204.

Welsh, et al., "Analysis of Gene Expression Profiles in Normal and Neoplastic Ovarian Tissue Samples Identifies Candidate Molecular Markers of Epithelial Ovarian Cancer", Proceedings of the National Academy of Sciences, vol. 98, No. 3, Jan. 2001, pp. 1176-1181.

Weast, "Handbook of Chemistry and Physics", 49th Edition, The Chemical Rubber Co.: Cleveland, Ohio., 1968, p. A-245.

Watanabe-Fukunaga, et al., "Lymphoproliferation Disorder in Mice Explained by Defects in Fas Antigen that Mediates Apoptosis", Nature, vol. 356, Mar. 1992, pp. 314-317.

Shoker, et al., "Heightened CD40 Ligand Gene Expression in Peripheral CD4+ T Cells from Patients with Kidney Allograft Rejection", Transplantation, vol. 70, No. 3, 2000, pp. 497-505.

Vu, "A Method for Quantification of Absolute Amounts of Nucleic Acids by (RT)-PCR and a New Mathematical Model for Data Analysis", Nucleic Acids Research 28(7):e18, 2000, 9 pages.

Vincenti, et al., "Multicenter Trial Exploring Calcineurin Inhibitors Avoidance in Renal Transplantation", Transplantation, vol. 71, No. 9, May 2001, pp. 1282-1287.

Vignali, "Multiplexed Particle-Based Flow Cytometric Assays", Journal of Immunological Methods, vol. 243 2000, pp. 243-255.

Vasconcellos, et al., "Cytotoxic Lymphocyte Gene Expression in Peripheral Blood Leukocytes Correlates with Rejecting Renal Allografts", Transplantation, vol. 66, No. 5, Sep. 1998, pp. 562-566.

Vandevyver, "Cytokine mRNA Profile of Myelin Basic Protein Reactive T-Cell Clones in Patients with Multiple Sclerosis", Autoimmunity, vol. 28, 1998, pp. 77-89.

Shou-Nee, et al., "Serum Interferon in Systemic Lupus Erythematosus", British Journal of Dermatology, vol. 117, 1987, pp. 155-159.

Tamayo, et al., "Interpreting Patterns of Gene Expression with Self-Organizing Maps: Methods and Application to Hematopoietic Differentiation", Proceedings of the National Academy of Sciences of the United States of America, vol. 96 Mar. 1999, pp. 2907-2912.

Vallin, "Anti-Double-Stranded DNA Antibodies and Immunostimulatory Plasmid DNA in Combination Mimic the Endogenous IFN-Alpha Inducer in Systemic Lupus Erythematosus", The Journal of Immunology, vol. 163, 1999, pp. 6306-6313.

Umek, et al., "Electronic Detection of Nucleic Acids: A Versatile Platform for Molecular Diagnostics", Journal of Molecular Diagnostics, vol. 3, No. 2, May 2001, pp. 74-84.

Tusher, "Significance Analysis of Microarrays Applied to the Ionizing Radiation Response", Proceedings of the National Academy of Sciences, vol. 98, No. 9, 2001, pp. 5116-5121.

Tsutamoto, et al., "Angiotensin II Type 1 Receptor Antagonist Decreases Plasma Levels of Tumor Necrosis Factor Alpha, Interleukin-6 and Soluble Adhesion Molecules in Patients with Chronic Heart Failure", Journal of the American College of Cardiology, vol. 35, No. 3, Mar. 2000, pp. 714-721.

Torre-Amione, et al., "Proinflammatory Cytokine Levels in Patients with Depressed Left Ventricular Ejection Fraction: A Report from the Studies of Left Ventricular Dysfunction (SOLVD)", Journal of the American College of Cardiology, vol. 27, No. 5, Apr. 1996, pp. 1201-1206.

Toronen, et al., "Analysis of Gene Expression Data Using Self-Organizing Maps", FEBS Letters, vol. 451, 1999, pp. 142-146.

Toogood, et al., "The Immune Response Following Small Bowel Transplantation", Transplantation, vol. 62, No. 6, 1996, pp. 851-855.

Tibshirani, "Diagnosis of Multiple Cancer Types by Shrunken Centroids of Gene Expression", Proceedings of the National Academy of Sciences, vol. 99, No. 1, 2002, pp. 6567-6572.

Thomas, "Subtyping of Juvenile Idiopathic Arthritis Using Latent Class Analysis", Arthritis & Rheumatism, vol. 43, No. 7, 2000, pp. 1496-1503.

Shulzhenko, et al., "Intragraft Activation of Genes Encoding Cytotoxic T Lymphocyte Effector Molecules Precedes the Histological Evidence of Rejection in Human Cardiac Transplantation", Transplantation, vol. 72, No. 10, 2001, pp. 1705-1708.

Tan, et al., "The 1982 Revised Criteria for the Classification of Systemic Lupus Erythematosus", Arthritis and Rheumatism, vol. 25, No. 2, Nov. 1982, pp. 1271-1277.

Tan, "Sequential Monitoring of Peripheral T-Lymphocyte Cytokine Gene Expression in the Early Post Renal Allograft Period", Transplantation, vol. 71, No. 6, Mar. 2001, pp. 751-759.

Deng et al., "The Relation of Interleukin-6, Tumor Necrosis Factor-Alpha, IL-2, and IL-2 Receptor Levels to Cellular Rejection, Allograft Dysfunction, and Clinical Events Early After Cardiac Transplantation", Transplantation, vol. 60, No. 10, Nov. 1995, pp. 1118-1124.

European Search Report received for European Patent Application No. 06770255.5, issued on Dec. 22, 2009, 10 pages.

Extended European Search Report received for European Patent Application No. 07861283.5, mailed on Dec. 27, 2010, 17 pages.

European Search Report and Written Opinion received for European Patent Application No. 08016970.9, mailed on Apr. 28, 2010, 10 pages.

Office Action received for U.S. Appl. No. 10/512,028, mailed on Sep. 19, 2008, 6 pages.

Office Action received for U.S. Appl. No. 10/990,275, mailed on Jul. 18, 2008, 4 pages.

Office Action received for U.S. Appl. No. 10/990,298, mailed on Oct. 5, 2007, 5 pages.

Extended European Search Report received for European Patent Application No. 10157687.4, mailed on Oct. 28, 2010, 9 pages.

Office Action received for U.S. Appl. No. 11/223,492, mailed on Dec. 4, 2008, 18 pages.

Office Action received for U.S. Appl. No. 11/433,191, mailed on Jul. 22, 2010, 13 pages.
Office Action received for U.S. Appl. No. 11/784,998, mailed on May 29, 2009, 28 pages.
Notice of Allowance received for U.S. Appl. No. 11/893,236, mailed on Dec. 10, 2010, 18 pages.
Office Action received for U.S. Appl. No. 11/893,236, mailed on May 29, 2009, 12 pages.
Notice of Allowance received for U.S. Appl. No. 12/584,615, mailed on Sep. 29, 2010, 31 pages.
Office Action received for U.S. Appl. No. 12/628,168, mailed on Dec. 10, 2010, 35 pages.
Office Action received for U.S. Appl. No. 12/635,438, mailed on Sep. 27, 2010, 13 pages.
Office Action received for U.S. Appl. No. 12/635,438, mailed on Mar. 23, 2010, 8 pages.
Notice of Allowance received for U.S. Appl. No. 12/823,090, mailed on Jan. 25, 2011, 27 pages.
Notice of Allowance received for U.S. Appl. No. 12/855,178, mailed on Sep. 17, 2010, 25 pages.
Notice of Reasons for Rejection received for Japanese patent Application No. 2003-587333, mailed on May 26, 2009, 15 pages, including English translation 9 pages.
Office Action received for Japanese Patent Application No. 2003-587333, mailed on Jan. 15, 2010, 4 pages of English translation.
Notice of Reasons for Rejection received Japanese Patent Application No. 2004-549874, mailed on Apr. 27, 2009, 9 pages of English translation only.
Office Action received for Japanese Patent Application No. 2004-549874, mailed on Nov. 5, 2010, 13 pages, including English translation 8 pages.
Affymetrix Webstie, Available at: https://www.affymetrix.com/analysis/netaffx/showresults.affx, downloaded on Jan. 13, 2011.
Benner et al., "Evolution, Language and Analogy in Functional Genomics", Trends in Genetics, vol. 17, No. 7, Jul. 2001, pp. 414-418.
Bennett et al., "Interferon and Granulopoiesis Signatures in Systemic Lupus Erythematosus Blood", The Journal of Experimental Medicine, vol. 197, No. 6, Mar. 17, 2003, pp. 711-723.
Bergholdt et al., "Characterization of New Polymorphisms in the 5' UTR of the Human Interleukin-1 Receptor Type 1 (IL1R1) Gene: Linkage to Type 1 Diabetes and Correlation to IL-1 RI Plasma Level", Genes and Immunity 1, 2000, pp. 495-500.
Carow et al., "Expression of the hematopoietic growth factor receptor FLT3 (STK-1/Flk2) in human leukemias", Blood, American Society of Hematology, vol. 87, No. 3, 1996, pp. 1089-1096.
Centola et al., "Genome-Scale Assessment of Molecular Pathology in Systemic Autoimmune Diseases Using Microarray Technology: A Potential Breakthrough Diagnostic and Individualized Therapy-Design Tool", Scandinavian Journal of Immunology, vol. 64, 2006, pp. 236-242.
Crow et al., "Microarray Analysis of Gene Expression in Lupus", Arthritis Research & Therapy, vol. 5, No. 6, 2003, pp. 279-287.
Non Final Office Action received for U.S. Appl. No. 12/985,314, mailed on Feb. 22, 2011, 73 pages.
Dozmorov, et al., "5α-Androstane-3α, 17β-Diol Selectively Activates the Canonical PI3K/AKT Pathway: A Bioinformatics-Based Evidence for Androgen-Activated Cytolplasmic Signaling", Genomic Medicine, vol. 1, 2007, pp. 139-146.
Eitner, "Chemokine Receptor (CXCR4) mRNA-Expressing Leukocytes are Increased in Human Renal Allograft Rejection.", Transplantation, vol. 66, No. 11, 1998, pp. 1551-1557.
Garraway et al., "Array-based approaches to cancer genome analysis", Drug Discovery Today: Disease Mechanisms, Elsevier, vol. 2, No. 2, Jan. 2005, pp. 171-177.
Hayashi et al., "Effects of glucocorticoids on gene transcription", European Journal of Pharmacology, Elsevier BV, NL, vol. 500, No. 1-3, Oct. 2004, pp. 51-62.
Horwitz et al., "Detection of Cardiac Allograft Rejection and Response to Immunosuppressive Therapy with Peripheral Blood Gene Expression", Circulation, vol. 110, 2004, pp. 3815-3821.
Ing et al., "Steroid Hormones Regulate Gene Expression Post-transcriptionally by Altering the Stabilities of Messenger RNAs", Biology of Reproduction, vol. 72, 2005, pp. 1290-1296.
Kaufman et al., "Functional Significance of Donor Islet Interleukin-1 Receptor Type 1 (IL-1 Rt1) Expression in Islet Transplantation", Transplantation Proceedings, 29, 1997, pp. 772-773.
Keembiyehetty, "Mouse Glucose Transporter 9 Splice Variants Are Expressed in Adult Liver and Kidney and Are Up-regulated in Diabetes", Molecular Endocrinology, vol. 20, No. 3, 2006, pp. 686-697.
Kelsen et al., "The Chemokine Receptor CXCR3 and its Splice Variant are Expressed in Human Airway Epithelial Cells", American Journal of Physiology-Lung Cellular and Molecular Physiology, vol. 287, 2004, pp. L584-L591.
Keshavjee et al., "Immunoregulatory influences on peripheral blood gene expression in lung transplant patients: the lung allograft rejection gene expression observational (LARGO) study", Journal of Heart and Lung Transplantation, Mosby-Year Book, Inc., St. Louis, MO, US, vol. 25, No. 2 Feb. 2006, p. S78.
Kirou, K. A. et al., "Coordinate Overexpression of Interferon-Induced Genes in Systemic Lupus Erythematosus", Arthritis & Rheumatism, 50(12), Dec. 2004, pp. 3958-3967.
Kronick, "Creation of the Whole human genome microarray", Expert Rev. Proteomics, vol. 1, No. 1, 2004, pp. 19-28.
Kuehn et al., "Identification of Steroid—Responsive Genes in Organ Cultured Human Eyes", Invest Ophthalmol Vis Sci. vol. 46, 2000: E-Abstract 3709, pp. 1-2.
Mandel et al., "Gene Expression Studies in Systemic Lupus Erythematosus", Lupus 15, 2006, pp. 451-456.
Mehra et al.,"131: Gene expression and prediction of early cardiac allograft rejection: Discovery of a gene-based corticosteroid efficacy measure", Journal of Heart and Lung Transplantation, Mosby-Year Book, Inc., St Louis, MO, US, vol. 26, No. 2, Feb. 2007, pp. S106-S107.
Mehra et al., "The Role of IL1R2 and FLT3 gene expression in cardiac allograft rejection: Aprecise measure of corticosteroid effect?", Circulation, vol. 114, No. 18, Oct. 2006, p. 709 (2 pages of Abstract).
Mehra et al., "Transcriptional Signals of T-cell and Corticosteroid-sensitive Genes Are Associated With Future Acute Cellular Rejection in Cardiac Allografts", Journal of Heart and Lung Transplantation, Mosby-Year Book, Inc., St Louis, MO, US, vol. 26, No. 12, Nov. 2007, pp. 1255-1263.
Michiels et al., "Prediction of cancer outcome with microarrays: a multiple random validation strategy", The Lancet, vol. 365 2005, pp. 488-492.
Non Final Office Action received for U.S. Appl. No. 11/938,227, mailed on Sep. 23, 2011, 46 pages.

PRIMER EFFICIENCY TESTING. A STANDARD CURVE OF Ct VERSUS LOG
OF THE STARTING RNA AMOUNT IS SHOWN FOR 2 GENES

| FIG. 3 | FIG. 3A |
|---|---|
| | FIG. 3B |
| | FIG. 3C |

KITS FOR DISCOVERY OF, OR APPLICATION OF DIAGNOSTIC GENE SETS

A. CONTENTS OF KIT FOR DISCOVERY OF DIAGNOSTIC GENE SETS USING MICROARRAYS

1. STERILE, ENDOTOXIN AND RNAse FREE BLOOD COLLECTION TUBES
2. ALCOHOL SWABS, TOURNIQUET, BLOOD COLLECTION SET
3. -PBS (PHOSPHATE BUFFER SALINE; NEEDED WHEN METHOD OF EXAMPLE 8 IS USED TO DERIVED MONONUCLEAR RNA)
4. CELL LYSIS BUFFER
5. RNA ISOLATION KIT
6. SUBSTRATES FOR LABELING OF RNA (MAY VARY FOR VARIOUS EXPRESSION PROFILING TECHNIQUES)
    FOR FLUORESCENCE MICROARRAY EXPRESSION PROFILING:
    REVERSE TRANSCRIPTASE AND 10x RT BUFFER
    T7(dT)24 PRIMER (PRIMER WITH T7 PROMOTER AT 5' END)
    DTT
    DEOXYNUCLEOTIDES 100mM EACH
    RNAse INHIBITOR
    $2^{ND}$ STRAND cDNA BUFFER
    DNA POLYMERASE
    RNASE H
    T7 RNA POLYMERASE
    RIBONUCLEOTIDES
    IN VITRO TRANSCRIPTION BUFFER
    Cy3 AND Cy5 LABELED RIBONUCLEOTIDES
7. MICROARRAYS CONTAINING CANDIDATE GENE LIBRARIES
8. COVER SLIPS FOR SLIDES
9. HYBRIDIZATION CHAMBERS
10. SOFTWARE PACKAGE FOR IDENTIFICATION OF DIAGNOSTIC GENE SET FROM DATA
    CONTAINS STATISTICAL METHODS
    ALLOWS ALTERATION IN DESIRED SENSITIVITY AND SPECIFICITY OF GENE SET
    SOFTWARE FACILITATES ACCESS TO AND DATA ANALYSIS BY CENTRALLY LOCATED DATABASE SERVER
11. PASSWORD AND ACCOUNT NUMBER TO ACCESS CENTRAL DATABASE SERVER
12. KIT USER MANUAL

FIG. 3A

KITS FOR DISCOVERY OF, OR APPLICATION OF DIAGNOSTIC GENE SETS

B. CONTENTS OF KIT FOR APPLICATION OF DIAGNOSTIC GENE SETS USING MICROARRAYS

1. STERILE, ENDOTOXIN AND RNAse FREE BLOOD COLLECTION TUBES
2. ALCOHOL SWABS, TOURNIQUET, BLOOD COLLECTION SET
3. -PBS (PHOSPHATE BUFFER SALINE; NEEDED WHEN METHOD OF EXAMPLE 7 IS USED TO DERIVED MONONUCLEAR RNA)
4. CELL LYSIS BUFFER
5. RNA ISOLATION KIT
6. SUBSTRATES FOR LABELING OF RNA (MAY VARY FOR VARIOUS EXPRESSION PROFILING TECHNIQUES)
    FOR FLUORESCENCE MICROARRAY EXPRESSION PROFILING:
    REVERSE TRANSCRIPTASE AND 10x RT BUFFER
    T7(dT)24 PRIMER (PRIMER WITH T7 PROMOTER AT 5' END)
    DTT
    DEOXYNUCLEOTIDES 100mM EACH
    RNAse INHIBITOR
    $2^{ND}$ STRAND cDNA BUFFER
    DNA POLYMERASE
    RNASE H
    T7 RNA POLYMERASE
    RIBONUCLEOTIDES
    IN VITRO TRANSCRIPTION BUFFER
    Cy3 AND Cy5 LABELED RIBONUCLEOTIDES
7. MICROARRAYS CONTAINING CANDIDATE GENE LIBRARIES
8. COVER SLIPS FOR SLIDES
9. HYBRIDIZATION CHAMBERS
10. SOFTWARE PACKAGE FOR IDENTIFICATION OF DIAGNOSTIC GENE SET FROM DATA
    CONTAINS STATISTICAL METHODS
    ALLOWS ALTERATION IN DESIRED SENSITIVITY AND SPECIFICITY OF GENE SET
    SOFTWARE FACILITATES ACCESS TO AND DATA ANALYSIS BY CENTRALLY LOCATED DATABASE SERVER
11. PASSWORD AND ACCOUNT NUMBER TO ACCESS CENTRAL DATABASE SERVER
12. KIT USER MANUAL

*FIG. 3B*

KITS FOR DISCOVERY OF, OR APPLICATION OF DIAGNOSTIC GENE SETS

C. CONTENTS OF KIT FOR APPLICATION OF DIAGNOSTIC GENE SETS USING REAL-TIME RT-PCR

1. STERILE, ENDOTOXIN AND RNAse FREE BLOOD COLLECTION TUBES
2. ALCOHOL SWABS, TOURNIQUET, BLOOD COLLECTION SET
3. -PBS (PHOSPHATE BUFFER SALINE; NEEDED WHEN METHOD OF EXAMPLE 7 IS USED TO DERIVED MONONUCLEAR RNA)
4. CELL LYSIS BUFFER
5. RNA ISOLATION KIT
6. SUBSTRATES FOR REAL TIME RT-PCR (MAY VARY FOR VARIOUS REAL-TIME PCR TECHNIQUES:
    POLY dT PRIMERS, RANDOM HEXAMER PRIMERS
    REVERSE TRANSCRIPTASE AND RT BUFFER
    DTT
    DEOXYNUCLEOTIDES 100 mM
    RNASE H
    PRIMER PAIRS FOR DIAGNOSTIC AND CONTROL GENE SET
    10x PCR REACTION BUFFER
    TAQ DNA POLYMERASE
    FLUORESCENT PROBES FOR DIAGNOSTIC AND CONTROL GENE SET (ALTERNATIVELY, FLUORESCENT DYE THAT BINDS TO ONLY DOUBLE STRANDED DNA)
    REACTION TUBES WITH OR WITHOUT BARCODE FOR SAMPLE TRACKING
    96-WELL PLATES WITH BARCODE FOR SAMPLE IDENTIFICATION, ONE BARCODE FOR ENTIRE SET, OR INDIVIDUAL BARCODE PER REACTION TUBE IN PLATE
7. SOFTWARE PACKAGE FOR IDENTIFICATION OF DIAGNOSTIC GENE SET FROM DATA
    CONTAINS STATISTICAL METHODS
    ALLOWS ALTERATION IN DESIRED SENSITIVITY AND SPECIFICITY OF GENE SET
    SOFTWARE FACILITATES ACCESS TO AND DATA ANALYSIS BY CENTRALLY LOCATED DATABASE SERVER
8. PASSWORD AND ACCOUNT NUMBER TO ACCESS CENTRAL DATABASE SERVER
9. KIT USER MANUAL

*FIG. 3C*

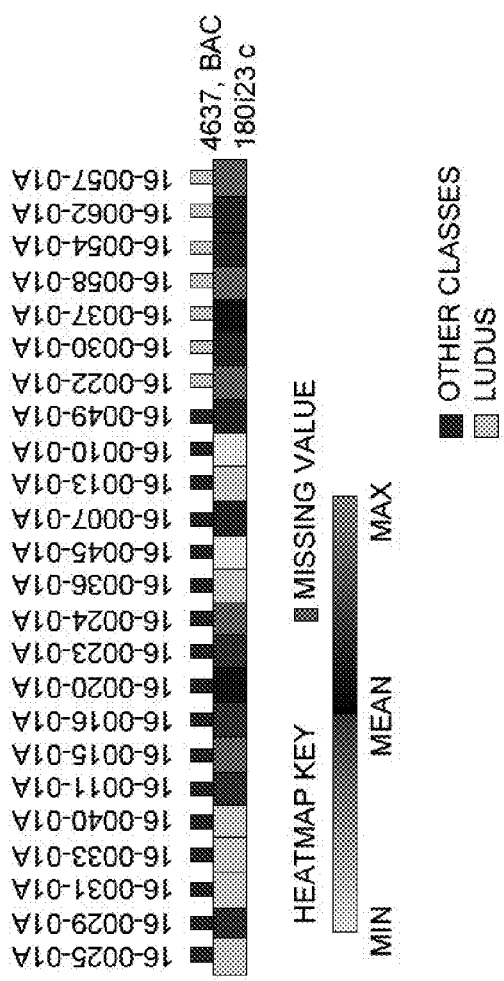

| MODEL | # GENES | RELATIVE COST | SEQ/OLIGO-ID | LOCUS | NOMINAL DESCRIPTION | CART SPLITTER | CART VALUE FOR Dx SLE |
|---|---|---|---|---|---|---|---|
| MODEL I | 2 | 0.118 | 2412 | NM_002946 | REPLICATION PROTEIN A2 (32kD) | CO-1ST | [(2412)*0.903-(2648)*0.431] <= 0.1909 |
| | | | 2648 | NM_004510 | INTERFERON-INDUCED PROTEIN 75 | CO-1ST | [(2412)*0.903-(2648)*0.431] <= 0.1909 |
| MODEL I | 3 | 0.125 | 2412 | NM_002946 | REPLICATION PROTEIN A2 (32kD) | CO-1ST | [(2412)*0.903-(2648)*0.431] <= 0.1909 |
| | | | 2648 | NM_004510 | INTERFERON-INDUCED PROTEIN 75 | CO-1ST | [(2412)*0.903-(2648)*0.431] <= 0.1909 |
| | | | 1436 | BC002409 | ACTIN, BETA (ACTB) | 2ND | (G1436) > 0.0868 |
| MODEL II | 1 | 0.612 | 5067 | W16552 | CAPICUA PROTEIN (CIC) mRNA | 1ST | (5067) > 0.1030 |
| MODEL II | 3 | 0.686 | 5067 | W16552 | CAPICUA PROTEIN (CIC) mRNA | 1ST | (5067) > 0.1030 |
| | | | 1025 | AK024756 | HYPOTHETICAL PROTEIN FLJ21103 | 2ND | (G1025) <= 0.3968 |
| | | | 1035 | AK024969 | HYPOTHETICAL PROTEIN DKFZp566I133 | 3RD | (G1035) <= 0.0073 |
| MODEL II | 5 | 0.745 | 5067 | W16552 | CAPICUA PROTEIN (CIC) mRNA | 1ST | (5067) > 0.1030 |
| | | | 1003 | AK024240 | cDNA FLJ14178 FIS | 2ND | (G1003) > 0.2105 |
| | | | 1025 | AK024756 | HYPOTHETICAL PROTEIN FLJ21103 | 2ND | (G1025) <= 0.3968 |
| | | | 1001 | AK024202 | HEAT SHOCK 90kD PROTEIN 1, ALPHA | 3RD | (G1001) <= -0.3107 |
| | | | 1035 | AK024969 | HYPOTHETICAL PROTEIN DKFZp566I133 | 3RD | (G1035) <= 0.0073 |

SLE DIAGNOSTIC GENES AND ALGORITHMS

*FIG. 5C*

| | MODEL | SENSITIVITY | SPECIFICITY | RELATIVE COST |
|---|---|---|---|---|
| TRAINING SET | MODEL 1 (2 GENES) | 100 | 94 | |
| | MODEL 1 (3 GENES) | 100 | 100 | |
| 10-FOLD CROSS VALIDATION | MODEL 1 (2 GENES) | 100 | 88 | 0.118 |
| | MODEL 1 (3 GENES) | 93 | 94 | 0.125 |
SLE DIAGNOSTIC GENES AND ALGORITHMS
FIG. 5D
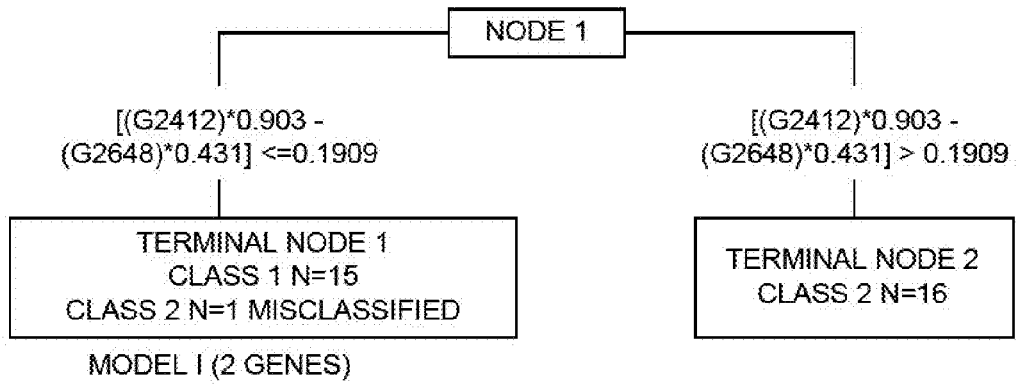
MODEL I (2 GENES)
SLE DIAGNOSTIC GENES AND ALGORITHMS
FIG. 5E
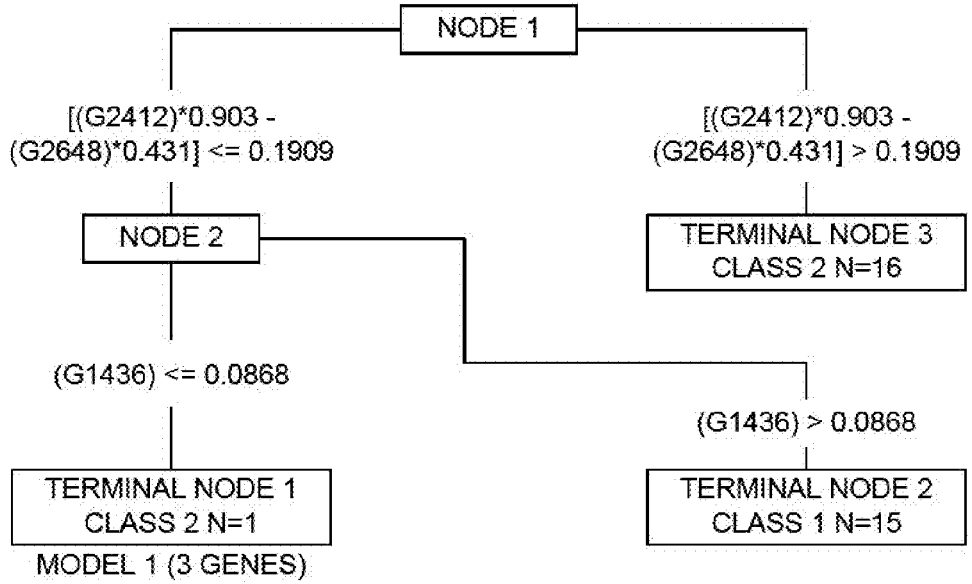
MODEL 1 (3 GENES)
SLE DIAGNOSTIC GENES AND ALGORITHMS
FIG. 5F

ENDPOINT TESTING OF PCR PRIMERS

ENDPOINT TESTING OF PCR PRIMERS

ENDPOINT TESTING OF PCR PRIMERS

ENDPOINT TESTING OF PCR PRIMERS

METHODS AND COMPOSITIONS FOR DIAGNOSING OR MONITORING AUTOIMMUNE AND CHRONIC INFLAMMATORY DISEASES

RELATED APPLICATIONS

This application is a continuation of application Ser. No. 12/235,969, filed Sep. 23, 2008, which is a divisional of application Ser. No. 10/990,298, filed Nov. 15, 2004, now U.S. Pat. No. 7,579,148, which is a divisional of application Ser. No. 10/131,827, filed Apr. 24, 2002, now U.S. Pat. No. 6,905,827, which is a continuation-in-part of application Ser. No. 10/006,290, filed Oct. 22, 2001, now abandoned, which claims the benefit of U.S. Provisional Application No. 60/296,764, filed Jun. 8, 2001, all of which are hereby incorporated by reference in their entirety.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 506612500101SeqList.txt, date recorded: Dec. 1, 2010, size: 1,709 KB).

FIELD OF THE INVENTION

This application is in the field of chronic inflammatory diseases. In particular, this invention relates to methods and compositions for diagnosing or monitoring chronic inflammatory diseases.

BACKGROUND OF THE INVENTION

Many of the current shortcomings in diagnosis, prognosis, risk stratification and treatment of disease can be approached through the identification of the molecular mechanisms underlying a disease and through the discovery of nucleotide sequences (or sets of nucleotide sequences) whose expression patterns predict the occurrence or progression of disease states, or predict a patient's response to a particular therapeutic intervention. In particular, identification of nucleotide sequences and sets of nucleotide sequences with such predictive value from cells and tissues that are readily accessible would be extremely valuable. For example, peripheral blood is attainable from all patients and can easily be obtained at multiple time points at low cost. This is a desirable contrast to most other cell and tissue types, which are less readily accessible, or accessible only through invasive and aversive procedures. In addition, the various cell types present in circulating blood are ideal for expression profiling experiments as the many cell types in the blood specimen can be easily separated if desired prior to analysis of gene expression. While blood provides a very attractive substrate for the study of diseases using expression profiling techniques, and for the development of diagnostic technologies and the identification of therapeutic targets, the value of expression profiling in blood samples rests on the degree to which changes in gene expression in these cell types are associated with a predisposition to, and pathogenesis and progression of a disease.

There is an extensive literature supporting the role of leukocytes, e.g., T- and B-lymphocytes, monocytes and granulocytes, including neutrophils, in a wide range of disease processes, including such broad classes as cardiovascular diseases, inflammatory, autoimmune and rheumatic diseases, infectious diseases, transplant rejection, cancer and malignancy, and endocrine diseases.

Of particular interest is the role of leukocytes and leukocyte gene expression in chronic inflammatory diseases such as Systemic Lupus Erythematosis and Rheumatoid Arthritis. Systemic lupus erythematosis (SLE) and Rheumatoid Arthritis (RA) are chonic autoimmune and inflammatory disorders characterized by dysregulation of the immune system, which causes damage to a variety of organs. These diseases clearly involve differential expression of genes in leukocytes. Diagnostic and disease monitoring tools are severly lacking for these patients and their physicians. Leukocyte expression profiling can be applied to discover expression markers for SLE and RA and apply them as patient management tools in the clinical setting. In addition, osteoarthirtis is a degenerative joint disease that can be confused with RA. This disease also involves leukocytes and expression profiling of leukocytes associated with osteoarthritis may lead to the discovery of new diagnostic and therapeutic approaches to the disease.

The accuracy of technologies based on expression profiling for the diagnosis, prognosis, and monitoring of disease would be dramatically increased if numerous differentially expressed nucleotide sequences, each with a measure of sensitivity and specificity for a disease in question, could be identified and assayed in a concerted manner. Using the expression of multiple genes (gene sets) for diagnostic applications helps overcome assay and population variability. In order to achieve this improved accuracy, the appropriate sets of nucleotide sequences need to be identified and validated against numerous samples in combination with relevant clinical data.

SUMMARY OF THE INVENTION

In order to meet these needs, the present invention identifies genes and gene sets that have clinical utility as diagnostic tools for the management of transplant recipients, lupus patients and patients with a variety of chronic inflammatory and autoimmune diseases. The present invention is thus directed to a method of diagnosing or monitoring chronic autoimmune or inflammatory disease in a patient. The method of the invention involves detecting in a patient expression of one or more genes such as those genes depicted in Table 8 and Table 10 A and surrogates derived therefrom. Exemplary surrogates are provided in Table 10C. The present invention is further directed to a method of diagnosing or monitoring an autoimmune or chronic inflammatory disease in a patient by detecting the expression level of one or more genes or surrogates derived therefrom in said patient to diagnose or monitor the autoimmune or chronic inflammatory disease in the patient wherein said genes include a nucleotide sequence selected from SEQ ID NO: 41; SEQ ID NO:328; SEQ ID NO:668; SEQ ID NO:855; SEQ ID NO:981; SEQ ID NO:1001; SEQ ID NO:1003; SEQ ID NO:1025; SEQ ID NO:1035; SEQ ID NO:1227; SEQ ID NO:1341; SEQ ID NO:1390; SEQ ID NO:1436; SEQ ID NO:1535; SEQ ID NO:1750; SEQ ID NO:2102; SEQ ID NO:2331; SEQ ID NO:2386; SEQ ID NO:2412; SEQ ID NO:2560; SEQ ID NO:2648; SEQ ID NO:2895; SEQ ID NO:3249; SEQ ID NO:3305; SEQ ID NO:3541; SEQ ID NO:3692; SEQ ID NO:3701; SEQ ID NO:3741; SEQ ID NO:3825; SEQ ID NO:3827; SEQ ID NO:3832; SEQ ID NO:4149; SEQ ID NO:4400; SEQ ID NO:4601; SEQ ID NO:4604; SEQ ID NO:4631; SEQ ID NO:4637; SEQ ID NO:5067; SEQ ID NO:5074; SEQ ID NO:5468; SEQ ID NO:5531; SEQ ID NO:5607; SEQ ID NO:6382; SEQ ID NO:6956; SEQ ID NO:7238; SEQ ID NO:7330; SEQ ID NO:7641; SEQ ID NO:8015 and SEQ ID NO:8095.

In the method of the invention, the chronic inflammatory disease or autoimmune disease may be systemic lupus erythematosis (SLE).

In one format, expression is detecting by measuring RNA levels or protein levels from the genes.

In the method of the invention, RNA may be isolated from the patient prior to detecting expression of a gene such as those depicted in Table 10A. RNA levels may be detected by PCR, hybridization. such as hybridization to an oligonucleotide. The nucleotide sequence may include comprises DNA, cDNA, PNA, genomic DNA, or synthetic oligonucleotides.

In the methods of the invention, the RNA may be detected by hybridization to an oligonucleotide having a nucleotide sequence selected from SEQ ID NO: 41; SEQ ID NO:328; SEQ ID NO:668; SEQ ID NO:855; SEQ ID NO:981; SEQ ID NO:1001; SEQ ID NO:1003; SEQ ID NO:1025; SEQ ID NO:1035; SEQ ID NO:1227; SEQ ID NO:1341; SEQ ID NO:1390; SEQ ID NO:1436; SEQ ID NO:1535; SEQ ID NO:1750; SEQ ID NO:2102; SEQ ID NO:2331; SEQ ID NO:2386; SEQ ID NO:2412; SEQ ID NO:2560; SEQ ID NO:2648; SEQ ID NO:2895, SEQ ID NO:3249; SEQ ID NO:3305; SEQ ID NO:3541; SEQ ID NO:3692; SEQ ID NO:3701; SEQ ID NO:3741; SEQ ID NO:3825; SEQ ID NO:3827; SEQ ID NO:3832; SEQ ID NO:4149; SEQ ID NO:4400; SEQ ID NO:4601; SEQ ID NO:4604; SEQ ID NO:4631; SEQ ID NO:4637; SEQ ID NO:5067; SEQ ID NO:5074; SEQ ID NO:5468; SEQ ID NO:5531; SEQ ID NO:5607; SEQ ID NO:6382; SEQ ID NO:6956; SEQ ID NO:7238; SEQ ID NO:7330; SEQ ID NO:7641; SEQ ID NO:8015 and SEQ ID NO:8095.

The present invention is further directed to a diagnostic oligonucleotide for detecting chronic or inflammatory disease wherein the oligonucleotide has a nucleotide sequence selected from SEQ ID NO: 4637, The diagnostic oligonucleotide of may include DNA, cDNA, PNA, genomic DNA, or synthetic oligonucleotides.

The present invention is further directed to a system or kit for diagnosing or monitoring chronic inflammatory or autoimmune disease in a patient comprising an isolated DNA molecule wherein the isolated DNA molecule detects expression of a gene listed in Table 10A. In the system of the invention, the DNA molecules may be synthetic DNA, genomic DNA, PNA or cDNA. The isolated DNA molecule may be immobilized on an array. Such arrays may include a chip array, a plate array, a bead array, a pin array, a membrane array, a solid surface array, a liquid array, an oligonucleotide array, polynucleotide array or a cDNA array, a microtiter plate, a membrane and a chip.

The present invention is further directed to a system or detecting differential gene expression. In one format, the system has one or more isolated DNA molecules wherein each isolated DNA molecule detects expression of a gene selected from the group of genes corresponding to the oligonucleotides depicted in the Sequence Listing. It is understood that the DNA sequences and oligonucleotides of the invention may have slightly different sequences than those identified herein. Such sequence variations are understood to those of ordinary skill in the art to be variations in the sequence which do not significantly affect the ability of the sequences to detect gene expression.

The sequences encompassed by the invention have at least 40-50, 50-60, 70-80, 80-85, 85-90, 90-95 or 95-100% sequence identity to the sequences disclosed herein. In some embodiments, DNA molecules are less than about any of the following lengths (in bases or base pairs): 10,000; 5,000; 2500; 2000; 1500; 1250; 1000; 750; 500; 300; 250; 200; 175; 150; 125; 100; 75; 50; 25; 10. In some embodiments, DNA molecule is greater than about any of the following lengths (in bases or base pairs): 10; 15; 20; 25; 30; 40; 50; 60; 75; 100; 125; 150; 175; 200; 250; 300; 350; 400; 500; 750; 1000; 2000; 5000; 7500; 10000; 20000; 50000. Alternately, a DNA molecule can be any of a range of sizes having an upper limit of 10,000; 5,000; 2500; 2000; 1500; 1250; 1000; 750; 500; 300; 250; 200; 175; 150; 125; 100; 75; 50; 25; or 10 and an independently selected lower limit of 10; 15; 20; 25; 30; 40; 50; 60; 75; 100; 125; 150; 175; 200; 250; 300; 350; 400; 500; 750; 1000; 2000; 5000; 7500 wherein the lower limit is less than the upper limit.

The gene expression system may be a candidate library, a diagnostic agent, a diagnostic oligonucleotide set or a diagnostic probe set. The DNA molecules may be genomic DNA, protein nucleic acid (PNA), cDNA or synthetic oligonucleotides.

In one format, the gene expression system is immobilized on an array. The array may be a chip array, a plate array, a bead array, a pin array, a membrane array, a solid surface array, a liquid array, an oligonucleotide array, a polynucleotide array, a cDNA array, a microfilter plate, a membrane or a chip.

BRIEF DESCRIPTION OF THE SEQUENCE LISTING

A brief description of the sequence listing is given below. There are 9090 entries. The Sequence Listing presents 50mer oligonucleotide sequences derived from human leukocyte, plant and viral genes. These are listed as SEQ IDs 1-8143. The 50mer sequences and their sources are also displayed in Table 8. Most of these 50mers were designed from sequences of genes in Tables 2, 3A, B and C and the Sequence listing.

SEQ IDs 8144-8766 are the cDNA sequences derived from human leukocytes that were not homologous to UniGene sequences or sequences found in dbEST at the time they were searched. Some of these sequences match human genomic sequences and are listed in Tables 3B and C. The remaining clones are putative cDNA sequences that contained less than 50% masked nucleotides when submitted to RepeatMasker, were longer than 147 nucleotides, and did not have significant similarity to the UniGene Unique database, dbEST, the NR nucleotide database of Genbank or the assembled human genome of Genbank.

SEQ IDs 8767-8770, 8828-8830 and 8832 are sequences that appear in the specification (primer, masked sequences, exemplary sequences, etc.).

SEQ IDs 8845-8893 are the full length gene sequences for the genes identified by an accession number in Table 10A.

SEQ IDs 8894-9085 are the primer sequences for lupus genes identified in Table 10B.

BRIEF DESCRIPTION OF THE FIGURES

FIG. 3 describes kits useful for the practice of the invention. FIG. 3A describes the contents of a kit useful for the discovery of diagnostic nucleotide sets using microarrays. FIG. 3B describes the contents of a kit useful for the application of diagnostic nucleotide sets using microarrays. FIG. 3C describes contents of a kit useful for the application of diagnostic nucleotide sets using real-time PCR.

FIG. 5 depicts Diagnostic genes, gene sets and diagnostic algorithms for Systemic Lupus Erythematosis are identified. FIG. 5A shows the relative expression level of oligonucleotide and SEQ ID #4637 (Sialyltransferase 4A) between Lupus and control samples is shown. The gene is identified as having a false detection rate for differential expression from the SAM algorithm of 0.5%. FIG. 5B shows the scaled ratios (non log) for Sialyltransferase (SEQ ID #4637) are given for the samples in the analysis. The average ratio of each group along with the standard deviation of the ratio is shown. The average fold change from control to Lupus is 1.48. FIG. 5C shows CART gene expression models for diagnosis of SLE. For each model, the number of genes used, the relative cost with 10 fold cross validation, the SEQ ID, Locus accession number, the name and the position and values in the CART model are given. The CART values given are the expression level thresholds for classification of the sample as SLE after the node. For example, in the single gene model II, the first node of the decision tree asks if expression of gene 5067 is >0.103. If yes, the sample is placed in the lupus class. FIG. 5D shows the sensitivity and specificity of Model 1. The sensitivity and specificity are given for both the 2 and 3 gene models and both the training set and on cross validation. The relative cost is given for cross-validation. FIG. 5E shows the CART Model I, 2 genes. The model uses 2 genes in a single node to classify samples as Lupus (Class 1) or non-Lupus (Class 2). FIG. 5F shows CART Model I, 3 genes. The model uses a second node to classify all samples correctly as lupus (class 1) or non-lupus (class 2) for the training set.

FIG. 6 shows endpoint testing of PCR primers. Electrophoresis and microfluidics are used to assess the product of gene specific PCR primers.

FIG. 7 shows the validation of differential expression of a gene discovered using microarrays using Real-time PCR.

BRIEF DESCRIPTION OF THE TABLES

Figure 1:
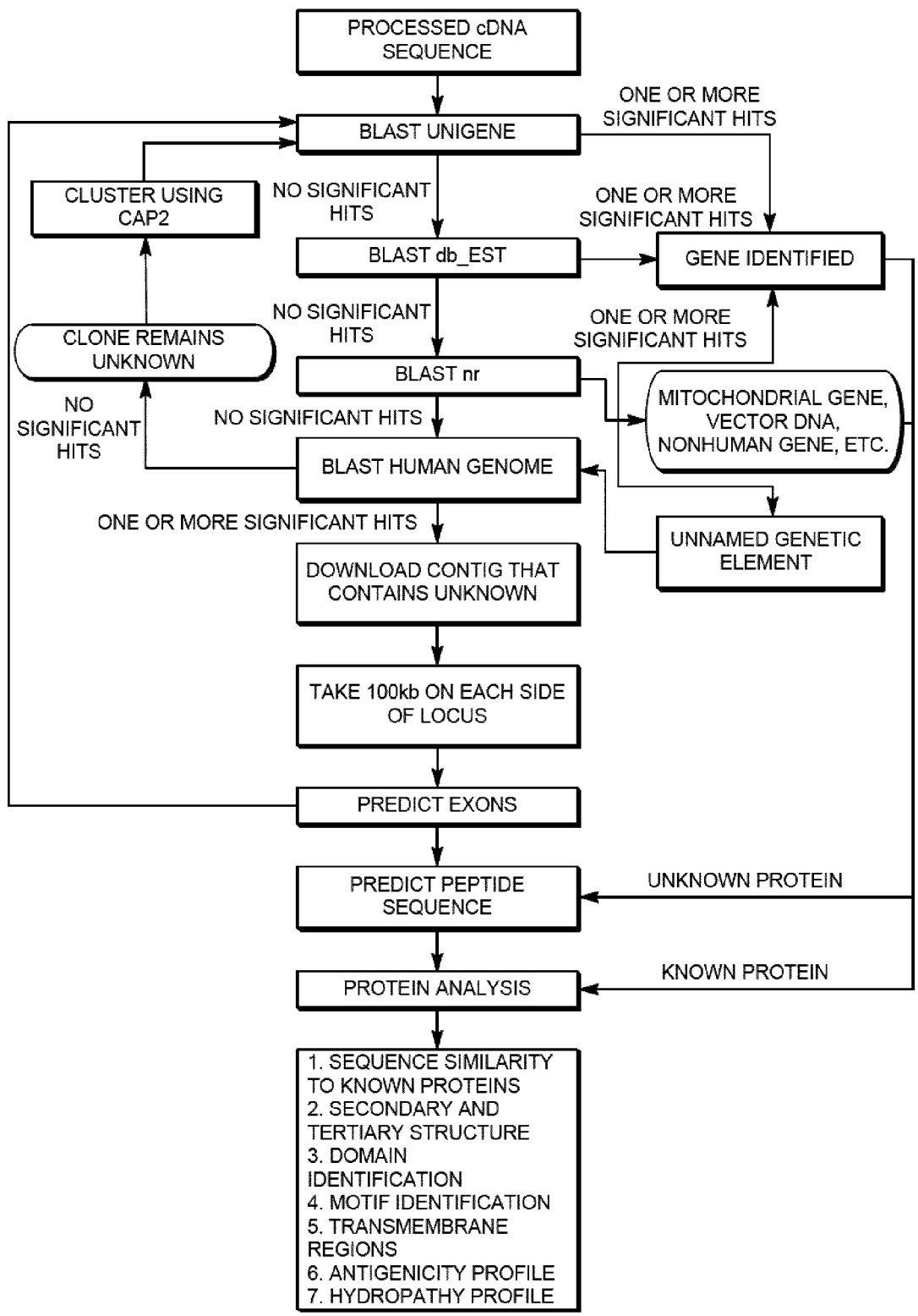
FIG. 1 is a schematic flow chart illustrating an instruction set for characterization of the nucleotide sequence and/or the predicted protein sequence of novel nucleotide sequences.

Table 1: Table 1 lists some of the diseases or conditions amenable to study by leukocyte profiling.

Table 2: Table 2 describes genes and other nucleotide sequences identified using data mining of publically available publication databases and nucleotide sequence databases. Corresponding Unigene (build 133) cluster numbers are listed with each gene or other nucleotide sequence.

Table 3A: Table 3A describes differentially expressed nucleotide sequences useful for the prediction of clinical outcomes. This table contains 4517 identified cDNAs and cDNA regions of genes that are members of a leukocyte candidate library, for use in measuring the expression of nucleotide sequences that could subsequently be correlated with human clinical conditions. The regions of similarity were found by searching three different databases for pair wise similarity using blastn. The three databases were UniGene Unique build Mar. 30, 2001, file Hs.seq.uniq.Z; the downloadable database located at the website ftp.ncbi.nlm-.nih.com/blast/db/est human.Z with date Apr. 8, 2001 which is a section of Genbank version 122; and the non-redundant section of Genbank ver 123. The Hs.XXXXX numbers represent UniGene accession numbers from the Hs.seq.uniq.Z file of Mar. 30, 2001. The clone sequences are not in the sequence listing.

Table 3B: Table 3B describes Identified Genomic Regions that code for novel mRNAs. The table contains 591 identified genomic regions that are highly similar to the cDNA clones. Those regions that are within ~100 to 200 Kb of each other on the same contig are likely to represent exons of the same gene. The indicated clone is exemplary of the cDNA clones that match the indicated genomic region. The "number clones" column indicates how many clones were isolated from the libraries that are similar to the indicated region of the chromosome. The probability number is the likelihood that region of similarity would occur by chance on a random sequence. The Accession numbers are from the Mar. 15, 2001 build of the human genome. The file date for the downloaded data was Apr. 17, 2001. These sequences may prove useful for the prediction of clinical outcomes.

Table 3C: Table 3C describes 48 clones whose sequences align to two or more non-contiguous sequences on the same assembled human contig of genomic sequence. The Accession numbers are from the Mar. 15, 2001 build of the human genome. The file date for the downloaded data was Apr. 17, 2001. The alignments of the clone and the contig are indicated in the table. The start and stop offset of each matching region is indicated in the table. The sequence of the clones themselves is included in the sequence listing. The alignments of these clones strongly suggest that they are novel nucleotide sequences. Furthermore, no EST or mRNA aligning to the clone was found in the database. These sequences may prove useful for the prediction of clinical outcomes.

Table 4: Database mining. The Library Browser at the NCBI UniGene web site was used to identify genes that are specifically expressed in leukocyte cell populations. The table lists the library name and type, the number of sequences in each library and the number used for the array.

Table 5: Table 5 describes the nucleotide sequence databases used in the sequence analysis described herein.

Table 6: Table 6 describes the algorithms and software packages used for exon and polypeptide prediction used in the sequence analysis described herein.

Table 7: Table 7 describes the databases and algorithms used for the protein sequence analysis described herein.

Table 8: Table 8 provides a listing of all oligonucleotides designed for the arrays and their associated genes. In this table, the sequence ID is given which corresponds to the sequence listing. The origin of the sequence for inclusion on the array is noted as coming from one of the cDNA libraries described in example 1, mining from databases as described in examples 2 and 11 or identification from the published literature. The unigene number, genebank accession and GI number are also given for each sequence when known. These data were obtained from the Unigene unique database, build 137. The name of the gene associated with the accession number is noted. The sequence of these genes as available from the databases are hereby incorporated by reference in their entirety. The strand is noted as −1 or 1, meaning that the probe was designed from the complement of the sequence (−1) or directly from the sequence (1). The nucleotide sequence of each probe is also given in the Sequence Listing.

Table 9: Table 9 shows viral genes for arrays. Viral genomes were used to design oligonucleotides for the microarrays. The accession numbers for the viral genomes used are given, along with the gene name and location of the region used for oligonucleotide design.

Table 10A. Table 10A shows Lupus gene expression markers. This table lists the oligonucleotides and associated genes identified as having value for the diagnosis and monitoring of lupus. The first column gives the SEQ ID that corresponds to the oligonucleotide in the sequence listing. The origin of the sequence for inclusion on the array is noted as coming from one of the cDNA libraries described in example 1, mining from databases as described in examples 2 and 11 or identification from the published literature. The unigene number, genebank accession and GI number are also given for each sequence when known. The SEQ ID for the sequence listing for the full-length genes corresponding to the accession numbers in the table are also given (SEQ ID ACC). These data were obtained from the Unigene unique database, build ###. The name of the gene associated with the accession number is noted. The strand is noted as −1 or 1, meaning that the probe was designed from the complement of the sequence (−1) or directly from the sequence (1). Next, the nucleotide sequence of each probe is also given. For each gene, the false detection rate (FDR) from the significance analsysis described in example 10 is given if applicable. Also, those genes that were identified by CART as a diagnostic gene are noted with the model and position in the model (see example 10 and FIG. 5).

Table 10B. Table 10B shows primers for PCR. For each of the lupus gene expression markers identified in Table 10A, 2 sets of PCR primer pairs are shown that were derived by the methods described in example 15. The melting temperature (Tm) for each primer is shown, as is the corresponding SEQ ID number for the primer in the sequence listing.

Table 10C. Table 10C shows surrogates for the lupus gene expression markers disclosed herein. For some of the lupus marker genes identified in Table 10A, genes are identified by the SEQ ID number as surrogates. The surrogates are identified as such by the CART algorithm or by hierarchical clustering as detailed below.

DETAILED DESCRIPTION OF THE INVENTION

Definitions

Unless defined otherwise, all scientific and technical terms are understood to have the same meaning as commonly used in the art to which they pertain. For the purpose of the present invention, the following terms are defined below.

In the context of the invention, the term "gene expression system" refers to any system, device or means to detect gene expression and includes diagnostic agents, candidate libraries oligonucleotide, oligonucleotide sets or probe sets.

The terms "diagnostic oligonucleotide" or "diagnostic oligonucleotide set" generally refers to an oligonucleotide or to a set of two or more oligonucleotides that, when evaluated for differential expression their corresponding diagnostic genes, collectively yields predictive data. Such predictive data typically relates to diagnosis, prognosis, monitoring of therapeutic outcomes, and the like. In general, the components of a diagnostic oligonucleotide or a diagnostic oligonucleotide set are distinguished from oligonucleotide sequences that are evaluated by analysis of the DNA to directly determine the genotype of an individual as it correlates with a specified trait or phenotype, such as a disease, in that it is the pattern of expression of the components of the diagnostic oligonucleotide set, rather than mutation or polymorphism of the DNA sequence that provides predictive value. It will be understood that a particular component (or member) of a diagnostic oligonucleotide set can, in some cases, also present one or more mutations, or polymorphisms that are amenable to direct genotyping by any of a variety of well known analysis methods, e.g., Southern blotting, RFLP, AFLP, SSCP, SNP, and the like.

A "diagnostic gene" is a gene whose expression is detected by a diagnostic oligonucleotide or diagnostic oligonucleotide set.

A "disease specific target oligonucleotide sequence" is a gene or other oligonucleotide that encodes a polypeptide, most typically a protein, or a subunit of a multi-subunit protein, that is a therapeutic target for a disease, or group of diseases.

A "candidate library" or a "candidate oligonucleotide library" refers to a collection of oligonucleotide sequences (or gene sequences) that by one or more criteria have an increased probability of being associated with a particular disease or group of diseases. The criteria can be, for example, a differential expression pattern in a disease state or in activated or resting leukocytes in vitro as reported in the scientific or technical literature, tissue specific expression as reported in a sequence database, differential expression in a tissue or cell type of interest, or the like. Typically, a candidate library has at least 2 members or components; more typically, the library has in excess of about 10, or about 100, or about 1000, or even more, members or components.

The term "disease criterion" is used herein to designate an indicator of a disease, such as a diagnostic factor, a prognostic factor, a factor indicated by a medical or family history, a genetic factor, or a symptom, as well as an overt or confirmed diagnosis of a disease associated with several indicators such as those selected from the above list. A disease criterian includes data describing a patient's health status, including retrospective or prospective health data, e.g. in the form of the patient's medical history, laboratory test results, diagnostic test result, clinical events, medications, lists, response(s) to treatment and risk factors, etc.

An autoimmune disorder is defined as a disease state in which a patient's immune system recognizes an antigen in that patient's organs or tissues as foreign and becomes activated. The activated immune cells can then cause damage to the inciting organ or tissue or can damage other organs or tissues. In some cases, the disorder may be caused by a dysregulation of the immune system cells, rather than by the recognition as a self-antigen as foreign. Dysregulated immune cells can secrete inflammatory cytokines that cause systemic inflammation or they can recognize self-antigens as foreign.

Examples of autoimmune diseases include: Autoimmune hepatitis, Multiple Sclerosis, Myasthenia Gravis, Type I diabetes, Rheumatoid Arthritis, Psoriasis, Systemic Lupus Erythematosis, Hashimoto's Thyroiditis, Grave's disease, Ankylosing Spondylitis Sjogrens Disease, CREST syndrome, Scleroderma and many more.

Most of the autoimmune diseases are also chronic inflammatory diseases. This is defined as a disease process associated with long-term (>6 months) activation of inflammatory cells (leukocytes). The chronic inflammation leads to damage of patient organs or tissues. Many diseases are chronic inflammatory disorders, but are not know to have an autoimmune basis. For example, Atherosclerosis, Congestive Heart Failure, Crohn's disease, Ulcerative Colitis, Polyarteritis nodosa, Whipple's Disease, Primary Sclerosing Cholangitis and many more.

The terms "molecular signature" or "expression profile" refers to the collection of expression values for a plurality (e.g., at least 2, but frequently about 10, about 100, about 1000, or more) of members of a candidate library. In many cases, the molecular signature represents the expression pattern for all of the nucleotide sequences in a library or array of candidate or diagnostic nucleotide sequences or genes. Alternatively, the molecular signature represents the expression pattern for one or more subsets of the candidate library. The term "oligonucleotide" refers to two or more nucleotides. Nucleotides may be DNA or RNA, naturally occurring or synthetic.

The term "healthy individual," as used herein, is relative to a specified disease or disease criterion. That is, the individual does not exhibit the specified disease criterion or is not diagnosed with the specified disease. It will be understood, that the individual in question, can, of course, exhibit symptoms, or possess various indicator factors for another disease.

Similarly, an "individual diagnosed with a disease" refers to an individual diagnosed with a specified disease (or disease criterion). Such an individual may, or may not, also exhibit a disease criterion associated with, or be diagnosed with another (related or unrelated) disease.

The term "monitoring" is used herein to describe the use of gene sets to provide useful information about an individual or an individual's health or disease status. "Monitoring" can include, determination of prognosis, risk-stratification, selection of drug therapy, assessment of ongoing drug therapy, prediction of outcomes, determining response to therapy, diagnosis of a disease or disease complication, following progression of a disease or providing any information relating to a patients health status.

An "array" is a spatially or logically organized collection, e.g., of oligonucleotide sequences or nucleotide sequence products such as RNA or proteins encoded by an oligonucleotide sequence. In some embodiments, an array includes antibodies or other binding reagents specific for products of a candidate library.

When referring to a pattern of expression, a "qualitative" difference in gene expression refers to a difference that is not assigned a relative value. That is, such a difference is designated by an "all or nothing" valuation. Such an all or nothing variation can be, for example, expression above or below a threshold of detection (an on/off pattern of expression). Alternatively, a qualitative difference can refer to expression of different types of expression products, e.g., different alleles (e.g., a mutant or polymorphic allele), variants (including sequence variants as well as post-translationally modified variants), etc.

In contrast, a "quantitative" difference, when referring to a pattern of gene expression, refers to a difference in expression that can be assigned a value on a graduated scale, (e.g., a 0-5 or 1-10 scale, a +−+++scale, a grade 1-grade 5 scale, or the like; it will be understood that the numbers selected for illustration are entirely arbitrary and in no-way are meant to be interpreted to limit the invention).

Gene Expression Systems and Methods of Detecting Gene Expression

The invention is directed to methods of detecting gene expression with a gene expression system having one or more DNA molecules wherein the one or more DNA molecules has a nucleotide sequence which detects expression of a gene corresponding to the oligonucleotides depicted in the Sequence Listing. In one format, the oligonucleotide detects expression of a gene that is differentially expressed in leukocytes. The gene expression system may be a candidate library, a diagnostic agent, a diagnostic oligonucleotide set or a diagnostic probe set. The DNA molecules may be genomic DNA, RNA, protein nucleic acid (PNA), cDNA or synthetic oligonucleotides. Following the procedures taught herein, one can identity sequences of interest for analyzing gene expression in leukocytes. Such sequences may be predictive of a disease state.

Diagnostic Oligonucleotides of the Invention

The invention relates to diagnostic oligonucleotides and diagnostic oligonucleotide set(s) comprising members of the leukocyte candidate library listed in Table 2, Table 3 and Tables 8-10 in the Sequence Listing, for which a correlation exists between the health status of an individual, and the individual's expression of RNA or protein products corresponding to the nucleotide sequence. In some instances, only one oligonucleotide is necessary for such detection. Members of a diagnostic oligonucleotide set may be identified by any means capable of detecting expression of RNA or protein products, including but not limited to differential expression screening, PCR, RT-PCR, SAGE analysis, high-throughput sequencing, microarrays, liquid or other arrays, protein-based methods (e.g., western blotting, proteomics, and other methods described herein), and data mining methods, as further described herein.

In one embodiment, a diagnostic oligonucleotide set comprises at least two oligonucleotide sequences listed in Table 2, Table 3 and Tables 8-10 or the Sequence Listing which are differentially expressed in leukocytes in an individual with at least one disease criterion for at least one leukocyte-implicated disease relative to the expression in individual without the at least one disease criterion, wherein expression of the two or more nucleotide sequences is correlated with at least one disease criterion, as described below.

In another embodiment, a diagnostic oligonucleotide set comprises at least one oligonucleotide having an oligonucleotide sequence listed in Table 2, 3 and Tables 8-10, or the Sequence Listing which is differentially expressed, and further wherein the differential expression/correlation has not previously been described. In some embodiments, the diagnostic oligonucleotide set is immobilized on an array.

In another embodiment, diagnostic oligonucleotides (or oligonucleotide sets) are related to the members of the leukocyte candidate library listed in Table 2, Table 3, Tables 8-10 and in the Sequence Listing, for which a correlation exists between the health status (or disease criterion) of an individual. The diagnostic oligonucleotides are partially or totally contained in (or derived from) full-length gene sequences (or predicted full-length gene sequences) for the members of the candidate library listed in Table 2, 3 and the Sequence Listing. This includes sequences from accession numbers and unigene numbers from Table 8. Table 8 shows the accession and unigene number (when known) for each oligonucleotide used on the 8134 gene leukocyte array described in examples 11-13. In some cases, oligonucleotide sequences are designed from EST or Chromosomal sequences from a public database. In these cases the full-length gene sequences may not be known. Full-length sequences in these cases can be predicted using gene prediction algorithms (Examples 4-6). Alternatively the full-length can be determined by cloning and sequencing the full-length gene or genes that contain the sequence of interest using standard molecular biology approaches described here. The same is true for olignonucleotides designed from our sequencing of cDNA libraries (see Examples 1-4) where the cDNA does not match any sequence in the public databases.

The diagnostic oligonucleotides may also be derived from other genes that are coexpressed with the correlated sequence or full-length gene. Genes may share expression patterns because they are regulated in the same molecular pathway. Because of the similarity of expression, behavior genes are identified as surrogates in that they can substitute for a diagnostic gene in a diagnostic gene set. Example 10 demonstrates the discovery of surrogates from the data and Table 10C and the sequence listing identify and give the sequence for surrogates for lupus diagnostic genes. Surrogate oligonucleotide and surrogate oligonucleotide sets can be utilized to detect expression of surrogate genes and thereby diagnose or monitor patients with a disease.

As used herein the term "gene cluster" or "cluster" refers to a group of genes related by expression pattern. In other words, a cluster of genes is a group of genes with similar regulation across different conditions, such as a patient having a chronic autoimmune or inflammatory disease or a patient without chronic autoimmune or inflammatory disease. The expression profile for each gene in a cluster should be correlated with the expression profile of at least one other gene in that cluster. Correlation may be evaluated using a variety of statistical methods. As used herein the term "surrogate" refers to a gene with an expression profile such that it can substitute for a diagnostic gene in a diagnostic assay. Such genes are often members of the same gene cluster as the diagnostic gene. For each member of a diagnostic gene set, a set of potential surrogates can be identified through identification of genes with similar expression patterns as described below.

Many statistical analyses produce a correlation coefficient to describe the relatedness between two gene expression patterns. Patterns may be considered correlated if the correlation coefficient is greater than or equal to 0.8. In preferred embodiments, the correlation coefficient should be greater than 0.85, 0.9 or 0.95. Other statistical methods produce a measure of mutual information to describe the relatedness between two gene expression patterns. Patterns may be considered correlated if the normalized mutual information value is greater than or equal to 0.7. In preferred embodiments, the normalized mutual information value should be greater than 0.8, 0.9 or 0.95. Patterns may also be considered similar if they cluster closely upon hierarchical clustering of gene expression data (Eisen et al. 1998). Similar patterns may be those genes that are among the 1, 2, 5, 10, 20, 50 or 100 nearest neighbors in a hierarchical clustering or have a similarity score (Eisen et al. 1998) of >0.5, 0.7, 0.8, 0.9, 0.95 or 0.99. Similar patterns may also be identified as those genes found to be surrogates in a classification tree by CART (Breiman et al. 1994). Often, but not always, members of a gene cluster have similar biological functions in addition to similar gene expression patterns.

Correlated genes, clusters and surrogates are identified for the diagnostic genes of the invention. These surrogates may be used as diagnostic genes in an assay instead of, or in addition to, the diagnostic genes for which they are surrogates.

The invention also provides diagnostic probe sets. It is understood that a probe includes any reagent capable of specifically identifying a nucleotide sequence of the diagnostic nucleotide set, including but not limited to amplified DNA, amplified RNA, cDNA, synthetic oligonucleotide, partial or full-length nucleic acid sequences. In addition, the probe may identify the protein product of a diagnostic nucleotide sequence, including, for example, antibodies and other affinity reagents.

It is also understood that each probe can correspond to one gene, or multiple probes can correspond to one gene, or both, or one probe can correspond to more than one gene.

Homologs and variants of the disclosed nucleic acid molecules may be used in the present invention. Homologs and variants of these nucleic acid molecules will possess a relatively high degree of sequence identity when aligned using standard methods. The sequences encompassed by the invention have at least 40-50, 50-60, 70-80, 80-85, 85-90, 90-95 or 95-100% sequence identity to the sequences disclosed herein.

It is understood that for expression profiling, variations in the disclosed sequences will still permit detection of gene expression. The degree of sequence identity required to detect gene expression varies depending on the length of the oligomer. For a 60 mer, (an oligonucleotide with 60 nucleotides) 6-8 random mutations or 6-8 random deletions in a 60 mer do not affect gene expression detection. Hughes, T R, et al. "Expression profiling using microarrays fabricated by an ink-jet oligonucleotide synthesizer. Nature Biotechnology, 19:343-347 (2001). As the length of the DNA sequence is increased, the number of mutations or deletions permitted while still allowing gene expression detection is increased.

As will be appreciated by those skilled in the art, the sequences of the present invention may contain sequencing errors. That is, there may be incorrect nucleotides, frameshifts, unknown nucleotides, or other types of sequencing errors in any of the sequences; however, the correct sequences will fall within the homology and stringency definitions herein.

The minimum length of an oligonucleotide probe necessary for specific hybridization in the human genome can be estimated using two approaches. The first method uses a statistical argument that the probe will be unique in the human genome by chance. Briefly, the number of independent perfect matches (Po) expected for an oligonucleotide of length L in a genome of complexity C can be calculated from the equation (Laird C D, Chromosoma 32:378 (1971):

$$Po = (1/4)^L * 2C$$

In the case of mammalian genomes, $2C = \sim 3.6 \times 10^9$, and an oligonucleotide of 14-15 nucleotides is expected to be represented only once in the genome. However, the distribution of nucleotides in the coding sequence of mammalian genomes is nonrandom (Lathe, R. J. Mol. Biol. 183:1 (1985) and longer oligonucleotides may be preferred in order to in increase the specificity of hybridization. In practical terms, this works out to probes that are 19-40 nucleotides long (Sambrook J et al., infra). The second method for estimating the length of a specific probe is to use a probe long enough to hybridize under the chosen conditions and use a computer to search for that sequence or close matches to the sequence in the human genome and choose a unique match. Probe sequences are chosen based on the desired hybridization properties as described in Chapter 11 of Sambrook et al, infra The PRIMER3 program is useful for designing these probes (S. Rozen and H. Skaletsky 1996, 1997; Primer3 code available at genome.wi.mitedu/genome_software/other/primer3.html, the website). The sequences of these probes are then compared pair wise against a database of the human genome sequences using a program such as BLAST or MEGA-BLAST (Madden, T. L et al. (1996) Meth. Enzymol. 266:131-141). Since most of the human genome is now contained in the database, the number of matches will be determined. Probe sequences are chosen that are unique to the desired target sequence.

In some embodiments, a diagnostic oligonucleotide or oligonucleotide probe set is immobilized on an array. The array is optionally comprises one or more of: a chip array, a plate array, a bead array, a pin array, a membrane array, a solid surface array, a liquid array, an oligonucleotide array, a polynucleotide array or a cDNA array, a microtiter plate, a pin array, a bead array, a membrane or a chip.

In some embodiments, the leukocyte-implicated disease is selected from the diseases listed in Table 1. In other embodiments, the disease is atherosclerosis or cardiac allograft rejection. In other embodiments, the disease is congestive heart failure, angina, myocardial infarction, chronic autoimmune and inflammatory diseases, systemic lupus erythematosis (SLE) and rheumatoid arthritis.

In some embodiments, diagnostic oligonucleotides of the invention are used as a diagnostic gene set in combination with genes that are know to be associated with a disease state ("known markers"). The use of the diagnostic oligonucleotides in combination with the known markers can provide information that is not obtainable through the known markers alone. The known markers include those identified by the prior art listing provided.

General Molecular Biology References

In the context of the invention, nucleic acids and/or proteins are manipulated according to well known molecular biology techniques. Detailed protocols for numerous such procedures are described in, e.g., in Ausubel et al. *Current Protocols in Molecular Biology* (supplemented through 2000) John Wiley & Sons, New York ("Ausubel"); Sambrook et al. *Molecular Cloning—A Laboratory Manual* (2nd Ed.), Vol. 1-3, Cold Spring Harbor Laboratory, Cold Spring Harbor, N.Y., 1989 ("Sambrook"), and Berger and Kimmel *Guide to Molecular Cloning Techniques, Methods in Enzymology* volume 152 Academic Press, Inc., San Diego, Calif. ("Berger").

In addition to the above references, protocols for in vitro amplification techniques, such as the polymerase chain reaction (PCR), the ligase chain reaction (LCR), Q-replicase amplification, and other RNA polymerase mediated techniques (e.g., NASBA), useful e.g., for amplifying cDNA probes of the invention, are found in Mullis et al. (1987) U.S. Pat. No. 4,683,202; *PCR Protocols A Guide to Methods and Applications* (Innis et al. eds) Academic Press Inc. San Diego, Calif. (1990) ("Innis"); Arnheim and Levinson (1990) *C&EN* 36; *The Journal Of NIH Research* (1991) 3:81; Kwoh et al. (1989) *Proc Natl Acad Sci USA* 86, 1173; Guatelli et al. (1990) *Proc Natl Acad Sci USA* 87:1874; Lomell et al. (1989) *J Clin Chem* 35:1826; Landegren et al. (1988) *Science* 241: 1077; Van Brunt (1990) *Biotechnology* 8:291; Wu and Wallace (1989) *Gene* 4: 560; Barringer et al. (1990) *Gene* 89:117, and Sooknanan and Malek (1995) *Biotechnology* 13:563. Additional methods, useful for cloning nucleic acids in the context of the present invention, include Wallace et al. U.S. Pat. No. 5,426,039. Improved methods of amplifying large nucleic acids by PCR are summarized in Cheng et al. (1994) *Nature* 369:684 and the references therein.

Certain polynucleotides of the invention, e.g., oligonucleotides can be synthesized utilizing various solid-phase strategies involving mononucleotide- and/or trinucleotide-based phosphoramidite coupling chemistry. For example, nucleic acid sequences can be synthesized by the sequential addition of activated monomers and/or trimers to an elongating polynucleotide chain. See e.g., Caruthers, M. H. et al. (1992) *Meth Enzymol* 211:3.

In lieu of synthesizing the desired sequences, essentially any nucleic acid can be custom ordered from any of a variety of commercial sources, such as The Midland Certified Reagent Company (mcrc@oligos.com), The Great American Gene Company (genco.com), ExpressGen, Inc. (expressgen.com), Operon Technologies, Inc. (operon.com), and many others.

Similarly, commercial sources for nucleic acid and protein microarrays are available, and include, e.g., Agilent Technologies, Palo Alto, Calif. and Affymetrix, Santa Clara, Calif.

Candidate Library

Libraries of candidate genes that are differentially expressed in leukocytes are substrates for the identification and evaluation of diagnostic oligonucleotides and oligonucleotide sets and disease specific target nucleotide sequences.

The term leukocyte is used generically to refer to any nucleated blood cell that is not a nucleated erythrocyte. More specifically, leukocytes can be subdivided into two broad classes. The first class includes granulocytes, including, most prevalently, neutrophils, as well as eosinophils and basophils at low frequency. The second class, the non-granular or mononuclear leukocytes, includes monocytes and lymphocytes (e.g., T cells and B cells). There is an extensive literature in the art implicating leukocytes, e.g., neutrophils, monocytes and lymphocytes in a wide variety of disease processes, including inflammatory and rheumatic diseases, neurodegenerative diseases (such as Alzheimer's dementia), cardiovascular disease, endocrine diseases, transplant rejection, malignancy and infectious diseases, and other diseases listed in Table 1. Mononuclear cells are involved in the chronic immune response, while granulocytes, which make up approximately 60% of the leukocytes, have a non-specific and stereotyped response to acute inflammatory stimuli and often have a life span of only 24 hours.

In addition to their widespread involvement and/or implication in numerous disease related processes, leukocytes are particularly attractive substrates for clinical and experimental evaluation for a variety of reasons. Most importantly, they are readily accessible at low cost from essentially every potential subject. Collection is minimally invasive and associated with little pain, disability or recovery time. Collection can be performed by minimally trained personnel (e.g., phlebotomists, medical technicians, etc.) in a variety of clinical and non-clinical settings without significant technological expenditure. Additionally, leukocytes are renewable, and thus available at multiple time points for a single subject.

Assembly of Candidate Libraries

At least two conceptually distinct approaches to the assembly of candidate libraries exist. Either, or both, or other, approaches can be favorably employed. The method of assembling, or identifying, candidate libraries is secondary to the criteria utilized for selecting appropriate library members. Most importantly, library members are assembled based on differential expression of RNA or protein products in leukocyte populations. More specifically, candidate nucleotide sequences are induced or suppressed, or expressed at increased or decreased levels in leukocytes from a subject with one or more disease or disease state (a disease criterion) relative to leukocytes from a subject lacking the specified disease criterion. Alternatively, or in addition, library members can be assembled from among nucleotide sequences that are differentially expressed in activated or resting leukocytes relative to other cell types.

Firstly, publication and sequence databases can be "mined" using a variety of search strategies. For example, currently available scientific and medical publication databases such as Medline, Current Contents, OMIM (online Mendelian inheritance in man) various Biological and Chemical Abstracts, Journal indexes, and the like can be searched using term or key-word searches, or by author, title, or other relevant search parameters. Many such databases are publicly available, and one of skill is well versed in strategies and procedures for identifying publications and their contents, e.g., genes, other nucleotide sequences, descriptions, indications, expression pattern, etc. Numerous databases are available through the internet for free or by subscription, see, e.g., the websites, ncbi.nlm.nih.gov/PubMed/; 3.infotrieve.com/; isinet.com/; sciencemag.org/. Additional or alternative publication or citation databases are also available that provide identical or similar types of information, any of which are favorably employed in the context of the invention. These databases can be searched for publications describing differential gene expression in leukocytes between patients with and without diseases or conditions listed in Table 1. We identified the nucleotide sequences listed in Table 2 and some of the sequences used to design oligonucleotides for microarrays (sequence listing), using data mining methods.

Alternatively, a variety of publicly available and proprietary sequence databases (including GenBank, dbEST, UniGene, and TIGR and SAGE databases) including sequences corresponding to expressed nucleotide sequences, such as expressed sequence tags (ESTs) are available. For example, the Genbank™ website located at ncbi.nlm.nih.gov/Genbank/ among others, can be readily accessed and searched via the internet. These and other sequence and clone database resources are currently available; however, any number of additional or alternative databases comprising nucleotide sequence sequences, EST sequences, clone repositories, PCR primer sequences, and the like corresponding to individual nucleotide sequence sequences are also suitable for the purposes of the invention. Nucleotide sequences can be identified that are only found in libraries derived from leukocytes or sub-populations of leukocytes, for example see Table 2 and Example 2.

Alternatively, the representation, or relative frequency, of a nucleotide sequence may be determined in a leukocyte-derived nucleic acid library and compared to the representation of the sequence in non-leukocyte derived libraries. The representation of a nucleotide sequence correlates with the relative expression level of the nucleotide sequence in leukocytes and non-leukocytes. An oligonucleotide sequence that has increased or decreased representation in a leukocyte-derived nucleic acid library relative to a non-leukocyte-derived libraries is a candidate for a leukocyte-specific gene.

Nucleotide sequences identified as having specificity to activated or resting leukocytes or to leukocytes from patients or patient samples with a variety of disease types can be isolated for use in a candidate library for leukocyte expression profiling through a variety of mechanisms. These include, but are not limited to, the amplification of the nucleotide sequence from RNA or DNA using nucleotide sequence specific primers for PCR or RT-PCR, isolation of the nucleotide sequence using conventional cloning methods, the purchase of an IMAGE consortium cDNA clone (EST) with complimentary sequence or from the same expressed nucleotide sequence, design of oligonucleotides, preparation of synthetic nucleic acid sequence, or any other nucleic-acid based method. In addition, the protein product of the nucleotide sequence can be isolated or prepared, and represented in a candidate library, using standard methods in the art, as described further below.

While the above discussion related primarily to "genomics" approaches, it is appreciated that numerous, analogous "proteomics" approaches are suitable to the present invention. For example, a differentially expressed protein product can, for example, be detected using western analysis, two-dimensional gel analysis, chromatographic separation, mass spectrometric detection, protein-fusion reporter constructs, colorometric assays, binding to a protein array, or by characterization of polysomal mRNA. The protein is further characterized and the nucleotide sequence encoding the protein is identified using standard techniques, e.g. by screening a cDNA library using a probe based on protein sequence information.

The second approach involves the construction of a differential expression library by any of a variety of means. Any one or more of differential screening, differential display or subtractive hybridization procedures, or other techniques that preferentially identify, isolate or amplify differentially expressed nucleotide sequences can be employed to produce a library of differentially expressed candidate nucleotide sequences, a subset of such a library, a partial library, or the like. Such methods are well known in the art. For example, peripheral blood leukocytes, (i.e., a mixed population including lymphocytes, monocytes and neutrophils), from multiple donor samples are pooled to prevent bias due to a single-donor's unique genotype. The pooled leukocytes are cultured in standard medium and stimulated with individual cytokines or growth factors e.g., with IL-2, IL-1, MCP1, TNFα, and/or IL8 according to well known procedures (see, e.g., Tough et al. (1999); Winston et al. (1999); Hansson et al. (1989)). Typically, leukocytes are recovered from Buffy coat preparations produced by centrifugation of whole blood. Alternatively, mononuclear cells (monocytes and lymphocytes) can be obtained by density gradient centrifugation of whole blood, or specific cell types (such as a T lymphocyte) can be isolated using affinity reagents to cell specific surface markers. When affinity reagents are used to isolate specific cell types, it is desirable to isolate the cells using negative selection to avoid activation of the desired cell type by binding of the antibody. Leukocytes may also be stimulated by incubation with ionomycin, and phorbol myristate acetate (PMA). This stimulation protocol is intended to non-specifically mimic "activation" of numerous pathways due to variety of disease conditions rather than to simulate any single disease condition or paradigm.

Using well-known subtractive hybridization procedures (as described in, e.g., U.S. Pat. Nos. 5,958,738; 5,589,339; 5,827,658; 5,712,127; 5,643,761) each of which are hereby incorporated by reference, a library is produced that is enriched for RNA species (messages) that are differentially expressed between test and control leukocyte populations. In some embodiments, the test population of leukocytes are simply stimulated as described above to emulate non-specific activation events, while in other embodiments the test population can be selected from subjects (or patients) with a specified disease or class of diseases. Typically, the control leukocyte population lacks the defining test condition, e.g., stimulation, disease state, diagnosis, genotype, etc. Alternatively, the total RNA from control and test leukocyte populations are prepared by established techniques, treated with DNAseI, and selected for messenger RNA with an intact 3' end (i.e., polyA(+) messenger RNA) e.g., using commercially available kits according to the manufacturer's instructions e.g. Clontech. Double stranded cDNA is synthesized utilizing reverse transcriptase. Double stranded cDNA is then cut with a first restriction enzyme (e.g., NlaIII, that cuts at the recognition site: CATG, and cuts the cDNA sequence at approximately 256 bp intervals) that cuts the cDNA molecules into conveniently sized fragments.

The cDNAs prepared from the test population of leukocytes are divided into (typically 2) "tester" pools, while cDNAs prepared from the control population of leukocytes are designated the "driver" pool. Typically, pooled populations of cells from multiple individual donors are utilized and in the case of stimulated versus unstimulated cells, the corresponding tester and driver pools for any single subtraction reaction are derived from the same donor pool.

A unique double-stranded adapter is ligated to each of the tester cDNA populations using unphosphorylated primers so that only the sense strand is covalently linked to the adapter. An initial hybridization is performed consisting of each of the tester pools of cDNA (each with its corresponding adapter) and an excess of the driver cDNA. Typically, an excess of about 10-100 fold driver relative to tester is employed, although significantly lower or higher ratios can be empirically determined to provide more favorable results. The initial hybridization results in an initial normalization of the cDNAs such that high and low abundance messages become more equally represented following hybridization due to a failure of driver/tester hybrids to amplify.

A second hybridization involves pooling un-hybridized sequences from initial hybridizations together with the addition of supplemental driver cDNA. In this step, the expressed sequences enriched in the two tester pools following the initial hybridization can hybridize. Hybrids resulting from the hybridization between members of each of the two tester pools are then recovered by amplification in a polymerase chain reaction (PCR) using primers specific for the unique adapters. Again, sequences originating in a tester pool that form hybrids with components of the driver pool are not amplified. Hybrids resulting between members of the same tester pool are eliminated by the formation of "panhandles" between their common 5' and 3' ends. For additional details, see, e.g., Lukyanov et al. (1997) *Biochem Biophys Res Commun* 230:285-8.

Typically, the tester and driver pools are designated in the alternative, such that the hybridization is performed in both directions to ensure recovery of messenger RNAs that are differentially expressed in either a positive or negative manner (i.e., that are turned on or turned off, up-regulated or down-regulated). Accordingly, it will be understood that the designation of test and control populations is to some extent arbitrary, and that a test population can just as easily be compared to leukocytes derived from a patient with the same of another disease of interest.

If so desired, the efficacy of the process can be assessed by such techniques as semi-quantitative PCR of known (i.e., control) nucleotide sequences, of varying abundance such as β-actin. The resulting PCR products representing partial cDNAs of differentially expressed nucleotide sequences are then cloned (i.e., ligated) into an appropriate vector (e.g., a commercially available TA cloning vector, such as pGEM from Promega) and, optionally, transformed into competent bacteria for selection and screening.

Either of the above approaches, or both in combination, or indeed, any procedure, which permits the assembly of a collection of nucleotide sequences that are expressed in leukocytes, is favorably employed to produce the libraries of candidates useful for the identification of diagnostic nucleotide sets and disease specific target nucleotides of the invention. Additionally, any method that permits the assembly of a collection of nucleotides that are expressed in leukocytes and preferentially associated with one or more disease or condition, whether or not the nucleotide sequences are differentially expressed, is favorably employed in the context of the invention. Typically, libraries of about 2,000-10,000 members are produced (although libraries in excess of 10,000 are not uncommon). Following additional evaluation procedures, as described below, the proportion of unique clones in the candidate library can approximate 100%.

A candidate oligonucleotide sequence may be represented in a candidate library by a full-length or partial nucleic acid sequence, deoxyribonucleic acid (DNA) sequence, cDNA sequence, RNA sequence, synthetic oligonucleotides, etc. The nucleic acid sequence can be at least 19 nucleotides in length, at least 25 nucleotides, at least 40 nucleotides, at least 100 nucleotides, or larger. Alternatively, the protein product of a candidate nucleotide sequence may be represented in a candidate library using standard methods, as further described below.

Characterization of Candidate Oligonucleotide Sequences

The sequence of individual members (e.g., clones, partial sequence listing in a database such as an EST, etc.) of the candidate oligonucleotide libraries is then determined by conventional sequencing methods well known in the art, e.g., by the dideoxy-chain termination method of Sanger et al. (1977) *Proc Natl Acad Sci USA* 74:5463-7; by chemical procedures, e.g., Maxam and Gilbert (1977) *Proc Natl Acad Sci USA* 74:560-4; or by polymerase chain reaction cycle sequencing methods, e.g., Olsen and Eckstein (1989) *Nuc Acid Res* 17:9613-20, DNA chip based sequencing techniques or variations, including automated variations (e.g., as described in Hunkapiller et al. (1991) *Science* 254:59-67; Pease et al. (1994) *Proc Natl Acad Sci USA* 91:5022-6), thereof. Numerous kits for performing the above procedures are commercially available and well known to those of skill in the art. Character strings corresponding to the resulting nucleotide sequences are then recorded (i.e., stored) in a database. Most commonly the character strings are recorded on a computer readable medium for processing by a computational device.

Generally, to facilitate subsequent analysis, a custom algorithm is employed to query existing databases in an ongoing fashion, to determine the identity, expression pattern and potential function of the particular members of a candidate library. The sequence is first processed, by removing low quality sequence. Next the vector sequences are identified and removed and sequence repeats are identified and masked. The remaining sequence is then used in a Blast algorithm against multiple publicly available, and/or proprietary databases, e.g., NCBI nucleotide, EST and protein databases, Unigene, and Human Genome Sequence. Sequences are also compared to all previously sequenced members of the candidate libraries to detect redundancy.

In some cases, sequences are of high quality, but do not match any sequence in the NCBI nr, human EST or Unigene databases. In this case the sequence is queried against the human genomic sequence. If a single chromosomal site is matched with a high degree of confidence, that region of genomic DNA is identified and subjected to further analysis with a gene prediction program such as GRAIL. This analysis may lead to the identification of a new gene in the genomic sequence. This sequence can then be translated to identify the protein sequence that is encoded and that sequence can be further analyzed using tools such as Pfam, Blast P, or other protein structure prediction programs, as illustrated in Table 7. Typically, the above analysis is directed towards the identification of putative coding regions, e.g., previously unidentified open reading frames, confirming the presence of known coding sequences, and determining structural motifs or sequence similarities of the predicted protein (i.e., the conceptual translation product) in relation to known sequences. In addition, it has become increasingly possible to assemble "virtual cDNAs" containing large portions of coding region, simply through the assembly of available expressed sequence tags (ESTs). In turn, these extended nucleic acid and amino acid sequences allow the rapid expansion of substrate sequences for homology searches and structural and functional motif characterization. The results of these analysis permits the categorization of sequences according to structural characteristics, e.g., as structural proteins, proteins involved in signal transduction, cell surface or secreted proteins etc.

It is understood that full-length nucleotide sequences may also be identified using conventional methods, for example, library screening, RT-PCR, chromosome walking, etc., as described in Sambrook and Ausubel, infra.

Candidate Nucleotide Library of the Invention

We identified members of a candidate nucleotide library that are differentially expressed in activated leukocytes and resting leukocytes. Accordingly, the invention provides the candidate leukocyte nucleotide library comprising the nucleotide sequences listed in Table 2, Table 3, Tables 8-10 and in the Sequence Listing. In another embodiment, the invention provides a candidate library comprising at least two nucleotide sequences listed in Table 2, Table 3, Tables 8-10 and the Sequence Listing. In another embodiment, at least two nucleotide sequences are 18 nucleotides in length, at least 35 nucleotides, at least 40 nucleotides or at least 100 nucleotides. In some embodiments, the nucleotide sequences comprises deoxyribonucleic acid (DNA) sequence, ribonucleic acid (RNA) sequence, synthetic oligonucleotide sequence, or genomic DNA sequence. It is understood that the nucleotide sequences may each correspond to one gene, or that several nucleotide sequences may correspond to one gene, or that a single nucleotide sequence may correspond to multiple genes.

The invention also provides probes to the candidate nucleotide library. In one embodiment of the invention, the probes comprise at least two nucleotide sequences listed in Table 2, Table 3, Tables 8-10, or the Sequence Listing which are differentially expressed in leukocytes in an individual with a least one disease criterion for at least one leukocyte-related disease and in leukocytes in an individual without the at least one disease criterion, wherein expression of the two or more nucleotide sequences is correlated with at least one disease criterion. It is understood that a probe may detect either the RNA expression or protein product expression of the candidate nucleotide library. Alternatively, or in addition, a probe can detect a genotype associated with a candidate nucleotide sequence, as further described below. In another embodiment, the probes for the candidate nucleotide library are immobilized on an array.

The candidate nucleotide library of the invention is useful in identifying diagnostic nucleotide sets of the invention, as described below. The candidate nucleotide sequences may be further characterized, and may be identified as a disease target nucleotide sequence and/or a novel nucleotide sequence, as described below. The candidate nucleotide sequences may also be suitable for use as imaging reagents, as described below.

Generation of Expression Patterns

RNA, DNA or Protein Sample Procurement

Following identification or assembly of a library of differentially expressed candidate nucleotide sequences, leukocyte expression profiles corresponding to multiple members of the candidate library are obtained. Leukocyte samples from one or more subjects are obtained by standard methods. Most typically, these methods involve trans-cutaneous venous sampling of peripheral blood. While sampling of circulating leukocytes from whole blood from the peripheral vasculature is generally the simplest, least invasive, and lowest cost alternative, it will be appreciated that numerous alternative sampling procedures exist, and are favorably employed in some circumstances. No pertinent distinction exists, in fact, between leukocytes sampled from the peripheral vasculature, and those obtained, e.g., from a central line, from a central artery, or indeed from a cardiac catheter, or during a surgical procedure which accesses the central vasculature. In addition, other body fluids and tissues that are, at least in part, composed of leukocytes are also desirable leukocyte samples. For example, fluid samples obtained from the lung during bronchoscopy may be rich in leukocytes, and amenable to expression profiling in the context of the invention, e.g., for the diagnosis, prognosis, or monitoring of lung transplant rejection, inflammatory lung diseases or infectious lung disease. Fluid samples from other tissues, e.g., obtained by endoscopy of the colon, sinuses, esophagus, stomach, small bowel, pancreatic duct, biliary tree, bladder, ureter, vagina, cervix or uterus, etc., are also suitable. Samples may also be obtained other sources containing leukocytes, e.g., from urine, bile, cerebrospinal fluid, feces, gastric or intestinal secretions, semen, or solid organ or joint biopsies.

Most frequently, mixed populations of leukocytes, such as are found in whole blood are utilized in the methods of the present invention. A crude separation, e.g., of mixed leukocytes from red blood cells, and/or concentration, e.g., over a sucrose, percoll or ficoll gradient, or by other methods known in the art, can be employed to facilitate the recovery of RNA or protein expression products at sufficient concentrations, and to reduce non-specific background. In some instances, it can be desirable to purify sub-populations of leukocytes, and methods for doing so, such as density or affinity gradients, flow cytometry, Fluorescence Activated Cell Sorting (FACS), immuno-magnetic separation, "panning," and the like, are described in the available literature and below.

Obtaining DNA, RNA and Protein Samples for Expression Profiling

A variety of techniques are available for the isolation of RNA from whole blood. Any technique that allows isolation of mRNA from cells (in the presence or absence of rRNA and tRNA) can be utilized. In brief, one method that allows reliable isolation of total RNA suitable for subsequent gene expression analysis is described as follows. Peripheral blood (either venous or arterial) is drawn from a subject, into one or more sterile, endotoxin free, tubes containing an anticoagulant (e.g., EDTA, citrate, heparin, etc.). Typically, the sample is divided into at least two portions. One portion, e.g., of 5-8 ml of whole blood is frozen and stored for future analysis, e.g., of DNA or protein. A second portion, e.g., of approximately 8 ml whole blood is processed for isolation of total RNA by any of a variety of techniques as described in, e.g, Sambook, Ausubel, below, as well as U.S. Pat. Nos. 5,728, 822 and 4,843,155.

Typically, a subject sample of mononuclear leukocytes obtained from about 8 ml of whole blood, a quantity readily available from an adult human subject under most circumstances, yields 5-20 µg of total RNA. This amount is ample, e.g., for labeling and hybridization to at least two probe arrays. Labeled probes for analysis of expression patterns of nucleotides of the candidate libraries are prepared from the subject's sample of RNA using standard methods. In many cases, cDNA is synthesized from total RNA using a polyT primer and labeled, e.g., radioactive or fluorescent, nucleotides. The resulting labeled cDNA is then hybridized to probes corresponding to members of the candidate nucleotide library, and expression data is obtained for each nucleotide sequence in the library. RNA isolated from subject samples (e.g., peripheral blood leukocytes, or leukocytes obtained from other biological fluids and samples) is next used for analysis of expression patterns of nucleotides of the candidate libraries.

In some cases, however, the amount of RNA that is extracted from the leukocyte sample is limiting, and amplification of the RNA is desirable. Amplification may be accomplished by increasing the efficiency of probe labeling, or by amplifying the RNA sample prior to labeling. It is appreciated that care must be taken to select an amplification procedure that does not introduce any bias (with respect to gene expression levels) during the amplification process.

Several methods are available that increase the signal from limiting amounts of RNA, e.g. use of the Clontech (Glass Fluorescent Labeling Kit) or Stratagene (Fairplay Microarray Labeling Kit), or the Micromax kit (New England Nuclear, Inc.). Alternatively, cDNA is synthesized from RNA using a T7-polyT primer, in the absence of label, and DNA dendrimers from Genisphere (3 DNA Submicro) are hybridized to the poly T sequence on the primer, or to a different "capture sequence" which is complementary to a fluorescently labeled sequence. Each 3DNA molecule has 250 fluorescent molecules and therefore can strongly label each cDNA.

Alternatively, the RNA sample is amplified prior to labeling. For example, linear amplification may be performed, as described in U.S. Pat. No. 6,132,997. A T7-polyT primer is used to generate the cDNA copy of the RNA. A second DNA strand is then made to complete the substrate for amplification. The T7 promoter incorporated into the primer is used by a T7 polymerase to produce numerous antisense copies of the original RNA. Fluorescent dye labeled nucleotides are directly incorporated into the RNA. Alternatively, amino allyl labeled nucleotides are incorporated into the RNA, and then fluorescent dyes are chemically coupled to the amino allyl groups, as described in Hughes et al. 2001. Other exemplary methods for amplification are described below.

It is appreciated that the RNA isolated must contain RNA derived from leukocytes, but may also contain RNA from other cell types to a variable degree. Additionally, the isolated RNA may come from subsets of leukocytes, e.g. monocytes and/or T-lymphocytes, as described above. Such consideration of cell type used for the derivation of RNA depends on the method of expression profiling used.

DNA samples may be obtained for analysis of the presence of DNA mutations, single nucleotide polymorphisms (SNPs), or other polymorphisms. DNA is isolated using standard techniques, e.g. Maniatus, supra.

Expression of products of candidate nucleotides may also be assessed using proteomics. Protein(s) are detected in samples of patient serum or from leukocyte cellular protein. Serum is prepared by centrifugation of whole blood, using standard methods. Proteins present in the serum may have been produced from any of a variety of leukocytes and non-leukocyte cells, and may include secreted proteins from leukocytes. Alternatively, leukocytes or a desired sub-population of leukocytes are prepared as described above. Cellular protein is prepared from leukocyte samples using methods well known in the art, e.g., Trizol (Invitrogen Life Technologies, cat #15596108; Chomczynski, P. and Sacchi, N. (1987) Anal. Biochem. 162, 156; Simms, D., Cizdziel, P. E., and Chomczynski, P. (1993) Focus® 15, 99; Chomczynski, P., Bowers-Finn, R., and Sabatini, L. (1987) J. of NIH Res. 6, 83; Chomczynski, P. (1993) Bio/Techniques 15, 532; Bracete, A. M., Fox, D. K., and Simms, D. (1998) Focus 20, 82; Sewall, A. and McRae, S. (1998) Focus 20, 36; Anal Biochem 1984 April; 138(1):141-3, A method for the quantitative recovery of protein in dilute solution in the presence of detergents and lipids; Wessel D, Flugge U I. (1984) Anal Biochem. 1984 April; 138(1):141-143.

Obtaining Expression Patterns

Expression patterns, or profiles, of a plurality of nucleotides corresponding to members of the candidate library are then evaluated in one or more samples of leukocytes. Typically, the leukocytes are derived from patient peripheral blood samples, although, as indicated above, many other sample sources are also suitable. These expression patterns constitute a set of relative or absolute expression values for some number of RNAs or protein products corresponding to the plurality of nucleotide sequences evaluated, which is referred to herein as the subject's "expression profile" for those nucleotide sequences. While expression patterns for as few as one independent member of the candidate library can be obtained, it is generally preferable to obtain expression patterns corresponding to a larger number of nucleotide sequences, e.g., about 2, about 5, about 10, about 20, about 50, about 100, about 200, about 500, or about 1000, or more. The expression pattern for each differentially expressed component member of the library provides a finite specificity and sensitivity with respect to predictive value, e.g., for diagnosis, prognosis, monitoring, and the like.

Clinical Studies, Data and Patient Groups

For the purpose of discussion, the term subject, or subject sample of leukocytes, refers to an individual regardless of health and/or disease status. A subject can be a patient, a study participant, a control subject, a screening subject, or any other class of individual from whom a leukocyte sample is obtained and assessed in the context of the invention. Accordingly, a subject can be diagnosed with a disease, can present with one or more symptom of a disease, or a predisposing factor, such as a family (genetic) or medical history (medical) factor, for a disease, or the like. Alternatively, a subject can be healthy with respect to any of the aforementioned factors or criteria. It will be appreciated that the term "healthy" as used herein, is relative to a specified disease, or disease factor, or disease criterion, as the term "healthy" cannot be defined to correspond to any absolute evaluation or status. Thus, an individual defined as healthy with reference to any specified disease or disease criterion, can in fact be diagnosed with any other one or more disease, or exhibit any other one or more disease criterion.

Furthermore, while the discussion of the invention focuses, and is exemplified using human sequences and samples, the invention is equally applicable, through construction or selection of appropriate candidate libraries, to non-human animals, such as laboratory animals, e.g., mice, rats, guinea pigs, rabbits; domesticated livestock, e.g., cows, horses, goats, sheep, chicken, etc.; and companion animals, e.g., dogs, cats, etc.

Methods for Obtaining Expression Data

Numerous methods for obtaining expression data are known, and any one or more of these techniques, singly or in combination, are suitable for determining expression profiles in the context of the present invention. For example, expression patterns can be evaluated by northern analysis, PCR, RT-PCR, Tag Man analysis, FRET detection, monitoring one or more molecular beacon, hybridization to an oligonucleotide array, hybridization to a cDNA array, hybridization to a polynucleotide array, hybridization to a liquid microarray, hybridization to a microelectric array, molecular beacons, cDNA sequencing, clone hybridization, cDNA fragment fingerprinting, serial analysis of gene expression (SAGE), subtractive hybridization, differential display and/or differential screening (see, e.g., Lockhart and Winzeler (2000) *Nature* 405:827-836, and references cited therein).

For example, specific PCR primers are designed to a member(s) of a candidate nucleotide library. cDNA is prepared from subject sample RNA by reverse transcription from a poly-dT oligonucleotide primer, and subjected to PCR. Double stranded cDNA may be prepared using primers suitable for reverse transcription of the PCR product, followed by amplification of the cDNA using in vitro transcription. The product of in vitro transcription is a sense-RNA corresponding to the original member(s) of the candidate library. PCR product may be also be evaluated in a number of ways known in the art, including real-time assessment using detection of labeled primers, e.g. TaqMan or molecular beacon probes. Technology platforms suitable for analysis of PCR products include the ABI 7700, 5700, or 7000 Sequence Detection Systems (Applied Biosystems, Foster City, Calif.), the MJ Research Opticon (MJ Research, Waltham, Mass.), the Roche Light Cycler (Roche Diagnositics, Indianapolis, Ind.), the Stratagene MX4000 (Stratagene, La Jolla, Calif.), and the Bio-Rad iCycler (Bio-Rad Laboratories, Hercules, Calif.). Alternatively, molecular beacons are used to detect presence of a nucleic acid sequence in an unamplified RNA or cDNA sample, or following amplification of the sequence using any method, e.g. IVT (In Vitro transcription) or NASBA (nucleic acid sequence based amplification). Molecular beacons are designed with sequences complementary to member(s) of a candidate nucleotide library, and are linked to fluorescent labels. Each probe has a different fluorescent label with non-overlapping emission wavelengths. For example, expression of ten genes may be assessed using ten different sequence-specific molecular beacons.

Alternatively, or in addition, molecular beacons are used to assess expression of multiple nucleotide sequences at once. Molecular beacons with sequence complimentary to the members of a diagnostic nucleotide set are designed and linked to fluorescent labels. Each fluorescent label used must have a non-overlapping emission wavelength. For example, 10 nucleotide sequences can be assessed by hybridizing 10 sequence specific molecular beacons (each labeled with a different fluorescent molecule) to an amplified or un-amplified RNA or cDNA sample. Such an assay bypasses the need for sample labeling procedures.

Alternatively, or in addition bead arrays can be used to assess expression of multiple sequences at once (See, e.g, LabMAP 100, Luminex Corp, Austin, Tex.). Alternatively, or in addition electric arrays are used to assess expression of multiple sequences, as exemplified by the e-Sensor technology of Motorola (Chicago, Ill.) or Nanochip technology of Nanogen (San Diego, Calif.)

Of course, the particular method elected will be dependent on such factors as quantity of RNA recovered, practitioner preference, available reagents and equipment, detectors, and the like. Typically, however, the elected method(s) will be appropriate for processing the number of samples and probes of interest. Methods for high-throughput expression analysis are discussed below.

Alternatively, expression at the level of protein products of gene expression is performed. For example, protein expression, in a sample of leukocytes, can be evaluated by one or more method selected from among: western analysis, two-dimensional gel analysis, chromatographic separation, mass spectrometric detection, protein-fusion reporter constructs, colorimetric assays, binding to a protein array and characterization of polysomal mRNA. One particularly favorable approach involves binding of labeled protein expression products to an array of antibodies specific for members of the candidate library. Methods for producing and evaluating antibodies are widespread in the art, see, e.g., Coligan, supra; and Harlow and Lane (1989) *Antibodies: A Laboratory Manual*, Cold Spring Harbor Press, NY ("Harlow and Lane"). Additional details regarding a variety of immunological and immunoassay procedures adaptable to the present invention by selection of antibody reagents specific for the products of candidate nucleotide sequences can be found in, e.g., Stites and Ten (eds.) (1991) *Basic and Clinical Immunology*, 7$^{th}$ ed., and Paul, supra. Another approach uses systems for performing desorption spectrometry. Commercially available systems, e.g., from Ciphergen Biosystems, Inc. (Fremont, Calif.) are particularly well suited to quantitative analysis of protein expression. Indeed, Protein Chip® arrays (see, e.g., the website, ciphergen.com) used in desorption spectrometry approaches provide arrays for detection of protein expression. Alternatively, affinity reagents, (e.g., antibodies, small molecules, etc.) are developed that recognize epitopes of the protein product. Affinity assays are used in protein array assays, e.g. to detect the presence or absence of particular proteins. Alternatively, affinity reagents are used to detect expression using the methods described above. In the case of a protein that is expressed on the cell surface of leukocytes, labeled affinity reagents are bound to populations of leukocytes, and leukocytes expressing the protein are identified and counted using fluorescent activated cell sorting (FACS).

It is appreciated that the methods of expression evaluation discussed herein, although discussed in the context of discovery of diagnostic nucleotide sets, are also applicable for expression evaluation when using diagnostic nucleotide sets for, e.g. diagnosis of diseases, as further discussed below.

High Throughput Expression Assays

A number of suitable high throughput formats exist for evaluating gene expression. Typically, the term high throughput refers to a format that performs at least about 100 assays, or at least about 500 assays, or at least about 1000 assays, or at least about 5000 assays, or at least about 10,000 assays, or more per day. When enumerating assays, either the number of samples or the number of candidate nucleotide sequences evaluated can be considered. For example, a northern analysis of, e.g., about 100 samples performed in a gridded array, e.g., a dot blot, using a single probe corresponding to a candidate nucleotide sequence can be considered a high throughput assay. More typically, however, such an assay is performed as a series of duplicate blots, each evaluated with a distinct probe corresponding to a different member of the candidate library. Alternatively, methods that simultaneously evaluate expression of about 100 or more candidate nucleotide sequences in one or more samples, or in multiple samples, are considered high throughput.

Numerous technological platforms for performing high throughput expression analysis are known. Generally, such methods involve a logical or physical array of either the subject samples, or the candidate library, or both. Common array formats include both liquid and solid phase arrays. For example, assays employing liquid phase arrays, e.g., for hybridization of nucleic acids, binding of antibodies or other receptors to ligand, etc., can be performed in multiwell, or microtiter, plates. Microtiter plates with 96, 384 or 1536 wells are widely available, and even higher numbers of wells, e,g, 3456 and 9600 can be used. In general, the choice of microtiter plates is determined by the methods and equipment, e.g., robotic handling and loading systems, used for sample preparation and analysis. Exemplary systems include, e.g., the ORCA™ system from Beckman-Coulter, Inc. (Fullerton, Calif.) and the Zymate systems from Zymark Corporation (Hopkinton, Mass.).

Alternatively, a variety of solid phase arrays can favorably be employed in to determine expression patterns in the context of the invention. Exemplary formats include membrane or filter arrays (e.g, nitrocellulose, nylon), pin arrays, and bead arrays (e.g., in a liquid "slurry"). Typically, probes corresponding to nucleic acid or protein reagents that specifically interact with (e.g., hybridize to or bind to) an expression product corresponding to a member of the candidate library are immobilized, for example by direct or indirect cross-linking, to the solid support. Essentially any solid support capable of withstanding the reagents and conditions necessary for performing the particular expression assay can be utilized. For example, functionalized glass, silicon, silicon dioxide, modified silicon, any of a variety of polymers, such as (poly)tetrafluoroethylene, (poly)vinylidenedifluoride, polystyrene, polycarbonate, or combinations thereof can all serve as the substrate for a solid phase array.

In a preferred embodiment, the array is a "chip" composed, e.g., of one of the above-specified materials. Polynucleotide probes, e.g., RNA or DNA, such as cDNA, synthetic oligonucleotides, and the like, or binding proteins such as antibodies, that specifically interact with expression products of individual components of the candidate library are affixed to the chip in a logically ordered manner, i.e., in an array. In addition, any molecule with a specific affinity for either the sense or anti-sense sequence of the marker nucleotide sequence (depending on the design of the sample labeling), can be fixed to the array surface without loss of specific affinity for the marker and can be obtained and produced for array production, for example, proteins that specifically recognize the specific nucleic acid sequence of the marker, ribozymes, peptide nucleic acids (PNA), or other chemicals or molecules with specific affinity.

Detailed discussion of methods for linking nucleic acids and proteins to a chip substrate, are found in, e.g., U.S. Pat. No. 5,143,854 "Large Scale Photolithographic Solid Phase Synthesis Of Polypeptides And Receptor Binding Screening Thereof" to Pirrung et al., issued, Sep. 1, 1992; U.S. Pat. No. 5,837,832 "Arrays Of Nucleic Acid Probes On Biological Chips" to Chee et al., issued Nov. 17, 1998; U.S. Pat. No. 6,087,112 "Arrays With Modified Oligonucleotide And Polynucleotide Compositions" to Dale, issued Jul. 11, 2000; U.S. Pat. No. 5,215,882 "Method Of Immobilizing Nucleic Acid On A Solid Substrate For Use In Nucleic Acid Hybridization Assays" to Bahl et al., issued Jun. 1, 1993; U.S. Pat. No. 5,707,807 "Molecular Indexing For Expressed Gene Analysis" to Kato, issued Jan. 13, 1998; U.S. Pat. No. 5,807,522 "Methods For Fabricating Microarrays Of Biological Samples" to Brown et al., issued Sep. 15, 1998; U.S. Pat. No. 5,958,342 "Jet Droplet Device" to Gamble et al., issued Sep. 28, 1999; U.S. Pat. No. 5,994,076 "Methods Of Assaying Differential Expression" to Chenchik et al., issued Nov. 30, 1999; U.S. Pat. No. 6,004,755 "Quantitative Microarray Hybridization Assays" to Wang, issued Dec. 21, 1999; U.S. Pat. No. 6,048,695 "Chemically Modified Nucleic Acids And Method For Coupling Nucleic Acids To Solid Support" to Bradley et al., issued Apr. 11, 2000; U.S. Pat. No. 6,060,240 "Methods For Measuring Relative Amounts Of Nucleic Acids In A Complex Mixture And Retrieval Of Specific Sequences Therefrom" to Kamb et al., issued May 9, 2000; U.S. Pat. No. 6,090,556 "Method For Quantitatively Determining The Expression Of A Gene" to Kato, issued Jul. 18, 2000; and U.S. Pat. No. 6,040,138 "Expression Monitoring By Hybridization To High Density Oligonucleotide Arrays" to Lockhart et al., issued Mar. 21, 2000 each of which are hereby incorporated by reference in their entirety.

For example, cDNA inserts corresponding to candidate nucleotide sequences, in a standard TA cloning vector are amplified by a polymerase chain reaction for approximately 30-40 cycles. The amplified PCR products are then arrayed onto a glass support by any of a variety of well-known techniques, e.g., the VSLIPS™ technology described in U.S. Pat. No. 5,143,854. RNA, or cDNA corresponding to RNA, isolated from a subject sample of leukocytes is labeled, e.g., with a fluorescent tag, and a solution containing the RNA (or cDNA) is incubated under conditions favorable for hybridization, with the "probe" chip. Following incubation, and washing to eliminate non-specific hybridization, the labeled nucleic acid bound to the chip is detected qualitatively or quantitatively, and the resulting expression profile for the corresponding candidate nucleotide sequences is recorded. It is appreciated that the probe used for diagnostic purposes may be identical to the probe used during diagnostic nucleotide sequence discovery and validation. Alternatively, the probe sequence may be different than the sequence used in diagnostic nucleotide sequence discovery and validation. Multiple cDNAs from a nucleotide sequence that are non-overlapping or partially overlapping may also be used.

In another approach, oligonucleotides corresponding to members of a candidate nucleotide library are synthesized and spotted onto an array. Alternatively, oligonucleotides are synthesized onto the array using methods known in the art, e.g. Hughes, et al. supra. The oligonucleotide is designed to be complementary to any portion of the candidate nucleotide sequence. In addition, in the context of expression analysis for, e.g. diagnostic use of diagnostic nucleotide sets, an oligonucleotide can be designed to exhibit particular hybridization characteristics, or to exhibit a particular specificity and/or sensitivity, as further described below.

Oligonucleotide probes are also prepared using the DNA sequence information for the candidate genes identified by differential hybridization screening (listed in Tables 3, 8-10 and the Sequence Listing) and/or the sequence information for the genes identified by database mining (listed in Table 2) is used to design complimentary oligonucleotide probes. Oligo probes are designed on a contract basis by various companies (for example, Compugen, Mergen, Affymetrix, Telechem), or designed from the candidate sequences using a variety of parameters and algorithms as indicated at the website genome.wi.mit.edu/cgi-bin/primer/primer3.cgi. Briefly, the length of the oligonucleotide to be synthesized is determined, preferably at least 16 nucleotides, generally 18-24 nucleotides, 24-70 nucleotides and, in some circumstances, more than 70 nucleotides. The sequence analysis algorithms and tools described above are applied to the sequences to mask repetitive elements, vector sequences and low complexity sequences. Oligonucleotides are selected that are specific to the candidate nucleotide sequence (based on a Blast n search of the oligonucleotide sequence in question against gene sequences databases, such as the Human Genome Sequence, UniGene, dbEST or the non-redundant database at NCBI), and have <50% G content and 25-70% G+C content. Desired oligonucleotides are synthesized using well-known methods and apparatus, or ordered from a company (for example Sigma). Oligonucleotides are spotted onto microarrays. Alternatively, oligonucleotides are synthesized directly on the array surface, using a variety of techniques (Hughes et al. 2001, Yershov et al. 1996, Lockhart et al 1996).

Hybridization signal may be amplified using methods known in the art, and as described herein, for example use of the Clontech kit (Glass Fluorescent Labeling Kit), Stratagene kit (Fairplay Microarray Labeling Kit), the Micromax kit (New England Nuclear, Inc.), the Genisphere kit (3DNA Submicro), linear amplification, e.g. as described in U.S. Pat. No. 6,132,997 or described in Hughes, T R, et al., Nature Biotechnology, 19:343-347 (2001) and/or Westin et al. *Nat. Biotech.* 18:199-204. In some cases, amplification techniques do not increase signal intensity, but allow assays to be done with small amounts of RNA.

Alternatively, fluorescently labeled cDNA are hybridized directly to the microarray using methods known in the art. For example, labeled cDNA are generated by reverse transcription using Cy3- and Cy5-conjugated deoxynucleotides, and the reaction products purified using standard methods. It is appreciated that the methods for signal amplification of expression data useful for identifying diagnostic nucleotide sets are also useful for amplification of expression data for diagnostic purposes.

Microarray expression may be detected by scanning the microarray with a variety of laser or CCD-based scanners, and extracting features with numerous software packages, for example, Imagene (Biodiscovery), Feature Extraction Software (Agilent), Scanalyze (Eisen, M. 1999. SCANALYZE User Manual; Stanford Univ., Stanford, Calif. Ver 2.32.), GenePix (Axon Instruments).

In another approach, hybridization to microelectric arrays is performed, e.g. as described in Umek et al (2001) *J Mol Diagn.* 3:74-84. An affinity probe, e.g. DNA, is deposited on a metal surface. The metal surface underlying each probe is connected to a metal wire and electrical signal detection system. Unlabelled RNA or cDNA is hybridized to the array, or alternatively, RNA or cDNA sample is amplified before hybridization, e.g. by PCR. Specific hybridization of sample RNA or cDNA results in generation of an electrical signal, which is transmitted to a detector. See Westin (2000) *Nat Biotech.* 18:199-204 (describing anchored multiplex amplification of a microelectronic chip array); Edman (1997) *NAR* 25:4907-14; Vignali (2000) *J Immunol Methods* 243:243-55.

In another approach, a microfluidics chip is used for RNA sample preparation and analysis. This approach increases efficiency because sample preparation and analysis are streamlined. Briefly, microfluidics may be used to sort specific leukocyte sub-populations prior to RNA preparation and analysis. Microfluidics chips are also useful for, e.g., RNA preparation, and reactions involving RNA (reverse transcription, RT-PCR). Briefly, a small volume of whole, anti-coagulated blood is loaded onto a microfluidics chip, for example chips available from Caliper (Mountain View, Calif.) or Nanogen (San Diego, Calif.) A microfluidics chip may contain channels and reservoirs in which cells are moved and reactions are performed. Mechanical, electrical, magnetic, gravitational, centrifugal or other forces are used to move the cells and to expose them to reagents. For example, cells of whole blood are moved into a chamber containing hypotonic saline, which results in selective lysis of red blood cells after a 20-minute incubation. Next, the remaining cells (leukocytes) are moved into a wash chamber and finally, moved into a chamber containing a lysis buffer such as guanidine isothyocyanate. The leukocyte cell lysate is further processed for RNA isolation in the chip, or is then removed for further processing, for example, RNA extraction by standard methods. Alternatively, the microfluidics chip is a circular disk containing ficoll or another density reagent. The blood sample is injected into the center of the disc, the disc is rotated at a speed that generates a centrifugal force appropriate for density gradient separation of mononuclear cells, and the separated mononuclear cells are then harvested for further analysis or processing.

It is understood that the methods of expression evaluation, above, although discussed in the context of discovery of diagnostic nucleotide sets, are also applicable for expression evaluation when using diagnostic nucleotide sets for, e.g. diagnosis of diseases, as further discussed below.

Evaluation of Expression Patterns

Expression patterns can be evaluated by qualitative and/or quantitative measures. Certain of the above described techniques for evaluating gene expression (as RNA or protein products) yield data that are predominantly qualitative in nature. That is, the methods detect differences in expression that classify expression into distinct modes without providing significant information regarding quantitative aspects of expression. For example, a technique can be described as a qualitative technique if it detects the presence or absence of expression of a candidate nucleotide sequence, i.e., an on/off pattern of expression. Alternatively, a qualitative technique measures the presence (and/or absence) of different alleles, or variants, of a gene product.

In contrast, some methods provide data that characterize expression in a quantitative manner. That is, the methods relate expression on a numerical scale, e.g., a scale of 0-5, a scale of 1-10, a scale of +-+++, from grade 1 to grade 5, a grade from a to z, or the like. It will be understood that the numerical, and symbolic examples provided are arbitrary, and that any graduated scale (or any symbolic representation of a graduated scale) can be employed in the context of the present invention to describe quantitative differences in nucleotide sequence expression. Typically, such methods yield information corresponding to a relative increase or decrease in expression.

Any method that yields either quantitative or qualitative expression data is suitable for evaluating expression of candidate nucleotide sequence in a subject sample of leukocytes. In some cases, e.g., when multiple methods are employed to determine expression patterns for a plurality of candidate nucleotide sequences, the recovered data, e.g., the expression profile, for the nucleotide sequences is a combination of quantitative and qualitative data.

In some applications, expression of the plurality of candidate nucleotide sequences is evaluated sequentially. This is typically the case for methods that can be characterized as low- to moderate-throughput. In contrast, as the throughput of the elected assay increases, expression for the plurality of candidate nucleotide sequences in a sample or multiple samples of leukocytes, is assayed simultaneously. Again, the methods (and throughput) are largely determined by the individual practitioner, although, typically, it is preferable to employ methods that permit rapid, e.g. automated or partially automated, preparation and detection, on a scale that is time-efficient and cost-effective.

It is understood that the preceding discussion, while directed at the assessment of expression of the members of candidate libraries, is also applies to the assessment of the expression of members of diagnostic nucleotide sets, as further discussed below.

Genotyping

In addition to, or in conjunction with the correlation of expression profiles and clinical data, it is often desirable to correlate expression patterns with the subject's genotype at one or more genetic loci or to correlate both expression profiles and genetic loci data with clinical data. The selected loci can be, for example, chromosomal loci corresponding to one or more member of the candidate library, polymorphic alleles for marker loci, or alternative disease related loci (not contributing to the candidate library) known to be, or putatively associated with, a disease (or disease criterion). Indeed, it will be appreciated, that where a (polymorphic) allele at a locus is linked to a disease (or to a predisposition to a disease), the presence of the allele can itself be a disease criterion.

Numerous well known methods exist for evaluating the genotype of an individual, including southern analysis, restriction fragment length polymorphism (RFLP) analysis, polymerase chain reaction (PCR), amplification length polymorphism (AFLP) analysis, single stranded conformation polymorphism (SSCP) analysis, single nucleotide polymorphism (SNP) analysis (e.g., via PCR, Taqman or molecular beacons), among many other useful methods. Many such procedures are readily adaptable to high throughput and/or automated (or semi-automated) sample preparation and analysis methods. Most, can be performed on nucleic acid samples recovered via simple procedures from the same sample of leukocytes as yielded the material for expression profiling. Exemplary techniques are described in, e.g., Sambrook, and Ausubel, supra.

Identification of the Diagnostic Oligonucleotides and Oligonucleotide Sets of the Invention Identification of diagnostic nucleotides and nucleotide sets and disease specific target nucleotide sequence proceeds by correlating the leukocyte expression profiles with data regarding the subject's health status to produce a data set designated a "molecular signature." Examples of data regarding a patient's health status, also termed "disease criteria(ion)", is described below and in the Section titled "selected diseases," below. Methods useful for correlation analysis are further described elsewhere in the specification.

Generally, relevant data regarding the subject's health status includes retrospective or prospective health data, e.g., in the form of the subject's medical history, as provided by the subject, physician or third party, such as, medical diagnoses, laboratory test results, diagnostic test results, clinical events, or medication lists, as further described below. Such data may include information regarding a patient's response to treatment and/or a particular medication and data regarding the presence of previously characterized "risk factors." For example, cigarette smoking and obesity are previously identified risk factors for heart disease. Further examples of health status information, including diseases and disease criteria, is described in the section titled Selected diseases, below.

Typically, the data describes prior events and evaluations (i.e., retrospective data). However, it is envisioned that data collected subsequent to the sampling (i.e., prospective data) can also be correlated with the expression profile. The tissue sampled, e.g., peripheral blood, bronchial lavage, etc., can be obtained at one or more multiple time points and subject data is considered retrospective or prospective with respect to the time of sample procurement.

Data collected at multiple time points, called "longitudinal data", is often useful, and thus, the invention encompasses the analysis of patient data collected from the same patient at different time points. Analysis of paired samples, such as samples from a patient at different times, allows identification of differences that are specifically related to the disease state since the genetic variability specific to the patient is controlled for by the comparison. Additionally, other variables that exist between patients may be controlled for in this way, for example, the presence or absence of inflammatory diseases (e.g., rheumatoid arthritis) the use of medications that may effect leukocyte gene expression, the presence or absence of co-morbid conditions, etc. Methods for analysis of paired samples are further described below. Moreover, the analysis of a pattern of expression profiles (generated by collecting multiple expression profiles) provides information relating to changes in expression level over time, and may permit the determination of a rate of change, a trajectory, or an expression curve. Two longitudinal samples may provide information on the change in expression of a gene over time, while three longitudinal samples may be necessary to determine the "trajectory" of expression of a gene. Such information may be relevant to the diagnosis of a disease. For example, the expression of a gene may vary from individual to individual, but a clinical event, for example, a heart attack, may cause the level of expression to double in each patient. In this example, clinically interesting information is gleaned from the change in expression level, as opposed to the absolute level of expression in each individual.

When a single patient sample is obtained, it may still be desirable to compare the expression profile of that sample to some reference expression profile. In this case, one can determine the change of expression between the patient's sample and a reference expression profile that is appropriate for that patient and the medical condition in question. For example, a reference expression profile can be determined for all patients without the disease criterion in question who have similar characteristics, such as age, sex, race, diagnoses etc.

Generally, small sample sizes of 10-40 samples from 10-20 individuals are used to identify a diagnostic nucleotide set. Larger sample sizes are generally necessary to validate the diagnostic nucleotide set for use in large and varied patient populations, as further described below. For example, extension of gene expression correlations to varied ethnic groups, demographic groups, nations, peoples or races may require expression correlation experiments on the population of interest.

Expression Reference Standards

Expression profiles derived from a patient (i.e., subjects diagnosed with, or exhibiting symptoms of, or exhibiting a disease criterion, or under a doctor's care for a disease) sample are compared to a control or standard expression RNA to facilitate comparison of expression profiles (e.g. of a set of candidate nucleotide sequences) from a group of patients relative to each other (i.e., from one patient in the group to other patients in the group, or to patients in another group).

The reference RNA used should have desirable features of low cost and simplicity of production on a large scale. Additionally, the reference RNA should contain measurable amounts of as many of the genes of the candidate library as possible.

For example, in one approach to identifying diagnostic nucleotide sets, expression profiles derived from patient samples are compared to a expression reference "standard." Standard expression reference can be, for example, RNA derived from resting cultured leukocytes or commercially available reference RNA, such as Universal reference RNA from Stratagene. See Nature, V406, 8-17-00, p. 747-752. Use of an expression reference standard is particularly useful when the expression of large numbers of nucleotide sequences is assayed, e.g. in an array, and in certain other applications, e.g. qualitative PCR, RT-PCR, etc., where it is desirable to compare a sample profile to a standard profile, and/or when large numbers of expression profiles, e.g. a patient population, are to be compared. Generally, an expression reference standard should be available in large quantities, should be a good substrate for amplification and labeling reactions, and should be capable of detecting a large percentage of candidate nucleic acids using suitable expression profiling technology.

Alternatively, or in addition, the expression profile derived from a patient sample is compared with the expression of an internal reference control gene, for example, β-actin or CD4. The relative expression of the profiled genes and the internal reference control gene (from the same individual) is obtained.

An internal reference control may also be used with a reference RNA. For example, an expression profile for "gene 1" and the gene encoding CD4 can be determined in a patient sample and in a reference RNA. The expression of each gene can be expressed as the "relative" ratio of expression the gene in the patient sample compared with expression of the gene in the reference RNA. The expression ratio (sample/reference) for gene 1 may be divided by the expression ration for CD4 (sample/reference) and thus the relative expression of gene 1 to CD4 is obtained.

The invention also provides a buffy coat control RNA useful for expression profiling, and a method of using control RNA produced from a population of buffy coat cells, the white blood cell layer derived from the centrifugation of whole blood. Buffy coat contains all white blood cells, including granulocytes, mononuclear cells and platelets. The invention also provides a method of preparing control RNA from buffy coat cells for use in expression profile analysis of leukocytes. Buffy coat fractions are obtained, e.g. from a blood bank or directly from individuals, preferably from a large number of individuals such that bias from individual samples is avoided and so that the RNA sample represents an average expression of a healthy population. Buffy coat fractions from about 50 or about 100, or more individuals are preferred. 10 ml buffy coat from each individual is used. Buffy coat samples are treated with an erthythrocyte lysis buffer, so that erthythrocytes are selectively removed. The leukocytes of the buffy coat layer are collected by centrifugation. Alternatively, the buffy cell sample can be further enriched for a particular leukocyte sub-populations, e.g. mononuclear cells, T-lymphocytes, etc. To enrich for mononuclear cells, the buffy cell pellet, above, is diluted in PBS (phosphate buffered saline) and loaded onto a non-polystyrene tube containing a polysucrose and sodium diatrizoate solution adjusted to a density of 1.077+/−0.001 g/ml. To enrich for T-lymphocytes, 45 ml of whole blood is treated with RosetteSep (Stem Cell Technologies), and incubated at room temperature for 20 minutes. The mixture is diluted with an equal volume of PBS plus 2% FBS and mixed by inversion. 30 ml of diluted mixture is layered on top of 15 ml DML medium (Stem Cell Technologies). The tube is centrifuged at 1200×g, and the enriched cell layer at the plasma:medium interface is removed, washed with PBS+2% FBS, and cells collected by centrifugation at 1200×g. The cell pellet is treated with 5 ml of erythrocyte lysis buffer (EL buffer, Qiagen) for 10 minutes on ice, and enriched T-lymphoctes are collected by centrifugation.

In addition or alternatively, the buffy cells (whole buffy coat or sub-population, e.g. mononuclear fraction) can be cultured in vitro and subjected to stimulation with cytokines or activating chemicals such as phorbol esters or ionomycin. Such stimuli may increase expression of nucleotide sequences that are expressed in activated immune cells and might be of interest for leukocyte expression profiling experiments.

Following sub-population selection and/or further treatment, e.g. stimulation as described above, RNA is prepared using standard methods. For example, cells are pelleted and lysed with a phenol/guanidinium thiocyanate and RNA is prepared. RNA can also be isolated using a silica gel-based purification column or the column method can be used on RNA isolated by the phenol/guanidinium thiocyanate method. RNA from individual buffy coat samples can be pooled during this process, so that the resulting reference RNA represents the RNA of many individuals and individual bias is minimized or eliminated. In addition, a new batch of buffy coat reference RNA can be directly compared to the last batch to ensure similar expression pattern from one batch to another, using methods of collecting and comparing expression profiles described above/below. One or more expression reference controls are used in an experiment. For example, RNA derived from one or more of the following sources can be used as controls for an experiment: stimulated or unstimulated whole buffy coat, stimulated or unstimulated peripheral mononuclear cells, or stimulated or unstimulated T-lymphocytes.

Alternatively, the expression reference standard can be derived from any subject or class of subjects including healthy subjects or subjects diagnosed with the same or a different disease or disease criterion. Expression profiles from subjects in two or more distinct classes are compared to determine which subset of nucleotide sequences in the candidate library can best distinguish between the subject classes, as further discussed below. It will be appreciated that in the present context, the term "distinct classes" is relevant to at least one distinguishable criterion relevant to a disease of interest, a "disease criterion." The classes can, of course, demonstrate significant overlap (or identity) with respect to other disease criteria, or with respect to disease diagnoses, prognoses, or the like. The mode of discovery involves, e.g., comparing the molecular signature of different subject classes to each other (such as patient to control, patients with a first diagnosis to patients with a second diagnosis, etc.) or by comparing the molecular signatures of a single individual taken at different time points. The invention can be applied to a broad range of diseases, disease criteria, conditions and other clinical and/or epidemiological questions, as further discussed above/below.

It is appreciated that while the present discussion pertains to the use of expression reference controls while identifying diagnostic nucleotide sets, expression reference controls are also useful during use of diagnostic nucleotide sets, e.g. use of a diagnostic nucleotide set for diagnosis of a disease, as further described below.

Analysis of Expression Profiles

In order to facilitate ready access, e.g., for comparison, review, recovery, and/or modification, the molecular signatures/expression profiles are typically recorded in a database. Most typically, the database is a relational database accessible by a computational device, although other formats, e.g., manually accessible indexed files of expression profiles as photographs, analogue or digital imaging readouts, spreadsheets, etc. can be used. Further details regarding preferred embodiments are provided below. Regardless of whether the expression patterns initially recorded are analog or digital in nature and/or whether they represent quantitative or qualitative differences in expression, the expression patterns, expression profiles (collective expression patterns), and molecular signatures (correlated expression patterns) are stored digitally and accessed via a database. Typically, the database is compiled and maintained at a central facility, with access being available locally and/or remotely.

As additional samples are obtained, and their expression profiles determined and correlated with relevant subject data, the ensuing molecular signatures are likewise recorded in the database. However, rather than each subsequent addition being added in an essentially passive manner in which the data from one sample has little relation to data from a second (prior or subsequent) sample, the algorithms optionally additionally query additional samples against the existing database to further refine the association between a molecular signature and disease criterion. Furthermore, the data set comprising the one (or more) molecular signatures is optionally queried against an expanding set of additional or other disease criteria. The use of the database in integrated systems and web embodiments is further described below.

Analysis of Expression Profile Data from Arrays

Expression data is analyzed using methods well known in the art, including the software packages Imagene (Biodiscovery, Marina del Rey, Calif.), Feature Extraction Software (Agilent, Palo Alto, Calif.), and Scanalyze (Stanford University). In the discussion that follows, a "feature" refers to an individual spot of DNA on an array. Each gene may be represented by more than one feature. For example, hybridized microarrays are scanned and analyzed on an Axon Instruments scanner using GenePix 3.0 software (Axon Instruments, Union City, Calif.). The data extracted by GenePix is used for all downstream quality control and expression evaluation. The data is derived as follows. The data for all features flagged as "not found" by the software is removed from the dataset for individual hybridizations. The "not found" flag by GenePix indicates that the software was unable to discriminate the feature from the background. Each feature is examined to determine the value of its signal. The median pixel intensity of the background ($B_n$) is subtracted from the median pixel intensity of the feature ($F_n$) to produce the background-subtracted signal (hereinafter, "BGSS"). The BGSS is divided by the standard deviation of the background pixels to provide the signal-to-noise ratio (hereinafter, "S/N"). Features with a S/N of three or greater in both the Cy3 channel (corresponding to the sample RNA) and Cy5 channel (corresponding to the reference RNA) are used for further analysis (hereinafter denoted "useable features"). Alternatively, different S/Ns are used for selecting expression data for an analysis. For example, only expression data with signal to noise ratios >3 might be used in an analysis. Alternatively, features with S/N values <3 may be flagged as such and included in the analysis. Such flagged data sets include more values and may allow one to discover expression markers that would be missed otherwise. However, such data sets may have a higher variablilty than filtered data, which may decrease significance of findings or performance of correlation statistics.

For each usable feature (i), the expression level (e) is expressed as the logarithm of the ratio (R) of the Background Subtracted Signal (hereinafter "BGSS") for the Cy3 (sample RNA) channel divided by the BGSS for the Cy5 channel (reference RNA). This "log ratio" value is used for comparison to other experiments.

$$R_i = \frac{BGSS_{sample}}{BGSS_{reference}} \quad (0.1)$$

$$e_i = \log r_i \quad (0.2)$$

Variation in signal across hybridizations may be caused by a number of factors affecting hybridization, DNA spotting, wash conditions, and labeling efficiency.

A single reference RNA may be used with all of the experimental RNAs, permitting multiple comparisons in addition to individual comparisons. By comparing sample RNAs to the same reference, the gene expression levels from each sample are compared across arrays, permitting the use of a consistent denominator for our experimental ratios.

Scaling

The data may be scaled (normalized) to control for labeling and hybridization variability within the experiment, using methods known in the art. Scaling is desirable because it facilitates the comparison of data between different experiments, patients, etc. Generally the BGSS are scaled to a factor such as the median, the mean, the trimmed mean, and percentile. Additional methods of scaling include: to scale between 0 and 1, to subtract the mean, or to subtract the median.

Scaling is also performed by comparison to expression patterns obtained using a common reference RNA, as described in greater detail above. As with other scaling methods, the reference RNA facilitates multiple comparisons of the expression data, e.g., between patients, between samples, etc. Use of a reference RNA provides a consistent denominator for experimental ratios.

In addition to the use of a reference RNA, individual expression levels may be adjusted to correct for differences in labeling efficiency between different hybridization experiments, allowing direct comparison between experiments with different overall signal intensities, for example. A scaling factor (a) may be used to adjust individual expression levels as follows. The median of the scaling factor (a), for example, BGSS, is determined for the set of all features with a S/N greater than three. Next, the BGSS; (the BGSS for each feature "i") is divided by the median for all features (a), generating a scaled ratio. The scaled ration is used to determine the expression value for the feature ($e_i$), or the log ratio.

$$S_i = \frac{BGSS_i}{a} \quad (0.3)$$

$$e_i = \log\left(\frac{Cy3S_i}{Cy5S_i}\right) \quad (0.4)$$

In addition, or alternatively, control features are used to normalize the data for labeling and hybridization variability within the experiment. Control feature may be cDNA for genes from the plant, *Arabidopsis thaliana*, that are included when spotting the mini-array. Equal amounts of RNA complementary to control cDNAs are added to each of the samples before they were labeled. Using the signal from these control genes, a normalization constant (L) is determined according to the following formula:

$$L_j = \frac{\frac{\sum_{i=1}^{N} BGSS_{j,i}}{N}}{\sum_{j=1}^{K} \frac{\sum_{i=1}^{N} BGSS_{j,i}}{N}}$$

where $BGSS_i$ is the signal for a specific feature, N is the number of *A. thaliana* control features, K is the number of hybridizations, and $L_j$ is the normalization constant for each individual hybridization.

Using the formula above, the mean for all control features of a particular hybridization and dye (e.g., Cy3) is calculated. The control feature means for all Cy3 hybridizations are averaged, and the control feature mean in one hybridization divided by the average of all hybridizations to generate a normalization constant for that particular Cy3 hybridization ($L_1$), which is used as a in equation (0.3). The same normalization steps may be performed for Cy3 and Cy5 values.

Many additional methods for normalization exist and can be applied to the data. In one method, the average ratio of Cy3 BGSS/Cy5 BGSS is determined for all features on an array.

This ratio is then scaled to some arbitrary number, such as 1 or some other number. The ratio for each probe is then multiplied by the scaling factor required to bring the average ratio to the chosen level. This is performed for each array in an analysis. Alternatively, the ratios are normalized to the average ratio across all arrays in an analysis.

If multiple features are used per gene sequence or oligonucleotide, these repeats can be used to derive an average expression value for each gene. If some of the replicate features are of poor qualitay and don't meet requirements for analysis, the remaining features can be used to represent the gene or gene sequence.

Correlation Analysis

Correlation analysis is performed to determine which array probes have expression behavior that best distinguishes or serves as markers for relevant groups of samples representing a particular clinical condition. Correlation analysis, or comparison among samples representing different disease criteria (e.g., clinical conditions), is performed using standard statistical methods. Numerous algorithms are useful for correlation analysis of expression data, and the selection of algorithms depends in part on the data analysis to be performed. For example, algorithms can be used to identify the single most informative gene with expression behavior that reliably classifies samples, or to identify all the genes useful to classify samples. Alternatively, algorithms can be applied that determine which set of 2 or more genes have collective expression behavior that accurately classifies samples. The use of multiple expression markers for diagnostics may overcome the variability in expression of a gene between individuals, or overcome the variability intrinsic to the assay. Multiple expression markers may include redundant markers (surrogates), in that two or more genes or probes may provide the same information with respect to diagnosis. This may occur, for example, when two or more genes or gene probes are coordinately expressed. For diagnostic application, it may be appropriate to utilize a gene and one or more of its surrogates in the assay. This redundancy may overcome failures (technical or biological) of a single marker to distinguish samples. Alternatively, one or more surrogates may have properties that make them more suitable for assay development, such as a higher baseline level of expression, better cell specificity, a higher fold change between sample groups or more specific sequence for the design of PCR primers or complimentary probes. It will be appreciated that while the discussion above pertains to the analysis of RNA expression profiles the discussion is equally applicable to the analysis of profiles of proteins or other molecular markers.

Prior to analysis, expression profile data may be formatted or prepared for analysis using methods known in the art. For example, often the log ratio of scaled expression data for every array probe is calculated using the following formula:

log (Cy 3 BGSS/Cy5 BGSS), where Cy 3 signal corresponds to the expression of the gene in the clinical sample, and Cy5 signal corresponds to expression of the gene in the reference RNA.

Data may be further filtered depending on the specific analysis to be done as noted below. For example, filtering may be aimed at selecting only samples with expression above a certain level, or probes with variability above a certain level between sample sets.

The following non-limiting discussion consider several statistical methods known in the art. Briefly, the t-test and ANOVA are used to identify single genes with expression differences between or among populations, respectively. Multivariate methods are used to identify a set of two or more genes for which expression discriminates between two disease states more specifically than expression of any single gene.

t-Test

The simplest measure of a difference between two groups is the Student's t test. See, e.g., Welsh et al. (2001) *Proc Natl Acad Sci USA* 98:1176-81 (demonstrating the use of an unpaired Student's t-test for the discovery of differential gene expression in ovarian cancer samples and control tissue samples). The t-test assumes equal variance and normally distributed data. This test identifies the probability that there is a difference in expression of a single gene between two groups of samples. The number of samples within each group that is required to achieve statistical significance is dependent upon the variation among the samples within each group. The standard formula for a t-test is:

$$t(e_i) = \frac{\bar{e}_{i,c} - \bar{e}_{i,t}}{\sqrt{(s_{i,c}^2/n_c) + (s_{i,t}^2/n_t)}},\qquad(0.5)$$

where $\bar{e}_i$ is the difference between the mean expression level of gene i in groups c and t, $s_{i,c}$ is the variance of gene x in group c and $s_{i,t}$ is the variance of gene x in group t. $n_c$ and $n_t$ are the numbers of samples in groups c and t.

The combination of the t statistic and the degrees of freedom [min($n_t$, $n_c$)−1] provides a p value, the probability of rejecting the null hypothesis. A p-value of $\leq 0.01$, signifying a 99 percent probability the mean expression levels are different between the two groups (a 1% chance that the mean expression levels are in fact not different and that the observed difference occurred by statistical chance), is often considered acceptable.

When performing tests on a large scale, for example, on a large dataset of about 8000 genes, a correction factor must be included to adjust for the number of individual tests being performed. The most common and simplest correction is the Bonferroni correction for multiple tests, which divides the p-value by the number of tests run. Using this test on an 8000 member dataset indicates that a p value of $\leq 0.00000125$ is required to identify genes that are likely to be truly different between the two test conditions.

Significance Analysis for Microarrays (SAM)

Significance analysis for microarrays (SAM) (Tusher 2001) is a method through which genes with a correlation between their expression values and the response vector are statistically discovered and assigned a statistical significance. The ratio of false significant to significant genes is the False Discovery Rate (FDR). This means that for each threshold there are a set of genes which are called significant, and the FDR gives a confidence level for this claim. If a gene is called differentially expressed between 2 classes by SAM, with a FDR of 5%, there is a 95% chance that the gene is actually differentially expressed between the classes. SAM takes into account the variability and large number of variables of microarrays. SAM will identity genes that are most globally differentially expressed between the classes. Thus, important genes for identifying and classifying outlier samples or patients may not be identified by SAM.

Wilcoxon's Signed Ranks Test

This method is non-parametric and is utilized for paired comparisons. See e.g., Sokal and Rohlf (1987) *Introduction to Biostatistics* $2^{nd}$ edition, WH Freeman, New York. At least 6 pairs are necessary to apply this statistic. This test is useful for analysis of paired expression data (for example, a set of patients who have had samples taken before and after administration of a pharmacologic agent).

ANOVA

Differences in gene expression across multiple related groups may be assessed using an Analysis of Variance (ANOVA), a method well known in the art (Michelson and Schofield, 1996).

Multivariate Analysis

Many algorithms suitable for multivariate analysis are known in the art (Katz 1999). Generally, a set of two or more genes for which expression discriminates between two disease states more specifically than expression of any single gene is identified by searching through the possible combinations of genes using a criterion for discrimination, for example the expression of gene X must increase from normal 300 percent, while the expression of genes Y and Z must decrease from normal by 75 percent. Ordinarily, the search starts with a single gene, then adds the next best fit at each step of the search. Alternatively, the search starts with all of the genes and genes that do not aid in the discrimination are eliminated step-wise.

Paired Samples

Paired samples, or samples collected at different timepoints from the same patient, are often useful, as described above. For example, use of paired samples permits the reduction of variation due to genetic variation among individuals. In addition, the use of paired samples has a statistical significance in that data derived from paired samples can be calculated in a different manner that recognizes the reduced variability. For example, the formula for a t-test for paired samples is:

$$t(e_x) = \frac{\overline{D}_{e_x}}{\sqrt{\frac{\sum D^2 - (\sum D)^2 / b}{b-1}}} \quad (0.5)$$

where D is the difference between each set of paired samples and b is the number of sample pairs. $\overline{D}$ is the mean of the differences between the members of the pairs. In this test, only the differences between the paired samples are considered, then grouped together (as opposed to taking all possible differences between groups, as would be the case with an ordinary t-test). Additional statistical tests useful with paired data, e.g., ANOVA and Wilcoxon's signed rank test, are discussed above.

Diagnostic Classification

Once a discriminating set of genes is identified, the diagnostic classifier (a mathematical function that assigns samples to diagnostic categories based on expression data) is applied to unknown sample expression levels.

Methods that can be used for this analysis include the following non-limiting list:

CLEAVER is an algorithm used for classification of useful expression profile data. See Raychaudhuri et al. (2001) *Trends Biotechnol* 19:189-193. CLEAVER uses positive training samples (e.g., expression profiles from samples known to be derived from a particular patient or sample diagnostic category, disease or disease criteria), negative training samples (e.g., expression profiles from samples known not to be derived from a particular patient or sample diagnostic category, disease or disease criteria) and test samples (e.g., expression profiles obtained from a patient), and determines whether the test sample correlates with the particular disease or disease criteria, or does not correlate with a particular disease or disease criteria. CLEAVER also generates a list of the 20 most predictive genes for classification.

Artificial neural networks (hereinafter, "ANN") can be used to recognize patterns in complex data sets and can discover expression criteria that classify samples into more than 2 groups. The use of artificial neural networks for discovery of gene expression diagnostics for cancers using expression data generated by oligonucleotide expression microarrays is demonstrated by Khan et al. (2001) *Nature Med.* 7:673-9. Khan found that 96 genes provided 0% error rate in classification of the tumors. The most important of these genes for classification was then determined by measuring the sensitivity of the classification to a change in expression of each gene. Hierarchical clustering using the 96 genes results in correct grouping of the cancers into diagnostic categories.

Golub uses cDNA microarrays and a distinction calculation to identify genes with expression behavior that distinguishes myeloid and lymphoid leukemias. See Golub et al. (1999) *Science* 286:531-7. Self organizing maps were used for new class discovery. Cross validation was done with a "leave one out" analysis. 50 genes were identified as useful markers. This was reduced to as few as 10 genes with equivalent diagnostic accuracy.

Hierarchical and non-hierarchical clustering methods are also useful for identifying groups of genes that correlate with a subset of clinical samples such as those with and without Lupus. Alizadeh used hierarchical clustering as the primary tool to distinguish different types of diffuse B-cell lymphomas based on gene expression profile data. See Alizadeh et al. (2000) *Nature* 403:503-11. Alizadeh used hierarchical clustering as the primary tool to distinguish different types of diffuse B-cell lymphomas based on gene expression profile data. A cDNA array carrying 17856 probes was used for these experiments, 96 samples were assessed on 128 arrays, and a set of 380 genes was identified as being useful for sample classification.

Perou demonstrates the use of hierarchical clustering for the molecular classification of breast tumor samples based on expression profile data. See Perou et al. (2000) *Nature* 406: 747-52. In this work, a cDNA array carrying 8102 gene probes was used. 1753 of these genes were found to have high variation between breast tumors and were used for the analysis.

Hastie describes the use of gene shaving for discovery of expression markers. Hastie et al. (2000) *Genome Biol.* 1(2): RESEARCH 0003.1-0003.21. The gene shaving algorithm identifies sets of genes with similar or coherent expression patterns, but large variation across conditions (RNA samples, sample classes, patient classes). In this manner, genes with a tight expression pattern within a diagnostic group, but also with high variability across the diagnoses are grouped together. The algorithm takes advantage of both characteristics in one grouping step. For example, gene shaving can identify useful marker genes with co-regulated expression. Sets of useful marker genes can be reduced to a smaller set, with each gene providing some non-redundant value in classification. This algorithm was used on the data set described in Alizadeh et al., supra, and the set of 380 informative gene markers was reduced to 234.

Supervised harvesting of expression trees (Hastie 2001) identifies genes or clusters that best distinguish one class from all the others on the data set. The method is used to identify the genes/clusters that can best separate one class versus all the others for datasets that include two or more classes or all classes from each other. This algorithm can be used for discovery or testing of a diagnostic gene set.

CART is a decision tree classification algorithm (Breiman 1984). From gene expression and or other data, CART can develop a decision tree for the classification of samples. Each node on the decision tree involves a query about the expression level of one or more genes or variables. Samples that are above the threshold go down one branch of the decision tree and samples that are not go down the other branch. See examples 10 and 16 for further description of its use in classification analysis and examples of its usefulness in discovering and implementing a diagnostic gene set. CART identifies surrogates for each splitter (genes that are the next best substitute for a useful gene inclassification.

Once a set of genes and expression criteria for those genes have been established for classification, cross validation is done. There are many approaches, including a 10 fold cross validation analysis in which 10% of the training samples are left out of the analysis and the classification algorithm is built with the remaining 90%. The 10% are then used as a test set for the algorithm. The process is repeated 10 times with 10% of the samples being left out as a test set each time. Through this analysis, one can derive a cross validation error which helps estimate the robustness of the algorithm for use on prospective (test) samples.

Clinical data are gathered for every patient sample used for expression analysis. Clinical variables can be quantitative or non-quantitative. A clinical variable that is quantitiative can be used as a variable for significance or classification analysis. Non-quantitative clinical variables, such as the sex of the patient, can also be used in a significance analysis or classification analysis with some statistical tool. It is appreciated that the most useful diagnostic gene set for a condition may be optimal when considered along with one or more predictive clinical variables. Clinical data can also be used as supervising vectors for a correlation analysis. That is to say that the clinical data associated with each sample can be used to divide the samples into meaningful diagnostic categories for analysis. For example, samples can be divided into 2 or more groups based on the presence or absence of some diagnostic criterion (a). In addition, clinical data can be utilized to select patients for a correlation analysis or to exclude them based on some undesirable characteristic, such as an ongoing infection, a medicine or some other issue. Clincial data can also be used to assess the pre-test probability of an outcome. For example, patients who are female are much more likely to be diagnosed as having systemic lupus erythematosis than patients who are male.

Once a set of genes are identified that classify samples with acceptable accuracy. These genes are validated as a set using new samples that were not used to discover the gene set. These samples can be taken from frozen archieves from the discovery clinical study or can be taken from new patients prospectively. Validation using a "test set" of samples can be done using expression profiling of the gene set with microarrays or using real-time PCR for each gene on the test set samples. Alternatively, a different expression profiling technology can be used.

Validation and Accuracy of Diagnostic Nucleotide Sets

Prior to widespread application of the diagnostic probe sets of the invention the predictive value of the probe set is validated. When the diagnostic probe set is discovered by microarray based expression analysis, the differential expression of the member genes may be validated by a less variable and more quantitive and accurate technology such as real time PCR. In this type of experiment the amplification product is measured during the PCR reaction. This enables the researcher to observe the amplification before any reagent becomes rate limiting for amplification. In kinetic PCR the measurement is of $C_T$ (threshold cycle) or $C_P$ (crossing point). This measurement ($C_T=C_P$) is the point at which an amplification curve crosses a threshold fluorescence value. The threshold is set to a point within the area where all of the reactions were in their linear phase of amplification. When measuring $C_T$, a lower $C_T$ value is indicative of a higher amount of starting material since an earlier cycle number means the threshold was crossed more quickly.

Several fluorescence methodologies are available to measure amplification product in real-time PCR. Taqman (Applied BioSystems, Foster City, Calif.) uses fluorescence resonance energy transfer (FRET) to inhibit signal from a probe until the probe is degraded by the sequence specific binding and Taq 3' exonuclease activity. Molecular Beacons (Stratagene, La Jolla, Calif.) also use FRET technology, whereby the fluorescence is measured when a hairpin structure is relaxed by the specific probe binding to the amplified DNA. The third commonly used chemistry is Sybr Green, a DNA-binding dye (Molecular Probes, Eugene, Oreg.). The more amplified product that is produced, the higher the signal. The Sybr Green method is sensitive to non-specific amplification products, increasing the importance of primer design and selection. Other detection chemistries can also been used, such as ethedium bromide or other DNA-binding dyes and many modifications of the fluorescent dye/quencher dye Taqman chemistry, for example scorpions.

Real-time PCR validation can be done as described in Example 15.

Typically, the oligonucleotide sequence of each probe is confirmed, e.g. by DNA sequencing using an oligonucleotide-specific primer. Partial sequence obtained is generally sufficient to confirm the identity of the oligonucleotide probe. Alternatively, a complementary polynucleotide is fluorescently labeled and hybridized to the array, or to a different array containing a resynthesized version of the oligo nucleotide probe, and detection of the correct probe is confirmed.

Typically, validation is performed by statistically evaluating the accuracy of the correspondence between the molecular signature for a diagnostic probe set and a selected indicator. For example, the expression differential for a nucleotide sequence between two subject classes can be expressed as a simple ratio of relative expression. The expression of the nucleotide sequence in subjects with selected indicator can be compared to the expression of that nucleotide sequence in subjects without the indicator, as described in the following equations.

$\Sigma E_x ai/N = E_x A$ the average expression of nucleotide sequence $x$ in the members of group $A$;

$\Sigma E_x bi/M = E_x B$ the average expression of nucleotide sequence $x$ in the members of group $B$;

$E_x A/ExB = \Delta E_x AB$ the average differential expression of nucleotide sequence $x$ between groups A and B:
where $\Sigma$ indicates a sum; Ex is the expression of nucleotide sequence x relative to a standard; ai are the individual members of group A, group A has N members; bi are the individual members of group B, group B has M members.

Individual components of a diagnostic probe set each have a defined sensitivity and specificity for distinguishing between subject groups. Such individual nucleotide sequences can be employed in concert as a diagnostic probe set to increase the sensitivity and specificity of the evaluation. The database of molecular signatures is queried by algorithms to identify the set of nucleotide sequences (i.e., corresponding to members of the probe set) with the highest average differential expression between subject groups. Typically, as the number of nucleotide sequences in the diagnostic probe set increases, so does the predictive value, that is, the sensitivity and specificity of the probe set. When the probe sets are defined they may be used for diagnosis and patient monitoring as discussed below. The diagnostic sensitivity and specificity of the probe sets for the defined use can be determined for a given probe set with specified expression levels as demonstrated above. By altering the expression threshold required for the use of each nucleotide sequence as a diagnostic, the sensitivity and specificity of the probe set can be altered by the practitioner. For example, by lowering the magnitude of the expression differential threshold for each nucleotide sequence in the set, the sensitivity of the test will increase, but the specificity will decrease. As is apparent from the foregoing discussion, sensitivity and specificity are inversely related and the predictive accuracy of the probe set is continuous and dependent on the expression threshold set for each nucleotide sequence. Although sensitivity and specificity tend to have an inverse relationship when expression thresholds are altered, both parameters can be increased as nucleotide sequences with predictive value are added to the diagnostic nucleotide set. In addition a single or a few markers may not be reliable expression markers across a population of patients. This is because of the variability in expression and measurement of expression that exists between measurements, individuals and individuals over time. Inclusion of a large number of candidate nucleotide sequences or large numbers of nucleotide sequences in a diagnostic nucleotide set allows for this variability as not all nucleotide sequences need to meet a threshold for diagnosis. Generally, more markers are better than a single marker. If many markers are used to make a diagnosis, the likelihood that all expression markers will not meet some thresholds based upon random variability is low and thus the test will give fewer false negatives. Surrogate markers are useful for these purposes. These are markers or genes that are coordinately expressed. Surrogate markers essential provide redundant information, but this redundancy can improve accuracy by decreasing errors due to assay variability.

It is appreciated that the desired diagnostic sensitivity and specificity of the diagnostic nucleotide set may vary depending on the intended use of the set. For example, in certain uses, high specificity and high sensitivity are desired. For example, a diagnostic nucleotide set for predicting which patient population may experience side effects may require high sensitivity so as to avoid treating such patients. In other settings, high sensitivity is desired, while reduced specificity may be tolerated. For example, in the case of a beneficial treatment with few side effects, it may be important to identify as many patients as possible (high sensitivity) who will respond to the drug, and treatment of some patients who will not respond is tolerated. In other settings, high specificity is desired and reduced sensitivity may be tolerated. For example, when identifying patients for an early-phase clinical trial, it is important to identify patients who may respond to the particular treatment. Lower sensitivity is tolerated in this setting as it merely results in reduced patients who enroll in the study or requires that more patients are screened for enrollment.

To discover and validate a gene set that can be applied to accurately diagnose or classify patients across the country or around the world, it is necessary to ensure that the gene set was developed and validated using samples that represent the types of patients that will be encountered in the clinical setting. For example, diverse ethnicity, drug usage and clinical practice patterns must all be represented in the discovery and validation to ensure that the test works on this variety of patients.

Selected Diseases

In principle, individual oligonucleotides and diagnostic oligonucleotide sets of the invention may be developed and applied to essentially any disease, or disease criterion, as long as at least one subset of oligonucleotide sequences is differentially expressed in samples derived from one or more individuals with a disease criteria or disease and one or more individuals without the disease criteria or disease, wherein the individual may be the same individual sampled at different points in time, or the individuals may be different individuals (or populations of individuals). For example, the subset of oligonucleotide sequences may be differentially expressed in the sampled tissues of subjects with the disease or disease criterion (e.g., a patient with a disease or disease criteria) as compared to subjects without the disease or disease criterion (e.g., patients without a disease (control patients)). Alternatively, or in addition, the subset of oligonucleotide sequence(s) may be differentially expressed in different samples taken from the same patient, e.g at different points in time, at different disease stages, before and after a treatment, in the presence or absence of a risk factor, etc.

Expression profiles corresponding to oligonucleotides and sets of oligonucleotide sequences that correlate not with a diagnosis, but rather with a particular aspect of a disease can also be used to identify the diagnostic oligonucleotide sets and disease specific target oligonucleotide sequences of the invention. For example, such an aspect, or disease criterion, can relate to a subject's medical or family history, e.g., occurance of an autoimmune disease, childhood illness, cause of death of a parent or other relative, prior surgery or other intervention, medications, laboratory values and results of diagnostic testing (radiology, pathology, etc.), symptoms (including onset and/or duration of symptoms), etc. Alternatively, the disease criterion can relate to a diagnosis, e.g., chronic inflammatory disease such as lupus, rheumatoid arthritis, osteoarthritis, or prognosis (e.g., prediction of future diagnoses, events or complications), e.g., renal failure from lupus, joint replacement surgery for rheumatoid arthritis, rheumatoid arthritis or systemic lupus erythematosis disease activity or the like. In other cases, the disease criterion corresponds to a therapeutic outcome, e.g., response to a medication, response to a surgery or physical therapy for a joint. Alternatively, the disease criteria correspond with previously identified or classic risk factors and may correspond to prognosis or future disease diagnosis. As indicated above, a disease criterion can also correspond to genotype for one or more loci. Disease criteria (including patient data) may be collected (and compared) from the same patient at different points in time, from different patients, between patients with a disease (criterion) and patients respresenting a control population, etc. Longitudinal data, i.e., data collected at different time points from an individual (or group of individuals) may be used for comparisons of samples obtained from an individual (group of individuals) at different points in time, to permit identification of differences specifically related to the disease state, and to obtain information relating to the change in expression over time, including a rate of change or trajectory of expression over time. The usefulness of longitudinal data is further discussed in the section titled "Identification of diagnostic nucleotide sets of the invention".

It is further understood that diagnostic oligonucleotides and oligonucleotide sets may be developed for use in diagnosing conditions for which there is no present means of diagnosis. For example, in rheumatoid arthritis, joint destruction is often well under way before a patient experience symptoms of the condition. A diagnostic nucleotide or nucleotide set may be developed that diagnoses rheumatic joint destruction at an earlier stage than would be possible using present means of diagnosis, which rely in part on the presentation of symptoms by a patient. Diagnostic nucleotide sets may also be developed to replace or augment current diagnostic procedures. For example, the use of a diagnostic nucleotide or nucleotide set to diagnose lupus may replace or supplement the current diagnostic tests and strategies.

It is understood that the following discussion of diseases is exemplary and non-limiting, and further that the general criteria discussed above, e.g. use of family medical history, are generally applicable to the specific diseases discussed below.

In addition to leukocytes, as described throughout, the general method is applicable to oligonucleotide sequences that are differentially expressed in any subject tissue or cell type, by the collection and assessment of samples of that tissue or cell type. However, in many cases, collection of such samples presents significant technical or medical problems given the current state of the art.

Systemic Lupus Erythematosis (SLE)

SLE is a chronic, systemic inflammatory disease characterized by dysregulation of the immune system, which effects up to 2 million patients in the US. Symptoms of SLE include rashes, joint pain, abnormal blood counts, renal dysfunction and damage, infections, CNS disorders, arthralgias and autoimmunity. Patients may also have early onset atherosclerosis. The diagnosis of SLE is difficult to make with certainty using current diagnostic tests and algorithms. Antibody tests can be specific for the disease, but often lack sensitivity. Clinical diagnosis may lack both high sensitivity and specificity. SLE is a disease that clearly involves differential gene expression in leukocytes compared to patients without the disease.

Diagnostic oligonucleotides and oligonucleotide sets are identified and validated for use in diagnosis and monitoring of SLE activity and progression. Disease criteria correspond to clinical data, e.g. symptom rash, joint pain, malaise, rashes, blood counts (white and red), tests of renal function e.g. creatinine, blood urea nitrogen (hereinafter, "bun") creative clearance, data obtained from laboratory tests, including complete blood counts with differentials, CRP, ESR, ANA, Serum IL6, Soluble CD40 ligand, LDL, HDL, Anti-DNA antibodies, rheumatoid factor, C3, C4, serum creatinine and any medication levels, the need for pain medications, cumulative doses or immunosuppressive therapy, symptoms or any manifestation of carotid atherosclerosis (e.g. ultrasound diagnosis or any other manifestations of the disease), data from surgical procedures such as gross operative findings and pathological evaluation of resected tissues and biopsies (e.g., renal, CNS), information on pharmacological therapy and treatment changes, clinical diagnoses of disease "flare", hospitalizations, death, response to medications, quantitative joint exams, results from health assessment questionnaires (HAQs), and other clinical measures of patient symptoms and disability. In addition, disease criteria correspond to the clinical score known as SLEDAI (Bombadier C, Gladman D D, Urowitz M B, Caron D, Chang C H and the Committee on Prognosis Studies in SLE: Derivation of the SLEDAI for Lupus Patients. *Arthritis Rheum* 35:630-640, 1992.). Diagnostic nucleotide sets may be useful for diagnosis of SLE, monitoring disease progression including progressive renal dysfunction, carotid atherosclerosis and CNS dysfunction, and predicting occurrence of side-effects, for example.

Rheumatoid Arthritis

Rheumatoid arthritis (RA) effects about two million patients in the US and is a chronic and debilitating inflammatory arthritis, particularly involving pain and destruction of the joints. RA often goes undiagnosed because patients may have no pain, but the disease is actively destroying the joint. Other patients are known to have RA, and are treated to alleviate symptoms, but the rate of progression of joint destruction can't easily be monitored. Drug therapy is available, but the most effective medicines are toxic (e.g., steroids, methotrexate) and thus need to be used with caution. A new class of medications (TNF blockers) is very effective, but the drugs are expensive, have side effects, and not all patients respond. Side-effects are common and include immune suppression, toxicity to organ systems, allergy and metabolic disturbances.

Diagnostic oligonucleotides and oligonucleotide sets of the invention are developed and validated for use in diagnosis and treatment of RA. Disease criteria correspond to disease symptoms (e.g., joint pain, joint swelling and joint stiffness and any of the American College for Rheumatology criteria for the diagnosis of RA, see Arnett et al (1988) *Arthr. Rheum.* 31:315-24), progression of joint destruction (e.g. as measured by serial hand radiographs, assessment of joint function and mobility), surgery, need for medication, additional diagnoses of inflammatory and non-inflammatory conditions, and clinical laboratory measurements including complete blood counts with differentials, CRP, ESR, ANA, Serum IL6, Soluble CD40 ligand, LDL, HDL, Anti-DNA antibodies, rheumatoid factor, C3, C4, serum creatinine, death, hospitalization and disability due to joint destruction. In addition, or alternatively, disease criteria correspond to response to drug therapy and presence or absence of side-effects or measures of improvement exemplified by the American College of Rheumatology "20%" and "50%" response/improvement rates. See Felson et al (1995) *Arthr Rheum* 38:531-37. Diagnostic nucleotide sets are identified that monitor and predict disease progression including flaring (acute worsening of disease accompanied by joint pain or other symptoms), response to drug treatment and likelihood of side-effects.

In addition to peripheral leukocytes, surgical specimens of rheumatoid joints can be used for leukocyte expression profiling experiments. Members of diagnostic nucleotide sets are candidates for leukocyte target nucleotide sequences, e.g. as a candidate drug target for rheumatoid arthritis. Synovial specimens can be used for expression profiling or cells derived and sorted from that tissue (such as subsets of leukocytes) can be used. Cells can be separated by fluorescence activated cell sorting or magnetic affinity reagent techniques or some other technique. Synovial specimens and blood can be obtained from the same patient and gene expression can be compared between these 2 sample types.

Osteoarthritis 20-40 million patients in the US have osteoarthritis. Patient groups are heterogeneous, with a subset of patients having earlier onset, more aggressive joint damage, involving more inflammation (leukocyte infiltration). Leukocyte diagnostics can be used to distinguish osteoarthritis from rheumatoid arthritis and other differntial diagnoses, define likelihood and degree of response to NSAID therapy (non-steroidal anti-inflammatory drugs) or other anti-inflammatory therapies. Rate of progression of joint damage can also be assessed. Diagnostic nucleotide sets may be developed for use in selection and titration of treatment therapies. Disease criteria correspond to response to therapy, and disease progression using certain therapies, response to medications, need for joint surgery, joint pain and disability.

In addition to peripheral leukocytes, surgical specimens of osteoarthritic joints can be used for leukocyte expression profiling experiments. Diagnostic oligonucleotides and diagnostic oligonucleotide sets are candidates for leukocyte target nucleotide sequences, e.g. as a candidate drug target for osteoarthritis. Synovial specimens can be used for expression profiling or cells derived and sorted from that tissue (such as subsets of leukocytes) can be used. Cells can be separated by fluorescence activated cell sorting or magnetic affinity reagent techniques or some other technique. Synovial specimens and blood can be obtained from the same patient and gene expression can be compared between these 2 sample types.

In another example, diagnostic nucleotide sets are developed and validated for use in diagnosis and therapy of peri-prosthetic osteolysis. In this disease, a prosthetic joint such as a knee or hip is found to loosen over time and requires repeat surgery. Loosening may occur in some patients due to an inflammatory response incited by the foreign material of the prosthesis. Disease criteria include joint loosening, radiographic evidence of peri-prosthetic osteolysis, need for repeat surgery, response to pharmacological therapy, and/or histological (from biopsy or surgery) or biochemical (markers of bone metabolism such as alkaline phosphatase) evidence of osteolysis. Tissues used for expression profiling can include peripheral leukocytes or leukocyte subsets, periprosthetic tissue, or synovial fluid. In addition, gene sets can be discovered using an in vitro model of the disease in which immune cells are exposed to prosthesis materials such as cement or titanium.

Pharmacogenomics

Pharmocogenomics is the study of the individual propensity to respond to a particular drug therapy (combination of therapies). In this context, response can mean whether a particular drug will work on a particular patient, e.g. some patients respond to one drug but not to another drug. Response can also refer to the likelihood of successful treatment or the assessment of progress in treatment. Titration of drug therapy to a particular patient is also included in this description, e.g. different patients can respond to different doses of a given medication. This aspect may be important when drugs with side-effects or interactions with other drug therapies are contemplated.

Diagnostic oligonucleotides and oligonucleotide sets are developed and validated for use in assessing whether a patient will respond to a particular therapy and/or monitoring response of a patient to drug therapy(therapies). Disease criteria correspond to presence or absence of clinical symptoms or clinical endpoints, presence of side-effects or interaction with other drug(s). The diagnostic nucleotide set may further comprise nucleotide sequences that are targets of drug treatment or markers of active disease.

Diagnostic oligonucleotides and oligonucleotide sets are developed and validated for use in assessing whether a patient has a particular drug toxicity or toxicity due to an environmental, work-related or other agent. Such exposures of the patient may also be related to biological or biochemical agents used in warfare. Diagnostic oligonucleotides and oligonucleotide sets may allow early diagnosis of a toxicity or exposure or may monitor the severity and course of toxic responses.

Methods of Using Diagnostic Oligonucleotides and Oligonucleotide Sets.

The invention also provide methods of using the diagnostic oligonucleotides and oligonucleotide sets to: diagnose or monitor disease; assess severity of disease; predict future occurrence of disease; predict future complications of disease; determine disease prognosis; evaluate the patient's risk, or "stratify" a group of patients; assess response to current drug therapy; assess response to current non-pharmacological therapy; determine the most appropriate medication or treatment for the patient; predict whether a patient is likely to respond to a particular drug; and determine most appropriate additional diagnostic testing for the patient, among other clinically and epidemiologically relevant applications.

The oligonucleotides and oligonucleotide sets of the invention can be utilized for a variety of purposes by physicians, healthcare workers, hospitals, laboratories, patients, companies and other institutions. As indicated previously, essentially any disease, condition, or status for which at least one nucleotide sequence is differentially expressed in leukocyte populations (or sub-populations) can be evaluated, e.g., diagnosed, monitored, etc. using the diagnostic nucleotide sets and methods of the invention. In addition to assessing health status at an individual level, the diagnostic nucleotide sets of the present invention are suitable for evaluating subjects at a "population level," e.g., for epidemiological studies, or for population screening for a condition or disease.

Collection and Preparation of Sample

RNA, protein and/or DNA are prepared using methods well-known in the art, as further described herein. It is appreciated that subject samples collected for use in the methods of the invention are generally collected in a clinical setting, where delays may be introduced before RNA samples are prepared from the subject samples of whole blood, e.g. the blood sample may not be promptly delivered to the clinical lab for further processing. Further delay may be introduced in the clinical lab setting where multiple samples are generally being processed at any given time. For this reason, methods that feature lengthy incubations of intact leukocytes at room temperature are not preferred, because the expression profile of the leukocytes may change during this extended time period. For example, RNA can be isolated from whole blood using a phenol/guanidine isothiocyanate reagent or another direct whole-blood lysis method, as described in, e.g., U.S. Pat. Nos. 5,346,994 and 4,843,155. This method may be less preferred under certain circumstances because the large majority of the RNA recovered from whole blood RNA extraction comes from erythrocytes since these cells outnumber leukocytes 1000:1. Care must be taken to ensure that the presence of erythrocyte RNA and protein does not introduce bias in the RNA expression profile data or lead to inadequate sensitivity or specificity of probes.

Alternatively, intact leukocytes may be collected from whole blood using a lysis buffer that selectively lyses erythrocytes, but not leukocytes, as described, e.g., in (U.S. Pat. Nos. 5,973,137, and 6,020,186). Intact leukocytes are then collected by centrifugation, and leukocyte RNA is isolated using standard protocols, as described herein. However, this method does not allow isolation of sub-populations of leukocytes, e.g. mononuclear cells, which may be desired. In addition, the expression profile may change during the lengthy incubation in lysis buffer, especially in a busy clinical lab where large numbers of samples are being prepared at any given time.

Alternatively, specific leukocyte cell types can be separated using density gradient reagents (Boyum, A, 1968.). For example, mononuclear cells may be separated from whole blood using density gradient centrifugation, as described, e.g., in U.S. Pat. Nos. 4,190,535, 4,350,593, 4,751,001, 4,818,418, and 5,053,134. Blood is drawn directly into a tube containing an anticoagulant and a density reagent (such as Ficoll or Percoll). Centrifugation of this tube results in separation of blood into an erythrocyte and granulocyte layer, a mononuclear cell suspension, and a plasma layer. The mononuclear cell layer is easily removed and the cells can be collected by centrifugation, lysed, and frozen. Frozen samples are stable until RNA can be isolated. Density centrifugation, however, must be conducted at room temperature, and if processing is unduly lengthy, such as in a busy clinical lab, the expression profile may change.

The quality and quantity of each clinical RNA sample is desirably checked before amplification and labeling for array hybridization, using methods known in the art. For example, one microliter of each sample may be analyzed on a Bioanalyzer (Agilent 2100 Palo Alto, Calif. USA) using an RNA 6000 nano LabChip (Caliper, Mountain View, Calif. USA). Degraded RNA is identified by the reduction of the 28S to 18S ribosomal RNA ratio and/or the presence of large quantities of RNA in the 25-100 nucleotide range.

It is appreciated that the RNA sample for use with a diagnostic oligonucleotide or oligonucleotide set may be produced from the same or a different cell population, sub-population and/or cell type as used to identify the diagnostic nucleotide set. For example, a diagnostic oligonucleotide or oligonucleotide set identified using RNA extracted from mononuclear cells may be suitable for analysis of RNA extracted from whole blood or mononuclear cells, depending on the particular characteristics of the members of the diagnostic nucleotide set. Generally, diagnostic oligonucleotides or oligonucleotide sets must be tested and validated when used with RNA derived from a different cell population, sub-population or cell type than that used when obtaining the diagnostic gene set. Factors such as the cell-specific gene expression of diagnostic nucleotide set members, redundancy of the information provided by members of the diagnostic nucleotide set, expression level of the member of the diagnostic nucleotide set, and cell-specific alteration of expression of a member of the diagnostic nucleotide set will contribute to the usefullness of a different RNA source than that used when identifying the members of the diagnostic nucleotide set. It is appreciated that it may be desirable to assay RNA derived from whole blood, obviating the need to isolate particular cell types from the blood.

Assessing Expression for Diagnostics

Expression profiles for the oligonucleotides or the set of diagnostic oligonucleotide sequences in a subject sample can be evaluated by any technique that determines the expression of each component oligonucleotide sequence. Methods suitable for expression analysis are known in the art, and numerous examples are discussed in the Sections titled "Methods of obtaining expression data" and "high throughput expression Assays", above.

In many cases, evaluation of expression profiles is most efficiently, and cost effectively, performed by analyzing RNA expression. Alternatively, the proteins encoded by each component of the diagnostic nucleotide set are detected for diagnostic purposes by any technique capable of determining protein expression, e.g., as described above. Expression profiles can be assessed in subject leukocyte sample using the same or different techniques as those used to identify and validate the diagnostic oligonucleotide or oligonucleotide set. For example, a diagnostic nucleotide set identified as a subset of sequences on a cDNA microarray can be utilized for diagnostic (or prognostic, or monitoring, etc.) purposes on the same array from which they were identified. Alternatively, the diagnostic nucleotide sets for a given disease or condition can be organized onto a dedicated sub-array for the indicated purpose. It is important to note that if diagnostic nucleotide sets are discovered using one technology, e.g. RNA expression profiling, but applied as a diagnostic using another technology, e.g. protein expression profiling, the nucleotide (or gene, or protein) sets must generally be validated for diagnostic purposes with the new technology. In addition, it is appreciated that diagnostic nucleotide sets that are developed for one use, e.g. to diagnose a particular disease, may later be found to be useful for a different application, e.g. to predict the likelihood that the particular disease will occur. Generally, the diagnostic nucleotide set will need to be validated for use in the second circumstance. As discussed herein, the sequence of diagnostic nucleotide set members may be amplified from RNA or cDNA using methods known in the art providing specific amplification of the nucleotide sequences.

Identification of Novel Nucleotide Sequences that are Differentially Expressed in Leukocytes Novel nucleotide sequences that are differentially expressed in leukocytes are also part of the invention. Previously unidentified open reading frames may be identified in a library of differentially expressed candidate nucleotide sequences, as described above, and the DNA and predicted protein sequence may be identified and characterized as noted above. We identified unnamed (not previously described as corresponding to a gene, or an expressed gene) nucleotide sequences in our candidate nucleotide library, depicted in Table 3A, 3B AND 3C and the sequence listing. Accordingly, further embodiments of the invention are the isolated nucleic acids described in Tables 3A and 3B AND 3C and in the sequence listing. The novel differentially expressed nucleotide sequences of the invention are useful in the diagnostic nucleotide set of the invention described above, and are further useful as members of a diagnostic nucleotide set immobilized on an array. The novel partial nucleotide sequences may be further characterized using sequence tools and publically or privately accessible sequence databases, as is well known in the art: Novel differentially expressed nucleotide sequences may be identified as disease target nucleotide sequences, described below. Novel nucleotide sequences may also be used as imaging reagent, as further described below.

As used herein, "novel nucleotide sequence" refers to (a) a nucleotide sequence containing at least one of the DNA sequences disclosed herein (as shown in FIGS. Table 3A, 3B and the sequence listing); (b) any DNA sequence that encodes the amino acid sequence encoded by the DNA sequences disclosed herein; (c) any DNA sequence that hybridizes to the complement of the coding sequences disclosed herein, contained within the coding region of the nucleotide sequence to which the DNA sequences disclosed herein (as shown in Table 3A, 3B AND 3C and the sequence listing) belong, under highly stringent conditions, e.g., hybridization to filter-bound DNA in 0.5 M $NaHPO_4$, 7% sodium dodecyl sulfate (SDS), 1 mM EDTA at 65° C., and washing in 0.1×SSC/0.1% SDS at 68° C. (Ausubel F. M. et al., eds., 1989, Current Protocols in Molecular Biology, Vol. I, Green Publishing Associates, Inc., and John Wiley & sons, Inc., New York, at p. 2.10.3), (d) any DNA sequence that hybridizes to the complement of the coding sequences disclosed herein, (as shown in Table 3A, 3B AND 3C and the sequence listing) contained within the coding region of the nucleotide sequence to which DNA sequences disclosed herein (as shown in TABLES 3A, 3B and the sequence listing) belong, under less stringent conditions, such as moderately stringent conditions, e.g., washing in 0.2×SSC/0.1% SDS at 42° C. (Ausubel et al., 1989, supra), yet which still encodes a functionally equivalent gene product; and/or (e) any DNA sequence that is at least 90% identical, at least 80% identical or at least 70% identical to the coding sequences disclosed herein (as shown in TABLES 3A, 3B AND 3C and the sequence listing), wherein % identity is determined using standard algorithms known in the art.

The invention also includes nucleic acid molecules, preferably DNA molecules, that hybridize to, and are therefore the complements of, the DNA sequences (a) through (c), in the preceding paragraph. Such hybridization conditions may be highly stringent or less highly stringent, as described above. In instances wherein the nucleic acid molecules are deoxyoligonucleotides ("oligos"), highly stringent conditions may refer, e.g., to washing in 6×SSC/0.05% sodium pyrophosphate at 37° C. (for 14-base oligos), 48° C. (for 17-base oligos), 55° C. (for 20-base oligos), and 60° C. (for 23-base oligos). These nucleic acid molecules may act as target nucleotide sequence antisense molecules, useful, for example, in target nucleotide sequence regulation and/or as antisense primers in amplification reactions of target nucleotide sequence nucleic acid sequences. Further, such sequences may be used as part of ribozyme and/or triple helix sequences, also useful for target nucleotide sequence regulation. Still further, such molecules may be used as components of diagnostic methods whereby the presence of a disease-causing allele, may be detected.

The Invention Also Encompasses Nucleic Acid Molecules Contained in Full-Length Gene Sequences That Are Related to Or Derived From Sequences In Tables 2, 3, 8-10 and the Sequence Listing. One Sequence May Map to More Than One Full-Length Gene.

The invention also encompasses (a) DNA vectors that contain any of the foregoing coding sequences and/or their complements (i.e., antisense); (b) DNA expression vectors that contain any of the foregoing coding sequences operatively associated with a regulatory element that directs the expression of the coding sequences; and (c) genetically engineered host cells that contain any of the foregoing coding sequences operatively associated with a regulatory element that directs the expression of the coding sequences in the host cell. As used herein, regulatory elements include but are not limited to inducible and non-inducible promoters, enhancers, operators and other elements known to those skilled in the art that drive and regulate expression. The invention includes fragments of any of the DNA sequences disclosed herein. Fragments of the DNA sequences may be at least 5, at least 10, at least 15, at least 19 nucleotides, at least 25 nucleotides, at least 50 nucleotides, at least 100 nucleotides, at least 200, at least 500, or larger.

In addition to the oligonucleotide sequences described above, homologues and orthologs of such sequences, as may, for example be present in other species, may be identified and may be readily isolated, without undue experimentation, by molecular biological techniques well known in the art, as well as use of gene analysis tools described above, and e.g., in Example 4. Further, there may exist nucleotide sequences at other genetic loci within the genome that encode proteins, which have extensive homology to one or more domains of such gene products. These nucleotide sequences may also be identified via similar techniques.

For example, the isolated differentially expressed nucleotide sequence may be labeled and used to screen a cDNA library constructed from mRNA obtained from the organism of interest. Hybridization conditions will be of a lower stringency when the cDNA library was derived from an organism different from the type of organism from which the labeled sequence was derived. Alternatively, the labeled fragment may be used to screen a genomic library derived from the organism of interest, again, using appropriately stringent conditions. Such low stringency conditions will be well known to those of skill in the art, and will vary predictably depending on the specific organisms from which the library and the labeled sequences are derived. For guidance regarding such conditions see, for example, Sambrook et al., 1989, Molecular Cloning, A Laboratory Manual, Cold Springs Harbor Press, N.Y.; and Ausubel et al., 1989, Current Protocols in Molecular Biology, Green Publishing Associates and Wiley Interscience, N.Y.

Protein Products

Novel nucleotide products include those proteins encoded by the novel nucleotide sequences described, above. Specifically, novel gene products may include polypeptides encoded by the novel nucleotide sequences contained in the coding regions of the nucleotide sequences to which DNA sequences disclosed herein (in TABLES 3A, 3B and the sequence listing).

In addition, novel protein products of novel nucleotide sequences may include proteins that represent functionally equivalent gene products. Such an equivalent novel gene product may contain deletions, additions or substitutions of amino acid residues within the amino acid sequence encoded by the novel nucleotide sequences described, above, but which result in a silent change, thus producing a functionally equivalent novel nucleotide sequence product. Amino acid substitutions may be made on the basis of similarity in polarity, charge, solubility, hydrophobicity, hydrophilicity, and/or the amphipathic nature of the residues involved.

For example, nonpolar (hydrophobic) amino acids include alanine, leucine, isoleucine, valine, proline, phenylalanine, tryptophan, and methionine; polar neutral amino acids include glycine, serine, threonine, cysteine, tyrosine, asparagine, and glutamine; positively charged (basic) amino acids include arginine, lysine, and histidine; and negatively charged (acidic) amino acids include aspartic acid and glutamic acid. "Functionally equivalent", as utilized herein, refers to a protein capable of exhibiting a substantially similar in vivo activity as the endogenous novel gene products encoded by the novel nucleotide described, above.

The novel gene products (protein products of the novel nucleotide sequences) may be produced by recombinant DNA technology using techniques well known in the art. Methods which are well known to those skilled in the art can be used to construct expression vectors containing novel nucleotide sequence protein coding sequences and appropriate transcriptional/translational control signals. These methods include, for example, in vitro recombinant DNA techniques, synthetic techniques and in vivo recombination/genetic recombination. See, for example, the techniques described in Sambrook et al., 1989, supra, and Ausubel et al., 1989, supra. Alternatively, RNA capable of encoding novel nucleotide sequence protein sequences may be chemically synthesized using, for example, synthesizers. See, for example, the techniques described in "Oligonucleotide Synthesis", 1984, Gait, M. J. ed., IRL Press, Oxford, which is incorporated by reference herein in its entirety. A variety of host-expression vector systems may be utilized to express the novel nucleotide sequence coding sequences of the invention. (Ruther et al., 1983, EMBO J. 2:1791; Inouye & Inouye, 1985, Nucleic Acids Res. 13:3101-3109; Van Heeke & Schuster, 1989, J. Biol. Chem. 264:5503; Smith et al., 1983, J. Virol. 46: 584; Smith, U.S. Pat. No. 4,215,051; Logan & Shenk, 1984, Proc. Natl. Acad. Sci. USA 81:3655-3659; Bittner et al., 1987, Methods in Enzymol. 153:516-544; Wigler, et al., 1977, Cell 11:223; Szybalska & Szybalski, 1962, Proc. Natl. Acad. Sci. USA 48:2026; Lowy, et al., 1980, Cell 22:817; Wigler, et al., 1980, Natl. Acad. Sci. USA 77:3567; O'Hare, et al., 1981, Proc. Natl. Acad. Sci. USA 78:1527;

Mulligan & Berg, 1981, Proc. Natl. Acad. Sci. USA 78:2072; Colberre-Garapin, et al., 1981, J. Mol. Biol. 150:1; Santerre, et al., 1984, Gene 30:147; Janknecht, et al., 1991, Proc. Natl. Acad. Sci. USA 88: 8972-8976

Where recombinant DNA technology is used to produce the protein encoded by the novel nucleotide sequence for such assay systems, it may be advantageous to engineer fusion proteins that can facilitate labeling, immobilization and/or detection.

Indirect labeling involves the use of a protein, such as a labeled antibody, which specifically binds to the protein encoded by the novel nucleotide sequence. Such antibodies include but are not limited to polyclonal, monoclonal, chimeric, single chain, Fab fragments and fragments produced by an Fab expression library.

Antibodies

The invention also provides for antibodies to the protein encoded by the novel nucleotide sequences. Described herein are methods for the production of antibodies capable of specifically recognizing one or more novel nucleotide sequence epitopes. Such antibodies may include, but are not limited to polyclonal antibodies, monoclonal antibodies (mAbs), humanized or chimeric antibodies, single chain antibodies, Fab fragments, F(ab')2 fragments, fragments produced by a Fab expression library, anti-idiotypic (anti-Id) antibodies, and epitope-binding fragments of any of the above. Such antibodies may be used, for example, in the detection of a novel nucleotide sequence in a biological sample, or, alternatively, as a method for the inhibition of abnormal gene activity, for example, the inhibition of a disease target nucleotide sequence, as further described below. Thus, such antibodies may be utilized as part of cardiovascular or other disease treatment method, and/or may be used as part of diagnostic techniques whereby patients may be tested for abnormal levels of novel nucleotide sequence encoded proteins, or for the presence of abnormal forms of the such proteins.

For the production of antibodies to a novel nucleotide sequence, various host animals may be immunized by injection with a novel protein encoded by the novel nucleotide sequence, or a portion thereof. Such host animals may include but are not limited to rabbits, mice, and rats, to name but a few. Various adjuvants may be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanin, dinitrophenol, and potentially useful human adjuvants such as BCG (bacille Calmette-Guerin) and *Corynebacterium parvum.*

Polyclonal antibodies are heterogeneous populations of antibody molecules derived from the sera of animals immunized with an antigen, such as novel gene product, or an antigenic functional derivative thereof. For the production of polyclonal antibodies, host animals such as those described above, may be immunized by injection with novel gene product supplemented with adjuvants as also described above.

Monoclonal antibodies, which are homogeneous populations of antibodies to a particular antigen, may be obtained by any technique which provides for the production of antibody molecules by continuous cell lines in culture. These include, but are not limited to the hybridoma technique of Kohler and Milstein, (1975, Nature 256:495-497; and U.S. Pat. No. 4,376,110), the human B-cell hybridoma technique (Kosbor et al., 1983, Immunology Today 4:72; Cole et al., 1983, Proc. Natl. Acad. Sci. USA 80:2026-2030), and the EBV-hybridoma technique (Cole et al., 1985, Monoclonal Antibodies And Cancer Therapy, Alan R. Liss, Inc., pp. 77-96). Such antibodies may be of any immunoglobulin class including IgG, IgM, IgE, IgA, IgD and any subclass thereof. The hybridoma producing the mAb of this invention may be cultivated in vitro or in vivo.

In addition, techniques developed for the production of "chimeric antibodies" (Morrison et al., 1984, Proc. Natl. Acad. Sci., 81:6851-6855; Neuberger et al., 1984, Nature, 312:604-608; Takeda et al., 1985, Nature, 314:452-454) by splicing the genes from a mouse antibody molecule of appropriate antigen specificity together with genes from a human antibody molecule of appropriate biological activity can be used. A chimeric antibody is a molecule in which different portions are derived from different animal species, such as those having a variable region derived from a murine mAb and a human immunoglobulin constant region.

Alternatively, techniques described for the production of single chain antibodies (U.S. Pat. No. 4,946,778; Bird, 1988, Science 242:423-426; Huston et al., 1988, Proc. Natl. Acad. Sci. USA 85:5879-5883; and Ward et al., 1989, Nature 334: 544-546) can be adapted to produce novel nucleotide sequence-single chain antibodies. Single chain antibodies are formed by linking the heavy and light chain fragments of the Fv region via an amino acid bridge, resulting in a single chain polypeptide.

Antibody fragments which recognize specific epitopes may be generated by known techniques For example, such fragments include but are not limited to: the F(ab')2 fragments which can be produced by pepsin digestion of the antibody molecule and the Fab fragments which can be generated by reducing the disulfide bridges of the F(ab')2 fragments. Alternatively, Fab expression libraries may be constructed (Huse et al., 1989, Science, 246:1275-1281) to allow rapid and easy identification of monoclonal Fab fragments with the desired specificity.

Disease Specific Target Oligonucleotide Sequences

The invention also provides disease specific target oligonucleotide sequences, and sets of disease specific target oligonucleotide sequences. The diagnostic oligonucleotide sets, subsets thereof, novel oligonucleotide sequences, and individual members of the diagnostic oligonucleotide sets identified as described above are also disease specific target oligonucleotide sequences. In particular, individual oligonucleotide sequences that are differentially regulated or have predictive value that is strongly correlated with a disease or disease criterion are especially favorable as disease specific target oligonucleotide sequences. Sets of genes that are co-regulated may also be identified as disease specific target oligonucleotide sets. Such oligonucleotide sequences and/or oligonucleotide sequence products are targets for modulation by a variety of agents and techniques. For example, disease specific target oligonucleotide sequences (or the products of such oligonucleotide sequences, or sets of disease specific target oligonucleotide sequences) can be inhibited or activated by, e.g., target specific monoclonal antibodies or small molecule inhibitors, or delivery of the oligonucleotide sequence or gene product of the oligonucleotide sequence to patients. Also, sets of genes can, be inhibited or activated by a variety of agents and techniques. The specific usefulness of the target oligonucleotide sequence(s) depends on the subject groups from which they were discovered, and the disease or disease criterion with which they correlate.

Kits

The present invention is optionally provided to a user as a kit. Typically, a kit contains one or more diagnostic nucleotide sets of the invention. Alternatively, the kit contains the candidate nucleotide library of the invention. Most often, the kit contains a diagnostic nucleotide probe set, or other subset of a candidate library, (e.g., as a cDNA, oligonucleotide or antibody microarray or reagents for performing an assay on a diagnostic gene set using any expression profiling technology), packaged in a suitable container. The kit may further comprise, one or more additional reagents, e.g., substrates, labels, primers, for labeling expression products, tubes and/or other accessories, reagents for collecting blood samples, buffers, e.g., erythrocyte lysis buffer, leukocyte lysis buffer, hybridization chambers, cover slips, etc., as well as a software package, e.g., including the statistical methods of the invention, e.g., as described above, and a password and/or account number for accessing the compiled database. The kit optionally further comprises an instruction set or user manual detailing preferred methods of using the diagnostic nucleotide sets in the methods of the invention.

This invention will be better understood by reference to the following non-limiting Examples:

EXAMPLES

Example 1: Generation of subtracted leukocyte candidate nucleotide library

Example 2: Identification of nucleotide sequences for candidate library using data mining techniques Example 3: DNA Sequencing and Processing of raw sequence data.

Example 4: Further sequence analysis of novel nucleotide sequences identified by subtractive hybridization screening Example 5: Further sequence analysis of novel Clone 596H6

Example 6: Further sequence analysis of novel Clone 486E11

Example 7: Preparation of RNA from Mononuclear Cells for Expression profiling

Example 8: Preparation of Universal Control RNA for Use in Leukocyte expression profiling Example 9: Identification of diagnostic oligonucleotide sets for use in diagnosis of rheumatoid arthritis.

Example 10: Identification of diagnostic oligonucleotide sets for diagnosis of Systemic Lupus Erythematosis Example 11: Probe selection for a 24,000 feature Array.

Example 12: Design of oligonucleotide probes.

Example 13: Production of an array of 8,000 spotted 50 mer oligonucleotides.

Example 14: Amplification, labeling and hybridization of total RNA to an oligonucleotide microarray.

Example 15: Real-time PCR validation of array expression results

Example 16: Correlation and Classification Analysis

Examples

Example 1

Generation of Subtracted Leukocyte Candidate Nucleotide Library

To produce a candidate nucleotide library with representatives from the spectrum of nucleotide sequences that are differentially expressed in leukocytes, subtracted hybridization libraries were produced from the following cell types and conditions:
1. Buffy Coat leukocyte fractions—stimulated with ionomycin and PMA
2. Buffy Coat leukocyte fractions—un-stimulated
3. Peripheral blood mononuclear cells—stimulated with ionomycin and PMA
4. Peripheral blood mononuclear cells—un-stimulated
5. T lymphocytes—stimulated with PMA and ionomycin
6. T lymphocytes—resting Cells were obtained from multiple individuals to avoid introduction of bias by using only one person as a cell source.

Buffy coats (platelets and leukocytes that are isolated from whole blood) were purchased from Stanford Medical School Blood Center. Four buffy coats were used, each of which was derived from about 350 ml of whole blood from one donor individual 10 ml of buffy coat sample was drawn from the sample bag using a needle and syringe. 40 ml of Buffer EL (Qiagen) was added per 10 ml of buffy coat to lyse red blood cells. The sample was placed on ice for 15 minutes, and cells were collected by centrifugation at 2000 rpm for 10 minutes. The supernatant was decanted and the cell pellet was resuspended in leukocyte growth media supplemented with DNase (LGM-3 from Clonetics supplemented with Dnase at a final concentration of 30 U/ml). Cell density was determined using a hemocytometer. Cells were plated in media at a density of $1 \times 10^6$ cells/ml in a total volume of 30 ml in a T-75 flask (Corning). Half of the cells were stimulated with ionomycin and phorbol myristate acetate (PMA) at a final concentration of 1 µg/ml and 62 ng/ml, respectively. Cells were incubated at 37° C. and at 5% $CO_2$ for 3 hours, then cells were scraped off the flask and collected into 50 ml tubes. Stimulated and resting cell populations were kept separate. Cells were centrifuged at 2000 rpm for 10 minutes and the supernatant was removed. Cells were lysed in 6 ml of phenol/guanidine isothyocyanate (Trizol reagent, GibcoBRL), homogenized using a rotary homogenizer, and frozen at 80°. Total RNA and mRNA were isolated as described below.

Two frozen vials of $5 \times 10^6$ pooled human peripheral blood mononuclear cells (PBMCs) were purchased from Clonetics (catalog number cc-2702). The cells were rapidly thawed in a 37° C. water bath and transferred to a 15 ml tube containing 10 ml of leukocyte growth media supplemented with DNase (prepared as described above). Cells were centrifuged at 200 µg for 10 minutes. The supernatant was removed and the cell pellet was resuspended in LGM-3 media supplemented with DNase. Cell density was determined using a hemocytometer. Cells were plated at a density of $1 \times 10^6$ cells/ml in a total volume of 30 ml in a T-75 flask (Corning). Half of the cells were stimulated with ionomycin and PMA at a final concentration of 1 µg/ml and 62 ng/ml, respectively. Cells were incubated at 37° C. and at 5% $CO_2$ for 3 hours, then cells were scraped off the flask and collected into 50 ml tubes. Stimulated and resting cell populations were kept separate. Cells were centrifuged at 2000 rpm and the supernatant was removed. Cells were lysed in 6 ml of phenol/guanidine isothyocyanate solution (TRIZOL reagent, GibcoBRL)), homogenized using a rotary homogenizer, and frozen at 80°. Total RNA and mRNA were isolated from these samples using the protocol described below.

45 ml of whole blood was drawn from a peripheral vein of four healthy human subjects into tubes containing anticoagulant. 50 µl RosetteSep (Stem Cell Technologies) T-cell isolation cocktail per ml of blood was added, mixed well, and incubated for 20 minutes at room temperature. The mixture was diluted with an equal volume of PBS+2% fetal bovine serum (FBS) and mixed by inversion. 30 ml of diluted mixture sample was layered on top of 15 ml DML medium (Stem Cell Technologies). The sample tube was centrifuged for 20 minutes at 1200×g at room temperature. The enriched T-lymphocyte cell layer at the plasma:medium interface was removed. Enriched cells were, washed with PBS+2% FBS and centrifuged at 1200×g. The cell pellet was treated with 5 ml of erythrocyte lysis buffer (EL buffer, Qiagen) for 10 minutes on ice. The sample was centrifuged for 5 min at 1200 g. Cells were plated at a density of 1×10⁶ cells/ml in a total volume of 30 ml in a T-75 flask (Corning). Half of the cells were stimulated with ionomycin and PMA at a final concentration of 1 µg/ml and 62 ng/ml, respectively. Cells were incubated at 37° C. and at 5% $CO_2$ for 3 hours, then cells were scraped off the flask and collected into 50 ml tubes. Stimulated and resting cell populations were kept separate. Cells were centrifuged at 2000 rpm and the supernatant was removed. Cells were lysed in 6 ml of phenol/guanidine isothyocyanate solution (TRIZOL reagent, GibcoBRL), homogenized using a rotary homogenizer, and frozen at 80°. Total RNA and mRNA were isolated as described below.

Total RNA and mRNA were isolated using the following procedure: the homogenized samples were thawed and mixed by vortexing. Samples were lysed in a 1:0.2 mixture of Trizol and chloroform, respectively. For some samples, 6 ml of Trizol-chloroform was added. Variable amounts of Trizol-chloroform was added to other samples. Following lysis, samples were centrifuged at 3000 g for 15 min at 4° C. The aqueous layer was removed into a clean tube and 4 volumes of Buffer RLT Qiagen) was added for every volume of aqueous layer. The samples were mixed thoroughly and total RNA was prepared from the sample by following the Qiagen Rneasy midi protocol for RNA cleanup (October 1999 protocol, Qiagen). For the final step, the RNA was eluted from the column twice with 250 µl Rnase-free water. Total RNA was quantified using a spectrophotometer. Isolation of mRNA from total RNA sample was done using The Oligotex mRNA isolation protocol (Qiagen) was used to isolate mRNA from total RNA, according to the manufacturer's instructions (Qiagen, 7/99 version). mRNA was quantified by spectrophotometry.

Subtracted cDNA libraries were prepared using Clontech's PCR-Select cDNA Subtraction Kit (protocol number PT-1117-1) as described in the manufacturer's protocol. The protocol calls for two sources of RNA per library, designated "Driver" and "Tester." The following 6 libraries were made:

| Library | Driver RNA | Tester RNA |
| --- | --- | --- |
| Buffy Coat Stimulated | Un-stimulated Buffy Coat | Stimulated Buffy Coat |
| Buffy Coat Resting | Stimulated Buffy Coat | Un-stimulated Buffy Coat |
| PBMC Stimulated | Un-stimulated PBMCs | Stimulated PBMCs |
| PBMC Resting | Stimulated PBMCs | Un-stimulated PBMCs |
| T-cell Stimulated | Un-stimulated T-cells | Stimulated T-cells |
| T-cell Resting | Stimulated T-cells | Un-stimulated T-cells |

The Clontech protocol results in the PCR amplification of cDNA products. The PCR products of the subtraction protocol were ligated to the pGEM T-easy bacterial vector as described by the vector manufacturer (Promega 6/99 version). Ligated vector was transformed into competent bacteria using well-known techniques, plated, and individual clones are picked, grown and stored as a glycerol stock at −80 C. Plasmid DNA was isolated from these bacteria by standard techniques and used for sequence analysis of the insert. Unique cDNA sequences were searched in the Unigene database (build 133), and Unigene cluster numbers were identified that corresponded to the DNA sequence of the cDNA. Unigene cluster numbers were recorded in an Excel spreadsheet.

Example 2

Identification of Nucleotide Sequences for Candidate Library Using Data Mining Techniques Existing and publicly available gene sequence databases were used to identify candidate nucleotide sequences for leukocyte expression profiling. Genes and nucleotide sequences with specific expression in leukocytes, for example, lineage specific markers, or known differential expression in resting or activated leukocytes were identified. Such nucleotide sequences are used in a leukocyte candidate nucleotide library, alone or in combination with nucleotide sequences isolated through cDNA library construction, as described above.

Leukocyte candidate nucleotide sequences were identified using three primary methods. First, the publically accessible publication database PubMed was searched to identify nucleotide sequences with known specific or differential expression in leukocytes. Nucleotide sequences were identified that have been demonstrated to have differential expression in peripheral blood leukocytes between subjects with and without particular disease(s) selected from Table 1. Additionally, genes and gene sequences that were known to be specific or selective for leukocytes or sub-populations of leukocytes were identified in this way.

Next, two publicly available databases of DNA sequences, Unigene located on the website at ncbi.nlm.nih.gov/UniGene and BodyMap located on the website at bodymap.ims.u-tokyo.ac.jp, were searched for sequenced DNA clones that showed specificity to leukocyte lineages, or subsets of leukocytes, or resting or activated leukocytes.

The human Unigene database (build 133) was used to identify leukocyte candidate nucleotide sequences that were likely to be highly or exclusively expressed in leukocytes. We used the Library Differential Display utility of Unigene located on the website at ncbi.nlm.nih.gov/UniGene/info/ddd.html, which uses statistical methods (The Fisher Exact Test) to identify nucleotide sequences that have relative specificity for a chosen library or group of libraries relative to each other. We compared the following human libraries from Unigene release 133:

546 NCI_CGAP_HSC1 (399)
848 Human_mRNA_from_cd34+stem_cells (122)
105 CD34+DIRECTIONAL (150)
3587 KRIBB_Human_CD4_intrathymic_T-cell_cDNA_library (134)
3586 KRIBB_Human_DP_intrathymic_T-cell_cDNA_library (179)
3585 KRIBB_Human_TN_intrathymic_T-cell_cDNA_library (127)
3586 323 Activated_T-cells_I (740)
376 Activated_T-cells_XX (1727)
327 Monocytes,_stimulated_II (110)
824 Proliferating_Erythroid_Cells_(LCB:ad_library) (665)
825 429 Macrophage_II (105)
387 Macrophage_I (137)
669 NCI_CGAP_CLL1 (11626)
129 Human_White_blood_cells (922)
1400 NIH_MGC_2 (422)
55 Human_promyelocyte (1220)
1010 NCI_CGAP_CML1 (2541)
2217 NCI_CGAP_Sub7 (218)
1395 NCI_CGAP_Sub6 (2764)
4874 NIH_MGC_48 (2524)

Sequences from these libraries were compared to sequences from non-leukocyte derived libraries in the Unigene database to identify genes that had some specificity for the leukcoyte-derived libraries.

BodyMap, like Unigene, contains cell-specific libraries that contain potentially useful information about genes that may serve as lineage-specific or leukocyte specific markers (Okubo et al. 1992). We compared three leukocyte specific libraries, Granulocyte, CD4 T cell, and CD8 T cell, with the other libraries. Nucleotide sequences that were found in one or more of the leukocyte-specific libraries, but absent in the others, were identified. Clones that were found exclusively in one of the three leukocyte libraries were also included in a list of nucleotide sequences that could serve as lineage-specific markers.

Next, the sequence of the nucleotide sequences identified in PubMed or BodyMap were searched in Unigene (version 133), and a human Unigene cluster number was identified for each nucleotide sequence. The cluster number was recorded in a Microsoft Excel™ spreadsheet, and a non-redundant list of these clones was made by sorting the clones by UniGene number, and removing all redundant clones using Microsoft Excel™ tools. The non-redundant list of UniGene cluster numbers was then compared to the UniGene cluster numbers of the cDNAs identified using subtractive cDNA hybridization, as described above in Example 1 (listed in Table 3 and the sequence listing). Only UniGene clusters that were not contained in the cDNA libraries were retained. Unigene clusters corresponding to 1911 candidate nucleotide sequences for leukocyte expression profiling were identified in this way and are listed in Table 3 and the sequence listing.

DNA clones corresponding to each UniGene cluster number are obtained in a variety of ways. First, a cDNA clone with identical sequence to part of, or all of the identified UniGene cluster is bought from a commercial vendor or obtained from the IMAGE consortium located on the web at image.llnl.gov/, the Integrated Molecular Analysis of Genomes and their Expression. Alternatively, PCR primers are designed to amplify and clone any portion of the nucleotide sequence from cDNA or genomic DNA using well-known techniques. Alternatively, the sequences of the identified UniGene clusters are used to design and synthesize oligonucleotide probes for use in oligonucleotide microarray based expression profiling.

Example 3

DNA Sequencing and Processing of Raw Sequence Data

Clones of differentially expressed cDNAs (identified by subtractive hybridization, described above) were sequenced on an MJ Research BaseStation™ slab gel based fluorescent detection system, using BigDye™ (Applied Biosystems, Foster City, Calif.) terminator chemistry was used (Heiner et al., Genome Res 1998 May; 8(5):557-61).

The fluorescent profiles were analyzed using the Phred sequence analysis program (Ewing et al, (1998), Genome Research 8: 175-185). Analysis of each clone results in a one pass nucleotide sequence and a quality file containing a number for each base pair with a score based on the probability that the determined base is correct. Each of the sequence files and its respective quality files were initially combined into single fasta format (Pearson, W R. Methods Mol Biol. 2000; 132:185-219), multi-sequence file with the appropriate labels for each clone in the headers for subsequent automated analysis.

Initially, known sequences were analyzed by pair wise similarity searching using the blastn option of the blastall program obtained from the National Center for Biological Information, National Library of Medicine, National Institutes of Health (NCBI) to determine the quality score that produced accurate matching (Altschul S F, et al. J Mol Biol. 1990 Oct. 5; 215(3):403-10.). Empirically, it was determined that a raw score of 8 was the minimum that contained useful information. Using a sliding window average for 16 base pairs, an average score was determined. The sequence was removed (trimmed) when the average score fell below 8. Maximum reads were 950 nucleotides long.

Next, the sequences were compared by similarity matching against a database file containing the flanking vector sequences used to clone the cDNA, using the blastall program with the blastn option. All regions of vector similarity were removed, or "trimmed" from the sequences of the clones using scripts in the GAWK programming language, a variation of AWK (Aho A V et al, The Awk Programming Language (Addison-Wesley, Reading Mass., 1988); Robbins, AD, "Effective AWK Programming" (Free Software Foundation, Boston Mass., 1997). It was found that the first 45 base pairs of all the sequences were related to vector; these sequences were also trimmed and thus removed from consideration. The remaining sequences were then compared against the NCBI vector database (Kitts, P. A. et al. National Center for Biological Information, National Library of Medicine, National Institutes of Health, Manuscript in preparation (2001) using blastall with the blastn option. Any vector sequences that were found were removed from the sequences.

Messenger RNA contains repetitive elements that are found in genomic DNA. These repetitive elements lead to false positive results in similarity searches of query mRNA sequences versus known mRNA and EST databases. Additionally, regions of low information content (long runs of the same nucleotide, for example) also result in false positive results. These regions were masked using the program RepeatMasker2 found on the website at repeatmasker.genome.washington.edu (Smit, AFA & Green, P "RepeatMasker" at the website at genome.washington.edu/RM/RepeatMasker.html. The trimmed and masked files were then subjected to further sequence analysis.

Example 4

Further Sequence Analysis of Novel Nucleotide Sequences Identified by Subtractive Hybridization Screening cDNA sequences were further characterized using BLAST analysis. The BLASTN program was used to compare the sequence of the fragment to the UniGene, dbEST, and nr databases at NCBI (GenBank release 123.0; see Table 5). In the BLAST algorithm, the expect value for an alignment is used as the measure of its significance. First, the cDNA sequences were compared to sequences in Unigene on the web at ncbi.nlm.nih.gov/UniGene. If no alignments were found with an expect value less than $10^{-25}$, the sequence was compared to the sequences in the dbEST database using BLASTN. If no alignments were found with an expect value less than $10^{-25}$, the sequence was compared to sequences in the nr database.

The BLAST analysis produced the following categories of results: a) a significant match to a known or predicted human gene, b) a significant match to a nonhuman DNA sequence, such as vector DNA or E. coli DNA, c) a significant match to an unidentified GenBank entry (a sequence not previously identified or predicted to be an expressed sequence or a gene), such as a cDNA clone, mRNA, or cosmid, or d) no significant alignments. If a match to a known or predicted human gene was found, analysis of the known or predicted protein product was performed as described below. If a match to an unidentified GenBank entry was found, or if no significant alignments were found, the sequence was searched against all known sequences in the human genome database located on the web at ncbi.nlm.nih.gov/genome/seq/page.cgi?F=HsBlast.html&&ORG=Hs, see Table 5.

If many unknown sequences were to be analyzed with BLASTN, the clustering algorithm CAP2 (Contig Assembly Program, version 2) was used to cluster them into longer, contiguous sequences before performing a BLAST search of the human genome. Sequences that can be grouped into contigs are likely to be cDNA from expressed genes rather than vector DNA, *E. coli* DNA or human chromosomal DNA from a noncoding region, any of which could have been incorporated into the library. Clustered sequences provide a longer query sequence for database comparisons with BLASTN, increasing the probability of finding a significant match to a known gene. When a significant alignment was found, further analysis of the putative gene was performed, as described below. Otherwise, the sequence of the original cDNA fragment or the CAP2 contig is used to design a probe for expression analysis and further approaches are taken to identify the gene or predicted gene that corresponds to the cDNA sequence, including similarity searches of other databases, molecular cloning, and Rapid Amplification of cDNA Ends (RACE).

In some cases, the process of analyzing many unknown sequences with BLASTN was automated by using the BLAST network-client program blastcl3, which was downloaded from ftp://ncbi.nlm.nih.gov/blast/network/netblast.

When a cDNA sequence aligned to the sequence of one or more chromosomes, a large piece of the genomic region around the loci was used to predict the gene containing the cDNA. To do this, the contig corresponding to the mapped locus, as assembled by the RefSeq project at NCBI, was downloaded and cropped to include the region of alignment plus 100,000 bases preceding it and 100,000 bases following it on the chromosome. The result was a segment 200 kb in length, plus the length of the alignment. This segment, designated a putative gene, was analyzed using an exon prediction algorithm to determine whether the alignment area of the unknown sequence was contained within a region predicted to be transcribed (see Table 6).

This putative gene was characterized as follows: all of the exons comprising the putative gene and the introns between them were taken as a unit by noting the residue numbers on the 200 kb+ segment that correspond to the first base of the first exon and the last base of the last exon, as given in the data returned by the exon prediction algorithm. The truncated sequence was compared to the UniGene, dbEST, and nr databases to search for alignments missed by searching with the initial fragment.

The predicted amino acid sequence of the gene was also analyzed. The peptide sequence of the gene predicted from the exons was used in conjunction with numerous software tools for protein analysis (see Table 7). These were used to classify or identify the peptide based on similarities to known proteins, as well as to predict physical, chemical, and biological properties of the peptides, including secondary and tertiary structure, flexibility, hydrophobicity, antigenicity (hydrophilicity), common domains and motifs, and localization within the cell or tissues. The peptide sequence was compared to protein databases, including SWISS-PROT, TrEMBL, GenPept, PDB, PIR, PROSITE, ProDom, PROSITE, Blocks, PRINTS, and Pfam, using BLASTP and other algorithms to determine similarities to known proteins or protein subunits.

Example 5

Further Sequence Analysis of Novel Clone 596H6

The sequence of clone 596H6 is provided below:

```
                                                (SEQ ID NO: 8767)
ACTATATTTA GGCACCACTG CCATAAACTA CCAAAAAAAA AATGTAATTC    50

CTAGAAGCTG TGAAGAATAG TAGTGTAGCT AAGCACGGTG TGTGGACAGT   100

GGGACATCTG CCACCTGCAG TAGGTCTCTG CACTCCCAAA AGCAAATTAC   150

ATTGGCTTGA ACTTCAGTAT GCCCGGTTCC ACCCTCCAGA AACTTTTGTG   200

TTCTTTGTAT AGAATTTAGG AACTTCTGAG GGCCACAAAT ACACACATTA   250

AAAAAGGTAG AATTTTTGAA GATAAGATTC TTCTAAAAAA GCTTCCCAAT   300

GCTTGAGTAG AAAGTATCAG TAGAGGTATC AAGGGAGGAG AGACTAGGTG   350

ACCACTAAAC TCCTTCAGAC TCTTAAAATT ACGATTCTTT TCTCAAAGGG   400

GAAGAACGTC AGTGCAGCGA TCCCTTCACC TTTAGCTAAA GAATTGGACT   450

GTGCTGCTCA AAATAAAGAT CAGTTGGAGG TANGATGTCC AAGACTGAAG   500

GTAAAGGACT AGTGCAAACT GAAAGTGATG GGGAAACAGA CCTACGTATG   550

GAAGCCATGT AGTGTTCTTC ACAGGCTGCT GTTGACTGAA ATTCCTATCC   600

TCAAATTACT CTAGACTGAA GCTGCTTCCC TTCAGTGAGC AGCCTCTCCT   650

TCCAAGATTC TGGAAAGCAC ACCTGACTCC AAACAAAGAC TTAGAGCCCT   700

GTGTCAGTGC TGCTGCTGCT TTTACCAGAT TCTCTAACCT TCCGGGTAGA   750

AGAG
```

This sequence was used as input for a series of BLASTN searches. First, it was used to search the UniGene database, build 132 located on the web at ncbi.nlm.nih.gov/BLAST. No alignments were found with an expect value less than the threshold value of $10^{-25}$. A BLASTN search of the database dbEST, release 041001, was then performed on the sequence and 21 alignments were found (http://www.ncbi.nlm.nih.gov/BLAST/). Ten of these had expect values less than $10^{-25}$, but all were matches to unidentified cDNA clones. Next, the sequence was used to run a BLASTN search of the nr database, release 123.0. No significant alignment to any sequence in nr was found. Finally, a BLASTN search of the human genome was performed on the sequence located on the web at ncbi.nlm.nih.gov/genome/seq/page.cgi?F=HsBlast.html&&ORG=Hs.

A single alignment to the genome was found on contig NT_004698.3 (e=0.0). The region of alignment on the contig was from base 1,821,298 to base 1,822,054, and this region was found to be mapped to chromosome 1, from base 105,552,694 to base 105,553,450. The sequence containing the aligned region, plus 100 kilobases on each side of the aligned region, was downloaded. Specifically, the sequence of chromosome 1 from base 105,452,694 to 105,653,450 was downloaded from the website at ncbi.nlm.nih.gov/cgi-bin/Entrez/seq_reg.cgi?chr=1&from=105452694&to =105653450.

This 200,757 bp segment of the chromosome was used to predict exons and their peptide products as follows. The sequence was used as input for the Genscan algorithm located on the web at genes.mit.edu/GENSCAN.html, using the following Genscan settings:

Organism: vertebrate
Suboptimal exon cutoff: 1.00 (no suboptimal exons)
Print options: Predicted CDS and peptides The region matching the sequence of clone 596H6 was known to span base numbers 100,001 to 100,757 of the input sequence. An exon was predicted by the algorithm, with a probability of 0.695, covering bases 100,601 to 101,094 (designated exon 4.14 of the fourth predicted gene). This exon was part of a predicted cistron that is 24,195 bp in length. The sequence corresponding to the cistron was noted and saved separately from the 200,757 bp segment. BLASTN searches of the Unigene, dbEST, and nr databases were performed on it.

At least 100 significant alignments to various regions of the sequence were found in the dbEST database, although most appeared to be redundant representations of a few exons. All matches were to unnamed cDNAs and mRNAs (unnamed cDNAs and mRNAs are cDNAs and mRNAs not previously identified, or shown to correspond to a known or predicted human gene) from various tissue types. Most aligned to a single region on the sequence and spanned 500 bp or less, but several consisted of five or six regions separated by gaps, suggesting the locations of exons in the gene. Several significant matches to entries in the UniGene database were found, as well, even after masking low-complexity regions and short repeats in the sequence. All matches were to unnamed cDNA clones.

At least 100 significant alignments were found in the nr database, as well. A similarity to hypothetical protein FLJ22457 (UniGene cluster Hs.238707) was found (e=0.0). The cDNA of this predicted protein has been isolated from B lymphocytes located on the web at ncbi.nlm.nih.gov/entrez/viewer.cgi?save=0&cmd=&cfm=on&f=1&view=gp&txt=0&val=13637988.

Other significant alignments were to unnamed cDNAs and mRNAs.

Using Genscan, the following 730 residue peptide sequence was predicted from the putative gene:

```
                                                        SEQ ID NO: 8768
              MDGLGRRLRA SLRLKRGHGG HWRLNEMPYM KHEFDGGPPQ DNSGEALKEP    50

ERAQEHSLPN FAGGQHFFEY LLVVSLKKKR SEDDYEPIIT YQFPKRENLL   100

RGQQEEEERL LKAIPLFCFP DGNEWASLTE YPSLSCKTPG LLAALVVEKA   150

QPRTCCHASA PSAAPQARGP DAPSPAAGQA LPAGPGPRLP KVYCIISCIG   200

CFGLFSKILD EVEKRHQISM AVIYPFMQGL REAAFPAPGK TVTLKSFIPD   250

SGTEFISLTR PLDSHLEHVD FSSLLHCLSF EQILQIFASA VLERKIIFLA   300

EGLREEEKDV RDSTEVRGAG ECHGFQRKGN LGKQWGLCVE DSVKMGDNQR   350

GTSCSTLSQC IHAAAALLYP FSWAHTYIPV VPESLLATVC CPTPFMVGVQ   400

MRFQQEVMDS PMEEIQPQAE IKTVNPLGVY EERGPEKASL CLFQVLLVNL   450

CEGTFLMSVG DEKDILPPKL QDDILDSLGQ GINELKTAEQ INEHVSGPFV   500

QFFVKIVGHY ASYIKREANG QGHFQERSFC KALTSKTNRR FVKKFVKTQL   550

FSLFIQEAEK SKNPPAEVTQ VGNSSTCVVD TWLEAAATAL SHHYNIFNTE   600

HTLWSKGSAS LHEVCGHVRT RVKRKILFLY VSLAFTMGKS IFLVENKAMN   650

MTIKWTTSGR PGHGDMFGVI ESWGAAALLL LTGRVRDTGK SSSSTGHRAS   700

KSLVWSQVCF PESWEERLLT EGKQLQSRVI
```

Multiple analyses were performed using this prediction. First, a pairwise comparison of the sequence above and the sequence of FLJ22457, the hypothetical protein mentioned above, using BLASTP version 2.1.2 located on the web at ncbi.nlm.nih.gov/BLAST, resulted in a match with an expect value of 0.0. The peptide sequence predicted from clone 596H6 was longer and 19% of the region of alignment between the two resulted from gaps in hypothetical protein FLJ22457. The cause of the discrepancy might be alternative mRNA splicing, alternative post-translational processing, or differences in the peptide-predicting algorithms used to create the two sequences, but the homology between the two is significant.

BLASTP and TBLASTN were also used to search for sequence similarities in the SWISS-PROT, TrEMBL, GenBank Translated, and PDB databases. Matches to several proteins were found, among them a tumor cell suppression protein, HTS1. No matches aligned to the full length of the peptide sequence, however, suggesting that similarity is limited to a few regions of the peptide.

TBLASTN produced matches to several proteins—both identified and theoretical—but again, no matches aligned to the full length of the peptide sequence. The best alignment was to the same hypothetical protein found in GenBank before (FLJ22457).

To discover similarities to protein families, comparisons of the domains (described above) were carried out using the Pfam and Blocks databases. A search of the Pfam database identified two regions of the peptide domains as belonging the DENN protein family (e=$2.1 \times 10^{-33}$). The human DENN protein possesses an RGD cellular adhesion motif and a leucine-zipper-like motif associated with protein dimerization, and shows partial homology to the receptor binding domain of tumor necrosis factor alpha. DENN is virtually identical to MADD, a human MAP kinase-activating death domain protein that interacts with type I tumor necrosis factor receptor located on the web at srs.ebi.ac.uk/srs6bin/cgi-bin/wgetz?-id+fS5n1GQsHf+-e+[INTERPRO:'IPR001194']. The search of the Blocks database also revealed similarities between regions of the peptide sequence and known protein groups, but none with a satisfactory degree of confidence. In the Blocks scoring system, scores over 1,100 are likely to be relevant. The highest score of any match to the predicted peptide was 1,058.

The Prosite, ProDom, PRINTS databases (all publicly available) were used to conduct further domain and motif analysis. The Prosite search generated many recognized protein domains. A BLASTP search was performed to identify areas of similarity between the protein query sequence and PRINTS, a protein database of protein fingerprints, groups of motifs that together form a characteristic signature of a protein family. In this case, no groups were found to align closely to any section of the submitted sequence. The same was true when the ProDom database was searched with BLASTP.

A prediction of protein structure was done by performing a BLAST search of the sequence against PDB, a database in which every member has tertiary structure information. No significant alignments were found by this method. Secondary and super-secondary structure was examined using the Garnier algorithm. Although it is only considered to be 60-65% accurate, the algorithm provided information on the locations and lengths of alpha-helices, beta-sheets, turns and coils.

The antigenicity of the predicted peptide was modeled by graphing hydrophilicity vs. amino acid number. This produced a visual representation of trends in hydrophilicity along the sequence. Many locations in the sequence showed antigenicity and five sites had antigenicity greater than 2. This information can be used in the design of affinity reagents to the protein.

Membrane-spanning regions were predicted by graphing hydrophobicity vs. amino acid number. Thirteen regions were found to be somewhat hydrophobic. The algorithm TMpred predicted a model with 6 strong transmembrane helices located on the web at ch.embnet.org/software/TMPRED_form.html.

NNPSL is a neural network algorithm developed by the Sanger Center. It uses amino acid composition and sequence to predict cellular location. For the peptide sequence submitted, its first choice was mitochondrial (51.1% expected accuracy). Its second choice was cytoplasmic (91.4% expected accuracy).

Example 6

Further Sequence Analysis of Novel Clone 486E11

The sequence of clone 486E11 is provided below:

```
                                                  SEQ ID NO: 8769
TAAAAGCAGG CTGTGCACTA GGGACCTAGT GACCTTACTA GAAAAAACTC    50

AAATTCTCTG AGCCACAAGT CCTCATGGGC AAAATGTAGA TACCACCACC   100

TAACCCTGCC AATTTCCTAT CATTGTGACT ATCAAATTAA ACCACAGGCA   150

GGAAGTTGCC TTGAAAACTT TITATAGTGT ATATTACTGT TCACATAGAT   200

NAGCAATTAA CTTTACATAT ACCCGTTTTT AAAAGATCAG TCCTGTGATT   250

AAAAGTCTGG CTGCCCTAAT TCACTTCGAT TATACATTAG GTTAAAGCCA   300

TATAAAAGAG GCACTACGTC TTCGGAGAGA TGAATGGATA TTACAAGCAG   350

TAATGTTGGC TTTGGAATAT ACACATAATG TCCACTTGAC CTCATCTATT   400

TGACACAAAA TGTAAACTAA ATTATGAGCA TCATTAGATA CCTTGGCCTT   450

TTCAAATCAC ACAGGGTCCT AGATCTNNNN NNNNNNNNNN NNNNNNNNNN   500

NNNNNNNNNN NNNNNNNNNN NNNNNNNNNN NNNNNNNNAC TTTGGGATTC   550

CTATATCTTT GTCAGCTGTC AACTTCAGTG TTTTCAGGTT AAATTCTATC   600

CATAGTCATC CCAATATACC TGCTTTAGAT GATACAACCT TCAAAAGATC   650

CGCTCTTCCT CGTAAAAAGT GGAG
```

The BLASTN program was used to compare the sequence to the UniGene and dbEST databases. No significant alignments were found in either. It was then searched against the nr database and only alignments to unnamed genomic DNA clones were found.

CAP2 was used to cluster a group of unknowns, including clone 486E11. The sequence for 486E11 was found to overlap others. These formed a contig of 1,010 residues, which is shown below:

were used to search the TrEMBL protein database located on the web at expasy.ch/sprot/) and the GenBank nr database located on the web at ncbi.nlm.hih.gov/BLAST, which includes data from the SwissProt, PIR, PRF, and PDB data-

```
                                              SEQ ID NO: 8832
CGGACAGGTA CCTAAAAGCA GGCTGTGCAC TAGGGACCTA GTGACCTTAC      50

TAGAAAAAAC TCAAATTCTC TGAGCCACAA GTCCTCATGG GCAAAATGTA     100

GATACCACCA CCTAACCCTG CCAATTTCCT ATCATTGTGA CTATCAAATT     150

AAACCACAGG CAGGAAGTTG CCTTGAAAAC TTTTTATAGT GTATATTACT     200

GTTCACATAG ATNAGCAATT AACTTTACAT ATACCCGTTT TTAAAAGATC     250

AGTCCTGTGA TTAAAAGTCT GGCTGCCCTA ATTCACTTCG ATTATACATT     300

AGGTTAAAGC CATATAAAAG AGGCACTACG TCTTCGGAGA GATGAATGGA     350

TATTACAAGC AGTAATTTTG GCTTTGGAAT ATACACATAA TGTCCACTTG     400

ACCTCATCTA TTTGACACAA AATGTAAACT AAATTATGAG CATCATTAGA     450

TACCTTGGGC CTTTTCAAAT CACACAGGGT CCTAGATCTG NNNNNNNNNN     500

NNNNNNNNNN NNNNNNNNNN NNNNNNNNNN NNNNNNNNNN NNNNNNNNNN     550

NACTTTGGAT TCTTATATCT TTGTCAGCTG TCAACTTCAG TGTTTTCAGG     600

NTAAATTCTA TCCATAGTCA TCCCAATATA CCTGCTTTAG ATGATACAAA     650

CTTCAAAAGA TCCGGCTCTC CCTCGTAAAA CGTGGAGGAC AGACATCAAG     700

GGGGTTTTCT GAGTAAAGAA AGGCAACCGC TCGGCAAAAA CTCACCCTGG     750

CACAACAGGA NCGAATATAT ACAGACGCTG ATTGAGCGTT TTGCTCCATC     800

TTCACTTCTG TTAAATGAAG ACATTGATAT CTAAAATGCT ATGAGTCTAA     850

CTTTGTAAAA TTAAAATAGA TTTGTAGTTA TTTTTCAAAA TGAAATCGAA     900

AAGATACAAG TTTTGAAGGC AGTCTCTTTT TCCACCCTGC CCCTCTAGTG     950

TGTTTTACAC ACTTCTCTGG CCACTCCAAC AGGGAAGCTG GTCCAGGGCC    1000

ATTATACAGG
```

The sequence of the CAP2 contig was used in a BLAST search of the human genome. 934 out of 1,010 residues aligned to a region of chromosome 21. A gap of 61 residues divided the aligned region into two smaller fragments. The sequence of this region, plus 100 kilobases on each side of it, was downloaded and analyzed using the Genscan site at MIT located on the web at genes.mit.edu/GENSCAN.html, with the following settings:
  Organism: vertebrate
  Suboptimal exon cutoff: 1.00 (no suboptimal exons)
  Print options: Predicted CDS and peptides
The fragment was found to fall within one of several predicted genes in the chromosome region. The bases corresponding to the predicted gene, including its predicted introns, were saved as a separate file and used to search GenBank again with BLASTN to find any ESTs or UniGene clusters identified by portions of the sequence not included in the original unknown fragment. The nr database contained no significant matches. At least 100 significant matches to various parts of the predicted gene were found in the dbEST database, but all of them were to unnamed cDNA clones. Comparison to UniGene produced fewer significant matches, but all matches were to unnamed cDNAs.

The peptide sequence predicted by Genscan was also saved. Multiple types of analyses were performed on it using the resources mentioned in Table 3. BLASTP and TBLASTN bases. No significant matches were found in any of these, so no gene identity or tertiary structure was discovered.

The peptide sequence was also searched for similarity to known domains and motifs using BLASTP with the Prosite, Blocks, Pfam, and ProDom databases. The searches produced no significant alignments to known domains. BLASTP comparison to the PRINTS database produced an alignment to the P450 protein family, but with a low probability of accuracy (e=6.9).

Two methods were used to predict secondary structure—the Garnier/Osguthorpe/Robson model and the Chou-Fasman model. The two methods differed somewhat in their results, but both produced representations of the peptide sequence with helical and sheet regions and locations of turns.

Antigenicity was plotted as a graph with amino acid number in the sequence on the x-axis and hydrophilicity on the y-axis. Several areas of antigenicity were observed, but only one with antigenicity greater than 2. Hydrophobicity was plotted in the same way. Only one region, from approximately residue 135 to residue 150, had notable hydrophobicity. TMpred, accessed through ExPASy, was used to predict transmembrane helices. No regions of the peptide sequence were predicted with reasonable confidence to be membrane-spanning helices.

NNPSL predicted that the putative protein would be found either in the nucleus (expected prediction accuracy=51.1%) or secreted from the cell (expected prediction accuracy=91.4%).

Example 7

Preparation of RNA from Mononuclear Cells for Expression Profiling

Blood was isolated from the subject for leukocyte expression profiling using the following methods:

Two tubes were drawn per patient. Blood was drawn from either a standard peripheral venous blood draw or directly from a large-bore intra-arterial or intravenous catheter inserted in the femoral artery, femoral vein, subclavian vein or internal jugular vein. Care was taken to avoid sample contamination with heparin from the intravascular catheters, as heparin can interfere with subsequent RNA reactions.

For each tube, 8 ml of whole blood was drawn into a tube (CPT, Becton-Dickinson order #362753) containing the anticoagulant Citrate, 25° C. density gradient solution (e.g. Ficoll, Percoll) and a polyester gel barrier that upon centrifugation was permeable to RBCs and granulocytes but not to mononuclear cells. The tube was inverted several times to mix the blood with the anticoagulant. The tubes were centrifuged at 1750×g in a swing-out rotor at room temperature for 20 minutes. The tubes were removed from the centrifuge and inverted 5-10 times to mix the plasma with the mononuclear cells, while trapping the RBCs and the granulocytes beneath the gel barrier. The plasma/mononuclear cell mix was decanted into a 15 ml tube and 5 ml of phosphate-buffered saline (PBS) is added. The 15 ml tubes were spun for 5 minutes at 1750×g to pellet the cells. The supernatant was discarded and 1.8 ml of RLT lysis buffer is added to the mononuclear cell pellet. The buffer and cells were pipetted up and down to ensure complete lysis of the pellet. The cell lysate was frozen and stored until it is convenient to proceed with isolation of total RNA.

Total RNA was purified from the lysed mononuclear cells using the Qiagen Rneasy Miniprep kit, as directed by the manufacturer (10/99 version) for total RNA isolation, including homogenization (Qiashredder columns) and on-column DNase treatment. The purified RNA was eluted in 50 ul of water.

Some samples were prepared by a different protocol, as follows:

Two 8 ml blood samples were drawn from a peripheral vein into a tube (CPT, Becton-Dickinson order #362753) containing anticoagulant (Citrate), 25° C. density gradient solution (Ficoll) and a polyester gel barrier that upon centrifugation is permeable to RBCs and granulocytes but not to mononuclear cells. The mononuclear cells and plasma remained above the barrier while the RBCs and granulocytes were trapped below. The tube was inverted several times to mix the blood with the anticoagulant, and the tubes were subjected to centrifugation at 1750×g in a swing-out rotor at room temperature for 20 min. The tubes were removed from the centrifuge, and the clear plasma layer above the cloudy mononuclear cell layer was aspirated and discarded. The cloudy mononuclear cell layer was aspirated, with care taken to rinse all of the mononuclear cells from the surface of the gel barrier with PBS (phosphate buffered saline). Approximately 2 mls of mononuclear cell suspension was transferred to a 2 ml microcentrifuge tube, and centrifuged for 3 min. at 16,000 rpm in a microcentrifuge to pellet the cells. The supernatant was discarded and 1.8 ml of RLT lysis buffer (Qiagen) were added to the mononuclear cell pellet, which lysed the cells and inactivated Rnases. The cells and lysis buffer were pipetted up and down to ensure complete lysis of the pellet. Cell lysate was frozen and stored until it was convenient to proceed with isolation of total RNA.

RNA samples were isolated from 8 mL of whole blood. Yields ranged from 2 ug to 20 ug total RNA for 8 mL blood. A260/A280 spectrophotometric ratios were between 1.6 and 2.0, indicating purity of sample. 2 ul of each sample were run on an agarose gel in the presence of ethidium bromide. No degradation of the RNA sample and no DNA contamination were visible.

In some cases, specific subsets of mononuclear cells were isolated from peripheral blood of human subjects. When this was done, the StemSep cell separation kits (manual version 6.0.0) were used from StemCell Technologies (Vancouver, Canada). This same protocol can be applied to the isolation of T cells, CD4 T cells, CD8 T cells, B cells, monocytes, NK cells and other cells. Isolation of cell types using negative selection with antibodies may be desirable to avoid activation of target cells by antibodies.

Example 8

Preparation of Universal Control RNA for Use in Leukocyte Expression Profiling

Control RNA was prepared using total RNA from Buffy coats and/or total RNA from enriched mononuclear cells isolated from Buffy coats, both with and without stimulation with ionomycin and PMA. The following control RNAs were prepared:

Control 1: Buffy Coat Total RNA
Control 2: Mononuclear cell Total RNA
Control 3: Stimulated buffy coat Total RNA
Control 4: Stimulated mononuclear Total RNA
Control 5: 50% Buffy coat Total RNA/50% Stimulated buffy coat Total RNA
Control 6: 50% Mononuclear cell Total RNA/50% Stimulated Mononuclear Total RNA.

Some samples were prepared using the following protocol: Buffy coats from 38 individuals were obtained from Stanford Blood Center. Each buffy coat is derived from ~350 mL whole blood from one individual. 10 ml buffy coat was removed from the bag, and placed into a 50 ml tube. 40 ml of Buffer EL (Qiagen) was added, the tube was mixed and placed on ice for 15 minutes, then cells were pelleted by centrifugation at 2000×g for 10 minutes at 4° C. The supernatant was decanted and the cell pellet was re-suspended in 10 ml of Qiagen Buffer EL. The tube was then centrifuged at 2000×g for 10 minutes at 4° C. The cell pellet was then re-suspended in 20 ml TRIZOL (GibcoBRL) per Buffy coat sample, the mixture was shredded using a rotary homogenizer, and the lysate was then frozen at −80° C. prior to proceeding to RNA isolation.

Other control RNAs were prepared from enriched mononuclear cells prepared from Buffy coats. Buffy coats from Stanford Blood Center were obtained, as described above. 10 ml buffy coat was added to a 50 ml polypropylene tube, and 10 ml of phosphate buffer saline (PBS) was added to each tube. A polysucrose (5.7 g/dL) and sodium diatrizoate (9.0 g/dL) solution at a 1.077+/−0.0001 g/ml density solution of equal volume to diluted sample was prepared (Histopaque 1077, Sigma cat. no 1077-1). This and all subsequent steps were performed at room temperature. 15 ml of diluted buffy coat/PBS was layered on top of 15 ml of the histopaque solution in a 50 ml tube. The tube was centrifuged at 400×g for 30 minutes at room temperature. After centrifugation, the upper layer of the solution to within 0.5 cm of the opaque interface containing the mononuclear cells was discarded. The opaque interface was transferred into a clean centrifuge tube. An equal volume of PBS was added to each tube and centrifuged at 350×g for 10 minutes at room temperature. The supernatant was discarded. 5 ml of Buffer EL (Qiagen) was used to resuspend the remaining cell pellet and the tube was centrifuged at 2000×g for 10 minutes at room temperature. The supernatant was discarded. The pellet was resuspended in 20 ml of TRIZOL (GibcoBRL) for each individual buffy coat that was processed. The sample was homogenized using a rotary homogenizer and frozen at −80 C until RNA was isolated.

RNA was isolated from frozen lysed Buffy coat samples as follows: frozen samples were thawed, and 4 ml of chloroform was added to each buffy coat sample. The sample was mixed by vortexing and centrifuged at 2000×g for 5 minutes. The aqueous layer was moved to new tube and then repurified by using the RNeasy Maxi RNA clean up kit, according to the manufacturer's instruction (Qiagen, PN 75162). The yield, purity and integrity were assessed by spectrophotometer and gel electrophoresis.

Some samples were prepared by a different protocol, as follows. The further use of RNA prepared using this protocol is described in Example 14.

50 whole blood samples were randomly selected from consented blood donors at the Stanford Medical School Blood Center. Each buffy coat sample was produced from ~350 mL of an individual's donated blood. The whole blood sample was centrifuged at 4,400×g for 8 minutes at room temperature, resulting in three distinct layers: a top layer of plasma, a second layer of buffy coat, and a third layer of red blood cells. 25 ml of the buffy coat fraction was obtained and diluted with an equal volume of PBS (phosphate buffered saline). 30 ml of diluted buffy coat was layered onto 15 ml of sodium diatrizoate solution adjusted to a density of 1.077+/−0.001 g/ml (Histopaque 1077, Sigma) in a 50 mL plastic tube. The tube was spun at 800 g for 10 minutes at room temperature. The plasma layer was removed to the 30 ml mark on the tube, and the mononuclear cell layer removed into a new tube and washed with an equal volume of PBS, and collected by centrifugation at 2000 g for 10 minutes at room temperature. The cell pellet was resuspended in 10 ml of Buffer EL (Qiagen) by vortexing and incubated on ice for 10 minutes to remove any remaining erthythrocytes. The mononuclear cells were spun at 2000 g for 10 minutes at 4 degrees Celsius. The cell pellet was lysed in 25 ml of a phenol/guanidinium thiocyanate solution (TRIZOL Reagent, Invitrogen). The sample was homogenized using a PowerGene 5 rotary homogenizer (Fisher Scientific) and Omini disposable generator probes (Fisher Scientific). The Trizol lysate was frozen at −80 degrees C. until the next step.

The samples were thawed out and incubated at room temperature for 5 minutes. 5 ml chloroform was added to each sample, mixed by vortexing, and incubated at room temperature for 3 minutes. The aqueous layers were transferred to new 50 ml tubes. The aqueous layer containing total RNA was further purified using the Qiagen RNeasy Maxi kit (PN 75162), per the manufacturer's protocol (October 1999). The columns were eluted twice with 1 ml Rnase-free water, with a minute incubation before each spin. Quantity and quality of RNA was assessed using standard methods. Generally, RNA was isolated from batches of 10 buffy coats at a time, with an average yield per buffy coat of 870 μg, and an estimated total yield of 43.5 mg total RNA with a 260/280 ratio of 1.56 and a 28S/18S ratio of 1.78.

Quality of the RNA was tested using the Agilent 2100 Bioanalyzer using RNA 6000 microfluidics chips. Analysis of the electrophorgrams from the Bioanalyzer for five different batches demonstrated the reproducibility in quality between the batches.

Total RNA from all five batches were combined and mixed in a 50 ml tube, then aliquoted as follows: 2×10 ml aliquots in 15 ml tubes, and the rest in 100 μl aliquots in 1.5 ml microcentrifuge tubes. The aliquots gave highly reproducible results with respect to RNA purity, size and integrity. The RNA was stored at −80° C.

Test Hybridization of Reference RNA.

Figure 4:
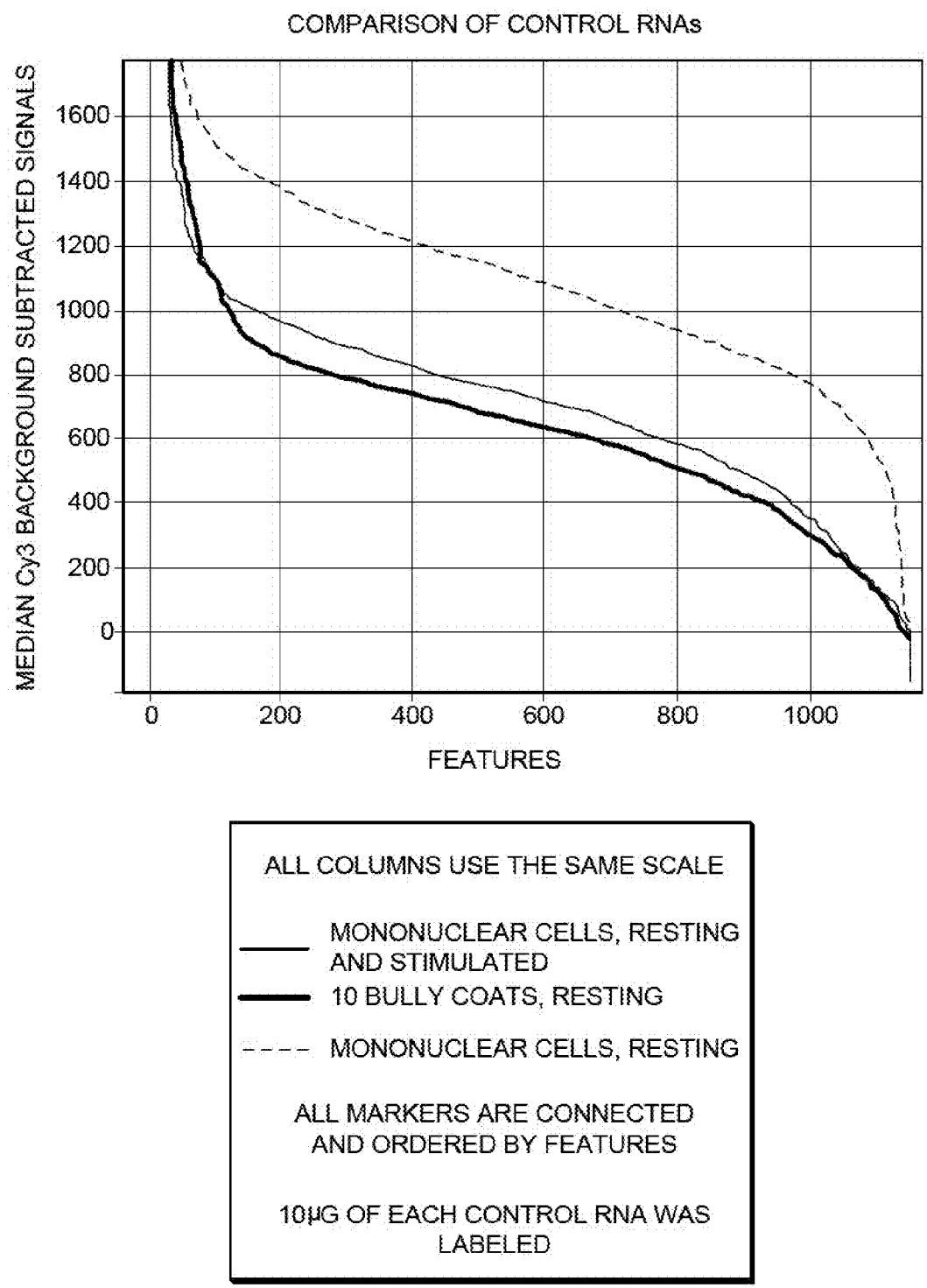
FIG. 4 depicts a graph comparing the median background subtracted expression signals for various leukocyte reference RNAs.

When compared with BC38 and Stimulated mononuclear reference samples, the R50 performed as well, if not better than the other reference samples as shown in FIG. 4.

In an analysis of hybridizations, where the R50 targets were fluorescently labeled with Cy-5 using methods described herein and the amplified and labeled aRNA was hybridized (as in example 14) to the olignoucleotide array described in example 13. The R50 detected 97.3% of probes with a Signal to Noise ratio (S/N) of greater than three and 99.9% of probes with S/N greater one.

Example 9

Identification of Diagnostic Oligonucleotides and Oligonucleotide Sets for Use in Monitoring Treatment and/or Progression of Rheumatoid Arthritis Rheumatoid arthritis (hereinafter, "RA") is a chronic and debilitating inflammatory arthritis. The diagnosis of RA is made by clinical criteria and radiographs. A new class of medication, TNF blockers, are effective, but the drugs are expensive, have side effects and not all patients respond to treatment. In addition, relief of disease symptoms does not always correlate with inhibition of joint destruction. For these reasons, an alternative mechanism for the titration of therapy is needed.

An observational study was conducted in which a cohort of patients meeting American College of Rheumatology (hereinafter "ARC") criteria for the diagnosis of RA was identified. Arnett et al. (1988) *Arthritis Rheum* 31:315-24. Patients gave informed consent and a peripheral blood mononuclear cell RNA sample was obtained by the methods as described herein. When available, RNA samples were also obtained from surgical specimens of bone or synovium from effected joints, and synovial fluid. Also, T-cells were isolated from the peripheral blood for some patients for expression analysis. This was done using the protocol given in Example 7.

From each patient, the following clinical information was obtained if available: Demographic information; information relating to the ACR criteria for RA; presence or absence of additional diagnoses of inflammatory and non-inflammatory conditions; data from laboratory test, including complete blood counts with differentials, CRP, ESR, ANA, Serum IL6, Soluble CD40 ligand, LDL, HDL, Anti-DNA antibodies, rheumatoid factor, C3, C4, serum creatinine and any medication levels; data from surgical procedures such as gross operative findings and pathological evaluation of resected tissues and biopsies; information on pharmacological therapy and treatment changes; clinical diagnoses of disease "flare"; hospitalizations; quantitative joint exams; results from health assessment questionnaires (HAQs); other clinical measures of patient symptoms and disability; physical examination results and radiographic data assessing joint involvement, synovial thickening, bone loss and erosion and joint space narrowing and deformity. In some cases, data includes pathological evaluation of synovial memebranes and joint tissues from RA and control patients. Pathology scoring systems were used to determine disease category, inflammation, type of inflammatory infiltrate, cellular and makeup of the synovial inflammation.

For some specimens of synovium, mononuclear cells or subsets of mononuclear cells (such as T cells) can be isolated for expression profiling. The relative number of lyphocyte subsets for some specimens can be determined by fluorescence activated cell sorting. Examples are determination of the CD4/CD8 T-cell ratio for a specimen. This information can be used as a variable to correlate to other outcomes or as an outcome for correlation analysis.

From these data, measures of improvement in RA are derived as exemplified by the ACR 20% and 50% response/improvement rates (Felson et al. 1996). Measures of disease activity over some period of time is derived from these data as are measures of disease progression. Serial radiography of effected joints is used for objective determination of progression (e.g., joint space narrowing, peri-articular osteoporosis, synovial thickening). Disease activity is determined from the clinical scores, medical history, physical exam, lab studies, surgical and pathological findings.

The collected clinical data (disease criteria) is used to define patient or sample groups for correlation of expression data. Patient groups are identified for comparison, for example, a patient group that possesses a useful or interesting clinical distinction, verses a patient group that does not possess the distinction. Examples of useful and interesting patient distinctions that can be made on the basis of collected clinical data are listed here:

Samples from patients during a clinically diagnosed RA flare versus samples from these same or different patients while they are asymptomatic.

Samples from patients who subsequently have high measures of disease activity versus samples from those same or different patients who have low subsequent disease activity.

Samples from patients who subsequently have high measures of disease progression versus samples from those same or different patients who have low subsequent disease progression.

Samples from patients who subsequently respond to a given medication or treatment regimen versus samples from those same or different patients who subsequently do not respond to a given medication or treatment regimen (for example, TNF pathway blocking medications).

Samples from patients with a diagnosis of osteoarthritis versus patients with rheumatoid arthritis.

Samples from patients with tissue biopsy results showing a high degree of inflammation versus samples from patients with lesser degrees of histological evidence of inflammation on biopsy.

Expression profiles correlating with progression of RA are identified. Subsets of the candidate library (or a previously identified diagnostic nucleotide set) are identified, according to the above procedures, that have predictive value for the progression of RA.

Diagnostic nucleotide set(s) are identified which predict respond to TNF blockade. Patients are profiled before and during treatment with these medications. Patients are followed for relief of symptoms, side effects and progression of joint destruction, e.g., as measured by hand radiographs. Expression profiles correlating with response to TNF blockade are identified. Subsets of the candidate library (or a previously identified diagnostic nucleotide set) are identified, according to the above procedures that have predictive value for response to TNF blockade.

Example 10

Identification of Diagnostic Oligonucleotide and Oligonucleotide Sets for Diagnosis of Systemic Lupus Erythematosis SLE is a chronic, systemic inflammatory disease characterized by dysregulation of the immune system. Clinical manifestations affect every organ system and include skin rash, renal dysfunction, CNS disorders, arthralgias and hematologic abnormalities. SLE clinical manifestations tend to both recur intermittently (or "flare") and progress over time, leading to permanent end-organ damage.

An observational study was conducted in which a cohort of patients meeting American College of Rheumatology (hereinafter "ACR") criteria for the diagnosis of SLE were identified. See Tan et al. (1982) Arthritis Rheum 25:1271-7. Patients gave informed consent and a peripheral blood mononuclear cell RNA sample or a peripheral T cell sample was obtained by the methods as described in example 7.

From each patient, the following clinical information was obtained if available: Demographic information, ACR criteria for SLE, additional diagnoses of inflammatory and non-inflammatory conditions, data from laboratory testing including complete blood counts with differentials, CRP, ESR, ANA, Serum IL6, Soluble CD40 ligand, LDL, HDL, Anti-DNA antibodies, rheumatoid factor, C3, C4, serum creatinine (and other measures of renal dysfunction), medication levels, data from surgical procedures such as gross operative findings and pathological evaluation of resected tissues and biopsies (e.g., renal, CNS), information on pharmacological therapy and treatment changes, clinical diagnoses of disease "flare", hospitalizations, quantitative joint exams, results from health assessment questionnaires (HAQs), SLEDAIs (a clinical score for SLE activity that assess many clinical variables; Bombadier C, Gladman D D, Urowitz M B, Caron D, Chang C H and the Committee on Prognosis Studies in SLE: Derivation of the SLEDAI for Lupus Patients. Arthritis Rheum 35:630-640, 1992), other clinical measures of patient symptoms and disability, physical examination results and carotid ultrasonography.

The collected clinical data (disease criteria) is used to define patient or sample groups for correlation of expression data. Patient groups are identified for comparison, for example, a patient group that possesses a useful or interesting clinical distinction, verses a patient group that does not possess the distinction. Measures of disease activity in SLE are derived from the clinical data described above to divide patients (and patient samples) into groups with higher and lower disease activity over some period of time or at any one point in time. Such data are SLEDAI scores and other clinical scores, levels of inflammatory markers or complement, number of hospitalizations, medication use and changes, biopsy results and data measuring progression of end-organ damage or end-organ damage, including progressive renal failure, carotid atherosclerosis, and CNS dysfunction.

Expression profiles correlating with progression of SLE are identified, including expression profiles corresponding to end-organ damage and progression of end-organ damage. Expression profiles are identified predicting disease progression or disease "flare", response to treatment or likelihood of response to treatment, predict likelihood of "low" or "high" disease measures (optionally described using the SLEDAI score), and presence or likelihood of developing premature carotid atherosclerosis. Subsets of the candidate library (or a previously identified diagnostic nucleotide set) are identified, according to the above procedures that have predictive value for the progression of SLE.

Further examples of useful and interesting patient distinctions that can be made on the basis of collected clinical data are listed here. Samples can be grouped and groups are compared to discover diagnostic gene sets:

1. Samples from patients during a clinically diagnosed SLE flare versus samples from these same or different patients while they are asymptomatic or while they have a documented infection.
2. Samples from patients who subsequently have high measures of disease activity versus samples from those same or different patients who have low subsequent disease activity.
3. Samples from patients who subsequently have high measures of disease progression versus samples from those same or different patients who have low subsequent disease progression.
4. Samples from patients who subsequently respond to a given medication or treatment regimen versus samples from those same or different patients who subsequently do not respond to a given medication or treatment regimen.
5. Samples from patients with premature carotid atherosclerosis on ultrasonography versus patients with SLE without premature atherosclerosis.

Identification of a Diagnostic Oligonucleotide or Oligonucleotide Set for Diagnosis of Lupus Mononuclear RNA samples were collected from patients with SLE and patients with Rheumatoid or Osteoarthritis (RA and OA) or controls using the protocol described in example 7. The patient diagnoses were determined using standard diagnostic algorithms such as those that are employed by the American College of Rheumatology (see example See Tan et al. (1982) *Arthritis Rheum* 25:1271-7; Arnett et al. (1988) *Arthritis Rheum* 31:315-24).

32 samples were included in the anaysis. 15 samples were derived from patients with a clinical diagnosis of SLE and the remainder were derived from patients with RA (9), OA (4) and subjects without known disease (4) who served as controls. Samples from patients with SLE or RA were classified as "Active" or "Controlled" (with respect to disease activity) by the patient's physician based on objective and subjective criteria, such as patient history, physical exam and lab studies. An attempt was made to match SLE patients and controls with respect to important variables such as medication use, sex, age and secondary diagnoses.

After preparation of RNA (example 7), amplification, labeling, hybridization, scanning, feature extraction and data processing were done as described in Example 14 using the oligonucleotide microarrays described in Example 13. The resulting log ratio of expression of Cy3 (patient sample)/Cy5 (R50 reference RNA) was used for analysis.

Initially, significance analysis for microarrays (SAM, Tusher 2001, Example 16) was used to discover that were differentially expressed between 7 of the Lupus samples and 17 control samples. 1 gene was identified that was expressed at a higher level in the lupus patients than in all controls. This gene had a 0.5% false detection rate using SAM. This means that there is statistically, a 99.5% chance that the gene is truly differentially expressed between the Lupus and control samples. This gene was oligonucleotide and SEQ ID #4637. The oligonucleotide: GCCTCTTGCTTGGCGTGATAAC-CCTGTCATCTTCCCAAAGCTCATTTATG detects a specific human gene: sialyltransferase (SIAT4A), Unigene: Hs.301698 Locus: NM_003033, GI: 4506950. Expression ratios for the gene are given for each sample in FIGS. 5A-B. The average fold change in expression between SLE and controls was 1.48.

When a larger data set was used, 15 SLE samples were compared to 17 controls. Using SAM, genes were identified as significantly differentially expressed between Lupus and controls. These genes and their FDRs are given in Table 10A. Supervised harvesting classification (X-Mine, Brisbane, Calif.) and CART (Salford Systems, San Diego Calif.) were also used on the same data to determine which set of genes best distinguish SLE from control samples (Example 16).

CART was used to build a decision tree for classification of samples as lupus or not lupus using the gene expression data from the arrays. The analysis identitifies sets of genes that can be used together to accurately identify samples derived from lupus patients. The set of genes and the identified threshold expression levels for the decision tree are referred to as "models". Multiple models for diagnosis of Lupus were derived by using different settings and parameters for the CART algorithm and using different sets of genes in the analysis. When using CART, it may be desirable to limit the number of independent variables. In the case of the genes on the arrays, a subset of ~8000 can be selected for analysis in CART based on significant differential expression discovered by using SAM or some other algorithm.

Model I was based on a data set consisting of thirty-two samples (fifteen SLE and seventeen non-SLE). These samples were used to derive the model and are referred to a the "training set'. Model I used the expression values for twenty-nine genes, which were found to be most significant in differentiating SLE and non-SLE samples in the analysis using SAM described above. SLE samples were designated as Class 1 and non-SLE samples were designated as Class 2. For this analysis, the following settings were used in the MODEL SETUP (CART, Salford Systems, San Diego, Calif.). In the Model settings, the tree type selected for the analysis was classification. In the Categorical settings, the default values were used. In the Testing settings, V-fold cross-validation was selected with a value of 10. In the Select Cases settings, the default values were used. In the Best Tree settings, the default values were used. In the Combine settings, the default values were used. In the Method settings, Symmetric Gini was selected as the type of classification tree and Linear combinations for splitting was also selected. The default values were used for the linear combinations. In the Advance Settings, the default values were used. In the Costs settings, the default values were used. In the Priors settings, Equal was selected as the priors for Class. In the penalty settings, the default values were used.

From this analysis, CART built two models, a two-gene model and a three-gene model (FIGS. 5C-E). The sensitivity and specificity for the identification of lupus in the training set samples of the two genes model were 100% and 94%, respectively. The sensitivity and specificity for the 10-fold cross validation set of the two-gene model were 100% and 88%, respectively, with a relative cost of 0.118. The sensitivity and specificity for the training set of the three genes model were 100% and 100%, respectively. The sensitivity and specificity for the 10-fold cross validation set of the three genes model were 93% and 94%, respectively, with a relative cost of 0.125.

Model II was based on a data set consisted of thirty-two samples, fifteen SLE and seventeen non-SLE (training set) and six thousand forty-four genes with expression values for at least 80% of the samples. The MODEL SETUP for the analysis of this data set was the same as for the analysis above, except for the following correction. In the Method settings, Linear combination for splitting was unchecked after the analysis yielded no classification tree. The change in the linear combination setting resulted in the following.

The sensitivity and specificity for the training set of the one gene model were 87% and 82%, respectively. The sensitivity and specificity for the 10-fold cross validation set of the one gene model were 80% and 59%, respectively, with a relative cost of 0.612. The sensitivity and specificity for the training set of the three genes model were 100% and 88%, respectively. The sensitivity and specificity for the 10-fold cross validation set of the three genes model were 67% and 65%, respectively, with a relative cost of 0.686. The sensitivity and specificity for the training set of the five genes model were 100% and 94%, respectively. The sensitivity and specificity for the 10-fold cross validation set of the five genes model were 67% and 59%, respectively, with a relative cost of 0.745. Results and models are summarized in FIGS. 5 C and F.

Those genes that were found to be useful for classification are noted in Table 10A.

These genes can be used alone or in association with other genes or variables to build a diagnostic gene set or a classification algorithm. These genes can be used in association with known gene markers for lupus (such as those identified in the prior art) to provide a diagnostic algorithm.

Primers for real-time PCR validation were designed for each of the genes as described in Example 15 and are listed in Table 10B.

Surrogates for some of the most useful genes were identified and are listed in Table 10C. Surrogates can be used in addition to or in place of a diagnostic gene in a method of detecting lupus or in diagnostic gene set. For genes that were splitters in CART, surrogates were identified and reported by the software. In these cases, the best available surrogates are listed. For other genes, hierarchical clustering of the data was performed with default settings (x-miner, X-mine, Brisbane, Calif.) and members of gene expression clusters were noted. A cluster was selected that included the gene of interest and the members of that cluster were recorded in Table 10C.

Example 11

Probe Selection for a 24,000 Feature Array

This Example describes the compilation of almost 8,000 unique genes and ESTs using sequences identified from the sources described below. The sequences of these genes and ESTs were used to design probes, as described in the following Example.

Tables 3A, 3B and 3C list the sequences identified in the subtracted leukocyte expression libraries. All sequences that were identified as corresponding to a known RNA transcript were represented at least once, and all unidentified sequences were represented twice—once by the sequence on file and again by the complementary sequence—to ensure that the sense (or coding) strand of the gene sequence was included.

Table 3A. Table 3A contained all those sequences in the subtracted libraries of example 1 that matched sequences in GenBank's nr, EST_Human, and UniGene databases with an acceptable level of confidence. All the entries in the table representing the sense strand of their genes were grouped together and all those representing the antisense strand were grouped. A third group contained those entries whose strand could not be determined. Two complementary probes were designed for each member of this third group.

Table 3B and 3C. Table 3B and 3C contained all those sequences in the leukocyte expression subtracted libraries of example 1 that did not match sequences in GenBank's nr, EST_Human, and UniGene databases with an acceptable level of confidence, but which had a high probability of representing real mRNA sequences. Sequences in Table 3B did not match anything in the databases above but matched regions of the human genome draft and were spatially clustered along it, suggesting that they were exons, rather than genomic DNA included in the library by chance. Sequences in Table 3C also aligned well to regions of the human genome draft, but the aligned regions were interrupted by genomic DNA, meaning they were likely to be spliced transcripts of multiple exon genes.

Table 3B lists 510 clones and Table 3C lists 48 clones that originally had no similarity with any sequence in the public databases. Blastn searches conducted after the initial filing have identified sequences in the public database with high similarity (E values less than 1e-40) to the sequences determined for these clones. Table 3B contained 272 clones and Table 3C contained 25 clones that were found to have high similarity to sequences in dbEST. The sequences of the similar dbEST clones were used to design probes. Sequences from clones that contained no similar regions to any sequence in the database were used to design a pair of complementary probes.

Probes were designed from database sequences that had the highest similarity to each of the sequenced clones in Tables 3A, 3B, and 3C. Based on BLASTn searches the most similar database sequence was identified by locus number and the locus number was submitted to GenBank using batch Entrez (located at the website ncbi.nlm.nih.gov/entrez/batchentrez.cgi?db=Nucleotide) to obtain the sequence for that locus. The GenBank entry sequence was used because in most cases it was more complete or was derived from multipass sequencing and thus would likely have fewer errors than the single pass cDNA library sequences. When only UniGene cluster IDs were available for genes of interest, the respective sequences were extracted from the UniGene_unique database, build 137, downloaded from NCBI (ftp://ncbi.nlm.nih.gov/repository/UniGene/). This database contains one representative sequence for each cluster in UniGene.

| Summary of library clones used in array probe design | | | |
|---|---|---|---|
| Table | Sense Strand | Antisnese Strand | Strand Undetermined |
| 3A | 3621 | 763 | 124 |
| 3B | 142 | 130 | 238 |
| 3C | 19 | 6 | 23 |
| Totals | 3782 | 899 | 385 |

Literature Searches

Example 2 describes searches of literature databases. We also searched for research articles discussing genes expressed only in leukocytes or involved in inflammation and particular disease conditions, including genes that were specifically expressed or down-regulated in a disease state. Searches included, but were not limited to, the following terms and various combinations of theses terms: inflammation, atherosclerosis, rheumatoid arthritis, osteoarthritis, lupus, SLE, allograft, transplant, rejection, leukocyte, monocyte, lymphocyte, mononuclear, macrophage, neutrophil, eosinophil, basophil, platelet, congestive heart failure, expression, profiling, microarray, inflammatory bowel disease, asthma, RNA expression, gene expression, granulocyte.

A UniGene cluster ID or GenBank accession number was found for each gene in the list. The strand of the corresponding sequence was determined, if possible, and the genes were divided into the three groups: sense (coding) strand, antisense strand, or strand unknown. The rest of the probe design process was carried out as described above for the sequences from the leukocyte subtracted expression library.

Database Mining

Database mining was performed as described in Example 2. In addition, the Library Browser at the NCBI UniGene web site (located on the web at ncbi.nlm.nih.gov/UniGene/lbrowse.cgi?ORG=Hs&DISPLAY=ALL) was used to identify genes that are specifically expressed in leukocyte cell populations. All expression libraries available at the time were examined and those derived from leukocytes were viewed individually. Each library viewed through the Library Browser at the UniGene web site contains a section titled "Shown below are UniGene clusters of special interest only" that lists genes that are either highly represented or found only in that library. Only the genes in this section were downloaded from each library. Alternatively, every sequence in each library is downloaded and then redundancy between libraries is reduced by discarding all UniGene cluster IDs that are represented more than once. A total of 439 libraries were downloaded, containing 35,819 genes, although many were found in more than one library. The most important libraries from the remaining set were separated and 3,914 genes remained. After eliminating all redundancy between these libraries and comparing the remaining genes to those listed in Tables 3A, 3B and 3C, the set was reduced to 2,573 genes in 35 libraries as shown in Table 4. From these, all genes in first 30 libraries were used to design probes. A random subset of genes was used from Library Lib.376, "Activated_T-cells_XX". From the last four libraries, a random subset of sequences listed as "ESTs, found only in this library" was used.

Angiogenesis Markers 215 sequences derived from an angiogenic endothelial cell subtracted cDNA library obtained from Stanford University were used for probe design. Briefly, using well known subtractive hybridization procedures, (as described in, e.g., U.S. Pat. Nos. 5,958,738; 5,589,339; 5,827,658; 5,712,127; 5,643,761; 5,565,340) modified to normalize expression by suppressing over-representation of abundant RNA species while increasing representation of rare RNA species, a library was produced that is enriched for RNA species (messages) that are differentially expressed between test (stimulated) and control (resting) HUVEC populations. The subtraction/suppression protocol was performed as described by the kit manufacturer (Clontech, PCR-select cDNA Subtraction Kit).

Pooled primary HUVECs (Clonetics) were cultured in 15% FCS, M199 (GibcoBRL) with standard concentrations of Heparin, Penicillin, Streptomycin, Glutamine and Endothelial Cell Growth Supplement. The cells were cultured on 1% gelatin coated 10 cm dishes. Confluent HUVECs were photographed under phase contrast microscopy. The cells formed a monolayer of flat cells without gaps. Passage 2-5 cells were used for all experiments. Confluent HUVECs were treated with trypsin/EDTA and seeded onto collagen gels. Collagen gels were made according to the protocol of the Collagen manufacturer (Becton Dickinson Labware). Collagen gels were prepared with the following ingredients: Rat tail collagen type I (Collaborative Biomedical) 1.5 mg/mL, mouse laminin (Collaborative Biomedical) 0.5 mg/mL, 10% 10× media 199 (Gibco BRL). 1N NaOH, 10×PBS and sterile water were added in amounts recommended in the protocol. Cell density was measured by microscopy. $1.2 \times 10^6$ cells were seeded onto gels in 6-well, 35 mm dishes, in 5% FCS M199 media. The cells were incubated for 2 hrs at 37 C with 5% $CO_2$. The media was then changed to the same media with the addition of VEGF (Sigma) at 30 ng/mL media. Cells were cultured for 36 hrs. At 12, 24 and 36 hrs, the cells were observed with phase contrast microscopy. At 36 hours, the cells were observed elongating, adhering to each other and forming lumen structures. At 12 and 24 hrs media was aspirated and refreshed. At 36 hrs, the media was aspirated, the cells were rinsed with PBS and then treated with Collagenase (Sigma) 2.5 mg/mL PBS for 5 min with active agitation until the collagen gels were liquefied. The cells were then centrifuged at 4 C, 2000 g for 10 min. The supernatant was removed and the cells were lysed with 1 mL Trizol Reagent (Gibco) per $5 \times 10^6$ cells. Total RNA was prepared as specified in the Trizol instructions for use. mRNA was then isolated as described in the micro-fast track mRNA isolation protocol from Invitrogen. This RNA was used as the tester RNA for the subtraction procedure.

Ten plates of resting, confluent, p4 HUVECs, were cultured with 15% FCS in the M199 media described above. The media was aspirated and the cells were lysed with 1 mL Trizol and total RNA was prepared according to the Trizol protocol. mRNA was then isolated according to the micro-fast track mRNA isolation protocol from Invitrogen. This RNA served as the control RNA for the subtraction procedure.

The entire subtraction cloning procedure was carried out as per the user manual for the Clontech PCR Select Subtraction Kit. The cDNAs prepared from the test population of HUVECs were divided into "tester" pools, while cDNAs prepared from the control population of HUVECs were designated the "driver" pool. cDNA was synthesized from the tester and control RNA samples described above. Resulting cDNAs were digested with the restriction enzyme RsaI. Unique double-stranded adapters were ligated to the tester cDNA. An initial hybridization was performed consisting of the tester pools of cDNA (with its corresponding adapter) and an excess of the driver cDNA. The initial hybridization results in a partial normalization of the cDNAs such that high and low abundance messages become more equally represented following hybridization due to a failure of driver/tester hybrids to amplify.

A second hybridization involved pooling unhybridized sequences from the first hybridization together with the addition of supplemental driver cDNA. In this step, the expressed sequences enriched in the two tester pools following the initial hybridization can hybridize. Hybrids resulting from the hybridization between members of each of the two tester pools are then recovered by amplification in a polymerase chain reaction (PCR) using primers specific for the unique adapters. Again, sequences originating in a tester pool that form hybrids with components of the driver pool are not amplified. Hybrids resulting between members of the same tester pool are eliminated by the formation of "panhandles" between their common 5' and 3' ends. The subtraction was done in both directions, producing two libraries, one with clones that are upregulated in tube-formation and one with clones that are down-regulated in the process.

The resulting PCR products representing partial cDNAs of differentially expressed genes were then cloned (i.e., ligated) into an appropriate vector according to the manufacturer's protocol (pGEM-Teasy from Promega) and transformed into competent bacteria for selection and screening. Colonies (2180) were picked and cultured in LB broth with 50 ug/mL ampicillin at 37 C overnight. Stocks of saturated LB+50 ug/mL ampicillin and 15% glycerol in 96-well plates were stored at −80 C. Plasmid was prepared from 1.4 mL saturated LB broth containing 50 ug/mL ampicillin. This was done in a 96 well format using commercially available kits according to the manufacturer's recommendations (Qiagen 96-turbo prep).

2 probes to represent 22 of these sequences required, therefore, a total of 237 probes were derived from this library.

Viral Genes

Several viruses may play a role in a host of disease including inflammatory disorders, atherosclerosis, and transplant rejection. Table 12 lists the viral genes represented by oligonucleotide probes on the microarray. Low-complexity regions in the sequences were masked using RepeatMasker before using them to design probes.

Strand Selection

It was necessary to design sense oligonucleotide probes because the labeling and hybridization protocol to be used with the microarray results in fluorescently-labeled antisense cRNA. All of the sequences we selected to design probes could be divided into three categories:

(1) Sequences known to represent the sense strand
(2) Sequences known to represent the antisense strand
(3) Sequences whose strand could not be easily determined from their descriptions It was not known whether the sequences from the leukocyte subtracted expression library were from the sense or antisense strand. GenBank sequences are reported with sequence given 5' to 3', and the majority of the sequences we used to design probes came from accession numbers with descriptions that made it clear whether they represented sense or antisense sequence. For example, all sequences containing "mRNA" in their descriptions were understood to be the sequences of the sense mRNA, unless otherwise noted in the description, and all IMAGE Consortium clones are directionally cloned and so the direction (or sense) of the reported sequence can be determined from the annotation in the GenBank record.

For accession numbers representing the sense strand, the sequence was downloaded and masked and a probe was designed directly from the sequence. These probes were selected as close to the 3' end as possible. For accession numbers representing the antisense strand, the sequence was downloaded and masked, and a probe was designed complementary to this sequence. These probes were designed as close to the 5' end as possible (i.e., complementary to the 3' end of the sense strand).

Minimizing Probe Redundancy.

Multiple copies of certain genes or segments of genes were included in the sequences from each category described above, either by accident or by design. Reducing redundancy within each of the gene sets was necessary to maximize the number of unique genes and ESTs that could be represented on the microarray.

Three methods were used to reduce redundancy of genes, depending on what information was available. First, in gene sets with multiple occurrences of one or more UniGene numbers, only one occurrence of each UniGene number was kept. Next, each gene set was searched by GenBank accession numbers and only one occurrence of each accession number was conserved. Finally, the gene name, description, or gene symbol were searched for redundant genes with no UniGene number or different accession numbers. In reducing the redundancy of the gene sets, every effort was made to conserve the most information about each gene.

We note, however, that the UniGene system for clustering submissions to GenBank is frequently updated and UniGene cluster IDs can change. Two or more clusters may be combined under a new cluster ID or a cluster may be split into several new clusters and the original cluster ID retired. Since the lists of genes in each of the gene sets discussed were assembled at different times, the same sequence may appear in several different sets with a different UniGene ID in each.

Sequences from Table 3A were treated differently. In some cases, two or more of the leukocyte subtracted expression library sequences aligned to different regions of the same GenBank entry, indicating that these sequences were likely to be from different exons in the same gene transcript. In these cases, one representative library sequence corresponding to each presumptive exon was individually listed in Table 3A.

Compilation.

After redundancy within a gene set was sufficiently reduced, a table of approximately 8,000 unique genes and ESTs was compiled in the following manner. All of the entries in Table 3A were transferred to the new table. The list of genes produced by literature and database searches was added, eliminating any genes already contained in Table 3A. Next, each of the remaining sets of genes was compared to the table and any genes already contained in the table were deleted from the gene sets before appending them to the table.

| Subtracted Leukocyte Expression Library | Probes |
| --- | --- |
| Table 3A | 4,872 |
| Table 3B | 796 |
| Table 3C | 85 |
| Literature Search Results | 494 |
| Database Mining | 1,607 |
| Viral genes | |
| a. CMV | 14 |
| b. EBV | 6 |
| c. HHV 6 | 14 |
| d. Adenovirus | 8 |
| Angiogenesis markers: 215, 22 of which needed two probes | 237 |
| *Arabidopsis thaliana* genes | 10 |
| Total sequences used to design probes | 8,143 |

Example 12

Design of Oligonucleotide Probes

By way of example, this section describes the design of four oligonucleotide probes using Array Designer Ver 1.1 (Premier Biosoft International, Palo Alto, Calif.). The major steps in the process are given first.

1) Obtain best possible sequence of mRNA from GenBank. If a full-length sequence reference sequence is not available, a partial sequence is used, with preference for the 3' end over the 5' end. When the sequence is known to represent the antisense strand, the reverse complement of the sequence is used for probe design. For sequences represented in the subtracted leukocyte expression library that have no significant match in GenBank at the time of probe design, our sequence is used.

2) Mask low complexity regions and repetitive elements in the sequence using an algorithm such as RepeatMasker.

3) Use probe design software, such as Array Designer, version 1.1, to select a sequence of 50 residues with specified physical and chemical properties. The 50 residues nearest the 3' end constitute a search frame. The residues it contains are tested for suitability. If they don't meet the specified criteria, the search frame is moved one residue closer to the 5' end, and the 50 residues it now contains are tested. The process is repeated until a suitable 50-mer is found.

4) If no such 50-mer occurs in the sequence, the physical and chemical criteria are adjusted until a suitable 50-mer is found.

5) Compare the probe to dbEST, the UniGene cluster set, and the assembled human genome using the BLASTn search tool at NCBI to obtain the pertinent identifying information and to verify that the probe does not have significant similarity to more than one known gene.

Clone 40H12

Clone 40H12 was sequenced and compared to the nr, dbEST, and UniGene databases at NCBI using the BLAST search tool. The sequence matched accession number NM_002310, a 'curated RefSeq project' sequence, see Pruitt et al. (2000) *Trends Genet.* 16:44-47, encoding leukemia inhibitory factor receptor (LIFR) mRNA with a reported E value of zero. An E value of zero indicates there is, for all practical purposes, no chance that the similarity was random based on the length of the sequence and the composition and size of the database. This sequence, cataloged by accession number NM_002310, is much longer than the sequence of clone 40H12 and has a poly-A tail. This indicated that the sequence cataloged by accession number NM_002310 is the sense strand and a more complete representation of the mRNA than the sequence of clone 40H12, especially at the 3' end. Accession number "NM_002310" was included in a text file of accession numbers representing sense strand mRNAs, and sequences for the sense strand mRNAs were obtained by uploading a text file containing desired accession numbers as an Entrez search query using the Batch Entrez web interface and saving the results locally as a FASTA file. The following sequence was obtained, and the region of alignment of clone 401-112 is outlined:

```
CTCTCTCCCAGAACGTGTCTCTGCTGCAAGGCACCGGGCCCTTTCGCTCTGCAGAACTGC

ACTTGCAAGACCATTATCAACTCCTAATCCCAGCTCAGAAAGGGAGCCTCTGCGACTCAT

TCATCGCCCTCCAGGACTGACTGCATTGCACAGATGATGGATATTTACGTATGTTTGAAA

CGACCATCCTGGATGGTGGACAATAAAAGAATGAGGACTGCTTCAAATTTCCAGTGGCTG

TTATCAACATTTATTCTTCTATATCTAATGAATCAAGTAAATAGCCAGAAAAAGGGGGCT

CCTCATGATTTGAAGTGTGTAACTAACAATTTGCAAGTGTGGAACTGTTCTTGGAAAGCA

CCCTCTGGAACAGGCCGTGGTACTGATTATGAAGTTTGCATTGAAAACAGGTCCCGTTCT

TGTTATCAGTTGGAGAAAACCAGTATTAAAATTCCAGCTCTTTCACATGGTGATTATGAA

ATAACAATAAATTCTCTACATGATTTTGGAAGTTCTACAAGTAAATTCACACTAAATGAA

CAAAACGTTTCCTTAATTCCAGATACTCCAGAGATCTTGAATTTGTCTGCTGATTTCTCA

ACCTCTACATTATACCTAAAGTGGAACGACAGGGGTTCAGTTTTTCCACACCGCTCAAAT

GTTATCTGGGAAATTAAAGTTCTACGTAAAGAGAGTATGGAGCTCGTAAAATTAGTGACC

CACAACACAACTCTGAATGGCAAAGATACACTTCATCACTGGAGTTGGGCCTCAGATATG

CCCTTGGAATGTGCCATTCATTTTGTGGAAATTAGATGCTACATTGACAATCTTCATTTT

TCTGGTCTCGAAGAGTGGAGTGACTGGAGCCCTGTGAAGAACATTTCTTGGATACCTGAT

TCTCAGACTAAGGTTTTTCCTCAAGATAAAGTGATACTTGTAGGCTCAGACATAACATTT

TGTTGTGTGAGTCAAGAAAAAGTGTTATCAGCACTGATTGGCCATACAAACTGCCCCTTG

ATCCATCTTGATGGGAAAATGTTGCAATCAAGATTCGTAATATTTCTGTTTCTGCAAGT

AGTGGAACAAATGTAGTTTTTACAACCGAAGATAACATATTTGGAACCGTTATTTTGCT

GGATATCCACCAGATACTCCTCAACAACTGAATTGTGAGACACATGATTTAAAAGAAATT

ATATGTAGTTGGAATCCAGGAAGGGTGACAGCGTTGGTGGGCCCACGTGCTACAAGCTAC

ACTTTAGTTGAAAGTTTTTCAGGAAAATATGTTAGACTTAAAAGAGCTGAAGCACCTACA

AACGAAAGCTATCAATTATTATTTCAAATGCTTCCAAATCAAGAAATATATAATTTTACT

TTGAATGCTCACAATCCGCTGGGTCGATCACAATCAACAATTTTAGTTAATATAACTGAA

AAAGTTTATCCCCATACTCCTACTTCATTCAAAGTGAAGGATATTAATTCAACAGCTGTT

AAACTTTCTTGGCATTTACCAGGCAACTTTGCAAAGATTAATTTTTTATGTGAAATTGAA
```

-continued

```
ATTAAGAAATCTAATTCAGTACAAGAGCAGCGGAATGTCACAATCAAGGAGTAGAAAAT

TCAAGTTATCTTGTTGCTCTGGACAAGTTAAATCCATACACTCTATATACTTTTCGGATT

CGTTGTTCTACTGAAACTTTCTGGAAATGGAGCAAATGGAGCAATAAAAAACAACATTTA

ACAACAGAAGCCAGTCCTTCAAAGGGGCCTGATACTTGGAGAGAGTGGAGTTCTGATGGA

AAAAATTTAATAATCTATTGGAAGCCTTTACCCATTAATGAAGCTAATGGAAAAATACTT

TCCTACAATGTATCGTGTTCATCAGATGAGGAAACACAGTCCCTTTCTGAAATCCCTGAT

CCTCAGCACAAAGCAGAGATACGACTTGATAAGAATGACTACATCATCAGCGTAGTGGCT

AAAAATTCTGTGGGCTCATCACCACCTTCCAAAATAGCGAGTATGGAAATTCCAAATGAT

GATCTCAAAATAGAACAAGTTGTTGGGATGGGAAAGGGGATTCTCCTCACCTGGCATTAC

GACCCCAACATGACTTGCGACTACGTCATTAAGTGGTGTAACTCGTCTCGGTCGGAACCA

TGCCTTATGGACTGGAGAAAAGTTCCCTCAAACAGCACTGAAACTGTAATAGAATCTGAT

GAGTTTCGACCAGGTATAAGATATAATTTTTTCCTGTATGGATGCAGAAATCAAGGATAT

CAATTATTACGCTCCATGATTGGATATATAGAAGAATTGGCTCCCATTGTTGCACCAAAT

TTTACTGTTGAGGATACTTCTGCAGATTCGATATTAGTAAAATGGGAAGACATTCCTGTG

GAAGAACTTAGAGGCTTTTTAAGAGGATATTTGTTTTACTTTGGAAAAGGAGAAAGAGAC

ACATCTAAGATGAGGGTTTTAGAATCAGGTCGTTCTGACATAAAAGTTAAGAATATTACT

GACATATCCCAGAAGACACTGAGAATTGCTGATCTTCAAGGTAAAACAAGTTACCACCTG

GTCTTGCGAGCCTATACAGATGGTGGAGTGGGCCCGGAGAAGAGTATGTATGTGGTGACA

AAGGAAAATTCTGTGGGATTAATTATTGCCATTCTCATCCCAGTGGCAGTGGCTGTCATT

GTTGGAGTGGTGACAAGTATCCTTTGCTATCGGAAACGAGAATGGATTAAAGAAACCTTC

TACCCTGATATTCCAAATCCAGAAAACTGTAAAGCATTACAGTTTCAAAAGAGTGTCTGT

GAGGGAAGCAGTGCTCTTAAAACATTGGAAATGAATCCTTGTACCCCAAATAATGTTGAG

GTTCTGGAAACTCGATCAGCATTTCCTAAAATAGAAGATACAGAAATAATTTCCCCAGTA

GCTGAGCGTCCTGAAGATCGCTCTGATGCAGAGCCTGAAAACCATGTGGTTGTGTCCTAT

TGTCCACCCATCATTGAGGAAGAAATACCAAACCCAGCCGCAGATGAAGCTGGAGGGACT

GCAAGGTTATTTACATTGATGTTCAGTCGATGTATCAGCCTCAAGCAAAACCAGAAGAA

GAACAAGAAAATGACCCTGTAGGAGGGGCAGGTATAAGCCACAGATGCACCTCCCCATT

AATTCTACTGTGGAAGATATAGCTGCAGAAGAGGACTTAGATAAAACTGCGGGTTACAGA

CCTCAGGCCAATGTAAATACATGGAATTTAGTGTCTCCAGACTCTCCTAGATCCATAGAC

AGCAACAGTGAGATTGTCTCATTTGGAAGTCCATGCTCCATTAATTCCCGACAATTTTTG

ATTCCTCCTAAAGATGAAGACTCTCCTAAATCTAATGGAGGAGGGTGGTCCTTTACAAAC

TTTTTTCAGAACAAACCAAACGATTAACAGTGTCACCGTGTCACTTCAGTCAGCCATCTC

AATAAGCTCTTACTGCTAGTGTTGCTACATCAGCACTGGGCATTCTTGGAGGGATCCTGT

GAAGTATTGTTAGGAGGTGAACTTCACTACATGTTAAGTTACACTGAAAGTTCATGTGCT

TTTAATGTAGTCTAAAAGCCAAAGTATAGTGACTCAGAATCCTCAATCCACAAAACTCAA

GATTGGGAGCTCTTTGTGATCAAGCCAAAGAATTCTCATGTACTCTACCTTCAAGAAGCA
```

-continued

```
TTTCAAGGCTAATACCTACTTGTACGTACATGTAAAACAAATCCCGCCGCAACTGTTTTC

TGTTCTGTTGTTTGTGGTTTTCTCATATGTATACTTGGTGGAATTGTAAGTGGATTTGCA

GGCCAGGGAGAAAATGTCCAAGTAACAGGTGAAGTTTATTTGCCTGACGTTTACTCCTTT

CTAGATGAAAACCAAGCACAGATTTTAAAACTTCTAAGATTATTCTCCTCTATCCAGAGC

ATTCACAAAAATTAATATAATTTTTAATGTAGTGACAGCGATTTAGTGTTTTGTTTGATA

AAGTATGCTTATTTCTGTGCCTACTGTATAATGGTTATCAAACAGTTGTCTCAGGGGTAC

AAACTTTGAAAACAAGTGTGACACTGACCAGCCCAAAT|CATAATCATGTTTTCTTGCTGT|

|GATAGGTTTTGCTTGCCTTTTCATTATTTTTTAGCTTTTATGCTTGCTTCCATTATTTCA|

|GTTGGTTGCCCTAATATTTAAAATTTACACTTCTAAGACTAGAGACCCACATTTTTTAAA|

|AATCATTTTATTTTGTGATACAGTGACAGCTTTATATGAGCAAATTCAATATTATTCATA|

|AGCATGTAATTCCAGTGACTTACTATGTGAGATGACTACTAAGCAATATCTAGCAGCGTT|

|AGTTCCATATAGTTCTGATTGGATTTCGTTCCTCCTGAGGAGACCATGCCGTTGAGCTTG|

|GCTACCCAGGCAGTGGTGATCTTTGACACCTTCTGGTGGATGTTCCTCCCACTCATGAGT|

|CTTTTCATCATGCCACATTATCTGATCCAGTCCTCACATTTTTAAATATAAAACTAAAGA|

|GAGAATGCTTCTTACAGGAACAGTTACCCAAGGGCTGTTTCTTAGTAACTGTCATAAACT|

|GATCTGGATCCATGGGCATACCTGTGTTCGAGGTGCAGCAATTGCTTGGTGAGCTGTGCA|

|GAATTGATTGCCTTCAGCACAGCATCCTCTGCCCACCCTTGTTTCTCATAAGCGATGTCT|

|GGAGTGATTGTGGTTCTTGGAAAAGCAGAAGGAAAAACTAAAAAGTGTATCTTGTATTTT|

|CCCTGCC|CCTCAGGTTGCCTATGTATTTTACCTTTTCATATTTAAGGCAAAAGTACTTGAA

AATTTTAAGTGTCCGAATAAGATATGTCTTTTTTGTTTGTTTTTTTTGGTTGGTTGTTTG

TTTTTTATCATCTGAGATTCTGTAATGTATTTGCAAATAATGGATCAATTAATTTTTTTT

GAAGCTCATATTGTATCTTTTTAAAAACCATGTTGTGGAAAAAAGCCAGAGTGACAAGTG

ACAAAATCTATTTAGGAACTCTGTGTATGAATCCTGATTTTAACTGCTAGGATTCAGCTA

AATTTCTGAGCTTTATGATCTGTGGAAATTTGGAATGAAATCGAATTCATTTTGTACATA

CATAGTATATTAAAACTATATAATAGTTCATAGAAATGTTCAGTAATGAAAAAATATATC

CATAGTATATTAAAACTATATAATAGTTCATAGAAATGTTCAGTAATGAAAAAATATATC

CAATCAGAGCCATCCCGAAAAAAAAAAAAAAA (SEQ ID NO: 8827)
```

The FASTA file, including the sequence of NM_002310, was masked using the RepeatMasker web interface (Smit, AFA & Green, P RepeatMasker at genome.washington.edu/RM/RepeatMasker.html, Smit and Green). Specifically, during masking, the following types of sequences were replaced with "N's": SINE/MIR & LINE/L2, LINE/L1, LTR/MaLR, LTR/Retroviral, Alu, and other low informational content sequences such as simple repeats. Below is the sequence following masking:

```
CTCTCTCCCAGAACGTGTCTCTGCTGCAAGGCACCGGGCCCTTTCGCTCTGCAGAACTG

CACTTGCAAGACCATTATCAACTCCTAATCCCAGCTCAGAAAGGGAGCCTCTGCGACTC
```

-continued

```
ATTCATCGCCCTCCAGGACTGACTGCATTGCACAGATGATGGATATTTACGTATGTTTG

AAACGACCATCCTGGATGGTGGACAATAAAAGAATGAGGACTGCTTCAAATTTCCAGTG

GCTGTTAATCAACATTTATTCTTCTATATCTAATGAATCAAGTAAATAGCCAGAAAAAGG

GGGCTCCTCATGATTTGAAGTGTGTAACTAACAATTTGCAAGTGTGGAACTGTTCTTGG

AAAGCACCCTCTGGAACAGGCCGTGGTACTGATTATGAAGTTTGCATTGAAAACAGGTC

CCGTTCTTGTTATCAGTTGGAGAAAACCAGTATTAAAATTCCAGCTCTTTCACATGGTG

ATTATGAAATAACAATAAATTCTCTACATGATTTTGGAAGTTCTACAAGTAAATTCACA

CTAAATGAACAAAACGTTTCCTTAATTCCAGATACTCCAGAGATCTTGAATTTGTCTGC

TGATTTCTCAACCTCTACATTATACCTAAAGTGGAACGACAGGGGTTCAGTTTTTCCAC

ACCGCTCAAATGTTATCTGGGAAATTAAAGTTCTACGTAAAGAGAGTATGGAGCTCGTA

AAATTAGTGACCCACAACACAACTCTGAATGGCAAAGATACACTTCATCACTGGAGTTG

GGCCTCAGATATGCCCTTGGAATGTGCCATTCATTTTGTGGAAATTAGATGCTACATTG

ACAATCTTCATTTTTCTGGTCTCGAAGAGTGGAGTGACTGGAGCCCTGTGAAGAACATT

TCTTGGATACCTGATTCTCAGACTAAGGTTTTTCCTCAAGATAAAGTGATACTTGTAGG

CTCAGACATAACATTTTGTTGTGTGAGTCAAGAAAAAGTGTTATCAGCACTGATTGGCC

ATACAAACTGCCCCTTGATCCATCTTGATGGGGAAAATGTTGCAATCAAGATTCGTAAT

ATTTCTGTTTCTGCAAGTAGTGGAACAAATGTAGTTTTTACAACCGAAGATAACATATT

TGGAACCGTTATTTTTGCTGGATATCCACCAGATACTCCTCAACAACTGAATTGTGAGA

CACATGATTTAAAAGAAATTATATGTAGTTGGAATCCAGGAAGGGTGACAGCGTTGGTG

GGCCCACGTGCTACAAGCTACACTTTAGTTGAAAGTTTTTCAGGAAAAATATGTTAGACT

TAAAAGAGCTGAAGCACCTACAAACGAAAGCTATCAATTATTATTTCAAATGCTTCCAA

ATCAAGAAATATATAATTTTACTTTGAATGCTCACAATCCGCTGGGTCGATCACAATCA

ACAATTTTAGTTAATATAACTGAAAAAGTTTATCCCCATACTCCTACTTCATTCAAAGT

GAAGGATATTAATTCAACAGCTGTTAAACTTTCTTGGCATTTACCAGGCAACTTTGCAA

AGATTAATTTTTTATGTGAAATTGAAATTAAGAAATCTAATTCAGTACAAGAGCAGCGG

AATGTCACAATCAAAGGAGTAGAAAATTCAAGTTATCTTGTTGCTCTGGACAAGTTAAA

TCCATACACTCTATATACTTTTCGGATTCGTTGTTCTACTGAAACTTTCTGGAAATGGA

GCAAATGGAGCAATAAAAAACAACATTTAACAACAGAAGCCAGTCCTTCAAAGGGGCCT

GATACTTGGAGAGAGTGGAGTTCTGATGGAAAAAATTTAATAATCTATTGGAAGCCTTT

ACCCATTAATGAAGCTAATGGAAAAATACTTTCCTACAATGTATCGTGTTCATCAGATG

AGGAAACACAGTCCCTTTCTGAAATCCCTGATCCTCAGCACAAAGCAGAGATACGACTT

GATAAGAATGACTACATCATCAGCGTAGTGGCTAAAAATTCTGTGGGCTCATCACCACC

TTCCAAAATAGCGAGTATGGAAATTCCAAATGATGATCTCAAAATAGAACAAGTTGTTG

GGATGGGAAGGGGATTCTCCTCACCTGGCATTACGACCCCAACATGACTTGCGACTAC

GTCATTAAGTGGTGTAACTCGTCTCGGTCGGAACCATGCCTTATGGACTGGAGAAAAGT

TCCCTCAAACAGCACTGAAACTGTAATAGAATCTGATGAGTTTCGACCAGGTATAAGAT
```

```
ATAATTTTTTCCTGTATGGATGCAGAAATCAAGGATATCAATTATTACGCTCCATGATT
GGATATATAGAAGAATTGGCTCCCATTGTTGCACCAAATTTTACTGTTGAGGATACTTC
TGCAGATTCGATATTAGTAAAATGGGAAGACATTCCTGTGGAAGAACTTAGAGGCTTTT
TAAGAGGATATTTGTTTTACTTTGGAAAAGGAGAAAGAGACACATCTAAGATGAGGGTT
TTAGAATCAGGTCGTTCTGACATAAAAGTTAAGAATATTACTGACATATCCCAGAAGAC
ACTGAGAATTGCTGATCTTCAAGGTAAAACAAGTTACCACCTGGTCTTGCGAGCCTATA
CAGATGGTGGAGTGGGCCCGGAGAAGAGTATGTATGTGGTGACAAAGGAAAATTCTGTG
GGATTAATTATTGCCATTCTCATCCCAGTGGCAGTGGCTGTCATTGTTGGAGTGGTGAC
AAGTATCCTTTGCTATCGGAAACGAGAATGGATTAAAGAAACCTTCTACCCTGATATTC
CAAATCCAGAAAACTGTAAAGCATTACAGTTTCAAAAGAGTGTCTGTGAGGGAAGCAGT
GCTCTTAAAACATTGGAAATGAATCCTTGTACCCCAAATAATGTTGAGGTTCTGGAAAC
TCGATCAGCATTTCCTAAAATAGAAGATACAGAAATAATTTCCCCAGTAGCTGAGCGTC
CTGAAGATCGCTCTGATGCAGAGCCTGAAAACCATGTGGTTGTGTCCTATTGTCCACCC
ATCATTGAGGAAGAAATACCAAACCCAGCCGCAGATGAAGCTGGAGGGACTGCACAGGT
TATTTACATTGATGTTCAGTCGATGTATCAGCCTCAAGCAAAACCAGAAGAAGAACAAG
AAAATGACCCTGTAGGAGGGGCAGGCTATAAGCCACAGATGCACCTCCCCATTAATTCT
ACTGTGGAAGATATAGCTGCAGAAGAGGACTTAGATAAAACTGCGGGTTACAGACCTCA
GGCCAATGTAAATACATGGAATTTAGTGTCTCCAGACTCTCCTAGATCCATAGACAGCA
ACAGTGAGATTGTCTCATTTGGAAGTCCATGCTCCATTAATTCCCGACAATTTTTGATT
CCTCCTAAAGATGAAGACTCTCCTAAATCTAATGGAGGAGGGTGGTCCTTTACAAACTT
TTTTCAGAACAAACCAAACGATTAACAGTGTCACCGTGTCACTTCAGTCAGCCATCTCA
ATAAGCTCTTACTGCTAGTGTTGCTACATCAGCACTGGGCATTCTTGGAGGGATCCTGT
GAAGTATTGTTAGGAGGTGAACTTCACTACATGTTAAGTTACACTGAAAGTTCATGTGC
TTTTAATGTAGTCTAAAAGCCAAAGTATAGTGACTCAGAATCCTCAATCCACAAAACTC
AAGATTGGGAGCTCTTTGTGATCAAGCCAAAGAATTCTCATGTACTCTACCTTTCAAGAA
GCATTTCAAGGCTAATACCTACTTGTACGTACATGTAAAACAAATCCCGCCGCAACTGT
TTTCTGTTCTGTTGTTTGTGGTTTTCTCATATGTATACTTGGTGGAATTGTAAGTGGAT
TTGCAGGCCAGGGAGAAAATGTCCAAGTAACAGGTGAAGTTTATTTGCCTGACGTTTAC
TCCTTTCTAGATGAAAACCAAGCACAGATTTTAAAACTTCTAAGATTATTCTCCTCTAT
CCACAGCATTCACNNNNNNNNNNNNNNNNNNNNNGTAGTGACAGCGATTTAGTGTTTT
GTTTGATAAAGTATGCTTATTTCTGTGCCTACTGTATAATGGTTATCAAACAGTTGTCT
CAGGGGTACAAACTTTGAAAACAAGTGTGACACTGACCAGCCCAAAT CATAATCATGTT
TTCTTGCTGTGATAGGTTTTGCTTGCCTTTTCATTATTTTTAGCTTTTATGCTTGCTT
CCATTATTTCAGTTGGTTGCCCTAATATTTAAAATTTACACTTCTAAGACTAGAGACCC
ACATTTTTTAAAAATCATTTTATTTTGTGATACAGTGACAGCTTTATATGAGCAAATTC
```

-continued

```
AATATTATTCATAAGCATGTAATTCCAGTGACTTACTATGTGAGATGACTACTAAGCAA

TATCTAGCAGCGTTAGTTCCATATAGTTCTGATTGGATTTCGTTCCTCCTGAGGAGACC

ATGCCGTTGAGCTTGGCTACCCAGGCAGTGGTGATCTTTGACACCTTCTGGTGGATGTT

CCTCCCACTCATGAGTCTTTTCATCATGCCACATTATCTGATCCAGTCCTCACATTTTT

AAATATAAAACTAAAGAGAGAATGCTTCTTACAGGAACAGTTACCCAAGGGCTGTTTCT

TAGTAACTGTCATAAACTGATCTGGATCCATGGGCATACCTGTGTTCGAGGTGCAGCAA

TTGCTTGGTGAGCTGTGCAGAATTGATTGCCTTCAGCACAGCATCCTCTGCCCACCCTT

GTTTCTCATAAGCGATGTCTGGAGTGATTGTGGTTCTTGGAAAAGCAGAAGGAAAAACT

AAAAAGTGTATCTTGTATTTTCCCTGCC CTCAGGTTGCCTATGTATTTTACCTTTTCAT
```

ATTTAAGGCAAAAGTACTTGAAAATTTTAAGTGTCCGAATAAGATATGTCTTTTTTGTT

TGTTTTTTTTGGTTGGTTGTTTGTTTTTTATCATCTGAGATTCTGTAATGTATTTGCAA

ATAATGGATCAATTAATTTTTTTTGAAGCTCATATTGTATCTTTTTAAAAACCATGTTG

TGGAAAAAAGCCAGAGTGACAAGTGACAAAATCTATTTAGGAACTCTGTGTATGAATCC

TGATTTTAACTGCTAGGATTCAGCTAAATTTCTGAGCTTTATGATCTGTGGAAATTTGG

AATGAAATCGAATTCATTTTGTACATACATAGTATATTAAAACTATATAATAGTTCAT<u>A</u>

<u>GAAATGTTCAGTAATGAAAAAATATATCCAATCAGAGCCATCCCGAAAAAAAAAAAAA</u>

<u>A</u> (SEQ ID NO: 8828).

The length of this sequence was determined using batch, automated computational methods and the sequence, as sense strand, its length, and the desired location of the probe sequence near the 3' end of the mRNA was submitted to Array Designer Ver 1.1 (Premier Biosoft International, Palo Alto, Calif.). Search quality was set at 100%, number of best probes set at 1, length range set at 50 base pairs, Target Tm set at 75 C. degrees plus or minus 5 degrees, Hairpin max deltaG at 6.0-kcal/mol., Self dimmer max deltaG at 6.0-kcal/mol, Run/repeat (dinucleotide) max length set at 5, and Probe site minimum overlap set at 1. When none of the 49 possible probes met the criteria, the probe site would be moved 50 base pairs closer to the 5' end of the sequence and resubmitted to Array Designer for analysis. When no possible probes met the criteria, the variation on melting temperature was raised to plus and minus 8 degrees and the number of identical base-pairs in a run increased to 6 so that a probe sequence was produced.

In the sequence above, using the criteria noted above, Array Designer Ver 1.1 designed a probe corresponding to oligo-nucleotide number 2280 in Table 8 and is indicated by under-lining in the sequence above. It has a melting temperature of 68.4 degrees Celsius and a max run of 6 nucleotides and represents one of the cases where the criteria for probe design in Array Designer Ver 1.1 were relaxed in order to obtain an oligonucleotide near the 3' end of the mRNA (Low melting temperature was allowed).

Clone 463D12

Clone 463D12 was sequenced and compared to the nr, dbEST, and UniGene databases at NCBI using the BLAST search tool. The sequence matched accession number AI184553, an EST sequence with the definition line "qd60a05.x1 Soares_testis_NHT *Homo sapiens* cDNA clone IMAGE:1733840 3' similar to gb:M29550 PROTEIN PHOSPHATASE 2B CATALYTIC SUBUNIT 1 (HUMAN); mRNA sequence." The E value of the alignment was $1.00 \times 10^{-118}$. The GenBank sequence begins with a poly-T region, suggesting that it is the antisense strand, read 5' to 3'. The beginning of this sequence is complementary to the 3' end of the mRNA sense strand. The accession number for this sequence was included in a text file of accession numbers representing antisense sequences. Sequences for antisense strand mRNAs were obtained by uploading a text file containing desired accession numbers as an Entrez search query using the Batch Entrez web interface and saving the results locally as a FASTA file. The following sequence was obtained, and the region of alignment of clone 463D12 is outlined:

TTTTTTTTTTTTTCTTAAATAGCATTTATTTTCTCTCAAAAAGCCTATTATGTACTAAC

AAGTGTTCCTCTAAATTAGAAAGGCATCACTACTAAAATTTTATACATATTTTTATATA

AGAGAAGGAATATTGGGTTACAATCTGAATTTCTCTTTATGATTTCTCTTAAAGTATAGA

```
ACAGCTATTAAAATGACTAATATTGCTAAAATGAAGGCTACTAAATTTCCCCAAGAATTT

CGGTGGAATGCCCAAAAATGGTGTTAAGATATGCAGAAGGGCCCATTTCAAGCAAAGCAA

TCTCTCCACCCCTTCATAAAAGATTTAAGCTAAAAAAAAAAAAAAAAGAAGAAAATCCA

ACAGCTGAAGACATTGGGCTATTTATAAATCTTCTCCCAGTCCCCCAGACAGCCTCACA

TGGGGGCTGTAAACAGCTAACTAAAATATCTTTGAGACTCTTATGTCCACACCCACTGA

CACAAGGAGAGCTGTAACCACAGTGAAACTAGACTTTGCTTTCCTTTAGCAAGTATGTG

CCTATGATAGTAAACTGGAGTAAATGTAACAGTAATAAAACAAATTTTTTTAAAAATA

AAAATTATACCTTTTTCTCCAACAAACGGTAAAGACCACGTGAAGACATCCATAAAATTA

GGCAACCAGTAAAGATGTGGAGAACCAGTAAACTGTCGAAATTCATCACATTATTTTCAT

ACTTTAATACAGCAGCTTTAATTATTGGAGAACATCAAAGTAATTAGGTGCCGAAAAACA

TTGTTATTAATGAAGGGAACCCCTGACGTTTGACCTTTTCTGTACCATCTATAGCCCTGG

ACTTGA    (SEQ ID NO: 8829)
```

The FASTA file, including the sequence of AA184553, was then masked using the RepeatMasker web interface, as shown below. The region of alignment of clone 463D12 is outlined.

```
TTTTTTTTTTTTTTCTTAAATAGCATTTATTTTCTCTCAAAAAGCCTATTATGTACTAAC

AAGTGTTCCTCTAAATTAGAAAGGCATCACTACNNNNNNNNNNNNNNNNNNNNNNNNNNN

NGAGAAGGAATATTGGGTTACAATCTGAATTTCTCTTTATGATTTCTCTTAAAGTATAGA

ACAGCTATTAAAATGACTAATATTGCTAAAATGAAGGCTACTAAATTTCCCCAAGAATTT

CGGTGGAATGCCCAAAAATGGTGTTAAGATATGCAGAAGGGCCCATTTCAAGCAAAGCAA

TCTCTCCACCCCTTCATAAAAGATTTAAGCTAAAAAAAAAAAAAAAAGAAGAAAATCCA

ACAGCTGAAGACATTGGGCTATTTATAAATCTTCTCCCAGTCCCCCAGACAGCCTCACA

TGGGGGCTGTAAACAGCTAACTAAAATATCTTTGAGACTCTTATGTCCACACCCACTGA

CACAAGGAGAGCTGTAACCACAGTGAAACTAGACTTTGCTTTCCTTTAGCAAGTATGTG

CCTATGATAGTAAACTGGAGTAAATGTAACAGNNNNNNNNNNNNNNNNNNNNNNNNNNN

NNNNNNNNNNCCTTTTCTCCAACAAACGGTAAAGACCACGTGAAGACATCCATAAAATTA

GGCAACCAGTAAAGATGTGGAGAACCAGTAAACTGTCGAAATTCATCACATTATTTTCAT

ACTTTAATACAGCAGCTTTAATTATTGGAGAACATCAAAGTAATTAGGTGCCGAAAAACA

TTGTTATTAATGAAGGGAACCCCTGACGTTTGACCTTTTCTGTACCATCTATAGCCCTGG

ACTTGA Masked version of 463D12 sequence, (SEQ ID NO: 8830)
```

The sequence was submitted to Array Designer as described above, however, the desired location of the probe was indicated at base pair 50 and if no probe met the criteria, moved in the 3' direction. The complementary sequence from Array Designer was used, because the original sequence was antisense. The oligonucleotide designed by Array Designer corresponds to oligonucleotide number 4342 in Table 8 and is complementary to the underlined sequence above. The probe has a melting temperature of 72.7 degrees centigrade and a max run of 4 nucleotides.

Clone 72D4

Clone 72D4 was sequenced and compared to the nr, dbEST, and UniGene databases at NCBI using the BLAST search tool. No significant matches were found in any of these databases. When compared to the human genome draft, significant alignments were found to three consecutive regions of the reference sequence NT_008060, as depicted below, suggesting that the insert contains three spliced exons of an unidentified gene.

| Residue numbers on clone 72D4 sequence | Matching residue numbers on NT_008060 |
|---|---|
| 1-198 | 478646-478843 |
| 197-489 | 479876-480168 |
| 491-585 | 489271-489365 |

Because the reference sequence contains introns and may represent either the coding or noncoding strand for this gene, BioCardia's own sequence file was used to design the oligonucleotide. Two complementary probes were designed to ensure that the sense strand was represented. The sequence of the insert in clone 72D4 is shown below, with the three putative exons outlined.

```
CAGGTCACACAGCACATCAGTGGCTACATGTGAGCTCAGACCTGGGTCTGCT
GCTGTCTGTCTTCCCAATATCCATGACCTTGACTGATGCAGGTGTCTAGGGAT
ACGTCCATCCCCGTCCTGCTGGAGCCCAGAGCACGGAAGCCTGGCCCTCCGA
GGAGACAGAAGGGAGTGTCGGACACCATGACGAGAGCTTGGCAGAATAAAT
AACTTCTTTAAACAATTTTACGGCATGAAGAAACTGGACCAGTTTATTAAAT
GGGATTTCTGCCACAAACCTTGGAAGAATCACATCATCTTANNCCCAAGTGA
AAACTGTGTTGCGTAACAAAGAACATGACTGCGCTCCACACATACATCATTG
CCCGGCGAGGCGGGACACAAGTCAACGACGGAACACTTGAGACAGGCCTAC
AACTGTGCACGGGTCAGAAGCAAGTTTAAGCCATACTTGCTGCAGTGAGACT
ACATTTCTGTCTATAGAAGATACCTGACTTGATCTGTTTTTCAGCTCCAGTTC
CCAGATGTGCGTGTTGTGGTCCCCAAGTATCACCTTCCAATTTCTGGGAGCA
GTGCTCTGGCCGGATCCTTGCCGCGCGGATAAAAAT  (SEQ ID NO: 8545)
```

The sequence was submitted to RepeatMasker, but no repetitive sequences were found. The sequence shown above was used to design the two 50-mer probes using Array Designer as described above. The probes are shown in bold typeface in the sequence depicted below. The probe in the sequence is oligonucleotide number 6415 (SEQ ID NO: 6415) in Table 8 and the complementary probe is oligonucleotide number 6805 (SEQ ID NO:6805).

```
CAGGTCACACAGCACATCAGTGGCTACATGTGAGCTCAGACCTGGGTCTGCTGCTGTCTG

TCTTCCCAATATCCATGACCTTGACTGATGCAGGTGTCTAGGGATACGTCCATCCCCGTC

CTGCTGGAGCCCAGAGCACGGAAGCCTGGCCCTCCGAGGAGACAGAAGGGAGTGTCGGAC

ACCCATGACGAGAGCTTGGCAGAATAAATAACTTCTTTAAACAATTTTACGCATGAAGAA

ATCTGGACCAGTTTATTAAATGGGATTTCTGCCACAAACCTTGGAAGAATCACATCATCT

TANNCCCAAGTGAAAACTGTGTTGCGTAACAAAGAACATGACTGCGCTCCACACATACAT

CATTGCCCGGCGAGGCGGGACACAAGTCAACGACGGAACACTTGAGACAGGCCTACAACT

GTGCACGGGTCAGAAGCAAGTTTAAGCCATACTTGCTGCAGTGAGACTACATTTCTGTCT

ATAGAAGATACCTGACTTGATCTGTTTTTCAGCTCCAGTTCCCAGATGTGC

◄-----GTCAAGGGTCTACACG

GTGTTGTGGTCCCCAAGTATCACCTTCCAATTTCTGGGAG----►
```

-continued

CACAACACCAGGGGTTCATAGTGGAAGGTTAAAG-5' (SEQ ID NO: 6805)

CAGTGCTCTGGCCGGATCCTTGCCGCGCGGATAAAAACT-----► (SEQ ID NO: 8545)

Confirmation of Probe Sequence

Following probe design, each probe sequence was confirmed by comparing the sequence against dbEST, the Uni-Gene cluster set, and the assembled human genome using BLASTn at NCBI. Alignments, accession numbers, gi numbers, UniGene cluster numbers and names were examined and the most common sequence used for the probe. The final probe set was compiled into Table 8. In this table, the sequence ID is given which corresponds to the sequence listing. The origin of the sequence for inclusion on the array is noted as coming from one of the cDNA libraries described in example 1, mining from databases as described in examples 2 and 11 or identification from the published literature. The unigene number, genebank accession and GI number are also given for each sequence when known. The name of the gene associated with the accession number is noted. The strand is noted as −1 or 1, meaning that the probe was designed from the complement of the sequence (−1) or directly from the sequence (1). Finally, the nucleotide sequence of each probe is also given.

Example 13

Production of an Array of 8000 Spotted 50mer Oligonucleotides

We produced an array of 8000 spotted 50mer oligonucleotides. Examples 11 and 12 exemplify the design and selection of probes for this array.

Sigma-Genosys (The Woodlands, Tex.) synthesized unmodified 50-mer oligonucleotides using standard phosphoramidite chemistry, with a starting scale of synthesis of 0.05 μmole (see, e.g., R. Meyers, ed. (1995) *Molecular Biology and Biotechnology: A Comprehensive Desk Reference*). Briefly, to begin synthesis, a 3' hydroxyl nucleoside with a dimethoxytrityl (DMT) group at the 5' end was attached to a solid support. The DMT group was removed with trichloroacetic acid (TCA) in order to free the 5'-hydroxyl for the coupling reaction. Next, tetrazole and a phosphoramidite derivative of the next nucleotide were added. The tetrazole protonates the nitrogen of the phosphoramidite, making it susceptible to nucleophilic attack. The DMT group at the 5'-end of the hydroxyl group blocks further addition of nucleotides in excess. Next, the inter-nucleotide linkage was converted to a phosphotriester bond in an oxidation step using an oxidizing agent and water as the oxygen donor. Excess nucleotides were filtered out and the cycle for the next nucleotide was started by the removal of the DMT protecting group. Following the synthesis, the oligo was cleaved from the solid support. The oligonucleotides were desalted, resuspended in water at a concentration of 100 or 200 μM, and placed in 96-deep well format. The oligonucleotides were re-arrayed into Whatman Uniplate 384-well polyproylene V bottom plates. The oligonucleotides were diluted to a final concentration 30 μM in 1× Micro Spotting Solution Plus (Telechem/arrayit.com, Sunnyvale, Calif.) in a total volume of 15 μl. In total, 8,031 oligonucleotides were arrayed into twenty-one 384-well plates.

Arrays were produced on Telechem/arrayit.com Super amine glass substrates (Telechem/arrayit.com), which were manufactured in 0.1 mm filtered clean room with exact dimensions of 25×76×0.96 mm. The arrays were printed using the Virtek Chipwriter with a Telechem 48 pin Micro Spotting Printhead. The Printhead was loaded with 48 Stealth SMP3B TeleChem Micro Spotting Pins, which were used to print oligonucleotides onto the slide with the spot size being 110-115 microns in diameter.

Example 14

Amplification, Labeling, and Hybridization of Total RNA to an Oligonucleotide Microarray Amplification, Labeling, Hybridization and Scanning Samples consisting of at least 2 μg of intact total RNA were further processed for array hybridization. Amplification and labeling of total RNA samples was performed in three successive enzymatic reactions. First, a single-stranded DNA copy of the RNA was made (hereinafter, "ss-cDNA"). Second, the ss-cDNA was used as a template for the complementary DNA strand, producing double-stranded cDNA (hereinafter, "ds-cDNA, or cDNA"). Third, linear amplification was performed by in vitro transcription from a bacterial $T_7$ promoter. During this step, fluorescent-conjugated nucleotides were incorporated into the amplified RNA (hereinafter, "aRNA").

The first strand cDNA was produced using the Invitrogen kit (Superscript II). The first strand cDNA was produced in a reaction composed of 50 mM Tris-HCl (pH 8.3), 75 mM KCl, and 3 mM $MgCl_2$ (1× First Strand Buffer, Invitrogen), 0.5 mM dGTP, 0.5 mM dATP, 0.5 mM dTTP, 0.5 mM dCTP, 10 mM DTT, 10 U reverse transcriptase (Superscript II, Invitrogen, #18064014), 15 U RNase inhibitor (RNAGuard, Amersham Pharmacia, #27-0815-01), 5 μM T7T24 primer (5'-GGCCAGTGAATTGTAATACGACTCACTATAGGGAGG CGGTTTTTTTTTTTT TTTTTTTTTTTT-3'), (SEQ ID NO:8831) and 2 μg of selected sample total RNA. Several purified, recombinant control mRNAs from the plant *Arabidopsis thaliana* were added to the reaction mixture: 2-20 pg of the following genes CAB, RCA, LTP4, NAC1, RCP1, XCP2, RBCL, LTP6, TIM, and PRKase (Stratagene, #252201, #252202, #252204, #252208, #252207, #252206, #252203, #252205, #252209, #252210 respectively). The control RNAs allow the estimate of copy numbers for individual mRNAs in the clinical sample because corresponding sense oligonucleotide probes for each of these plant genes are present on the microarray. The final reaction volume of 20 μl was incubated at 42° C. for 60 min.

For synthesis of the second cDNA strand, DNA polymerase and RNase were added to the previous reaction, bringing the final volume to 150 μl. The previous contents were diluted and new substrates were added to a final concentration of 20 mM Tris-HCl (pH 7.0) (Fisher Scientific, Pittsburgh, Pa. #BP1756-100), 90 mM KCl (Teknova, Half Moon Bay, Calif., #0313-500), 4.6 mM $MgCl_2$ (Teknova, Half Moon Bay, Calif., #0304-500), 10 mM$(NH_4)_2SO_4$ (Fisher Scientific #A702-500) (1× Second Strand buffer, Invitrogen), 0.266 mM dGTP, 0.266 mM dATP, 0.266 mM dTTP, 0.266 mM dCTP, 40 U E. coli DNA polymerase (Invitrogen, #18010-025), and 2 U RNaseH (Invitrogen, #18021-014). The second strand synthesis took place at 16° C. for 120 minutes.

Following second-strand synthesis, the ds-cDNA was purified from the enzymes, dNTPs, and buffers before proceeding to amplification, using phenol-chloroform extraction followed by ethanol precipitation of the cDNA in the presence of glycogen.

Alternatively, a silica-gel column is used to purify the cDNA (e.g. Qiaquick PCR cleanup from Qiagen, #28104). The cDNA was collected by centrifugation at >10,000×g for 30 minutes, the supernatant is aspirated, and 150 µl of 70% ethanol, 30% water was added to wash the DNA pellet. Following centrifugation, the supernatant was removed, and residual ethanol was evaporated at room temperature.

Linear amplification of the cDNA was performed by in vitro transcription of the cDNA. The cDNA pellet from the step described above was resuspended in 7.4 µl of water, and in vitro transcription reaction buffer was added to a final volume of 20 µl containing 7.5 mM GTP, 7.5 mM ATP, 7.5 mM TTP, 2.25 mM CTP, 1.025 mM Cy3-conjugated CTP (PerkinElmer; Boston, Mass., #NEL-580), 1× reaction buffer (Ambion, Megascript Kit, Austin, Tex. and #1334) and 1% $T_7$ polymerase enzyme mix (Ambion, Megascript Kit, Austin, Tex. and #1334). This reaction was incubated at 37° C. overnight. Following in vitro transcription, the RNA was purified from the enzyme, buffers, and excess NTPs using the RNeasy kit from Qiagen (Valencia, Calif.; #74106) as described in the vendor's protocol. A second elution step was performed and the two eluates were combined for a final volume of 60 µl. RNA is quantified using an Agilent 2100 bioanalyzer with the RNA 6000 nano LabChip.

Reference RNA was prepared as described above, except Cy5-CTP was incorporated instead of Cy3CTP. Reference RNA from five reactions, each reaction started with 2 ug total RNA, was pooled together and quantitated as described above.

Hybridization to an Array

RNA was prepared for hybridization as follows: for an 18 mm×55 mm array, 20 µg of amplified RNA (aRNA) was combined with 20 µg of reference aRNA. The combined sample and reference aRNA was concentrated by evaporating the water to 10 µl in a vacuum evaporator. The sample was fragmented by heating the sample at 95° C. for 30 minutes to fragment the RNA into 50-200 bp pieces. Alternatively, the combined sample and reference aRNA was concentrated by evaporating the water to 5 µl in a vacuum evaporator. Five µl of 20 mM zinc acetate was added to the aRNA and the mix incubated at 60° C. for 10 minutes. Following fragmentation, 40 µl of hybridization buffer was added to achieve final concentrations of 5×SSC and 0.20% SDS with 0.1 µg/ul of Cot-1 DNA (Invitrogen) as a competitor DNA. The final hybridization mix was heated to 98° C., and then reduced to 50° C. at 0.1° C. per second.

Alternatively, formamide is included in the hybridization mixture to lower the hybridization temperature.

The hybridization mixture was applied to a pre-heated 65° C. microarray, surface, covered with a glass coverslip (Corning, #2935-246), and placed on a pre-heated 65° C. hybridization chamber (Telechem, AHC-10). 15 ul of 5×SSC was placed in each of the reservoir in the hybridization chamber and the chamber was sealed and placed in a water bath at 62° C. for overnight (16-20 hrs). Following incubation, the slides were washed in 2×SSC, 0.1% SDS for five minutes at 30° C., then in 2×SSC for five minutes at 30° C., then in 2×SSC for another five minutes at 30° C., then in 0.2×SSC for two minutes at room temperature. The arrays were spun at 1000×g for 2 minutes to dry them. The dry microarrays are then scanned by methods described above.

The microarrays were imaged on the Agilent (Palo Alto, Calif.) scanner G2565AA. The scan settings using the Agilent software were as follows: for the PMT Sensitivity (100% Red and 100% Green); Scan Resolution (10 microns); red and green dye channels; used the default scan region for all slides in the carousel; using the largest scan region; scan date for Instrument ID; and barcode for Slide ID. The full image produced by the Agilent scanner was flipped, rotated, and split into two images (one for each signal channel) using TIFFSplitter (Agilent, Palo Alto, Calif.). The two channels are the output at 532 nm (Cy3-labeled sample) and 633 nm (Cy5-labeled R50). The individual images were loaded into GenePix 3.0 (Axon Instruments, Union City, Calif.) for feature extraction, each image was assigned an excitation wavelength corresponding the file opened; Red equals 633 nm and Green equals 532 nm. The setting file (gal) was opened and the grid was laid onto the image so that each spot in the grid overlaped with >50% of the feature. Then the GenePix software was used to find the features without setting minimum threshold value for a feature. For features with low signal intensity, GenePix reports "not found". For all features, the diameter setting was adjusted to include only the feature if necessary.

The GenePix software determined the median pixel intensity for each feature ($F_i$) and the median pixel intensity of the local background for each feature ($B_i$) in both channels. The standard deviation ($SDF_i$ and $SDB_i$) for each is also determined. Features for which GenePix could not discriminate the feature from the background were "flagged" as described below.

Following feature extraction into a .gpr file, the header information of the .gpr file was changed to carry accurate information into the database. An Excel macro was written to change the headers. The steps in that macro were:

1. Open .gpr file.
2. Check the value in the first row, first column. If it is "ATF", then the header has likely already been reformatted. The file is skipped and the user is alerted. Otherwise, proceed through the following steps.
3. Store the following values in variables.
   a. Name of .tif image file: parsed from row 11.
   b. SlideID: parsed from name of .tif image file.
   c. Version of the feature extraction software: parsed from row 25
   d. GenePix Array List file: parsed from row 6
   e. GenePix Settings file: parsed from row 5
4. Delete rows 1-8, 10-12, 20, 22, and 25.
5. Arrange remaining values in rows 15-29.
6. Fill in rows 1-14 with the following:
   Row 1: ScanID (date image file was last modified, formatted as yyyy.mm.dd-hh.mm.ss)
   Row 2: SlideID, from stored value
   Row 3: Name of person who scanned the slide, from user input
   Row 4: Image file name, from stored value
   Row 5: Green PMT setting, from user input
   Row 6: Red PMT setting, from user input
   Row 7: ExtractID (date .gpr file was created, formatted as yyyy.mm.dd-hh.mm.ss)
   Row 8: Name of person who performed the feature extraction, from user input
   Row 9: Feature extraction software used, from stored value
   Row 10: Results file name (same as the .gpr file name)
   Row 11: GenePix Array List file, from stored value Row 12: GenePix Settings file, from stored value
Row 13: StorageCD, currently left blank
Row 14: Extraction comments, from user input (anything about the scanning or feature extraction of the image the user feels might be relevant when selecting which hybridizations to include in an analysis)

Pre-Processing with Excel Templates

Following analysis of the image and extraction of the data, the data from each hybridization was pre-processed to extract data that was entered into the database and subsequently used for analysis. The complete GPR file produced by the feature extraction in GenePix was imported into an excel file pre-processing template. The same excel template was used to process each GPR file. The template performs a series of calculations on the data to differentiate poor features from others and to combine triplicate feature data into a single data point for each probe.

Each GPR file contained 31 rows of header information, followed by rows of data for 24093 features. The last of these rows was retained with the data. Rows 31 through the end of the file were imported into the excel template. Each row contained 43 columns of data. The only columns used in the pre-processing were: Oligo ID, F633 Median (median value from all the pixels in the feature for the Cy5 dye), B633 Median (the median value of all the pixels in the local background of the selected feature for Cy5), B633 SD (the standard deviation of the values for the pixels in the local background of the selected feature for Cy5), F532 Median (median value from all the pixels in the feature for the Cy3 dye), B532 Median (the median value of all the pixels in the local background of the selected feature for Cy3), B532 SD (the standard deviation of the values for the pixels in the local background of the selected feature for Cy3), and Flags. The GenePix Flags column contains the flags set during feature extraction. "−75" indicates there were no features printed on the array in that position, "−50" indicates that GenePix could not differentiate the feature signal from the local background, and "−100" indicates that the user marked the feature as bad.

Once imported, the rows with −75 flags were deleted. Then the median of B633 SD and B532 SD were calculated over all features with a flag value of "0". The minimum values of B633 Median and B532 Median were identified, considering only those values associated with a flag value of "0". For each feature, the signal to noise ratio (S/N) was calculated for both dyes by taking the fluorescence signal minus the local background (BGSS) and dividing it by the standard deviation of the local background:

$$S/N = \frac{F_i - B_i}{SDB_i}$$

If the S/N was less than 3, then an adjusted background-subtracted signal was calculated as the fluorescence minus the minimum local background on the slide. An adjusted S/N was then calculated as the adjusted background subtracted signal divided by the median noise over all features for that channel. If the adjusted S/N was greater than three and the original S/N were less than three, a flag of 25 was set for the Cy5 channel, a flag of 23 was set for the Cy3 channel, and if both met these criteria, then a flag of 20 was set. If both the adjusted S/N and the original S/N were less than three, then a flag of 65 was set for Cy5, 63 set for Cy3, and 60 set if both dye channels had an adjusted S/N less than three. All signal to noise calculations, adjusted background-subtracted signal, and adjusted S/N were calculated for each dye channel. If the BGSS value was greater than or equal to 64000, a flag was set to indicate saturation; 55 for Cy5, 53 for Cy3, 50 for both.

The BGSS used for further calculations was the original BGSS if the original S/N was greater than or equal to three. If the original S/N ratio was less than three and the adjusted S/N ratio was greater than or equal to three, then the adjusted BGSS was used. If the adjusted S/N ratio was less than three, then the adjusted BGSS was used, but with knowledge of the flag status.

To facilitate comparison among arrays, the Cy3 and Cy5 data were scaled to have a median of 1. For each dye channel, the median value of all features with flags=0, 20, 23, or 25 was calculated. The BGSS for each dye in each feature was then divided by this median value. The Cy3/Cy5 ratio was calculated for each feature using the scaled $$BGSS: R_n = \frac{Cy3S_i}{Cy5S_i}$$

The flag setting for each feature was used to determine the expression ratio for each probe, a combination of three features. If all three features had flag settings in the same category (categories=negatives, 0 to 25, 50-55, and 60-65), then the average and CV of the three feature ratios was calculated. If the CV of all three features was less than 15, the average was used. If the CV was greater than 15, then the CV of each combination of two of the features was calculated and the two features with the lowest CV were averaged. If none of the combinations of two features had a CV less than 15, then the median ratio of the three features was used as the probe feature.

If the three features do not have flags in the same category, then the features with the best quality flags were used (0>25>23>20>55>53>50>65>63>60). Features with negative flags were never used. When the best flags were two features in the same category, the average was used. If a single feature had a better flag category than the other two then that feature was used.

Once the probe expression ratio was calculated from the three features, the log of the ratio was taken as described below and stored for use in analyzing the data. Whichever features were used to calculate the probe value, the worst of the flags from those features was carried forward and stored as the flag value for that probe. 2 different data sets can be used for analysis. Flagged data uses all values, including those with flags. Filtered data sets are created by removing flagged data from the set before analysis.

Example 15

Real-Time PCR Validation of Array Expression Results

In example 10, leukocyte gene expression was used to discover expression markers and diagnostic gene sets for clinical outcomes. It is desirable to validate the gene expression results for each gene using a more sensitive and quantitative technology such as real-time PCR. Further, it is possible for the diagnostic nucleotide sets to be implemented as a diagnostic test as a real-time PCR panel. Alternatively, the quantitative information provided by real-time PCR validation can be used to design a diagnostic test using any alternative quantitative or semi-quantitative gene expression technology.

To validate the results of the microarray experiments we used real-time, or kinetic, PCR. In this type of experiment the amplification product is measured during the PCR reaction. This enables the researcher to observe the amplification before any reagent becomes rate limiting for amplification. In kinetic PCR the measurement is of $C_T$ (threshold cycle) or $C_P$ (crossing point). This measurement ($C_T=C_P$) is the point at which an amplification curve crosses a threshold fluorescence value. The threshold is set to a point within the area where all of the reactions were in their linear phase of amplification. When measuring $C_T$, a lower $C_T$ value is indicative of a higher amount of starting material since an earlier cycle number means the threshold was crossed more quickly.

Several fluorescence methodologies are available to measure amplification product in real-time PCR. Taqman (Applied BioSystems, Foster City, Calif.) uses fluorescence resonance energy transfer (FRET) to inhibit signal from a probe until the probe is degraded by the sequence specific binding and Taq 3' exonuclease activity. Molecular Beacons (Stratagene, La Jolla, Calif.) also use FRET technology, whereby the fluorescence is measured when a hairpin structure is relaxed by the specific probe binding to the amplified DNA. The third commonly used chemistry is Sybr Green, a DNA-binding dye (Molecular Probes, Eugene, Oreg.). The more amplified product that is produced, the higher the signal. The Sybr Green method is sensitive to non-specific amplification products, increasing the importance of primer design and selection. Other detection chemistries can also been used, such as ethedium bromide or other DNA-binding dyes and many modifications of the fluorescent dye/quencher dye Taqman chemistry, for example scorpions.

Initially, samples are chosen for validation, which have already been used for microarray based expression analysis. They are also chosen to represent important disease classes or disease criteria. For the first steps of this example (primer design, primer endpoint testing, and primer efficiency testing) we examined β-actin and β-GUS. These genes are considered "housekeeping" genes because they are required for maintenance in all cells. They are commonly used as a reference that is expected to not change with experimental treatment. We chose these two particular genes as references because they varied the least in expression across 5 mRNA samples examined by real-time PCR.

The inputs for real time PCR reaction are gene-specific primers, cDNA from specific patient samples, and the standard reagents. The cDNA was produced from mononuclear RNA (prepared as in example 7) by reverse transcription using OligodT primers (Invitrogen, 18418-012) and random hexamers (Invitrogen, 48190-011) at a final concentration of 0.5 ng/µl and 3 ng/µl respectively. For the first strand reaction mix, 1.45 µg/µl of total RNA (R50, universal leukocyte reference RNA as described in Example 8) and 1 µl of the Oligo dT/Random Hexamer Mix, were added to water to a final volume of 11.5 µl. The sample mix was then placed at 70° C. for 10 minutes. Following the 70° C. incubation, the samples were chilled on ice, spun down, and 88.5 µl of first strand buffer mix dispensed into the reaction tube. The final first strand buffer mix produced final concentrations of 1× first strand buffer (Invitrogen, Y00146, Carlsbad, Calif.), 0.01 mM DTT (Invitrogen, Y00147), 0.1 mM dATP (NEB, N0440S, Beverly, Mass.), 0.1 mM dGTP (NEB, N0442S), 0.1 mM dTTP (NEB, N0443S), 0.1 mM dCTP (NEB, N0441S), 2U of reverse transcriptase (Superscript II, Invitrogen, 18064-014), and 0.18U of RNase inhibitor (RNAGaurd Amersham Pharmacia, 27-0815-01, Piscataway, N.J.). The reaction was incubated at 42° C. for 1 hour. After incubation the enzyme was heat inactivated at 70° C. for 15 minutes, 1 µl of RNAse H added to the reaction tube, and incubated at 37° C. for 20 minutes.

Primer Design

Two methods were used to design primers. The first was to use the software, Primer Express™ and recommendations for primer design that are provided with the GeneAmp® 7700 Sequence Detection System supplied by Applied BioSystems (Foster City, Calif.). The second method used to design primers was the PRIMER3 ver 0.9 program that is available from the Whitehead Research Institute, Cambridge, Mass. The program can also be accessed on the World Wide Web at: genome.wi.mit.edu/cgi-bin/primer/primer3_www.cgi. Primers and Taqman/hybridization probes were designed as described below using both programs.

The Primer Express literature explains that primers should be designed with a melting temperature between 58 and 60 degrees C. while the Taqman probes should have a melting temperature of 68 to 70 under the salt conditions of the supplied reagents. The salt concentration is fixed in the software. Primers should be between 15 and 30 basepairs long. The primers should produce and amplicon in size between 50 and 150 base pairs, have a C-G content between 20% and 80%, have no more than 4 identical base pairs next to one another, and no more than 2 C's and G's in the last 5 bases of the 3' end. The probe cannot have a G on the 5' end and the strand with the fewest G's should be used for the probe.

Primer3 has a large number of parameters. The defaults were used for all except for melting temperature and the optimal size of the amplicon was set at 100 bases. One of the most critical is salt concentration as it affects the melting temperature of the probes and primers. In order to produce primers and probes with melting temperatures equivalent to Primer Express, a number of primers and probes designed by Primer Express were examined using PRIMER3. Using a salt concentration of 50 mM these primers had an average melting temperature of 3.7 degrees higher than predicted by Primer Express. In order to design primers and probes with equivalent melting temperatures as Primer Express using PRIMER3, a melting temperature of 62.7 plus/minus 1.0 degree was used in PRIMER3 for primers and 72.7 plus/minus 1.0 degrees for probes with a salt concentration of 50 mM.

The C source code for Primer3 was downloaded and complied on a Sun Enterprise 250 server using the GCC complier. The program was then used from the command line using a input file that contained the sequence for which we wanted to design primers and probes along with the input parameters as described by help files that accompany the software. Using scripting it was possible to input a number of sequences and automatically generate a number of possible probes and primers.

Primers for β-Actin (Beta Actin, Genbank Locus: NM_001101) and β-GUS: glucuronidase, beta, (GUSB, Genbank Locus: NM_000181), two reference genes, were designed using both methods and are shown here as examples.

The first step was to mask out repetitive sequences found in the mRNA sequences using RepeatMasker program that can be accessed at the web site located at repeatmasker.genome. washington.edu/cgi-bin/RepeatMasker (Smit, AFA & Green, P "RepeatMasker" at the web site located at ftp. genome. washington.edu/RM/RepeatMasker.html).

The last 500 basepairs on the last 3' end of masked sequence was then submitted to PRIMER3 using the following exemplary input file:
PRIMER_SEQUENCE_ID=>ACTB Beta Actin
PRIMER_EXPLAIN_FLAG=1
PRIMER_MISPRIMING_LIBRARY=
SEQUENCE=TTGGCTTGACTCAGGATTTAAAAACTGGAACGGTGAAGGTGACAGCAGTCGGTTGGACGAGCA TCCCCCAAAGTTCACAATGTGGCCGAGGACTTTGATTGCACATTGTTGTTTTTTAATAGTCATTCCAAATATGAGATGCATTGTTACAGGAAGTCCCTTGCCATCCTAAAAGCACCCCACTTCTCTCTAAGGAGAATGGCCCAG TCCTCTCCCAAGTCCACACAGGGGAGGGATAGCATTGCTTTCGTGTAAATTATGTAATGCAAAATTTTTTTA ATCTTCGCCTTAATCTTTTTTATTTTGTTTTATTTTGAATGATGAGCCTTCGTGCCCCCCCTTCCCCCTTTT
TTCCCCCAACTTGAGATGTATGAAGGCTTTTGGTCTCCCTGGGAGTGGGTGGAGGCAGCCGGGCTTACCTGT ACACTGACTTGAGACCAGTTGAATAAAAGTGCACACCTTA (SEQ ID NO: 8833)
PRIMER_PRODUCT_OPT_SIZE=100
PRIMER_NUM_RETURN=100
PRIMER_MAX_END_STABILITY=9.0
PRIMER_MAX_MISPRIMING=12.00
PRIMER_PAIR_MAX_MISPRIMING=24.00
PRIMER_MIN_SIZE=18
PRIMER_OPT_SIZE=20
PRIMER_MAX_SIZE=32
PRIMER_MIN_TM=61.7
PRIMER_OPT_TM=62.7
PRIMER_MAX_TM=63.7
PRIMER_MAX_DIFF_TM=100.0
PRIMER_MIN_GC=20.0
PRIMER_MAX_GC=80.0
PRIMER_SELF_ANY=8.00
PRIMER_SELF_END=3.00
PRIMER_NUM_NS_ACCEPTED=0
PRIMER_MAX_POLY_X=4
PRIMER_OUTSIDE_PENALTY=0
PRIMER_GC_CLAMP=0
PRIMER_SALT_CONC=50.0
PRIMER_DNA_CONC=50.0
PRIMER_LIBERAL_BASE=1
PRIMER_MIN_QUALITY=0
PRIMER_MIN_END_QUALITY=0
PRIMER_QUALITY_RANGE_MIN=0
PRIMER_QUALITY_RANGE_MAX=100
PRIMER_WT_TM_LT=1.0
PRIMER_WT_TM_GT=1.0
PRIMER_WT_SIZE_LT=1.0
PRIMER_WT_SIZE_GT=1.0
PRIMER_WT_GC_PERCENT_LT=0.0
PRIMER_WT_GC_PERCENT_GT=0.0
PRIMER_WT_COMPL_ANY=0.0
PRIMER_WT_COMPL_END=0.0
PRIMER_WT_NUM_NS=0.0
PRIMER_WT_REP_SIM=0.0
PRIMER_WT_SEQ_QUAL=0.0
PRIMER_WT_END_QUAL=0.0
PRIMER_WT_POS_PENALTY=0.0
PRIMER_WT_END_STABILITY=0.0
PRIMER_PAIR_WT_PRODUCT_SIZE_LT=0.05
PRIMER_PAIR_WT_PRODUCT_SIZE_GT=0.05
PRIMER_PAIR_WT_PRODUCT_TM_LT=6.0
PRIMER_PAIR_WT_PRODUCT_TM_GT=0.0
PRIMER_PAIR_WT_DIFF_TM=0.0
PRIMER_PAIR_WT_COMPL_ANY=0.0
PRIMER_PAIR_WT_COMPL_END=0.0
PRIMER_PAIR_WT_REP_SIM=0.0
PRIMER_PAIR_WT_PR_PENALTY=1.0
PRIMER_PAIR_WT_IO_PENALTY=0.0
PRIMER_INTERNAL_OLIGO_MIN_SIZE=18
PRIMER_INTERNAL_OLIGO_OPT_SIZE=20
PRIMER_INTERNAL_OLIGO_MAX_SIZE=35
PRIMER_INTERNAL_OLIGO_MIN_TM=71.7
PRIMER_INTERNAL_OLIGO_OPT_TM=72.7
PRIMER_INTERNAL_OLIGO_MAX_TM=73.7
PRIMER_INTERNAL_OLIGO_MIN_GC=20.0
PRIMER_INTERNAL_OLIGO_MAX_GC=80.0
PRIMER_INTERNAL_OLIGO_SELF_ANY=12.00
PRIMER_INTERNAL_OLIGO_SELF_END=12.00
PRIMER_INTERNAL_OLIGO_NUM_NS=0
PRIMER_INTERNAL_OLIGO_MAX_POLY_X=5
PRIMER_INTERNAL_OLIGO_MISHYB_LIBRARY=
PRIMER_INTERNAL_OLIGO_MAX_MISHYB=12.00
PRIMER_INTERNAL_OLIGO_MIN_QUALITY=0
PRIMER_INTERNAL_OLIGO_SALT_CONC=50.0
PRIMER_INTERNAL_OLIGO_DNA_CONC=50.0
PRIMER_IO_WT_TM_LT=1.0
PRIMER_IO_WT_TM_GT=1.0
PRIMER_IO_WT_SIZE_LT=1.0
PRIMER_IO_WT_SIZE_GT=1.0
PRIMER_IO_WT_GC_PERCENT_LT=0.0
PRIMER_IO_WT_GC_PERCENT_GT=0.0
PRIMER_IO_WT_COMPL_ANY=0.0
PRIMER_IO_WT_NUM_NS=0.0
PRIMER_IO_WT_REP_SIM=0.0
PRIMER_IO_WT_SEQ_QUAL=0.0
PRIMER_TASK=pick_per_primers_and_hyb_probe
PRIMER_PRODUCT_SIZE_RANGE=50-150
PRIMER_FIRST_BASE_INDEX=1
PRIMER_PICK_ANYWAY=1
=
PRIMER_SEQUENCE_ID=>GUSB
PRIMER_EXPLAIN_FLAG=1
PRIMER_MISPRIMING_LIBRARY=
SEQUENCE=GAAGAGTACAGAAAAGTCTGCTAGAGCAGTACCATCTGGGTCTGGATCAAAAACGCAGAAAA TATGTGGTTGGAGAGCTCATTTGGAATTTTGCCGATTTCATGACTGAACAGTCACCGACGAGAGTGCTGGGGAATAAAAGGGGATCTTCACTCGGCAGAGACAACCAAAAAGTGCAGCGTTCCTTTTGCGAGAGAGATACTGG AAGATTGCCAATGAAACCAGGTATCCCCACTCAGTAGCCAAGTCACAATGTTTGGAAAACAGCCCGTTTACT TGAGCAAGACTGATACCACCTGCGTGTCCCTTCCTCCCCGAGTCAGGGCGACTTCCACAGCAGCAGAACAAG
TGCCTCCTGGACTGTTCACGGCAGACCAGAACGTTTCTGGCCTGGGTTTTGTGGTCATCTATTCTAGCAGGG AACACTAAAGGTGGAAATAAAAGATTTTCTATTATGGAAATAAAGAGTTGGCATGAAAGTCGCTACTG (SEQ ID NO: 8834)
PRIMER_PRODUCT_OPT_SIZE=100
PRIMER_NUM_RETURN=100
PRIMER_MAX_END_STABILITY=9.0
PRIMER_MAX_MISPRIMING=12.00
PRIMER_PAIR_MAX_MISPRIMING=24.00
PRIMER_MIN_SIZE=18

PRIMER_OPT_SIZE=20
PRIMER_MAX_SIZE=32
PRIMER_MIN_TM=61.7
PRIMER_OPT_TM=62.7
PRIMER_MAX_TM=63.7
PRIMER_MAX_DIFF_TM=100.0
PRIMER_MIN_GC=20.0
PRIMER_MAX_GC=80.0
PRIMER_SELF_ANY=8.00
PRIMER_SELF_END=3.00
PRIMER_NUM_NS_ACCEPTED=0
PRIMER_MAX_POLY_X=4
PRIMER_OUTSIDE_PENALTY=0
PRIMER_GC_CLAMP=0
PRIMER_SALT_CONC=50.0
PRIMER_DNA_CONC=50.0
PRIMER_LIBERAL_BASE=1
PRIMER_MIN_QUALITY=0
PRIMER_MIN_END_QUALITY=0
PRIMER_QUALITY_RANGE_MIN=0
PRIMER_QUALITY_RANGE_MAX=100
PRIMER_WT_TM_LT=1.0
PRIMER_WT_TM_GT=1.0
PRIMER_WT_SIZE_LT=1.0
PRIMER_WT_SIZE_GT=1.0
PRIMER_WT_GC_PERCENT_LT=0.0
PRIMER_WT_GC_PERCENT_GT=0.0
PRIMER_WT_COMPL_ANY=0.0
PRIMER_WT_COMPL_END=0.0
PRIMER_WT_NUM_NS=0.0
PRIMER_WT_REP_SIM=0.0
PRIMER_WT_SEQ_QUAL=0.0
PRIMER_WT_END_QUAL=0.0
PRIMER_WT_POS_PENALTY=0.0
PRIMER_WT_END_STABILITY=0.0
PRIMER_PAIR_WT_PRODUCT_SIZE_LT=0.05
PRIMER_PAIR_WT_PRODUCT_SIZE_GT=0.05
PRIMER_PAIR_WT_PRODUCT_TM_LT=0.0
PRIMER_PAIR_WT_PRODUCT_TM_GT=0.0
PRIMER_PAIR_WT_DIFF_TM=0.0
PRIMER_PAIR_WT_COMPL_ANY=0.0
PRIMER_PAIR_WT_COMPL_END=0.0
PRIMER_PAIR_WT_REP_SIM=0.0
PRIMER_PAIR_WT_PR_PENALTY=1.0
PRIMER_PAIR_WT_IO_PENALTY=0.0
PRIMER_INTERNAL_OLIGO_MIN_SIZE=18
PRIMER_INTERNAL_OLIGO_OPT_SIZE=20
PRIMER_INTERNAL_OLIGO_MAX_SIZE=35
PRIMER_INTERNAL_OLIGO_MIN_TM=71.7
PRIMER_INTERNAL_OLIGO_OPT_TM=72.7
PRIMER_INTERNAL_OLIGO_MAX_TM=73.7
PRIMER_INTERNAL_OLIGO_MIN_GC=20.0
PRIMER_INTERNAL_OLIGO_MAX_GC=80.0
PRIMER_INTERNAL_OLIGO_SELF_ANY=12.00
PRIMER_INTERNAL_OLIGO_SELF_END=12.00
PRIMER_INTERNAL_OLIGO_NUM_NS=0
PRIMER_INTERNAL_OLIGO_MAX_POLY_X=5
PRIMER_INTERNAL_OLIGO_MISHYB_LIBRARY=
PRIMER_INTERNAL_OLIGO_MAX_MISHYB=12.00
PRIMER_INTERNAL_OLIGO_MIN_QUALITY=0
PRIMER_INTERNAL_OLIGO_SALT_CONC=50.0
PRIMER_INTERNAL_OLIGO_DNA_CONC=50.0
PRIMER_IO_WT_TM_LT=1.0
PRIMER_IO_WT_TM_GT=1.0
PRIMER_IO_WT_SIZE_LT=1.0
PRIMER_IO_WT_SIZE_GT=1.0
PRIMER_IO_WT_GC_PERCENT LT=0.0
PRIMER_IO_WT_GC_PERCENT GT=0.0
PRIMER_IO_WT_COMPL_ANY=0.0
PRIMER_IO_WT_NUM_NS=0.0
PRIMER_IO_WT_REP_SIM=0.0
PRIMER_IO_WT_SEQ_QUAL=0.0
PRIMER_TASK=pick_per_primers_and_hyb_probe
PRIMER_PRODUCT_SIZE_RANGE=50-150
PRIMER_FIRST_BASE_INDEX=1
PRIMER_PICK_ANYWAY=1

After running PRIMER3, 100 sets of primers and probes were generated for ACTB and GUSB. From this set, nested primers were chosen based on whether both left primers could be paired with both right primers and a single Taqman probe could be used on an insert of the correct size. With more experience we have decided not use the mix and match approach to primer selection and just use several of the top pairs of predicted primers.

For ACTB this turned out to be:
Forward 75 CACAATGTGGCCGAGGACTT (SEQ ID NO: 8835),
Forward 80 TGTGGCCGAGGACTTTGATT (SEQ ID NO: 8836),
Reverse 178 TGGCTTTTAGGATGGCAAGG (SEQ ID NO: 8837), and
Reverse 168 GGGGGCTTAGTTTGCTTCCT (SEQ ID NO: 8838).
Upon testing, the F75 and R178 pair worked best.
For GUSB the following primers were chosen:
Forward 59 AAGTGCAGCGTTCCTTTTGC (SEQ ID NO: 8839),
Forward 65 AGCGTTCCTTTTGCGAGAGA (SEQ ID NO: 8840),
Reverse 158 CGGGCTGTTTTCCAAACATT (SEQ ID NO: 8841) and
Reverse 197 GAAGGGACACGCAGGTGGTA (SEQ ID NO: 8842).
No combination of these GUSB pairs worked well.
In addition to the primer pairs above, Primer Express predicted the following primers for GUSB: Forward 178 TAC-CACCTGCGTGTCCCTTC (SEQ ID NO: 8843) and Reverse 242 GAGGCACTTGTTCTGCTGCTG (SEQ ID NO: 8844). This pair of primers worked to amplify the GUSB mRNA.

The parameters used to predict these primers in Primer Express were:
Primer Tm: min 58, Max=60, opt 59, max difference=2 degrees
Primer GC: min=20% Max=80% no 3' G/C clamp
Primer: Length: min=9 max=40 opt=20
Amplicon: min Tm=0 max Tm=85
  min=50 bp max=150 bp
Probe: Tm 10 degrees>primers, do not begin with a G on 5' end
Other: max base pair repeat=3
  max number of ambiguous residues=0
  secondary structure: max consec bp=4, max total bp=8
  Uniqueness: max consec match=9
    max % match=75
    max 3' consecutive match=7
Using this approach, multiple primers were designed for genes that were shown to have expression patterns that correlated with clinical data in example 10. These primer pairs are shown in Table 10B and are added to the sequence listing. Primers can be designed from any region of a target gene using this approach.

Granzyme B is an important marker of CMV infection and transplant rejection. For Granzyme B the following sequence (NM_004131) was used as input for Primer3:
GGGGACTCTGGAGGCCCTCTTGTGTG-
TAACAAGGTGGCCCAGGGCATTGT CTCCTATGGAC-
GAAACAATGGCATGCCTCCACGAGCCTG-
CACCAAAGTCT
CAAGCTTTGTACACTGGATAAAGAAAAC-
CATGAAACGCTACTAACTACAG GAAGCAAAC-
TAAGCCCCCGCTGTAATGAAACACCT-
TCTCTGGAGCCAAGT
CCAGATTTACACTGGGAGAGGTGCCAG-
CAACTGAATAAATACCTCTCCCA GTGTAAATCTG-
GAGCCAAGTCCAGATTTACACTGG-
GAGAGGTGCCAGCAA
CTGAATAAATACCTCTTAGCTGAGTGG (SEQ ID No: 9086)

For Granzyme B the following primers were chosen for testing:
Forward 81 ACGAGCCTGCACCAAAGTCT (SEQ ID No: 9087)
Forward 63 AAACAATGGCATGCCTCCAC (SEQ ID No: 9088)
Reverse 178 TCATTACAGCGGGGGCTTAG (SEQ ID No: 9089)
Reverse 168 GGGGGCTTAGTTTGCTTCCT (SEQ ID No: 9090)

Testing demonstrated that F81 and R178 worked well in amplifying a product.

Primer Endpoint Testing

Primers were first tested to examine whether they would produce the correct size product without non-specific amplification. The standard real-time PCR protocol was used without the Rox and Sybr green dyes. Each primer pair was tested on cDNA made from universal mononuclear leukocyte reference RNA that was produced from 50 individuals as described in Example 8 (R50).

The PCR reaction consisted of 1× RealTime PCR Buffer (Ambion, Austin, Tex.), 3 mM MgCl2 (Applied BioSystems, B02953), 0.2 mM dATP (NEB), 0.2 mM dTTP (NEB), 0.2 mM dCTP (NEB), 0.2 mM dGTP (NEB), 1.25U AmpliTaq Gold (Applied BioSystems, Foster City, Calif.), 0.3 µM of each primer to be used (Sigma Genosys, The Woodlands, Tex.), 5 µl of the R50 reverse-transcription reaction and water to a final volume of 19 µl.

Figure 6B:
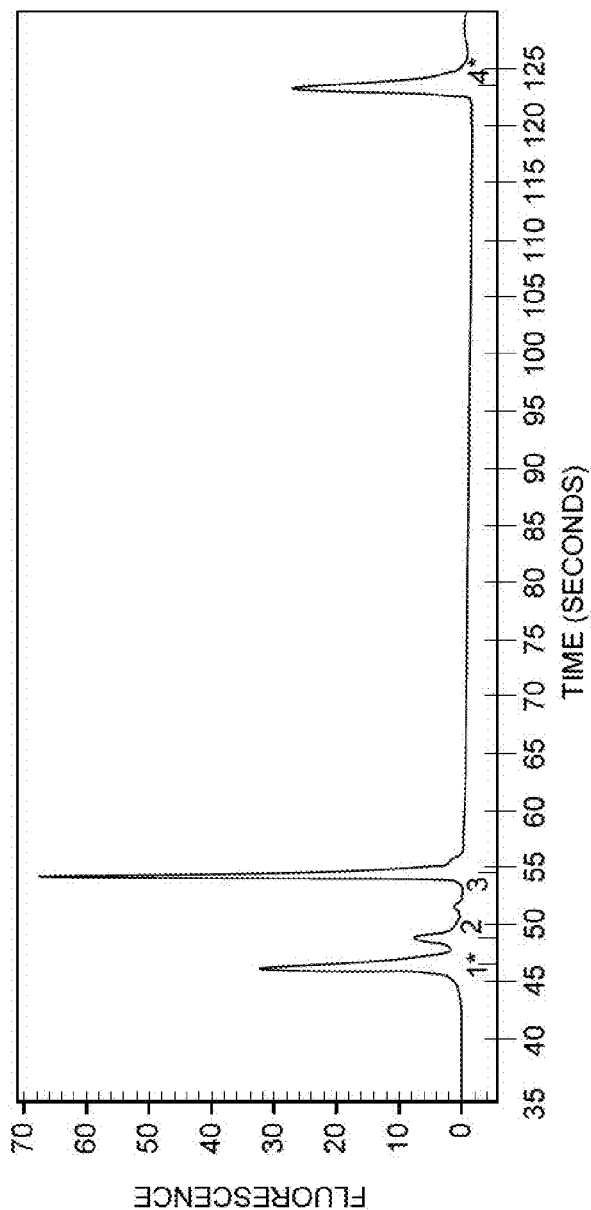
FIG. 6B shows the electropherogram of β-GUS primers F178 and R242, a graphical representation of Lane 3 from the gel image.
Figure 6A:
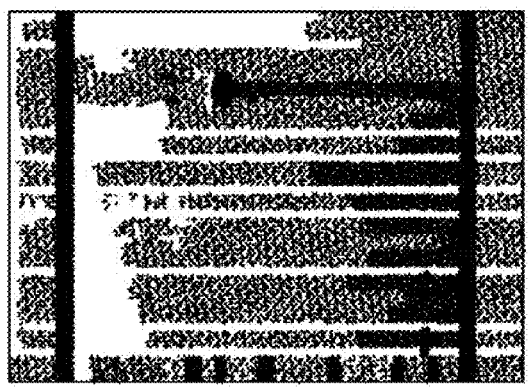
FIG. 6A is a β-GUS gel image. Lane 3 is the image for primers F178 and R242. Lanes 2 and 1 correspond to the no-template control and –RT control, respectively.
Figures 6C, 6D:
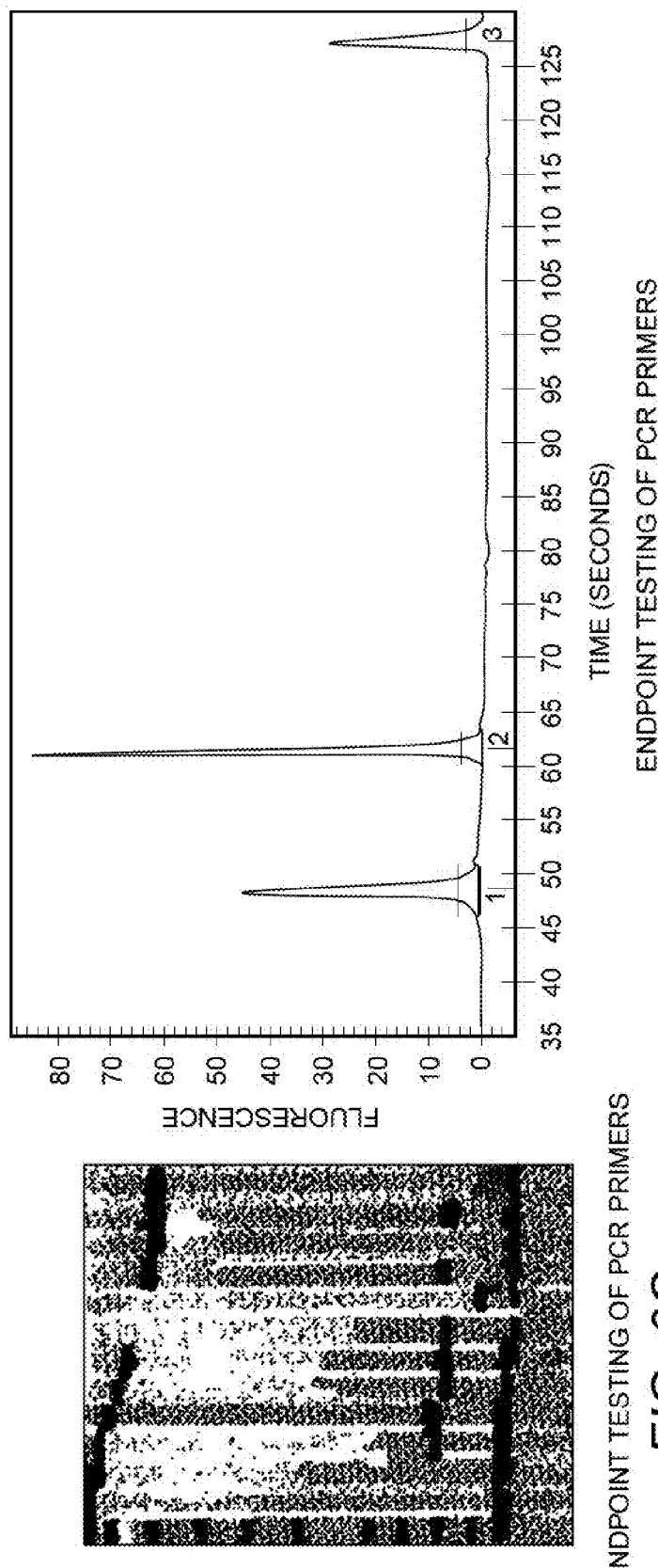
FIG. 6C shows a β-Actin gel image. Lane 3 is the image for primers F75 and R178. Lanes 2 and 1 correspond to the no-template control and –RT control, respectively.
FIG. 6D shows the electropherogram of β-Actin primers F75 and R178, a graphical representation of Lave 3 from the gel image.

Following 40 cycles of PCR, one microliter of the product was examined by agarose gel electrophoresis and on an Agilent Bioanalyzer, DNA1000 chip (Palo Alto, Calif.). Results for 2 genes are shown in FIG. 6. From the primer design and the sequence of the target gene, one can calculate the expected size of the amplified DNA product. Only primer pairs with amplification of the desired product and minimal amplification of contaminants were used for real-time PCR. Primers that produced multiple products of different sizes are likely not specific for the gene of interest and may amplify multiple genes or chromosomal loci.

Primer Optimization/Efficiency

Once primers passed the end-point PCR, the primers were tested to determine the efficiency of the reaction in a real-time PCR reaction. cDNA was synthesized from starting total RNA as described above. A set of 5 serial dilutions of the R50 reverse-transcribed cDNA (as described above) were made in water: 1:10, 1:20, 1:40, 1:80, and 1:160.

The Sybr Green real-time PCR reaction was performed using the Taqman PCR Reagent kit (Applied BioSystems, Foster City, Calif., N808-0228). A master mix was made that consisted of all reagents except the primes and template. The final concentration of all ingredients in the reaction was 1× Taqman Buffer A (Applied BioSystems), 2 mM MgCl2 (Applied BioSystems), 200 µM dATP (Applied BioSystems), 200 µM dCTP (Applied BioSystems), 200 µM dGTP (Applied BioSystems), 400 µM dUTP (Applied BioSystems), 1:400,000 diluted Sybr Green dye (Molecular Probes), 1.25U AmpliTaq Gold (Applied BioSystems). The master mix for 92 reactions was made to a final volume of 2112 µl. 1012 µl of PCR master mix was dispensed into two, light-tight tubes. Each β-Actin primer F75 and R178 (Genosys), was added to one tube of PCR master mix and Each β-GUS primer F178 and R242 (Genosys), was added to the other tube of PCR master mix to a final primer concentration of 300 nM, and a final volume of 1035 µl per reaction tube. 45 µl of the β-Actin master mix was dispensed into 23 wells, in a 96 well plate (Applied BioSystems). 45 µl of the β-GUS master mix was dispensed into 23 wells, in a 96well plate (Applied BioSystems). 5 µl of the template dilution series was dispensed into triplicate wells for each primer. The reaction was run on an ABI 7700 Sequence Detector (Applied BioSystems).

The Sequence Detector v1.7 software was used to analyze the fluorescent signal from each well. A threshold value was selected that allowed most of the amplification curves to cross the threshold during the linear phase of amplification. The cycle number at which each amplification curve crossed the threshold ($C_T$) was recorded and the file transferred to MS Excel for further analysis. The $C_T$ values for triplicate wells were averaged. The data were plotted as a function of the $\log_{10}$ of the calculated starting concentration of RNA. The starting RNA concentration for each cDNA dilution was determined based on the original amount of RNA used in the RT reaction, the dilution of the RT reaction, and the amount used (5 µl) in the real-time PCR reaction. For each gene, a linear regression line was plotted through all of the dilutions series points. The slope of the line was used to calculate the efficiency of the reaction for each primer set using the equation:

$$E = 10^{\left(\frac{-1}{slope}\right)}$$

Figure 2:
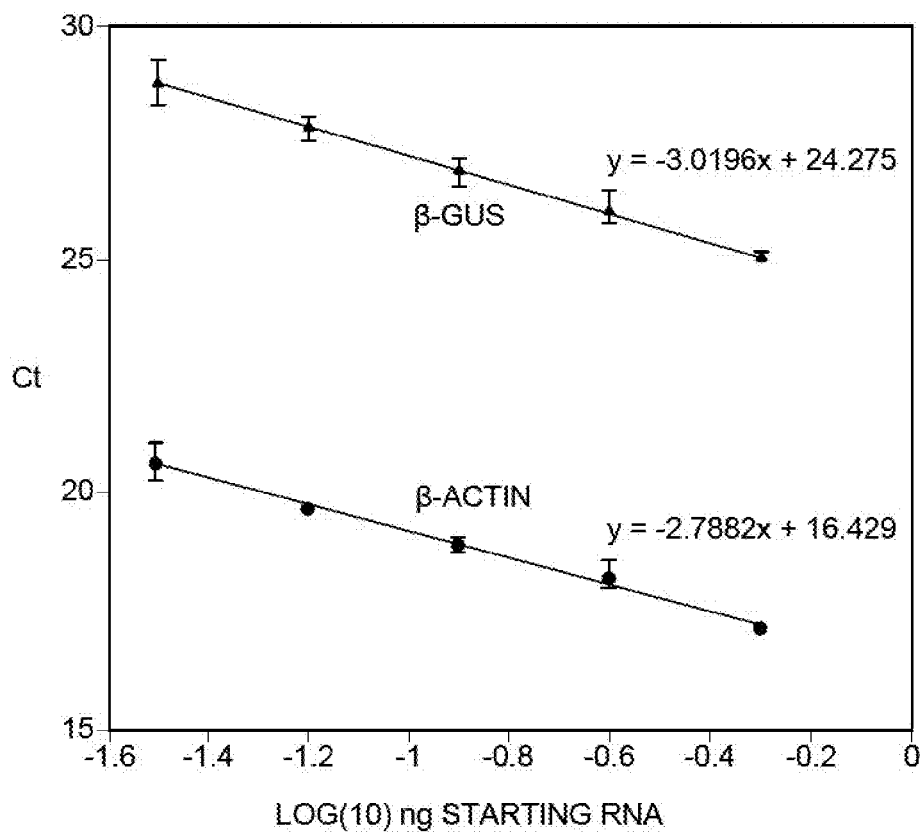
FIG. 2 shows PCR Primer efficiency testing. A standard curve of Ct versus log of the starting RNA amount is shown for 2 genes.

Using this equation (Pfaffl 2001), the efficiency for these β-actin primers is 2.28 and the efficiency for these β-GUS primers is 2.14 (FIG. 2). This efficiency was used when comparing the expression levels among multiple genes and multiple samples. This same method was used to calculate reaction efficiency for primer pairs for each gene we studied.

Assay and Results

Once primers were designed and tested and efficiency analysis was completed, primers were used examine expression of a single gene among many clinical samples. The basic design was to examine expression of both the experimental gene and a reference gene in each sample and, at the same time, in a control sample. The control sample we used was the universal mononuclear leukocyte reference RNA described in example 8 (R50).

In this example, three patient samples from patients with known CMV infection were compared to three patient samples from patients with no diagnosis of CMV infection based on standard diagnostic algorithms for active CMV infection (including viral PCR assays, serologies, culture and other tests). cDNA was made from all six RNA samples and the R50 control as described above. The cDNA was diluted 1:10 in water and 5 µl of this dilution was used in the 50 µl PCR reaction. Each 96-well plate consisted of 32 reactions, each done in triplicate. There were 17 templates and 3 primer sets. The three primer sets were β-GUS, β-Actin, and Granzyme B AS described above. Each of the three primer sets was used to measure template levels in 8 templates: the six experimental samples, R50, and water (no-template control). The β-GUS primers were also used to measure template levels a set of 8 templates identical except for the absence of the reverse transcriptase enzyme in the cDNA synthesis reaction (−RT). The real-time PCR reactions were performed as described above in "primer optimization/efficiency".

Figure 7B:
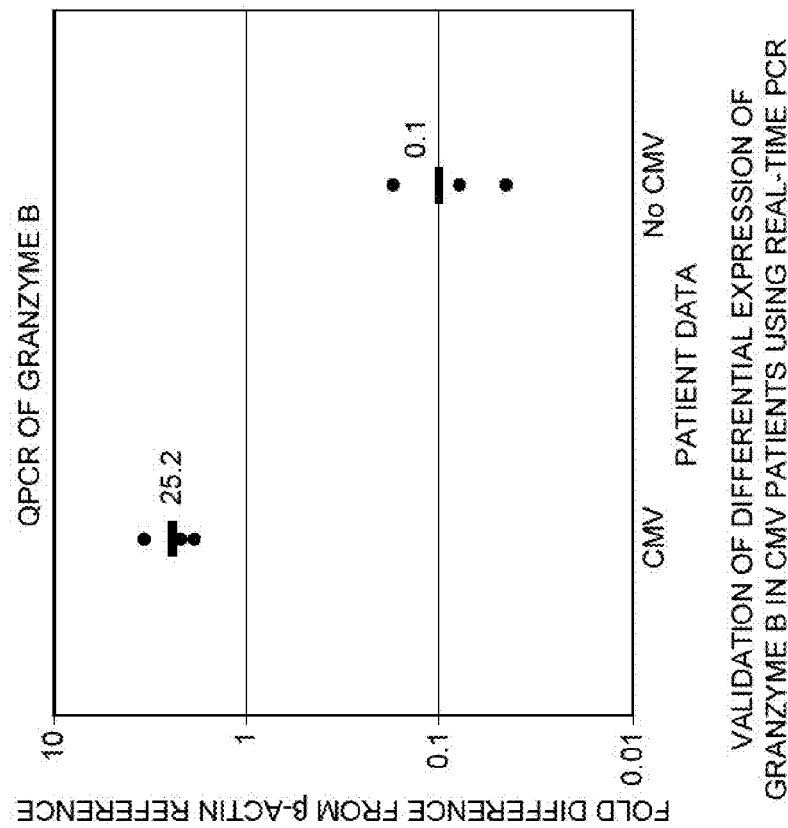
FIG. 7B shows the fold difference between the expression of Granzyme B and an Actin reference is shown for 3 samples from patients with and without CMV disease.
Figure 7A:
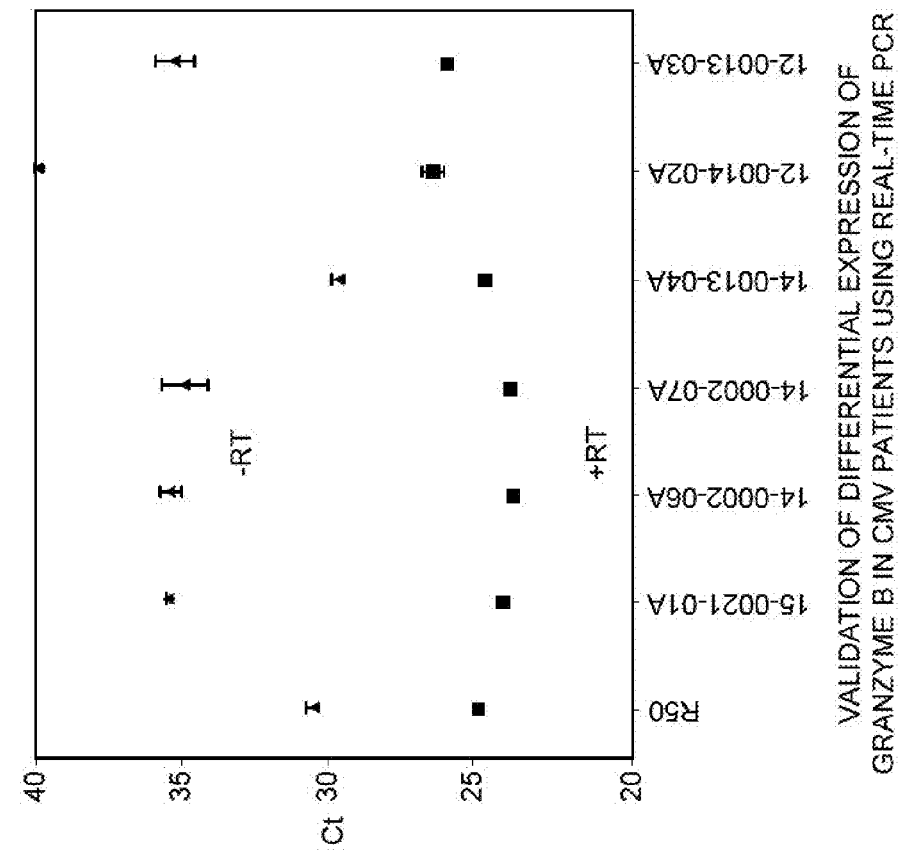
FIG. 7A shows the Ct for each patient sample on multiple assays is shown along with the Ct in the R50 control RNA. Triangles represent –RT (reverse transcriptase) controls.

The β-GUS amplification with +RT and −RT cDNA synthesis reaction templates were compared to measure the amount of genomic DNA contamination of the patient RNA sample (FIG. 7A). The only source of amplifiable material in the −RT cDNA synthesis reaction is contaminating genomic DNA. Separation by at least four $C_T$ between the −RT and +RT for each sample was required to consider the sample useful for analysis of RNA levels. Since a $C_T$ decrease of one is a two-fold increase in template, a difference of four $C_T$ would indicate that genomic DNA contamination level in the +RT samples was 6.25% of the total signal. Since we used these reactions to measure 30% or greater differences, a 6% contamination would not change the result.

For samples with sufficiently low genomic DNA contamination the data were used to identify differences in gene expression by measuring RNA levels. $C_T$ values from the triplicate wells for each reaction were averaged and the coefficient of variation (CV) determined. Samples with high CV (>2%) were examined and outlier reaction wells were discarded from further analysis. The average of the wells for each sample was taken as the $C_T$ value for each sample. For each gene, the $\Delta C_T$ was the R50 control $C_T$ minus the sample $C_T$. The equation below was then used to identify an expression ratio compared to a reference gene (β-Actin) and control sample (R50) for Granzyme B expression in each experimental sample (Pfaffl, M. W. 2001). E is the amplification efficiency determined above.

$$\text{ratio} = \frac{(E_{target})^{\Delta C_T target(control-sample)}}{(E_{ref})^{\Delta C_T ref(control-sample)}}$$

The complete experiment was performed in duplicate and the average of the two ratios taken for each gene. When β-Actin was used as the reference gene, the data show that Granzyme B is expressed at 25-fold higher levels in mononuclear cell RNA from patients with CMV than from patients without CMV (FIG. 7B). In this graph, each circle represents a patient sample and the black bars are the average of the three samples in each category.

Example 16

Correlation and Classification Analysis

After generation and processing of expression data sets from microarrays as described in Example 14, a log ratio value is used for most subsequent analysis. This is the logarithm of the expression ratio for each gene between sample and universal reference. The processing algorithm assigns a number of flags to data that are of low signal to noise or are in some other way of uncertain quality. Correlation analysis can proceed with all the data (including the flagged data) or can be done on filtered data sets where the flagged data is removed from the set. Filtered data should have less variability and may result in more significant results. Flagged data contains all information available and may allow discovery of genes that are missed with the filtered data set.

In addition to expression data, clinical data are included in the analysis. Continuous variables, such as the ejection fraction of the heart measured by echocardiography or the white blood cell count can be used for correlation analysis. In some cases, it may be desirable to take the logarithm of the values before analysis. These variables can be included in an analysis along with gene expression values, in which case they are treated as another "gene". Sets of markers can be discovered that work to diagnose a patient condition and these can include both genes and clinical parameters. Categorical variables such as male or female can also be used as variables for correlation analysis. For example, the sex of a patient may be an important splitter for a classification tree.

Clinical data are used as supervising vectors for the significance or classification analysis. In this case, clinical data associated with the samples are used to divide samples in to clinically meaningful diagnostic categories for correlation or classification analsysis. For example, pathologic specimens from kidney biopsies can be used to divide lupus patients into groups with and without kidney disease. A third or more categories can also be included (for example "unknown" or "not reported"). After generation of expression data and definition of using supervising vectors, correlation, significance and classification analysis is used to determine which set of genes are most appropriate for diagnosis and classification of patients and patient samples.

Significance Analysis for Microarrays (SAM)

Significance analysis for microarrays (SAM) (Tusher 2001) is a method through which genes with a correlation between their expression values and the response vector are statistically discovered and assigned a statistical significance. The ratio of false significant to significant genes is the False Discovery Rate (FDR). This means that for each threshold there are a set of genes which are called significant, and the FDR gives a confidence level for this claim. If a gene is called differentially expressed between 2 classes by SAM, with a FDR of 5%, there is a 95% chance that the gene is actually differentially expressed between the classes. SAM takes into account the variability and large number of variables of microarrays. SAM will identify genes that are most globally differentially expressed between the classes. Thus, important genes for identifying and classifying outlier samples or patients may not be identified by SAM.

After generation of data from patient samples and definition of categories using clinical data as supervising vectors, SAM is used to detect genes that are likely to be differentially expressed between the groupings. Those genes with the highest significance can be validated by real-time PCR (Example 15) or can be used to build a classification algorithm as described here.

Classification

Supervised harvesting of expression trees (Hastie 2001) identifies genes or clusters that best distinguish one class from all the others on the data set. The method is used to identify the genes/clusters that can best separate one class versus all the others for datasets that include two or more classes from each other. This algorithm can be used to identify genes that are used to create a diagnostic algorithm. Genes that are identified can be used to build a classification tree with algorithms such as CART.

CART is a decision tree classification algorithm (Breiman 1984). From gene expression and or other data, CART can develop a decision tree for the classification of samples. Each node on the decision tree involves a query about the expression level of one or more genes or variables. Samples that are above the threshold go down one branch of the decision tree and samples that are not go down the other branch. Genes from expression data sets can be selected for classification building using CART by significant differential expression in SAM analysis (or other significance test), identification by supervised tree-harvesting analysis, high fold change between sample groups, or known relevance to classification of the target diseases. In addition, clinical data can also be used as variables for CART that are of know importance to the clinical question or are found to be significant predictors by multivariate analysis or some other technique. CART identifies surrogates for each splitter (genes that are the next best substitute for a useful gene in classification). Analysis is performed in CART by weighting misclassification costs to optimize desired performance of the assay. For example, it may be most important the sensitivity of a test for a given diagnosis be near 100% while specificity is less important.

Once a set of genes and expression criteria for those genes have been established for classification, cross validation is done. There are many approaches, including a 10 fold cross validation analysis in which 10% of the training samples are left out of the analysis and the classification algorithm is built with the remaining 90%. The 10% are then used as a test set for the algorithm. The process is repeated 10 times with 10% of the samples being left out as a test set each time. Through this analysis, one can derive a cross validation error which helps estimate the robustness of the algorithm for use on prospective (test) samples. When a gene set is established for a diagnosis with a low cross validation error, this set of genes is tested using samples that were not included in the initial analysis (test samples). These samples may be taken from archives generated during the clinical study. Alternatively, a new prospective clinical study can be initiated, where samples are obtained and the gene set is used to predict patient diagnoses.

Lengthy table referenced here

US08110364-20120207-T00001

Please refer to the end of the specification for access instructions.

Lengthy table referenced here

US08110364-20120207-T00002

Please refer to the end of the specification for access instructions.

Lengthy table referenced here

US08110364-20120207-T00003

Please refer to the end of the specification for access instructions.

Lengthy table referenced here

US08110364-20120207-T00004

Please refer to the end of the specification for access instructions.

Lengthy table referenced here

US08110364-20120207-T00005

Please refer to the end of the specification for access instructions.

Lengthy table referenced here

US08110364-20120207-T00006

Please refer to the end of the specification for access instructions.

Lengthy table referenced here

US08110364-20120207-T00007

Please refer to the end of the specification for access instructions.

Lengthy table referenced here

US08110364-20120207-T00008

Please refer to the end of the specification for access instructions.

Lengthy table referenced here

US08110364-20120207-T00009

Please refer to the end of the specification for access instructions.

Lengthy table referenced here

US08110364-20120207-T00010

Please refer to the end of the specification for access instructions.

| Lengthy table referenced here | | Lengthy table referenced here |
|---|---|---|
| US08110364-20120207-T00011 | | US08110364-20120207-T00013 |
| Please refer to the end of the specification for access instructions. | | Please refer to the end of the specification for access instructions. |

| Lengthy table referenced here | | Lengthy table referenced here |
|---|---|---|
| US08110364-20120207-T00012 | | US08110364-20120207-T00014 |
| Please refer to the end of the specification for access instructions. | | Please refer to the end of the specification for access instructions. |

LENGTHY TABLES

The patent contains a lengthy table section. A copy of the table is available in electronic form from the USPTO web site (http://seqdata.uspto.gov/?pageRequest=docDetail&DocID=US08110364B2). An electronic copy of the table will also be available from the USPTO upon request and payment of the fee set forth in 37 CFR 1.19(b)(3).

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US08110364B2). An electronic copy of the "Sequence Listing" will also be available from the USPTO upon request and payment of the fee set forth in 37 CFR 1.19(b)(3).

We claim:

1. A method of diagnosing or monitoring an autoimmune or chronic inflammatory disease in a patient, comprising detecting the expression level of a nucleic acid in said patient to diagnose or monitor said autoimmune or chronic inflammatory disease in said patient wherein said nucleic acid comprises the nucleotide sequence SEQ ID NO: 3305.

2. The method of claim 1 wherein said autoimmune or chronic inflammatory disease is systemic lupus erythematosis (SLE).

3. The method of claim 1 wherein said expression level is detected by measuring the RNA level expressed by said nucleic acid.

4. The method of claim 3, further comprising isolating RNA from said patient prior to detecting said RNA level expressed by said nucleic acid.

5. The method of claim 3 wherein said RNA level is detected by PCR.

6. The method of claim 3 wherein said RNA level is detected by hybridization.

7. The method of claim 3 wherein said RNA level is detected by hybridization to an oligonucleotide.

8. The method of claim 7 wherein said oligonucleotide comprises DNA, RNA, cDNA, PNA, genomic DNA, or synthetic oligonucleotides.

* * * * *